(12) United States Patent
Burgess et al.

(10) Patent No.: US 9,096,567 B2
(45) Date of Patent: *Aug. 4, 2015

(54) 6-SUBSTITUTED PHENOXYCHROMAN CARBOXYLIC ACID DERIVATIVES

(71) Applicant: Array BioPharma Inc., Boulder, CO (US)

(72) Inventors: Laurence E. Burgess, Boulder, CO (US); Christopher T. Clark, Denver, CO (US); Adam Cook, Boulder, CO (US); Christopher P. Corrette, Boulder, CO (US); Robert Kirk DeLisle, Lyons, CO (US); George A. Doherty, Libertyville, IL (US); Kevin W. Hunt, Boulder, CO (US); Todd T. Romoff, Memphis, TN (US); Ganghyeok Kim, Superior, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/231,356

(22) Filed: Mar. 31, 2014

(65) Prior Publication Data
US 2014/0221342 A1      Aug. 7, 2014

Related U.S. Application Data

(63) Continuation of application No. 14/013,898, filed on Aug. 29, 2013, now Pat. No. 8,716,498, which is a continuation of application No. 13/001,201, filed as application No. PCT/US2009/048499 on Jun. 24, 2009, now Pat. No. 8,569,522.

(60) Provisional application No. 61/075,615, filed on Jun. 25, 2008.

(51) Int. Cl.
| | |
|---|---|
| A61K 31/352 | (2006.01) |
| C07D 311/04 | (2006.01) |
| C07D 311/58 | (2006.01) |
| C07D 405/12 | (2006.01) |
| C07D 407/12 | (2006.01) |

(52) U.S. Cl.
CPC ............ *C07D 311/58* (2013.01); *C07D 311/04* (2013.01); *C07D 405/12* (2013.01); *C07D 407/12* (2013.01)

(58) Field of Classification Search
CPC ......................... A61K 31/352; C07D 311/04
USPC ........... 549/356, 381, 405; 514/449, 453, 456
See application file for complete search history.

(56) References Cited

U.S. PATENT DOCUMENTS

| | | | |
|---|---|---|---|
| 5,059,609 | A | 10/1991 | Eggler et al. |
| 5,952,326 | A | 9/1999 | Eggler et al. |
| 6,239,147 | B1 | 5/2001 | Obach et al. |
| 8,569,522 | B2 | 10/2013 | Burgess et al. |
| 8,716,498 | B2 | 5/2014 | Burgess et al. |
| 8,785,445 | B2 * | 7/2014 | Cook et al. ............... 514/252.01 |
| 2010/0173955 | A1 | 7/2010 | Doherty et al. |
| 2010/0273850 | A1 | 10/2010 | Doherty |

FOREIGN PATENT DOCUMENTS

| | | |
|---|---|---|
| WO | 03029239 A1 | 4/2003 |
| WO | 2004058164 A2 | 7/2004 |
| WO | 2007144625 A1 | 12/2007 |
| WO | 2008024746 A1 | 2/2008 |
| WO | 2008054675 A2 | 5/2008 |

(Continued)

OTHER PUBLICATIONS

Norman, "Indole-Based CRTH2 Antagonists", Expert Opinion, Ther. Patents 15 (12), 1817-1823 (2005).
Pettipher et al., "Antagonism of the Prostaglandin D2 Receptors DP1 and CRTH2 as an Approach to Treat Allergic Diseases", Nature Reviews, Drug Discovery, vol. 6, 313-325 (2007).
Gunnewegh, et al., "Environmentally friendly synthesis of coumarin derivatives employing heterogeneous catalysis", Recl. Trav. Chim. Pays-Bas, vol. 115, 226-230 (1996).

(Continued)

*Primary Examiner* — Golam M M Shameem

(57) ABSTRACT

Provided herein is a method of treating an allergic inflammatory disease selected from asthma, dermatitis, allergic rhinitis, urticaria, anaphylaxis, angioedemea, allergies, contact hypersensitivity, drug hypersensitivity, and allergic conjunctivitis in a mammal, comprising administering a therapeutically effective amount of a compound of Formula I

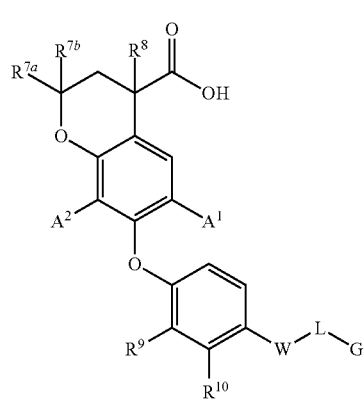

or a pharmaceutically acceptable salt thereof, to said mammal in need thereof, wherein $A^1$, $A^2$, W, L, G, $R^{7a}$, $R^{7b}$, $R^8$, $R^9$ and $R^{10}$ are as defined herein.

31 Claims, No Drawings

(56) References Cited

FOREIGN PATENT DOCUMENTS

| WO | 2008137027 | A2 | 11/2008 |
| WO | 2009061730 | A2 | 5/2009 |

OTHER PUBLICATIONS

Kamal M. Dawood, Tetrahedron, vol. 63, Issue 39, Sep. 2007, pp. 9642-9651.

* cited by examiner

6-SUBSTITUTED PHENOXYCHROMAN CARBOXYLIC ACID DERIVATIVES

This application is a continuation of U.S. patent application Ser. No. 14/013,898, filed Aug. 29, 2013, which is a continuation of U.S. patent application Ser. No. 13/001,201, filed Dec. 23, 2010, now U.S. Pat. No. 8,569,522, which is a 371 filing of PCT/US09/048,499, filed Jun. 24, 2009, which claims priority to U.S. Provisional Patent Application Ser. No. 61/075,615 filed Jun. 25, 2008, each of which is incorporated herein in its entirety.

The present invention relates to novel compounds, to pharmaceutical compositions comprising compounds of this invention, to a process for making compounds of this invention and to the use of compounds of this invention in therapy. More particularly, this invention relates to certain 6-substituted phenoxychroman carboxylic acid derivatives useful in the treatment and prevention of allergic diseases such as asthma, allergic rhinitis and atopic dermatitis and other inflammatory diseases mediated by prostaglandin $D_2$ ($PGD_2$).

DP2 is a G-protein coupled receptor that is selectively expressed on cell types that mediate allergic inflammation including mast cells, basophils, eosinophils and Th2 cells and there is growing evidence that it plays a critical role in the pathophysiology of allergy (Hirai et. al., Journal of Experimental Medicine (2001) 193:255-261). The endogenous ligands for DP2 (PGD2 and its active metabolites) are made by activated mast cells and by Th2 cells, and can be readily detected at sites of allergic disease. Agonism of DP2 promotes the migration and or activation of basophils, eosinophils and Th2 cells in vitro and in vivo (Kostenis and Ulven, Trends in Molecular Medicine (2006) 12:1471-148-158), suggesting that this receptor may drive disease processes in vivo. In support of this mice made deficient in DP2 by gene inactivation through homologous recombination show evidence of reduced allergic responses in pre-clinical models of asthma and atopic dermatitis. Similar results have been reported using selective small molecule inhibitors of DP2 (reviewed in Pettipher, et. al., Nature Reviews Drug Discovery (2007) 6:313-325).

Clinical validation for DP2 as a target for allergic disease is also provided by Ramatroban (BAY u34505). Ramatroban was originally developed as a Thromboxane A2 (TP) receptor antagonist but showed unexpected clinical activity in allergy, which could not be readily explained by its activity against TP. It has recently been shown that Ramatroban is also an inhibitor of DP2 and its activity in pre-clinical models of allergy can be recapitulated using selective inhibitors of DP2 but not of TP (Sugimoto et. al., Journal of Pharmacology and Experimental Therapeutics (2003) 305:347-352; Takeshiti et. al., International Immunology (2004) 16:947-959). These findings support the view that the clinical efficacy seen with Ramatroban in allergic disease is due to its activity against DP2. Ramatroban is currently approved in Japan for the treatment of seasonal allergic rhinitis. Based on the validation of DP2 as a drug target in allergy many have sought to develop inhibitors of DP2 for the treatment of allergic disease, and the first of these has now entered clinical development.

International patent application, publication number WO 2004/058164 discloses inter alia, certain 2-substituted phenoxyphenylacetic acid derivatives that modulate the $PGD_2$-selective receptor CRTH2 (chemoattractant receptor-homologous molecule expressed on Th2 cells), now more commonly referred to as DP2. The compounds are said to be useful in the treatment of immunologic diseases such as asthma and allergic inflammation.

It has now been found that certain phenoxychroman carboxylic acid derivatives having an amide-linked group at the 4-position of the phenoxy moiety are DP2 receptor antagonists.

According to one aspect, the present invention provides a compound of general Formula I:

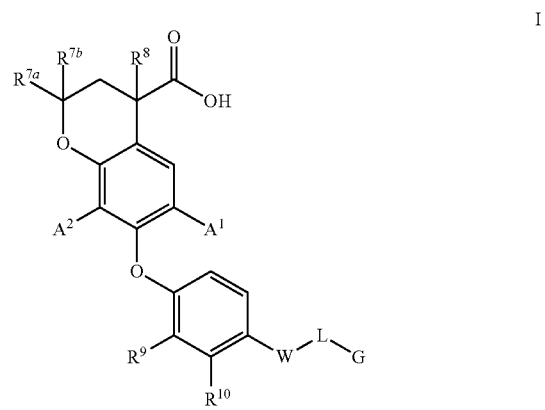

or a pharmaceutically acceptable salt thereof, wherein:

$A^1$ is hydrogen, CN, Cl, F, Br, OMe, (1-4C alkyl) or cyclopropyl;

$A^2$ is hydrogen, Cl, Br, F, (1-4C alkyl) or cyclopropyl;

W is —C(=O)NR$^1$— or —NR$^2$C(=O)—;

$R^1$ and $R^2$ are each hydrogen or methyl;

L is a bond, —(CR$^3$R$^4$)$_n$—(CR$^a$R$^b$)$_m$—(CR$^5$R$^6$)—*, (2-4C)alkenylene, —O(1-4C alkyl)-*, -(1-4C alkyl)-O—*, -(1-4C alkyl)-S—*, (3-6C)cycloalkylene, or hetCyc$^1$, wherein the * indicates the point of attachment to G, provided that when W is —C(=O)NR$^2$— then L is not —(CH=CH)—;

m=0, 1 or 2;

n=0 or 1;

$R^a$ and $R^b$ are independently selected from hydrogen and (1-4C alkyl);

$R^3$ is hydrogen, (1-4C alkyl) or CH$_2$OH;

$R^4$ is hydrogen or methyl;

$R^5$ is hydrogen, (1-4C alkyl), OH, —O(1-4C alkyl) or F;

$R^6$ is hydrogen, F or methyl, or $R^5$ and $R^6$ together with the carbon to which they are attached form a cyclopropyl ring, provided that when m=0 and n=0, then $R^5$ and $R^6$ do not form a ring with the carbon to which they are attached;

hetCyc$^1$ is a group having the formula

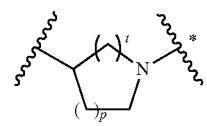

where t is 1 or 2 and p is 0 or 1, and the * indicates the point of attachment to G;

G is Ar$^1$, Ar$^2$, naphthyl, a benzo-fused (5-6C)cycloalkyl ring optionally substituted with one or more substituents independently selected from Cl and OMe, a benzo-fused 5-6 membered heterocyclic ring having 1-2 heteroatoms independently selected from O and N, a (3-6C)cycloalkyl ring optionally substituted with one or more substituents independently selected from (1-4C)alkyl, an oxaspirononanyl ring, or t-butyl;

Ar$^1$ is phenyl optionally substituted with one or more substituents independently selected from F, Cl, Br, CF$_3$, (1-4C) alkyl, OH, —O(1-4C alkyl), —S(1-3C alkyl), —SCF$_3$, cyclopropyl, —CH$_2$N(1-3C alkyl)$_2$, —O-(2-3C)fluoroalkyl, —O-(1-3C)difluoroalkyl —O-(1-3C)trifluoroalkyl, —OCH$_2$(cyclopropyl), and (3-4C)alkynyl;

Ar$^2$ is phenyl which is substituted with Ar$^3$, —O—Ar$^4$, hetAr$^1$ or —O-hetAr$^2$, wherein Ar$^2$ is optionally further substituted with one or more substituents independently selected from F, Cl and CF$_3$;

Ar$^3$ is phenyl optionally substituted with one or more substituents independently selected from F, Cl, Br and (1-4C alkyl);

Ar$^4$ is phenyl optionally substituted with one or more substituents independently selected from F, Cl, Br and (1-4C alkyl);

hetAr$^1$ is a 6-membered heteroaryl having 1-2 nitrogen atoms and optionally substituted with one or more substituents independently selected from (1-4C alkyl);

hetAr$^2$ is a 6-membered heteroaryl having 1-2 nitrogen atoms and optionally substituted with one or more substituents independently selected from (1-4C alkyl) and CF$_3$;

R$^{7a}$, R$^{7b}$ and R$^8$ are each independently hydrogen or methyl;

R$^9$ is hydrogen, methyl, fluoro or NO$_2$; and

R$^{10}$ is hydrogen, methyl or fluoro.

Compounds according to the present invention have been found to be DP2 antagonists and are useful in the treatment of immunologic diseases such as asthma and allergic inflammation.

It will be appreciated that certain compounds according to the invention may contain one or more centers of asymmetry and may therefore be prepared and isolated in a mixture of isomers such as a racemic mixture, or in an enantiomerically pure form.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

Examples of salts of Formula I include alkali metal salts, such as lithium, sodium or potassium salts, or alkaline earth metal salts, such as calcium salts. Particular mention is made of the sodium salt.

A further example of a salt includes a tromethamine salt (IUPAC name: 2-amino-2-(hydroxymethyl)-1,3-propanediol; also known as Tris).

It will further be appreciated that the compounds of Formula I or their salts may be isolated in the form of solvates, and accordingly that any such solvate is included within the scope of the present invention.

The term "(1-4C)alkyl" used herein refers to a saturated linear or branched-chain monovalent hydrocarbon radical of one to four carbon atoms. Examples of alkyl groups include, but are not limited to, methyl, ethyl, 1-propyl, 2-propyl, 1-butyl, 2-methyl-1-propyl, 2-butyl, and 2-methyl-2-propyl.

The term "(2-4C)alkenylene" as used herein refers to a linear or branched-chain bivalent hydrocarbon radical of two to four carbon atoms having a double bond. The double bond may be in the cis- or trans-orientation.

The term "(3-4C)alkynyl" as used herein refers to a linear or branched-chain monovalent hydrocarbon radical of 3-4 carbons having a triple bond.

The term "(2-3C)fluoroalkyl" as used herein refers to a C$_2$-C$_3$ alkyl group wherein one of the hydrogen atoms is replaced by a fluorine atom.

The term "(1-3C)difluoroalkyl" as used herein refers to a C$_1$-C$_3$ alkyl group wherein two of the hydrogen atoms are each replaced by a fluorine atom.

The term "(1-3C)trifluoroalkyl" as used herein refers to a C$_1$-C$_3$ alkyl group wherein three of the hydrogen atoms are each replaced by a fluorine atom.

In certain embodiments, A$^1$ is CN, Cl, (1-4C alkyl) or cyclopropyl.

In certain embodiments, A$^1$ is CN, Cl, methyl or cyclopropyl.

In certain embodiments, A$^1$ is CN, Cl or cyclopropyl.

In certain embodiments, A$^1$ is CN or Cl.

In certain embodiments, A$^1$ is hydrogen. In certain embodiments, A$^1$ is CN. In certain embodiments, A$^1$ is Cl. In certain embodiments, A$^1$ is (1-4C alkyl). An example of A$^1$ is methyl. In certain embodiments, A$^1$ is cyclopropyl. In certain embodiments, A$^1$ is OMe. In certain embodiments, A$^1$ is Br.

In certain embodiments, A$^2$ is selected from H, Br, Cl, cyclopropyl and methyl.

In certain embodiments, A$^2$ is selected from H, Br, Cl, and cyclopropyl.

In certain embodiments, A$^2$ is selected from hydrogen and Br.

In certain embodiments, A$^2$ is selected from hydrogen and Cl.

In certain embodiments, A$^2$ is selected from hydrogen and cyclopropyl.

In certain embodiments, A$^2$ is hydrogen. In certain embodiments, A$^2$ is Cl. In certain embodiments, A$^2$ is Br. In certain embodiments, A$^2$ is (1-4C alkyl). A particular example is methyl. In certain embodiments, A$^2$ is cyclopropyl.

In certain embodiments, A$^1$ is selected from Cl, CN and cyclopropyl, and A$^2$ is selected from H, Cl and cyclopropyl.

In certain embodiments, A$^1$ is selected from CN, Cl and cyclopropyl, and A$^2$ is H.

In certain embodiments, A$^1$ is CN and A$^2$ is hydrogen.

In certain embodiments, A$^1$ is Cl and A$^2$ is hydrogen.

In certain embodiments, A$^1$ is cyclopropyl and A$^2$ is hydrogen.

In certain embodiments, A$^1$ is Cl and A$^2$ is Br.

In certain embodiments, A$^1$ and A$^2$ are both Cl.

In certain embodiments, A$^1$ is Cl and A$^2$ is cyclopropyl.

In certain embodiments, A$^1$ and A$^2$ are both cyclopropyl.

In certain embodiments, A$^1$ and A$^2$ are both hydrogen.

In certain embodiments, R$^{7a}$ and R$^{7b}$ are both hydrogen.

In certain embodiments, R$^{7a}$ and R$^{7b}$ are both methyl.

In certain embodiments, R$^{7a}$ is hydrogen and R$^{7b}$ is methyl.

In certain embodiments, R$^8$ is hydrogen. In certain embodiments, R$^8$ is methyl.

In certain embodiments, each of R$^{7a}$, R$^{7b}$ and R$^8$ is hydrogen.

In certain embodiments, R$^9$ is hydrogen or fluoro.

In certain embodiments, R$^9$ is hydrogen. In certain embodiments, R$^9$ is fluoro. In certain embodiments, R$^9$ is methyl. In certain embodiments, R$^9$ is NO$_2$.

In certain embodiments, R$^{10}$ is hydrogen or fluoro.

In certain embodiments, R$^{10}$ is hydrogen. In certain embodiments, R$^{10}$ is fluoro.

In certain embodiments, R$^{10}$ is methyl.

In certain embodiments, each of R$^9$ and R$^{10}$ is hydrogen.

In certain embodiments, each of R$^{7a}$, R$^{7b}$, R$^8$, R$^9$ and R$^{10}$ is hydrogen.

In one embodiment, W is —CONR$^1$—. An example of a particular value for R$^1$ is hydrogen. In one embodiment, W is —NR²CO—. In one embodiment R² is hydrogen. In another embodiment, R² is methyl. Examples of values for W are —C(=O)NH—, —NHC(=O)— and —N(CH₃)CO—.

In a particular embodiment, W is —C(=O)NH—.

In one embodiment, L is a bond.

In one embodiment, L is —(CR³R⁴)ₙ—(CRᵃRᵇ)ₘ—(CR⁵R⁶)—*.

In certain embodiments when L is —(CR³R⁴)ₙ—(CRᵃRᵇ)ₘ—(CR⁵R⁶)—*, n is 0 or 1 and m is 0, 1 or 2. In certain embodiments, each of R³, R⁴, Rᵃ, Rᵇ, R⁵ and R⁶ is hydrogen such that L is selected from —CH₂—, —CH₂CH₂—, —CH₂CH₂CH₂— and —CH₂CH₂CH₂CH₂—.

In certain embodiments when L is —(CR³R⁴)ₙ—(CRᵃRᵇ)ₘ—(CR⁵R⁶)—* where one of m or n is 0.

In certain embodiments, L is a bond and CH₂CH₂.

In certain embodiments when L is —(CR³R⁴)ₙ—(CRᵃRᵇ)ₘ—(CR⁵R⁶)—*, n is 0 or 1, m is 1 or 2, and R⁵ and R⁶ together with the atom to which they are attached form a cyclopropyl ring. In certain embodiments, each of R³ and R⁴ is hydrogen when n is 1 and each of Rᵃ and Rᵇ is hydrogen. Particular values for L include —CH₂(cycloprop-1,1,-diyl) and —CH₂CH₂(cycloprop-1,1,-diyl) groups having the structures:

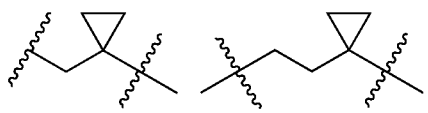

In certain embodiments when L is —(CR³R⁴)ₙ—(CRᵃRᵇ)ₘ—(CR⁵R⁶)—*, R⁵ is hydrogen, (1-4C alkyl), OH, —O(1-4C alkyl) or F, and R⁶ is hydrogen, F or methyl. In certain embodiments, n is 1 and m is 0. In certain embodiments, each of R³ and R⁴ is hydrogen. Particular values for L include the structures:

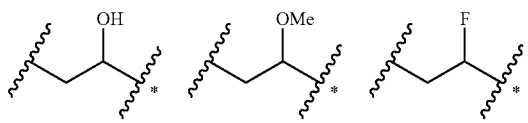

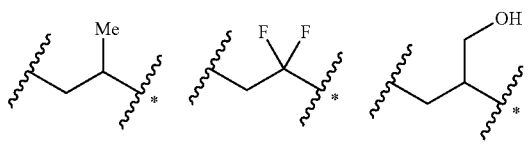

wherein the asterisk indicates the point of attachment to the G group.

In certain embodiments when L is —(CR³R⁴)ₙ—(CRᵃRᵇ)ₘ—(CR⁵R⁶)—*, n is 1, m is 0, 1 or 2, R³ is hydrogen, (1-4C alkyl) or —CH₂OH, and R⁴ is hydrogen or methyl. In certain embodiments, each of Rᵃ, Rᵇ, R⁵ and R⁶ is hydrogen. In certain embodiments, m is 0 and each of R⁵ and R⁶ is hydrogen. Particular values for L include the structures:

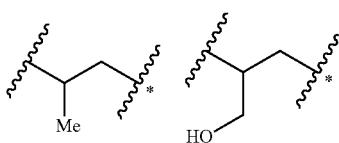 [SMILES: *CC(*)C ; *CC(*)CO]

wherein the asterisk indicates the point of attachment to the G group.

In certain embodiments, L is (2-4C)alkenylene. Particular values for L include —CH₂=CH₂— and —CH₂CH₂CH=CH₂—.

In certain embodiments, L is —O(1-4C alkyl)-* wherein the asterisk indicates the point of attachment to the G group. A particular value is —OCH₂—*.

In certain embodiments, L is -(1-4C alkyl)-O—* wherein the asterisk indicates the point of attachment to the G group. A particular value is —CH₂CH₂O—*.

In certain embodiments, L is -(1-4C alkyl)-S—* wherein the asterisk indicates the point of attachment to the G group. A particular value is —CH₂CH₂S—*.

In certain embodiments, L is (3-6C)cycloalkylene, that is, a divalent cycloalkyl ring having from 3-6 carbon atoms in the ring, wherein the radicals are located on different carbon atoms within the ring. Examples include cyclopropylene, cyclobutylene, cyclopentylene, and cyclohexylene rings. Particular values for L include the structures:

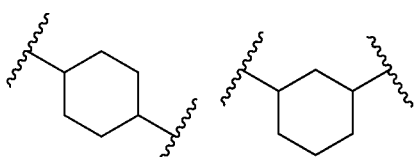

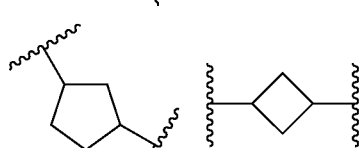

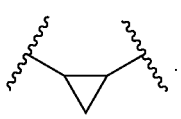

In certain embodiments, L is hetCyc¹ which is represented the formula

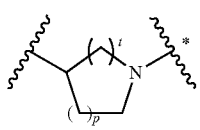

where t and p are as defined herein and the asterisk indicates the point of attachment to the G group. Particular values for L include the structures:

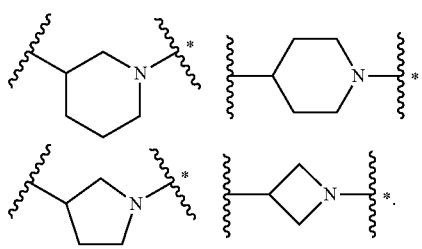

In certain embodiments of Formula I, L is selected from a bond, —(CR³R⁴)ₙ—(CRᵃRᵇ)ₘ—(CR⁵R⁶)—*, (3-6C)cycloalkylene, —O(1-4C alkyl)-*, -(1-4C alkyl)-O—*, and -(1-4C alkyl)-S—.

In certain embodiments of Formula I, L is selected from hetCyc¹, —O(1-4C alkyl)-*, -(1-4C alkyl)-O—*, and -(1-4C alkyl)-S—*.

In certain embodiments of Formula I, L is selected from —O(1-4C alkyl)-*, -(1-4C alkyl)-O—*, and -(1-4C alkyl)-S—*.

In certain embodiments of Formula I, L is hetCyc¹.

In certain embodiments of Formula I, L is selected from a bond, —(CR³R⁴)ₙ—(CRᵃRᵇ)ₘ—(CR⁵R⁶)—*, and (3-6C)cycloalkylene.

In certain embodiments of Formula I, L is selected from a bond and (CR³R⁴)ₘ—(CRᵃRᵇ)ₘ—(CR⁵R⁶)—*.

In certain embodiments of Formula I, L is selected from a bond and CH₂CH₂.

In certain embodiments, the G group is Ar¹.

In certain embodiments, Ar¹ is phenyl optionally substituted with one or more substituents independently selected from F, Cl, Br, CF₃, (1-4C)alkyl, OH, —O(1-4C alkyl), —S(1-3C alkyl), —SCF₃, cyclopropyl, —CH₂N(1-3C alkyl)₂, —O-(2-3C)fluoroalkyl, —O-(1-3C)difluoroalkyl —O-(1-3C)trifluoroalkyl, —OCH₂(cyclopropyl), and (3-4C) alkynyl.

In particular embodiments, Ar¹ is phenyl optionally substituted with one or more substituents independently selected from F, Cl, Br, CF₃, methyl, ethyl, propyl, tert-butyl, OH, methoxy, ethoxy, propoxy, isopropoxy, tert-butoxy, SMe, SCF₃, cyclopropyl, CH₂NMe₂, OCH₂CH₂F, OCH₂CH₂CH₂F, OCHF₂, OCF₃, —OCH₂(cyclopropyl), and propynyl. In certain embodiments, Ar¹ is phenyl optionally substituted with 2 of said substituents. In certain embodiments, Ar¹ is phenyl optionally substituted with 3 of said substituents.

Particular values for G when represented by Ar¹ include phenyl, 2-chlorophenyl, 3-chlorophenyl, 4-chlorophenyl, 2,6-dichlorophenyl, 3,4-dichlorophenyl, 2,4-dichlorophenyl, 2,5-dichlorophenyl, 2,3-dichlorophenyl, 3,5-dichlorophenyl, 2-chloro-6-fluorophenyl, 2-chloro-4-fluorophenyl, 2-fluorophenyl, 3-fluorophenyl, 4-fluorophenyl, 2,4-difluorophenyl, 2-bromophenyl, 4-bromophenyl, 2-trifluoromethylphenyl, 3-trifluoromethylphenyl, 4-trifluoromethylphenyl, 2-methylphenyl, 3-methylphenyl, 4-methylphenyl, 2,4-dimethylphenyl, 2-hydroxyphenyl, 3-hydroxyphenyl, 4-hydroxyphenyl, 2-methoxyphenyl, 3-methoxyphenyl, 4-methoxyphenyl, 2-tert-butoxyphenyl, 2-ethoxyphenyl, 3-isopropoxyphenyl, 2-trifluoromethoxyphenyl, 2-thiomethylphenyl, 3-thiomethylphenyl, 4-thiomethylphenyl, 4-trifluoromethylthiophenyl, 2-cyclopropylphenyl, 4-cyclopropylphenyl, 3-tert-butylphenyl, 4-tert-butylphenyl, 4-(dimethylamino)methylphenyl, 3,4-dimethoxyphenyl, 2,3-dimethoxyphenyl, 2,4-dimethoxyphenyl, 3-methoxy-4-chlorophenyl, 2-chloro-4-methoxyphenyl, 2-methoxy-4-bromophenyl, 2-methoxy-4-chlorophenyl, 2-methoxy-4-fluorophenyl, 2-methoxy-4-trifluoromethylphenyl, 2-methoxy-4-cyclopropylphenyl, 2-fluoro-5-chlorophenyl, 2-chloro-4-trifluoromethylphenyl, 2-chloro-4-bromophenyl, 2-methyl-4-chlorophenyl, 2,5-dimethoxyphenyl, 2-methoxy-5-bromophenyl, 2-bromo-4-chlorophenyl, 2-chloro-4-cyclopropylphenyl, 2-cyclopropyl-4-chlorophenyl, 2,4-dichloro-6-methoxyphenyl, 3-methoxy-4-chlorophenyl, 4-difluoromethoxyphenyl, 2-chloro-4,6-dimethoxyphenyl, 2,6-dimethoxyphenyl, 4-chloro-2,6-dimethoxyphenyl, 2-chloro-6-methoxyphenyl, 2,4-dichloro-6-ethoxyphenyl, 2-methyl-4-chlorophenyl, 2-ethyl-4-chlorophenyl, 2-propyl-4-chlorophenyl, 2,6-dichloro-4-methoxyphenyl, 2-trifluoromethyl-4-chlorophenyl, 2,4-diethoxyphenyl, 3,5-dimethoxyphenyl, 2-methoxy-3-chlorophenyl, 3-chloro-5-methoxyphenyl, 2,4-trifluoromethylphenyl, 2-ethylphenyl, 2-thiomethyl-4-chlorophenyl, 2-ethoxy-4-methoxyphenyl, 2-methoxy-5-chlorophenyl, 2-ethoxy-4-chlorophenyl, 2-trifluoromethoxy-4-chlorophenyl, 2-tert-butoxy-4-chlorophenyl, 2-cyclopropylmethoxy-4-chlorophenyl, 2-isopropoxy-4-chlorophenyl, 2-ethoxy-4-chlorophenyl, 2-propoxy-5-chlorophenyl, 4-chloro-2-(2-fluoroethoxy)phenyl, 4-chloro-2-(3-fluoropropoxy)phenyl, and 2-chloro-4-(propyn-1-yl) phenyl.

Additional values for G when represented by Ar¹ include 2,4-di(trifluoromethyl)phenyl, 2-cyclopropyl-4-trifluoromethylphenyl, 2,4,6-trimethoxyphenyl, 2-methoxy-4-ethoxyphenyl, 2-fluoro-4-chlorophenyl and 2-hydroxy-4-chlorophenyl.

In certain embodiments of Formula I, G is Ar².

In certain embodiments, Ar² is a phenyl group substituted with Ar³, wherein Ar² is optionally further substituted with one or more substituents independently selected from F, Cl and CF₃. Examples of Ar³ include phenyl, 2-chlorophenyl, 3-chlorophenyl, 4-chlorophenyl, 3-methylphenyl, 4-methylphenyl, 3,4-dimethylphenyl, and 2,3-dimethylphenyl.

Particular values for G when represented by Ar² include the structures:

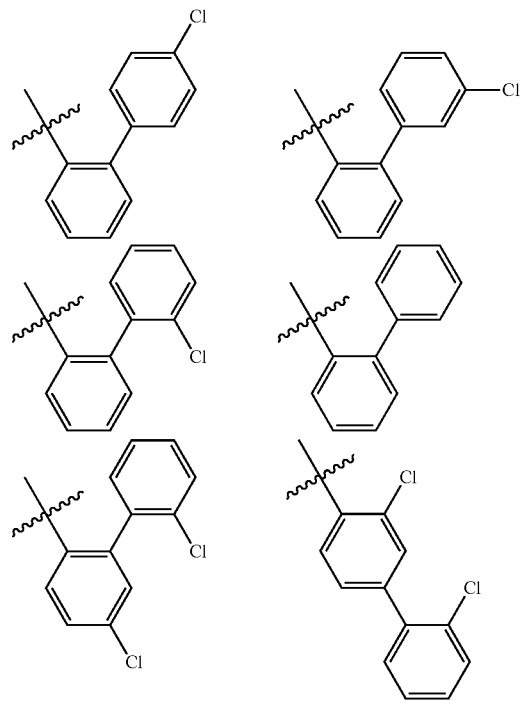

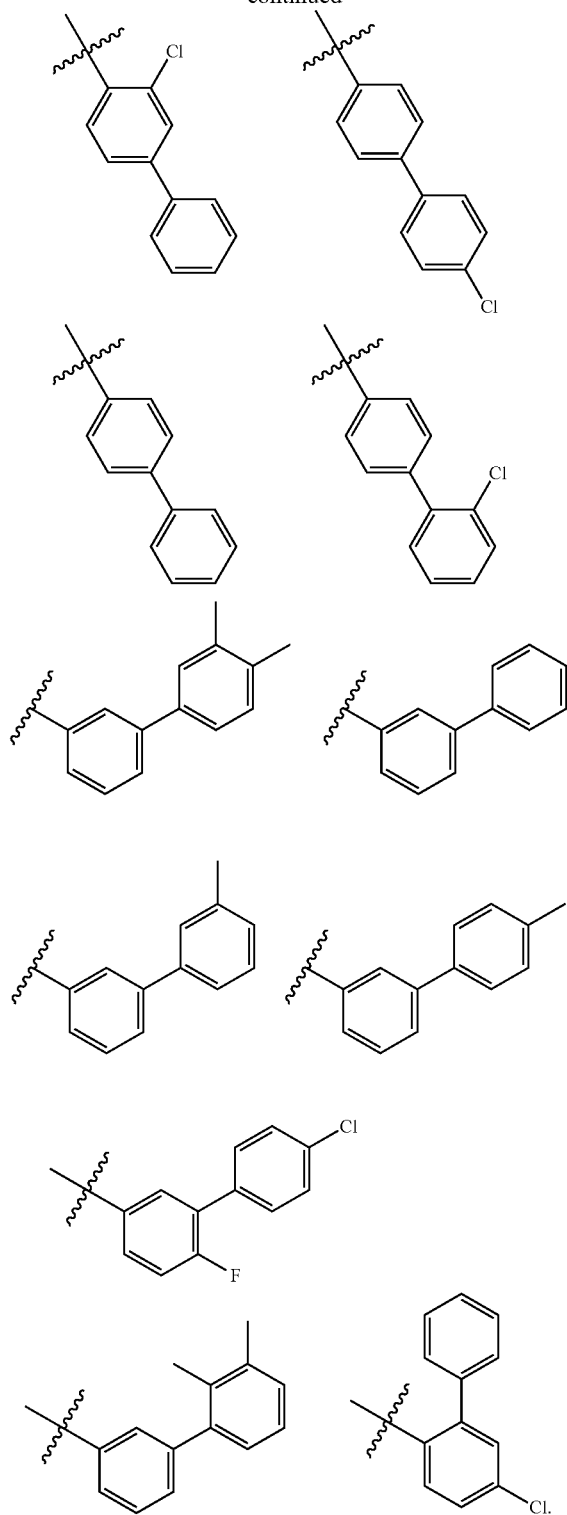

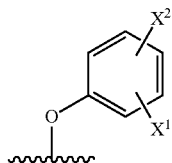

where $X^1$ and $X^2$ are independently selected from fluoro, chloro and bromo.

Examples of G when represented by $Ar^2$ include the structures:

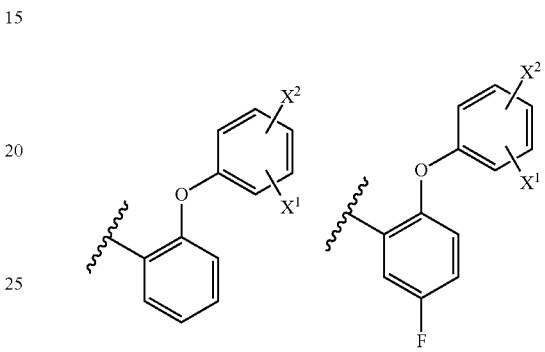

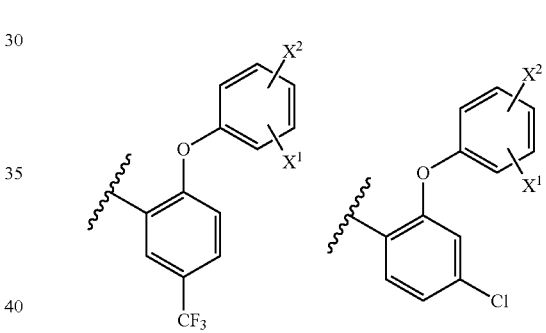

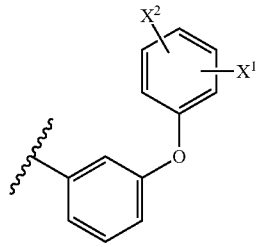

wherein $X^1$ and $X^2$ are independently selected from fluoro, chloro and bromo. Particular examples of G when represented by $Ar^2$ include the structures:

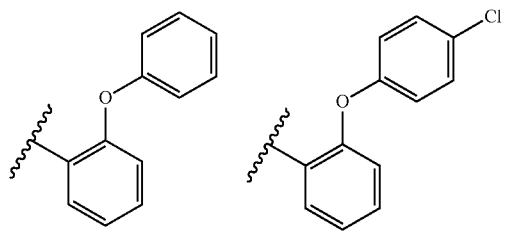

In certain embodiments of Formula I, G is $Ar^2$ and $Ar^2$ is phenyl substituted with O—$Ar^4$, wherein the $Ar^2$ group is optionally further substituted with one or more substituents independently selected from F, Cl and $CF_3$. Examples of O—$Ar^4$ substituents include phenoxy groups optionally substituted with fluoro, chloro or bromo. Particular examples of O—$Ar^4$ can be represented by the structure:

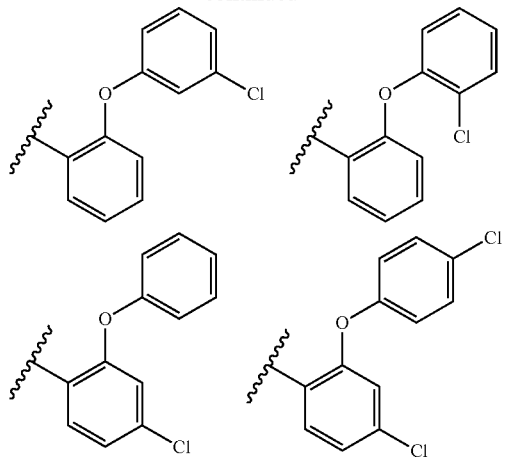

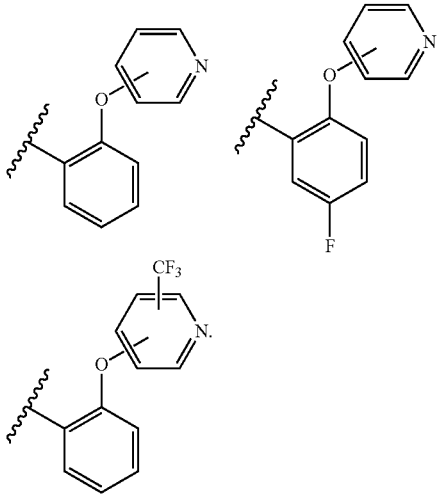

Particular examples of G when represented by $Ar^2$ include the structures:

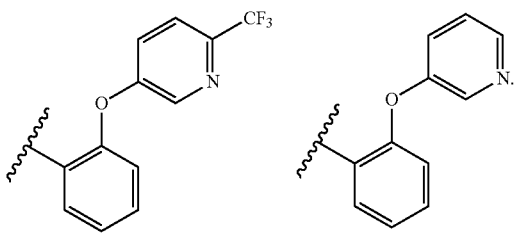

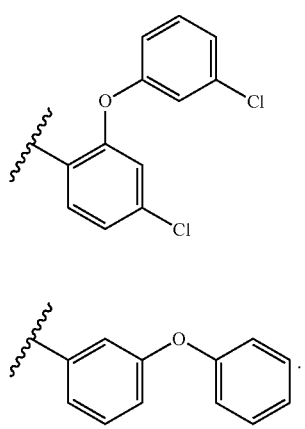

In certain embodiments of Formula I, G is $Ar^2$ and $Ar^2$ is phenyl substituted with $hetAr^1$, wherein said $Ar^2$ is optionally further substituted with one or more substituents independently selected from F, Cl and $CF_3$. Examples of $hetAr^1$ substituents include pyridyl and pyrimidyl rings. In certain embodiments, $hetAr^1$ is substituted with one or more (1-4C alkyl) groups, for example, one or more methyl groups. Particular examples of $hetAr^1$ include methylpyrimidyl groups, such as 2-methylpyrimidyl. A particular example of G when represented by $Ar^2$ is the structure:

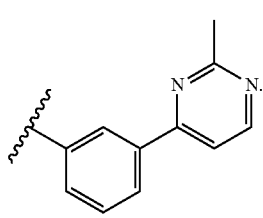 [SMILES: *c1cccc(-c2ccnc(C)n2)c1]

In certain embodiments of Formula I, G is $Ar^2$ wherein $Ar^2$ is phenyl substituted with —O-$hetAr^2$, wherein said $Ar^2$ is optionally further substituted with one or more substituents independently selected from F, Cl and $CF_3$. Examples of O-$hetAr^2$ include pyridinyloxy and pyrimidinyloxy groups, each of which is optionally substituted with $CF_3$. Examples of G when represented by $Ar^2$ include the structures:

In certain embodiments, G is naphthyl. Examples include 1-naphthyl and 2-naphthyl.

In certain embodiments, G is a benzo-fused (5-6C)cycloalkyl ring optionally substituted with one or more substituents independently selected from Cl and OMe. Examples of benzo-fused (5-6C)cycloalkyl ring include unsubstituted and substituted 2,3-dihydro-1H-indenyl and tetrahydronaphthyl rings, for example unsubstituted and substituted 2,3-dihydro-1H-inden-1-yl, 2,3-dihydro-1H-inden-2-yl, 1,2,3,4-tetrahydronaphth-2-yl rings. Particular values for the G group include the structures:

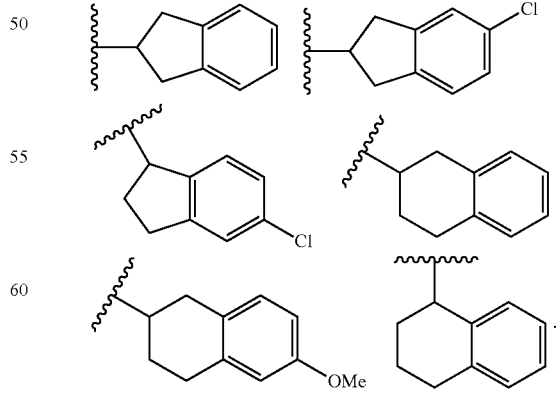

In certain embodiments, G is a benzo-fused 5-6 membered heterocycle having 1-2 ring heteroatoms independently selected from O and N. Examples include chromanyl, tetrahydroquinolinyl, and benzodioxolyl rings. Particular values for G include the structures:

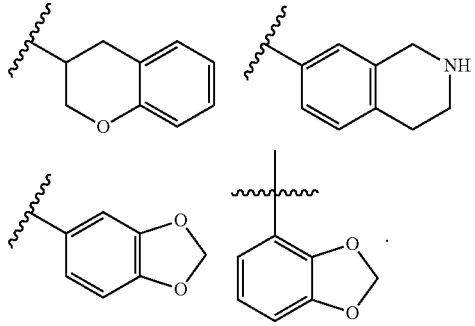

In certain embodiments, G is a (3-6C)cycloalkyl ring optionally substituted with one or more substituents independently selected from (1-4C)alkyl. Examples include cyclopropyl, cyclobutyl, cyclopentyl and cyclohexyl rings optionally substituted with one or more alkyl groups, such as one or more methyl, ethyl, propyl, isopropyl, butyl and t-butyl groups. In certain embodiments G is a cycloalkyl group substituted with one or more methyl or t-butyl groups. Particular examples of G include the structures:

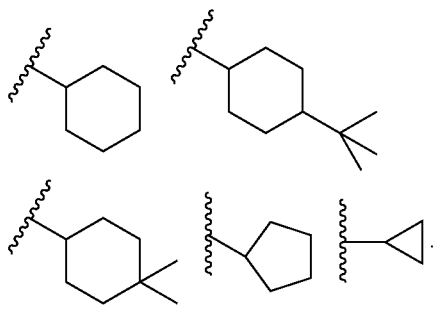

In certain embodiments, G is an oxaspirononanyl ring. A particular example is 1-oxaspiro[4.4]nonanyl.

In certain embodiments, G is a tert-butyl group.

In certain embodiments, G is selected from $Ar^1$, $Ar^2$ and a (3-6C)cycloalkyl ring.

In certain embodiments, G is selected from $Ar^1$ and $Ar^2$.

In certain embodiments, G is selected from $Ar^1$ and $Ar^2$, where $Ar^2$ is phenyl substituted with $Ar^3$.

Particular embodiments of Formula I include compounds wherein:

$Ar^1$ is phenyl optionally substituted with one or more substituents independently selected from F, Cl, Br, $CF_3$, methyl, ethyl, propyl, tert-butyl, OH, methoxy, ethoxy, propoxy, isopropoxy, tert-butoxy, SMe, $SCF_3$, cyclopropyl, $CH_2NMe_2$, $OCH_2CH_2F$, $OCH_2CH_2CH_2F$, $OCHF_2$, $OCF_3$, —$OCH_2$(cyclopropyl), and propynyl;

$Ar^3$ is selected from phenyl, 2-chlorophenyl, 3-chlorophenyl, 4-chlorophenyl, 3-methylphenyl, 4-methylphenyl, 3,4-dimethylphenyl, and 2,3-dimethylphenyl;

—O—$Ar^4$ is selected from groups having the formula

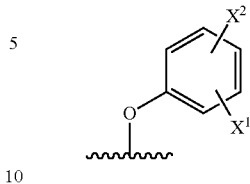

where $X^1$ and $X^2$ are independently selected from fluoro, chloro and bromo;

$hetAr^1$ is selected from a pyridyl and pyrimidyl ring, each of which is optionally substituted with one or more (1-4C alkyl) groups; and O-$hetAr^2$ is selected from pyridinyloxy and pyrimidinyloxy groups, each of which is optionally substituted with $CF_3$.

Examples of particular values for -L-G- groups include groups wherein:

L is a bond and G is $Ar^1$, $Ar^2$, naphthyl, a benzo-fused (5-6 C)cycloalkyl ring, a benzofused-5-6 membered heterocyclic ring, a (3-6C)cycloalkyl ring, or an oxaspirononanyl ring;

L is $CH_2$ and G is $Ar^1$, naphthyl, or a benzo-fused (5-6 C)cycloalkyl ring;

L is $CH_2CH_2$ and G is $Ar^1$, $Ar^2$, naphthyl, (3-6C cycloalkyl), or tert-butyl;

L is —$(CR^3R^4)_n$—$(CR^aR^b)_m$—$(CR^5R^6)$— and G is $Ar^1$;

L is $CH_2CH_2CH{=}CH$ and G is $Ar^1$;

L is —$OCH_2$ and G is $Ar^1$;

L is $CH_2CH_2S$— and G is $Ar^1$;

L is $CH_2CH_2O$— and G is $Ar^1$;

L is $hetCyc^1$ and G is $Ar^1$; and

L is (3-6C)cycloalkylene and G is $Ar^1$;

wherein each of the above G groups is optionally substituted as defined herein.

In certain embodiments of Formula I, -L-G- is a group wherein L is a bond or $CH_2CH_2$ and G is $Ar^1$, $Ar^2$, naphthyl, (3-6C cycloalkyl), or tert-butyl, or a group wherein L is —$(CR^3R^4)_n$—$(CR^aR^b)_m$—$(CR^5R^6)$— where one of m or n is 0 and G is $Ar^1$.

In particular embodiments of Formula I, -L-G- is a group wherein L is a bond or $CH_2CH_2$ and G is $Ar^1$, $Ar^2$ or a (3-6C)cycloalkyl ring, or a group wherein L is —$(CR^3R^4)_n$—$(CR^aR^b)_m$—$(CR^5R^6)$— and G is $Ar^1$.

In certain embodiments of Formula I, -L-G- is a group wherein L is a bond or $CH_2CH_2$ and G is $Ar^1$ or $Ar^2$, or a group wherein L is —$(CR^3R^4)_n$—$(CR^aR^b)_m$—$(CR^5R^6)$— and G is $Ar^1$.

In certain embodiments of Formula I, -L-G- is a group wherein L is a bond or —$(CR^3R^4)_n$—$(CR^aR^b)_m$—$(CR^5R^6)$— and G is $Ar^1$.

In each of the above-described -L-G- combinations, G is optionally substituted as described for Formula I.

In certain embodiments of the -L-G- combinations above, W is C(=O)NH.

Compounds of Formula I include compounds of Formula Ia wherein:

$A^1$ is CN, Cl, or cyclopropyl;

$A^2$ is hydrogen, Cl, Br, or cyclopropyl;

W is —C(=O)NH—;

L is as defined for Formula I;

G is $Ar^1$, $Ar^2$, naphthyl, a benzo-fused (5-6C)cycloalkyl ring optionally substituted with one or more substituents independently selected from Cl and OMe, a benzo-fused 5-6 membered heterocyclic ring having 1-2 heteroatoms independently selected from O and N, or a (3-6C)cycloalkyl ring optionally substituted with one or more substituents independently selected from (1-4C)alkyl;

Ar¹ is as defined for Formula I;
Ar² is as defined for Formula I;
$R^{7a}$, $R^{7b}$, and $R^8$ are each independently hydrogen;
$R^9$ is hydrogen, methyl, fluoro or $NO_2$; and
$R^{10}$ is hydrogen, methyl or fluoro.

Compounds of Formula I also include compounds of Formula Ib wherein:
$A^1$ is CN, Cl, or cyclopropyl;
$A^2$ is hydrogen, Cl, Br, or cyclopropyl;
W is —C(=O)NH—;
L is as defined for Formula I;
G is Ar¹, Ar², naphthyl, or a (3-6C)cycloalkyl ring optionally substituted with one or more substituents independently selected from (1-4C)alkyl;
Ar¹ is as defined for Formula I;
Ar² is as defined for Formula I;
$R^{7a}$, $R^{7b}$ and $R^8$ are each independently hydrogen;
$R^9$ is hydrogen, methyl, fluoro or $NO_2$; and
$R^{10}$ is hydrogen, methyl or fluoro.

Compounds of Formula I also include compounds of Formula Ic wherein:
$A^1$ is CN, Cl, or cyclopropyl;
$A^2$ is hydrogen, Cl, Br, or cyclopropyl;
W is —C(=O)NH—;
L is a bond or —$(CR^3R^4)_n$—$(CR^aR^b)_m$—$(CR^5R^6)$— wherein $R^3$, $R^4$, $R^a$, $R^b$, $R^5$ and $R^6$ are as defined for Formula I;
G is Ar¹, Ar², naphthyl, a benzo-fused (5-6C)cycloalkyl ring optionally substituted with one or more substituents independently selected from Cl and OMe, a benzo-fused 5-6 membered heterocyclic ring having 1-2 heteroatoms independently selected from O and N, or a (3-6C)cycloalkyl ring optionally substituted with one or more substituents independently selected from (1-4C)alkyl;
Ar¹ is as defined for Formula I;
Ar² is as defined for Formula I;
$R^{7a}$, $R^{7b}$ and $R^8$ are each independently hydrogen;
$R^9$ is hydrogen, methyl, fluoro or $NO_2$; and
$R^{10}$ is hydrogen, methyl or fluoro.

In a particular embodiment of Formula Ic, L is a bond or $CH_2CH_2$.

Compounds of Formula I also include compounds of Formula Id wherein:
$A^1$ is CN, Cl, or cyclopropyl;
$A^2$ is hydrogen, Cl, Br, or cyclopropyl;
W is —C(=O)NH—;
L is a bond or —$(CR^3R^4)_n$—$(CR^aR^b)_m$—$(CR^5R^6)$— wherein $R^3$, $R^4$, $R^a$, $R^b$, $R^5$ and $R^6$ are as defined for Formula I;
G is Ar¹, Ar², naphthyl or a (3-6C)cycloalkyl ring optionally substituted with one or more substituents independently selected from (1-4C)alkyl;
Ar¹ is as defined for Formula I;
Ar² is as defined for Formula I;
$R^{7a}$, $R^{7b}$ and $R^8$ are each independently hydrogen;
$R^9$ is hydrogen, methyl, fluoro; and
$R^{10}$ is hydrogen, methyl or fluoro.

In a particular embodiment of Formula Id, L is a bond or $CH_2CH_2$.

In certain embodiments of Formula Id, G is Ar¹, wherein Ar¹ is phenyl optionally substituted with one or more substituents independently selected from F, Cl, Br, $CF_3$, methyl, ethyl, propyl, tert-butyl, OH, methoxy, ethoxy, propoxy, iso-propoxy, tert-butoxy, SMe, $SCF_3$, cyclopropyl, $CH_2NMe_2$, $OCH_2CH_2F$, $OCH_2CH_2CH_2F$, $OCHF_2$, $OCF_3$, —$OCH_2$(cyclopropyl), and propynyl. In certain embodiments, Ar¹ is substituted with one to three of said substituents. In certain embodiments, Ar¹ is substituted with two of said substituents.

According to another aspect, the present invention provides a process for the preparation of a compound of Formula I or a salt thereof as defined hereinabove, which comprises:

(a) for a compound of Formula I in which $A^1$ is CN and $A^2$ is hydrogen, reacting a corresponding compound having the formula (II):

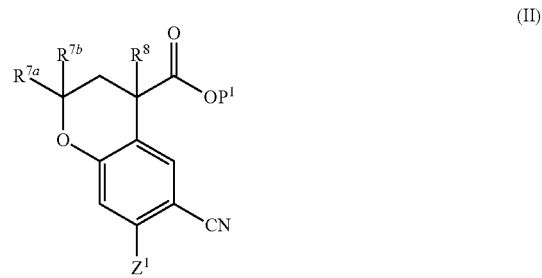

(II)

in which $P^1$ represents a hydrogen atom or a carboxyl protecting group and $Z^1$ represents a leaving atom or group, with a corresponding compound having the formula (III)

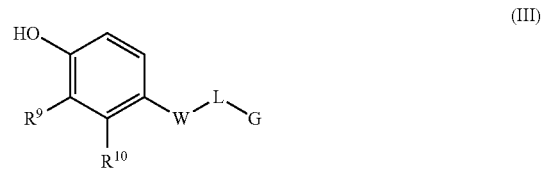

(III)

in the presence of a base; or (b) coupling a compound of formula (IV)

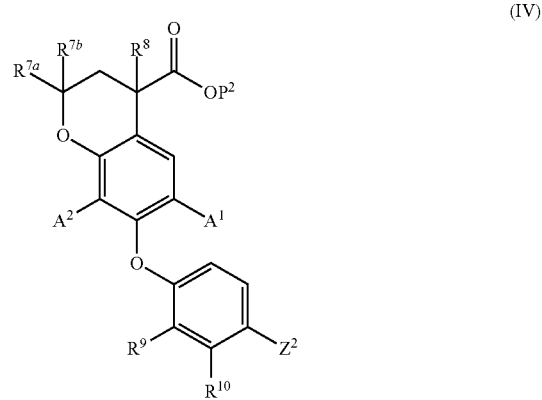

(IV)

in which $P^2$ is as defined for $P^1$ and $Z^2$ represents —$NH_2$ or —C(=O)OH, or a reactive derivative thereof, with a compound of formula (V)

H—$Z^3$-L-G (V)

in which $Z^3$ represents OC(=O) or NH, respectively, or a reactive derivative thereof; or (c) for a compound of Formula I in which $A^1$ is Cl, (1-4C alkyl), OMe or cyclopropyl and $A^2$ is (1-4C alkyl), chloro, bromo or cyclopropyl, coupling a compound having the formula (VI)

(VI)

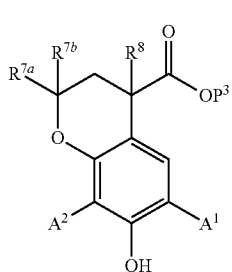

in which P³ is as defined for P¹ and A¹ is Cl, (1-4C alkyl), or cyclopropyl, and A² is (1-4C alkyl), chloro, bromo or cyclopropyl, with a corresponding compound having the formula (VII)

(VII)

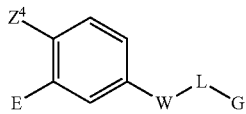

wherein E is an electron withdrawing group and Z⁴ is a leaving atom, in the presence of a base, and if desired removing said electron withdrawing group; or (d) for a compound of Formula I where G is Ar$^x$ where Ar$^x$ is (1) Ar¹ substituted with cyclopropyl or (1-4C)alkyl and optionally further substituted as defined for Ar¹, or (2) Ar² where Ar² is phenyl substituted with Ar³ and optionally further substituted with F or Cl, reacting a corresponding compound having the formula (VIII)

(VIII)

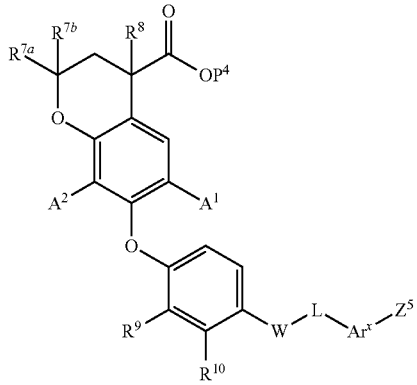

where P⁴ is as defined for P¹ and Z⁵ is a leaving atom or group, with a compound having the formula Y—B(OH)₂ where Y is cyclopropyl, (1-4 C alkyl) or Ar³, in the presence of a transition metal catalyst and a ligand; or (e) for a compound of Formula I where L is a bond and G is Ar¹ or Ar², reacting a corresponding compound having the formula (IX)

(IX)

wherein P⁵ is as defined for P¹, with a compound having the formula Ar¹—Z⁶ or Ar²—Z⁶ where Z⁶ is a leaving atom or group, in the presence of a metal catalyst and a ligand; or (f) for a compound of Formula I where A¹ is chloro, A² is cyclopropyl, R⁹ and R¹⁰ are hydrogen, and W is C(=O)NH, reacting a corresponding compound having the formula (X)

(X)

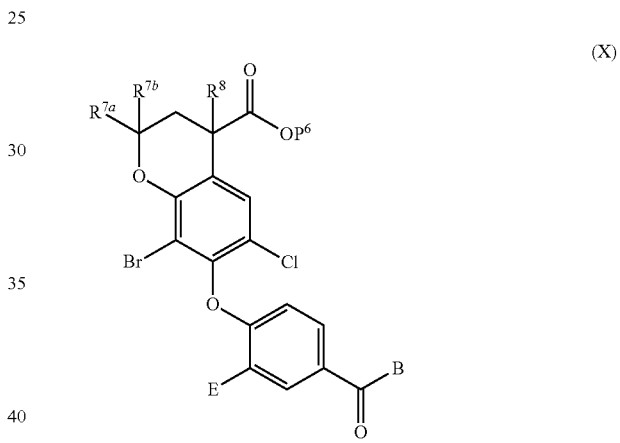

wherein P⁶ is as defined for P¹, E is an electron withdrawing group, and B is O-tertbutyl, NH₂ or NH-L-G, with about 2 equivalents of cyclopropylboronic acid in the presence of a suitable base, a metal catalyst and a ligand at temperatures between about 100° C. and about 150° C., followed by removal of the electron withdrawing group, if desired, and coupling with a compound having the formula H₂N-L-G when B is O-tBu or coupling with a compound having the formula X-L-G when B is NH₂, where X is a leaving group or atom; or (g) for a compound of Formula I where A¹ is cyclopropyl, A² is cyclopropyl, R⁹ and R¹⁰ are hydrogen and W is C(=O) NH, reacting a corresponding compound having the formula (X) with about 4 equivalents of cyclopropylboronic acid in the presence of a suitable base, a metal catalyst and a ligand at temperatures between about 100° C. and 150° C., followed by removal of the electron withdrawing group, if desired, and coupling with a compound having the formula H₂N-L-G when B is O-tBu or coupling with a compound having the formula X-L-G when B is NH₂, where X is a leaving group or atom; or (h) for a compound of Formula I where A¹ is cyclopropyl, A² is hydrogen, R⁹ and R¹⁰ are hydrogen and W is C(=O) NH, reacting a corresponding compound having the formula (XI)

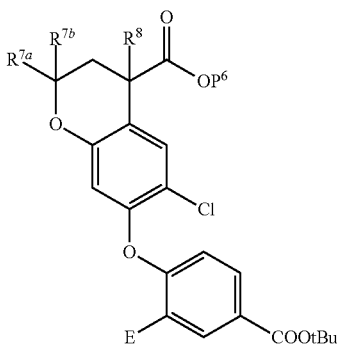

(XI)

with about 3 equivalents of cyclopropylboronic acid in the presence of a suitable base, a metal catalyst and a ligand at temperatures between about 90° C. and 150° C., for example 120° C., followed by removal of the electron withdrawing group, if desired, and coupling with a compound having the formula $H_2N$-L-G when B is O-tBu or coupling with a compound having the formula X-L-G when B is $NH_2$, where X is a leaving group or atom; and removing any protecting group or groups and, if desired, forming a salt.

The carboxyl protecting groups in any of the above methods may be any convenient carboxyl protecting group, for example as described in Greene & Wuts, eds., "Protecting Groups in Organic Synthesis", John Wiley & Sons, Inc. Examples of carboxyl protecting groups include (1-6C)alkyl groups, such as methyl, ethyl and t-butyl. Removal of the carboxyl protecting group may be performed using methods known in the art. For example, alkyl protecting groups can be removed by hydrolysis, for example, by treating the protected compound with a metal hydroxide, for example lithium, potassium or sodium hydroxide, in a suitable solvent such as THF or an alcohol (for example ethanol) or mixtures thereof. Tert-butyl protecting groups can be removed by acid hydrolysis, for example with TFA or hydrogen chloride in an organic solvent.

Referring to process (a), the leaving atom represented by $Z^1$ may be, for example, a halogen atom such as a fluorine atom. Alternatively, $Z^1$ may be a leaving group such as a triflate or tosylate. The base may be, for example, an alkali metal hydride or carbonate, such as sodium hydride, sodium carbonate or potassium carbonate, or a tertiary amine, such as triethylamine, or N,N-diisopropylethylamine. Convenient solvents include N-methylpyrrolidinone, or amides, sulfoxides and nitriles, such as DMF, DMSO or acetonitrile. The reaction can be performed at an elevated temperature, such as in the range of from 50 to 150° C.

Compounds of formula (II) are known or can be prepared by treating the corresponding bromo derivative having formula (IIa)

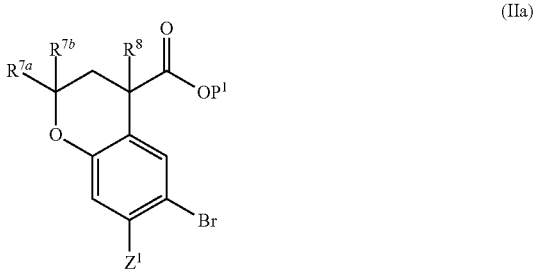

(IIa)

with Cu(I)CN in an appropriate solvent, such as N-methylpyrrolidone. The reaction is conveniently performed at elevated temperatures, for example between 100 and 200° C., such as at 160° C.

Compounds of formula (IIa) can be prepared by treating the corresponding derivative having formula (IIb)

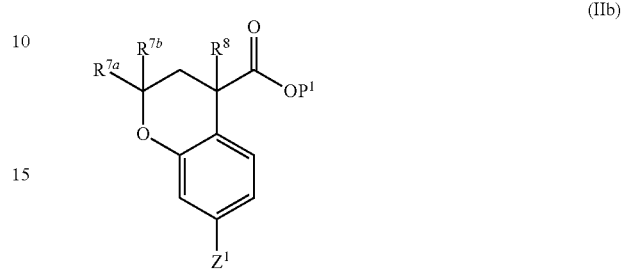

(IIb)

with N-bromosuccinimide in an appropriate solvent, such as DMF. The reaction is conveniently performed at temperatures between ambient temperature and 100° C., for example at 50° C.

Compounds of formula (IIb) wherein $R^8$ is Me can be prepared by reacting a corresponding compound of formula (IIb) wherein $R^8$ is H with methyl iodide in the presence of a suitable base, such as an alkali metal carbonate (e.g., sodium carbonate, potassium carbonate or cesium carbonate) or an alkali metal hydride (e.g., sodium hydride).

Compounds of formula (IIb) can be prepared by homologating a corresponding compound having formula (IIc)

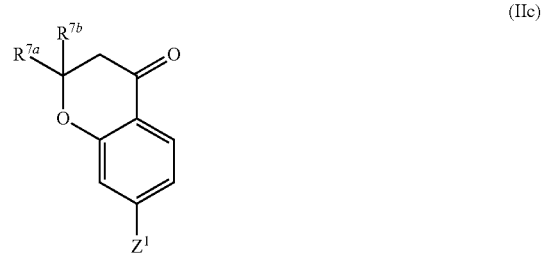

(IIc)

using methodologies known in the art [such as via enol ethers, epoxides, cyanohydrins, α,β-unsaturated sulfones, ketene thioacetals, glycidic esters, nitriles and α-acetoxyacrylonitriles], to add the one carbon unit followed by reductive hydrolysis with tin(II)chloride under acidic conditions. For example, in one embodiment, the compound of formula (IIc) can be treated with trimethylsilylnitrile and a catalyst such as zinc iodide or $I_2$, either neat or in a suitable solvent, for example dichloromethane. The reaction is conveniently performed at ambient temperature.

Compound of formula (IIb) wherein $R^{7a}$ and $R^{7b}$ are each Me can be prepared by cyclizing a compound having the formula

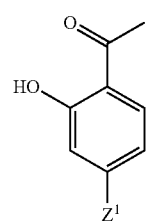

with 2-propanone in the presence of a suitable base, for example an amine base such as pyrrolidine. The reaction is conveniently preformed at elevated temperatures, such as between 50-100° C., for example 80° C.

Referring to process (b), the coupling of the compound of formula (IV) with a compound of formula (V) may be performed using conventional amide bond formation conditions, for example by treating the carboxylic acid with an activating agent, followed by addition of the amine in the presence of a base. Suitable activating agents include oxalyl chloride, thionyl chloride, EDCI, HATU, and HOBt. Suitable bases include amine bases, for example triethylamine, diisopropylethylamine, pyridine, or excess ammonia. Suitable solvents include DCM, DCE, THF, and DMF.

Alternatively, the amide bond formation can be performed by coupling a reactive derivative of a carboxylic acid, for example an acid halide, such as an acid chloride.

In a particular embodiment, a compound of formula (IV) where $A^1$ is Cl, $A^2$ is hydrogen and $Z^2$ is $CO_2H$ can be prepared by coupling a compound having the formula (IVa)

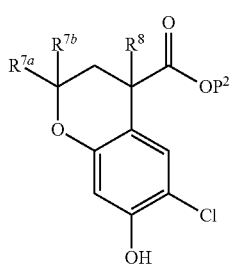

IVa with a corresponding compound having the formula

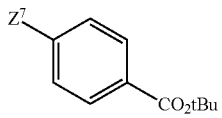

where $Z^7$ is a leaving atom or group, in the presence of copper(I) chloride and an inorganic base, followed by hydrolysis of the ester to form the corresponding acid. Suitable inorganic bases include carbonates, such as cesium carbonate. Leaving atoms represented by $Z^7$ include halogen atoms, for example Br or I. Alternatively, $Z^7$ can be a leaving group such as an alkylsulfonyl or arylsulfonyl group, for example, a triflate group.

Referring to process (c), examples of leaving atoms represented by $Z^4$ include halogen atoms, for example F and Cl. Alternatively, $Z^5$ can be a leaving group such as an alkylsulfonyl or arylsulfonyl group, for example, a triflate group. Examples of electron withdrawing groups include $NO_2$. In embodiments wherein the electron withdrawing group is $NO_2$, this group can be removed, if desired, by reducing the nitro group to an amino group using any convenient reducing conditions (for example, Zn and $NH_4Cl$) followed by cleavage of the amino group (for example, by treating the amino compound with isobutyl nitrite).

Referring to process (d), examples of a leaving atom represented by $Z^5$ include F, Cl, Br and I. Alternatively, $Z^5$ can be a leaving group such as an alkylsulfonyl or arylsulfonyl group, for example, a triflate group. Suitable transition metal catalysts include palladium catalysts, such as Pd(II) catalysts, for example $Pd(OAc)_2$ in the presence of a suitable ligand. The ligand can be a phosphine ligand, such as $PPh_3$. Suitable bases include inorganic bases, for example alkali metal carbonates such as potassium carbonate, sodium carbonate or cesium carbonate. The reaction is conveniently performed in a suitable solvent such as DMF, DMA, DMSO, NMP or dioxane, at temperatures ranging from about 50-160° C.

Referring to method (e), the leaving atom represented by $Z^6$ can be a halogen atom, for example F, Cl, Br, or I. Alternatively, $Z^5$ can be a leaving group such as an alkylsulfonyl or arylsulfonyl group, for example, a triflate group. Suitable metal catalysts include palladium catalysts, such as Pd(II) catalysts, for example $Pd(OAc)_2$ in the presence of a suitable ligand. The ligand can be a phosphine ligand, such as $PPh_3$. The reaction is conveniently performed in the presence of an inorganic base such as an alkali metal carbonate (for example sodium carbonate or cesium carbonate) in a suitable solvent, such as toluene, DMF, THF, or NMP. The reaction is conveniently performed at temperatures ranging from 50-160° C.

Referring to processes (f), (g) and (h), suitable bases include inorganic bases, for example alkali metal phosphates, such as potassium phosphate. Suitable catalysts include palladium catalysts, such as Pd(II) catalysts, for example $Pd(OAc)_2$ in the presence of a suitable ligand. The ligand can be a phosphine ligand, such as tricyclohexylphosphine. Examples of electron withdrawing groups include $NO_2$. In embodiments wherein the electron withdrawing group is $NO_2$, this group can be removed, if desired, by reducing the nitro group to an amino group using any convenient reducing conditions (for example, Zn and $NH_4Cl$) followed by cleavage of the amino group (for example, by treating the amino compound with isobutyl nitrite). Suitable solvents include xylene and toluene. The reaction is conveniently performed at the reflux temperature of the solvent.

The compounds of Formulas (IV), (VI), (VIII), (IX), (X) and (XI) are also believed to be novel and are provided as further aspects of this invention.

Also provided herein is a compound of general Formula Ie:

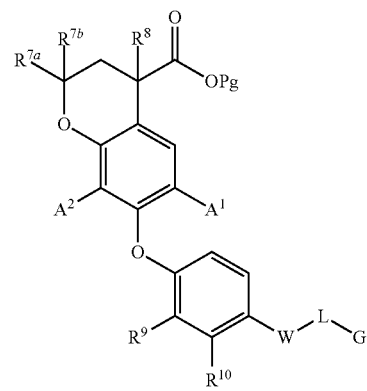

Ie or a salt thereof, wherein:
Pg is a carboxyl protecting group;
$A^1$ is hydrogen, CN, Cl, F, Br, OMe, (1-4C alkyl) or cyclopropyl;
$A^2$ is hydrogen, Cl, Br, F, (1-4C alkyl) or cyclopropyl;
W is —C(=O)NR$^1$— or —NR$^2$C(=O)—;
$R^1$ and $R^2$ are each hydrogen or methyl;
L is a bond, —(CR$^3$R$^4$)$_n$—(CR$^a$R$^b$)$_m$—(CR$^5$R$^6$)—*, (2-4C)alkenylene, —O(1-4C alkyl)-*, -(1-4C alkyl)-O—*, -(1-4C alkyl)-S—*, (3-6C)cycloalkylene, or hetCyc$^1$, wherein the * indicates the point of attachment to G, provided that when W is —NR²C(=O)— then L is not —(CH=CH)—;

m=0, 1 or 2;
n=0 or 1;
$R^a$ and $R^b$ are independently selected from hydrogen and (1-4C alkyl);
$R^3$ is hydrogen, (1-4C alkyl) or $CH_2OH$;
$R^4$ is hydrogen or methyl;
$R^5$ is hydrogen, (1-4C alkyl), OH, —O(1-4C alkyl) or F;
$R^6$ is hydrogen, F or methyl,
or $R^5$ and $R^6$ together with the carbon to which they are attached form a cyclopropyl ring;
hetCyc¹ is a group having the formula

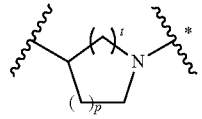

where t is 1 or 2 and p is 0 or 1, and the * indicates the point of attachment to G;
G is $Ar^1$, $Ar^2$, naphthyl, a benzo-fused (5-6C)cycloalkyl ring optionally substituted with one or more substituents independently selected from Cl and OMe, a benzo-fused 5-6 membered heterocyclic ring having 1-2 heteroatoms independently selected from O and N, a (3-6C)cycloalkyl ring optionally substituted with one or more substituents independently selected from (1-4C)alkyl, an oxaspirononanyl ring, or t-butyl;
$Ar^1$ is phenyl optionally substituted with one or more substituents independently selected from F, Cl, Br, $CF_3$, (1-4C) alkyl, OH, —O(1-4C alkyl), —S(1-3C alkyl), —$SCF_3$, cyclopropyl, —$CH_2N(1-3C\ alkyl)_2$, —O-(2-3C)fluoroalkyl, —O-(1-3 C)difluoroalkyl —O(1-3C)trifluoroalkyl, —$OCH_2$(cyclopropyl), and (3-4C)alkynyl;
$Ar^2$ is phenyl which is substituted with $Ar^3$, —O—$Ar^4$, $hetAr^1$ or —O-$hetAr^2$, wherein $Ar^2$ is optionally further substituted with one or more substituents independently selected from F, Cl and $CF_3$;
$Ar^3$ is phenyl optionally substituted with one or more substituents independently selected from F, Cl, Br and (1-4C alkyl);
$Ar^4$ is phenyl optionally substituted with one or more substituents independently selected from F, Cl, Br and (1-4C alkyl);
$hetAr^1$ is a 6-membered heteroaryl having 1-2 nitrogen atoms and optionally substituted with one or more substituents independently selected from (1-4C alkyl);
$hetAr^2$ is a 6-membered heteroaryl having 1-2 nitrogen atoms and optionally substituted with one or more substituents independently selected from (1-4C alkyl) and $CF_3$;
$R^{7a}$, $R^{7b}$ and $R^8$ are each independently hydrogen or methyl;
$R^9$ is hydrogen, methyl, fluoro or $NO_2$; and
$R^{10}$ is hydrogen, methyl or fluoro.

The protecting group represented by Pg in Formula Ie may be any convenient carboxyl protecting group, for example as described in Greene & Wuts, eds., "Protecting Groups in Organic Synthesis", John Wiley & Sons, Inc. Examples of carboxyl protecting groups include (1-6C)alkyl groups, such as methyl, ethyl and t-butyl.

It will be appreciated that the aforementioned processes can comprise the formation of an intermediate of Formula Ie in which Pg is a carboxyl protecting group (for example (1-6C)alkyl, such as methyl or ethyl), which protecting group is removed to afford a compound of Formula I. Such compounds form a further aspect of the invention. Compounds of Formula Ie may also function as prodrugs of compounds of Formula I.

The ability of test compounds to act as DP2 receptor antagonists may be demonstrated by the assay described in Example A.

Compounds which are antagonists of DP2 are useful in the treatment of diseases or disorders mediated by $PGD_2$, for example, diseases or disorders associated with overproduction or dysregulation of $PGD_2$.

As used herein, the term treatment includes prophylaxis as well as treatment of an existing condition.

Examples of disorders or diseases that may be treated with compounds according to the invention include immunologic diseases. In addition, compounds of the invention may be useful for treating inflammatory diseases and disorders. Compounds of the invention may also be useful for treating itching/pruritis.

Examples of immunologic diseases include allergic inflammatory disease such as asthma, dermatitis, allergic rhinitis, urticaria, anaphylaxis, angioedemea, allergies, contact hypersensitivity (e.g., nickel sensitivity), drug hypersensitivity, and allergic conjunctivitis in addition to inflammatory autoimmune diseases such as hyper-eosinophilic syndromes, psoriasis, systemic mast cell disorders, chronic obstructive pulmonary disease, inflammatory bowel disease, and arthritis.

Examples of immunologic diseases include allergic inflammatory diseases, such as asthma, atopic dermatitis, allergic rhinitis, seasonal allergies, food allergies, contact hypersensitivity (e.g., nickel sensitivity), hyper-eosinophilic syndromes, and allergic conjunctivitis.

Further examples of allergic inflammatory diseases include asthma (including mild-to-moderate asthma, severe asthma, refractory asthma, steroid-resistant asthma, steroid-insensitive asthma, and exercise-induced asthma), allergies such as severe allergy/anaphylaxis, food allergies, plant allergies, drug allergies, latex allergy, allergic reactions to venemous stings, seasonal allergic rhinitis, and perrennial allergic rhinitis, chronic rhinosinusitis, cystic fibrosis, eosinophilic diseases and disorders (including eosinophilic gastroenteritis, eosinophilic esophagitis, acute eosinophilic pneumonia, chronic eosinophilic pneumonia, pulmonary eosinophilia (Loeffler's Disease), eosinophilia-myalgia syndrome, Chrug-Strauss syndrome, eosinophilic fasciitis, familial eosinophilic cellulitis, cutaneous eosinophilia, non-allergic rhinitis with eosinophilia syndrome, familial eosinophilia, and drug reaction with eosinophilia and systemic symptoms), hyper IgE syndrome, allergic diseases of the gastrointestinal tract, celiac sprue, gluten enteropathy, gluten intolerance, acute hypersensitivy reaction, and delayed hypersensitivity reaction.

Further examples of allergic inflammatory diseases include severe allergy/anaphylaxis, eosinophilic gastroenteritis, eosinophilic esophagitis, severe asthma, refractory asthma, steroid-resistance asthma, allergic diseases of the gastrointestinal tract, celiac sprue, gluten enteropathy, gluten intolerance, acute hypersensitivy reaction, and delayed hypersensitivity reaction.

Additional diseases or disorders which may be treated with compounds of this invention include inflammatory bowel diseases such as Crohn's disease, ulcerative colitis, ileitis and enteritis, vasculitis, Behcet's syndrome, psoriasis and inflammatory dermatoses such as dermatitis, eczema, urticaria, viral cutaneous pathologies such as those derived from human papillomavirus, HIV or RLV infection, bacterial, fungal and other parasital cutaneous pathologies, and cutaneous lupus erythematosus, respiratory allergic diseases such as persensitivity lung diseases, chronic obstructive pulmonary disease and the like, autoimmune diseases, such as arthritis (including rheumatoid and psoriatic), systemic lupus erythematosus, type I diabetes, myasthenia gravis, multiple sclerosis, Graves' disease, glomerulonephritis and the like, graft rejection (including allograft rejection and graft-v-host disease), e.g., skin graft rejection, solid organ transplant rejection, bone marrow transplant rejection, fever, cardiovascular disorders such as acute heart failure, hypotension, hypertension, angina pectoris, myocardial infarction, cardiomyopathy, congestive heart failure, atherosclerosis, coronary artery disease, restenosis, thrombosis and vascular stenosis, cerebrovascular disorders such as traumatic brain injury, stroke, ischemic reperfusion injury and aneurysm, cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system, fibrosis, connective tissue disease and sarcoidosis, genital and reproductive conditions such as erectile dysfunction, gastrointestinal disorders such as gastritis, ulcers, nausea, pancreatitis and vomiting; neurological disorders, such as Alzheimer's disease, sleep disorders such as insomnia, narcolepsy, sleep apnea syndrome and Pickwick Syndrome, pain, renal disorders, ocular disorders such as glaucoma, infectious diseases, viral infections such as HIV, and bacterial infections such as sepsis, inflammation, flushing, nasal congestion, and otitis media.

Additional diseases or disorders which may be treated with compounds of this invention include inflammatory bowel diseases such as IgA deficiency, inflammatory dermatoses such as chronic urticaria, acute urticaria, seborrheic dermatitis, contact dermatitis, pemphigus, and exfoliative dermatitis (etythroderma), dermatitis herpetiformis, trichinosis, visceral larva migraines, trichuriasis, ascariasis, strongyloidiasis, hookworm infection, clonorchiasis, pragonimiasis, fascioliasis, cysticerosis, echinococcosis, filariasis, schistocomiasis, brucellosis, cat scratch fever, infectious lymphocytosis, acute coccidiodomycosis, infectious mononucleosis, mycobacterial disease, scarlet fever, tuberculosis, and cutaneous lupus erythematosus, respiratory allergic diseases such as hypersensitivity lung diseases, allergic broncopulmonary aspergillosis, tropical pulmonary eosinophilia, and the like, autoimmune diseases such as mastocytosis, leukocytoclastic vasculitis, urticarial vasculitis, basophilic leukocytosis, adrenal hypofunction and the like, cardiovascular disorders such as Coombs'-positive hemolytic anemias, Hashimoto's thyroiditis, Goodpasture's syndrome, serum sickness, polyarteritis nodosa, Dressler's syndrome, Wiskott-Aldrich syndrome, scleroderma, cirrhosis, and sarcoidosis, and ocular disorders such as vernal keratoconjunctivitis, atopic keartoconjunctivitis, giant papullary conjunctvitis.

Accordingly, another aspect of this invention provides a method of treating diseases or medical conditions in a mammal mediated by PGD2, comprising administering to said mammal one or more compounds of Formula I or a pharmaceutically acceptable salt or prodrug thereof in an amount effective to treat or prevent said disorder.

Another aspect of this invention provides a method of treating diseases or medical conditions in a mammal mediated by the DP2 receptor comprising administering to said mammal one or more compounds of Formula I or a pharmaceutically acceptable salt or prodrug thereof in an amount effective to treat or prevent said disorder.

Another aspect of this invention provides a method of treating diseases or medical conditions in a mammal involving the Th2 T cell via production of IL-4, IL-5 and/or IL-13 comprising administering to said mammal one or more compounds of Formula I or a pharmaceutically acceptable salt or prodrug thereof in an amount effective to treat or prevent said disorder.

Another aspect of this invention provides a method of treating diseases or medical conditions in a mammal involving the activation and trafficking of granulocytes (mast cell, eosinophil, neutrophil, basophil, etc.) comprising administering to said mammal one or more compounds of Formula I or a pharmaceutically acceptable salt or prodrug thereof in an amount effective to treat or prevent said disorder.

The phrase "effective amount" means an amount of compound that, when administered to a mammal in need of such treatment, is sufficient to (i) treat or prevent a particular disease, condition, or disorder mediated by PGD2, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

This invention also provides compounds of Formula I for use in the treatment of PGD2-mediated conditions.

An additional aspect of the invention is the use of a compound of Formula I in the preparation of a medicament for therapy, such as for the treatment or prevention PGD2-mediated conditions. Further, compounds which are antagonists of DP2 are useful in the treatment of diseases and disorders mediated by metabolites of PGD2 and other prostaglandins (and their corresponding metabolites) that may be acting via the DP2 receptor.

Compounds of the present invention can be used in combination with one or more additional drugs that work by the same or a different mechanism of action. Examples include anti-inflammatory compounds, steroids (e.g., dexamethasone, cortisone and fluticasone), NSAIDs (e.g., ibuprofen, indomethacin, and ketoprofen), anti-histamines, and anti-leukotrienes (e.g., Singulair®).

Compounds of the invention may be administered by any convenient route, e.g., by dermal application (i.e., topical application to the skin), transdermally, or into the gastrointestinal tract (e.g. rectally or orally), nose, lungs, musculature or vasculature.

Compounds may be administered in any convenient administrative form, e.g., creams, tablets, powders, capsules, solutions, dispersions, suspensions, syrups, sprays, suppositories, gels, emulsions, and drug delivery devices such as patches, etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

According to another aspect, the present invention provides a compound of formula (I) or a pharmaceutically acceptable salt thereof, for use in treating an immunologic disorder.

According to a further aspect, the present invention provides the use of a compound of Formula I or a pharmaceutically acceptable salt thereof, in the manufacture of a medicament to treat an immunologic disorder, as defined hereinabove.

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane ($CH_2Cl_2$, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$HNMR spectra were obtained as $CDCl_3$ or $CD_3OD$ solutions (reported in ppm), using tetramethylsilane (0.00 ppm) or residual solvent ($CDCl_3$: 7.25 ppm; $CD_3OD$: 3.31 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Separation of racemic mixtures to isolate enantiomers was performed as described below on a CHIRALCEL® OJ-H column (Chiral Technologies, West Chester, Pa.), in which the packing composition is cellulose tris(4-methylbenzoate) coated on 5 µM silica gel. Enantiomeric purity was determined using a CHIRALPAK® QD-AX column ((Chiral Technologies, West Chester, Pa.), which is a quinidine (QD) based column.

Particular compounds of the invention include:
6-Cyano-7-(4-(4-chlorophenylcarbamoyl)phenoxy)chroman-4-carboxylic acid;
7-(4-(4-chlorophenylcarbamoyl)phenoxy)-6-cyano-4-methylchroman-4-carboxylic acid;
7-(4-(4-Chlorophenylcarbamoyl)phenoxy)-6-cyano-2,2-dimethylchroman-4-carboxylic acid;
6-Cyano-7-(4-(2,4-dichlorophenylcarbamoyl)phenoxy)chroman-4-carboxylic acid;
6-Cyano-7-(4-(phenethylcarbamoyl)phenoxy)chroman-4-carboxylic acid;
6-Cyano-7-(4-(2,3-dihydro-1H-inden-2-ylcarbamoyl)phenoxy)chroman-4-carboxylic acid;
7-(4-(4-Chlorobenzyloxycarbamoyl)phenoxy)-6-cyano-chroman-4-carboxylic acid;
6-Cyano-7-(4-(3,4-dichlorophenylcarbamoyl)phenoxy)chroman-4-carboxylic acid;
6-Chloro-7-(4-(4-chlorophenethylcarbamoyl)-2-nitrophenoxy)chroman-4-carboxylic acid;
6-Chloro-7-(4-(4-chlorophenethylcarbamoyl)phenoxy)chroman-4-carboxylic acid;
6-Chloro-7-(4-(4-chlorophenethylcarbamoyl)phenoxy)chroman-4-carboxylic acid;
6-chloro-7-(4-(phenethylcarbamoyl)phenoxy)chroman-4-carboxylic acid;
6-chloro-7-(4-(4-phenylbutylcarbamoyl)phenoxy)chroman-4-carboxylic acid;
6-chloro-7-(4-(4-(3-chlorophenyl)butylcarbamoyl)phenoxy)chroman-4-carboxylic acid;
6-chloro-7-(4-(4-(4-chlorophenyl)butylcarbamoyl)phenoxy)chroman-4-carboxylic acid;
(Z)-6-chloro-7-(4-(4-(2-chlorophenyl)but-3-enylcarbamoyl)phenoxy)chroman-4-carboxylic acid;
6-chloro-7-(4-(4-(2-chlorophenyl)butylcarbamoyl)phenoxy)chroman-4-carboxylic acid;
(Z)-6-chloro-7-(4-(4-(2,4-dichlorophenyl)but-3-enylcarbamoyl)phenoxy)chroman-4-carboxylic acid;
6-chloro-7-(4-(4-(2,4-dichlorophenyl)butylcarbamoyl)phenoxy)chroman-4-carboxylic acid;
6-chloro-7-(4-(2-methylphenethylcarbamoyl)phenoxy)chroman-4-carboxylic acid;
6-chloro-7-(4-(2,4-dimethylphenethylcarbamoyl)phenoxy)chroman-4-carboxylic acid;
6-chloro-7-(4-(4-methylphenethylcarbamoyl)phenoxy)chroman-4-carboxylic acid;
7-(4-(4-bromophenethylcarbamoyl)phenoxy)-6-chlorochroman-4-carboxylic acid;
6-chloro-7-(4-(4-cyclopropylphenethylcarbamoyl)phenoxy)chroman-4-carboxylic acid;
6-chloro-7-(4-(2-cyclopropylethylcarbamoyl)phenoxy)chroman-4-carboxylic acid;
6-chloro-7-(4-(2-(2'-chlorobiphenyl-4-yl)ethylcarbamoyl)phenoxy)chroman-4-carboxylic acid;
6-chloro-7-(4-(4-chloro-2-methylphenethylcarbamoyl)phenoxy)chroman-4-carboxylic acid;
7-(4-(4-bromo-2-chlorophenethylcarbamoyl)phenoxy)-6-chlorochroman-4-carboxylic acid;
6-chloro-7-(4-(2-(2',3-dichlorobiphenyl-4-yl)ethylcarbamoyl)phenoxy)chroman-4-carboxylic acid;
6-chloro-7-(4-(2-chloro-4-cyclopropylphenethylcarbamoyl)phenoxy)chroman-4-carboxylic acid;
6-chloro-7-(4-(2-(3-chlorobiphenyl-4-yl)ethylcarbamoyl)phenoxy)chroman-4-carboxylic acid;
7-(4-(2-bromo-4-chlorophenethylcarbamoyl)phenoxy)-6-chlorochroman-4-carboxylic acid;
6-chloro-7-(4-(2-(2',5-dichlorobiphenyl-2-yl)ethylcarbamoyl)phenoxy)chroman-4-carboxylic acid;
6-chloro-7-(4-(4-chloro-2-cyclopropylphenethylcarbamoyl)phenoxy)chroman-4-carboxylic acid;
7-(4-(4-bromo-2-methoxyphenethylcarbamoyl)phenoxy)-6-chlorochroman-4-carboxylic acid;
6-chloro-7-(4-(4-cyclopropyl-2-methoxyphenethylcarbamoyl)phenoxy)chroman-4-carboxylic acid;
6-chloro-7-(4-(2,4-dichloro-6-methoxyphenethylcarbamoyl)phenoxy)chroman-4-carboxylic acid;
8-bromo-6-chloro-7-(4-(4-chlorophenethylcarbamoyl)phenoxy)chroman-4-carboxylic acid;
7-(4-(4-chlorophenethylcarbamoyl)phenoxy)-6,8-dicyclopropylchroman-4-carboxylic acid;
6,8-dicyclopropyl-7-(4-(2,4-dichlorophenethylcarbamoyl)phenoxy)chroman-4-carboxylic acid;
7-(4-(4-chlorophenethylcarbamoyl)phenoxy)-6-cyclopropylchroman-4-carboxylic acid;
6-cyclopropyl-7-(4-(2,4-dichlorophenethylcarbamoyl)phenoxy)chroman-4-carboxylic acid;

6-chloro-8-cyclopropyl-7-(4-(2,4-dichlorophenethylcarbamoyl)phenoxy)chroman-4-carboxylic acid;
6-Cyano-7-(4-(4-((dimethylamino)methyl)phenethylcarbamoyl)phenoxy)chroman-4-carboxylic acid;
6-Cyano-7-(4-(1,2,3,4-tetrahydroisoquinolin-7-ylcarbamoyl)phenoxy)chroman-4-carboxylic acid;
6,8-dichloro-7-(4-(4-chlorophenethylcarbamoyl)phenoxy)chroman-4-carboxylic acid;
7-(4-((2-Phenylcyclopropyl)carbamoyl)phenoxy)-6-cyano-3,4-dihydro-2H-chromene-4-carboxylic acid;
7-(4-((3-Methoxyphenethyl)carbamoyl)phenoxy)-6-cyano-3,4-dihydro-2H-chromene-4-carboxylic acid;
7-(4-((4-Fluorophenethyl)carbamoyl)phenoxy)-6-cyano-3,4-dihydro-2H-chromene-4-carboxylic acid;
7-(4-((4-(Trifluoromethyl)phenethyl)carbamoyl)phenoxy)-6-cyano-3,4-dihydro-2H-chromene-4-carboxylic acid;
7-(4-((2-(4-Chlorophenyl)cyclopropyl)carbamoyl)phenoxy)-6-cyano-3,4-dihydro-2H-chromene-4-carboxylic acid;
7-(4-(chroman-3-ylcarbamoyl)phenoxy)-6-cyanochroman-4-carboxylic acid
6-Cyano-7-(4-(6-methoxy-1,2,3,4-tetrahydronaphthalen-2-ylcarbamoyl)phenoxy)chroman-4-carboxylic acid;
6-Cyano-7-(4-(naphthalen-1-ylmethylcarbamoyl)phenoxy)chroman-4-carboxylic acid;
6-Cyano-7-(4-(2-(naphthalen-1-yl)ethylcarbamoyl)phenoxy)chroman-4-carboxylic acid;
6-Cyano-7-(4-(2-(naphthalen-2-yl)ethylcarbamoyl)phenoxy)chroman-4-carboxylic acid;
7-(4-(4-tert-Butylphenethylcarbamoyl)phenoxy)-6-cyanochroman-4-carboxylic acid;
7-(4-(2-(Biphenyl-4-yl)ethylcarbamoyl)phenoxy)-6-cyanochroman-4-carboxylic acid;
7-(4-(2-Biphenyl-4-yl)ethylcarbamoyl)phenoxy)-6-chlorochroman-4-carboxylic acid;
6-chloro-7-(4-((R)-2-phenylpropylcarbamoyl)phenoxy)chroman-4-carboxylic acid;
6-chloro-7-(4-((S)-2-phenylpropylcarbamoyl)phenoxy)chroman-4-carboxylic acid;
6-chloro-7-(4-(2-(4-chlorophenyl)propylcarbamoyl)phenoxy)chroman-4-carboxylic acid;
6-chloro-7-(4-(2-methoxyphenethylcarbamoyl)phenoxy)chroman-4-carboxylic acid;
6-chloro-7-(4-(2-(trifluoromethoxy)phenethylcarbamoyl)phenoxy)chroman-4-carboxylic acid;
6-chloro-7-(4-(2-phenoxyphenethylcarbamoyl)phenoxy)chroman-4-carboxylic acid;
6-Cyano-7-(4-(3',4'-dimethylbiphenyl-3-ylcarbamoyl)phenoxy)chroman-4-carboxylic acid;
7-(4-(Biphenyl-3-ylcarbamoyl)phenoxy)-6-cyanochroman-4-carboxylic acid;
7-(4-(Biphenyl-4-ylcarbamoyl)phenoxy)-6-cyanochroman-4-carboxylic acid;
7-(4-(4'-Chlorobiphenyl-4-ylcarbamoyl)phenoxy)-6-cyanochroman-4-carboxylic acid;
6-Cyano-7-(4-(3-(2-methylpyrimidin-4-yl)phenylcarbamoyl)phenoxy)chroman-4-carboxylic acid;
6-Chloro-7-(4-(4'-chloro-6-fluorobiphenyl-3-ylcarbamoyl)phenoxy)chroman-4-carboxylic acid;
6-Cyano-7-(4-(1,2,3,4-tetrahydronaphthalen-2-ylcarbamoyl)phenoxy)chroman-4-carboxylic acid;
7-(4-(5-Chloro-2,3-dihydro-1H-inden-2-ylcarbamoyl)phenoxy)-6-cyanochroman-4-carboxylic acid;
7-(4-(4-Chlorophenylcarbamoyl)phenoxy)-6-cyanochroman-4-carboxylic acid;
6-Cyano-7-(4-(4-(trifluoromethyl)phenylcarbamoyl)phenoxy)chroman-4-carboxylic acid;
6-Cyano-7-(4-(naphthalen-2-ylcarbamoyl)phenoxy)chroman-4-carboxylic acid;
6-chloro-7-(4-(3-(4-chlorophenyl)propylcarbamoyl)phenoxy)chroman-4-carboxylic acid;
6-chloro-7-(4-(3-phenylpropylcarbamoyl)phenoxy)chroman-4-carboxylic acid;
6-chloro-7-(4-(2-chlorophenethylcarbamoyl)phenoxy)chroman-4-carboxylic acid;
6-chloro-7-(4-(2,6-dichlorophenethylcarbamoyl)phenoxy)chroman-4-carboxylic acid;
6-chloro-7-(4-(2,4-difluorophenethylcarbamoyl)phenoxy)chroman-4-carboxylic acid;
6-chloro-7-(4-(2-chloro-6-fluorophenethylcarbamoyl)phenoxy)chroman-4-carboxylic acid;
6-chloro-7-(4-(3-hydroxyphenethylcarbamoyl)phenoxy)chroman-4-carboxylic acid;
6-chloro-7-(4-(4-hydroxyphenethylcarbamoyl)phenoxy)chroman-4-carboxylic acid;
6-chloro-7-(4-(4-fluorophenethylcarbamoyl)phenoxy)chroman-4-carboxylic acid;
6-chloro-7-(4-(2-(naphthalen-1-yl)ethylcarbamoyl)phenoxy)chroman-4-carboxylic acid;
6-chloro-7-(4-(2-(naphthalen-2-yl)ethylcarbamoyl)phenoxy)chroman-4-carboxylic acid;
6-chloro-7-(4-(2,5-dimethoxyphenethylcarbamoyl)phenoxy)chroman-4-carboxylic acid;
6-chloro-7-(4-(2,3-dimethoxyphenethylcarbamoyl)phenoxy)chroman-4-carboxylic acid;
7-(4-(5-bromo-2-methoxyphenethylcarbamoyl)phenoxy)-6-chlorochroman-4-carboxylic acid;
7-(4-(2-bromophenethylcarbamoyl)phenoxy)-6-chlorochroman-4-carboxylic acid;
7-(4-(2-(biphenyl-2-yl)ethylcarbamoyl)phenoxy)-6-chlorochroman-4-carboxylic acid;
6-chloro-7-(4-(2-cyclopropylphenethylcarbamoyl)phenoxy)chroman-4-carboxylic acid;
6-chloro-7-(4-(2-(4'-chlorobiphenyl-2-yl)ethylcarbamoyl)phenoxy)chroman-4-carboxylic acid;
6-chloro-7-(4-(2-(3'-chlorobiphenyl-2-yl)ethylcarbamoyl)phenoxy)chroman-4-carboxylic acid;
6-chloro-7-(4-(2-(2'-chlorobiphenyl-2-yl)ethylcarbamoyl)phenoxy)chroman-4-carboxylic acid;
6-chloro-7-(4-(2-chloro-4-fluorophenethylcarbamoyl)phenoxy)chroman-4-carboxylic acid;
6-chloro-7-(4-(2-chloro-4-(trifluoromethyl)phenethylcarbamoyl)phenoxy)chroman-4-carboxylic acid;
6-chloro-7-(4-(4-chloro-2-methoxyphenethylcarbamoyl)phenoxy)chroman-4-carboxylic acid;
6-chloro-7-(4-(2-chloro-4-methoxyphenethylcarbamoyl)phenoxy)chroman-4-carboxylic acid;
6-chloro-7-(4-(4-fluoro-2-methoxyphenethylcarbamoyl)phenoxy)chroman-4-carboxylic acid;
6-chloro-7-(4-(2-methoxy-4-(trifluoromethyl)phenethylcarbamoyl)phenoxy)chroman-4-carboxylic acid;
6-chloro-7-(4-(2,5-dichlorophenethylcarbamoyl)phenoxy)chroman-4-carboxylic acid;
6-chloro-7-(4-(5-chloro-2-fluorophenethylcarbamoyl)phenoxy)chroman-4-carboxylic acid;
6-chloro-7-(4-(2,4-dichlorophenethylcarbamoyl)-phenoxy)chroman-4-carboxylic acid;
Enantiomer 2 of 6-chloro-7-(4-(2,4-dichlorophenethylcarbamoyl)-phenoxy)chroman-4-carboxylic acid;
6-chloro-7-(4-(2,4-dichlorophenethylcarbamoyl)-phenoxy)chroman-4-carboxylic acid;
6-Cyano-7-(4-(4'-methylbiphenyl-3-ylcarbamoyl)phenoxy)chroman-4-carboxylic acid;

6-Cyano-7-(4-(3'-methylbiphenyl-3-ylcarbamoyl)phenoxy)chroman-4-carboxylic acid;
6-Cyano-7-(4-(2',3'-dimethylbiphenyl-3-ylcarbamoyl)phenoxy)chroman-4-carboxylic acid;
7-(4-(2-(benzo[d][1,3]dioxol-5-yl)ethylcarbamoyl)phenoxy)-6-chlorochroman-4-carboxylic acid;
6-chloro-7-(4-((2,3-dihydro-1H-inden-2-yl)methylcarbamoyl)phenoxy)chroman-4-carboxylic acid;
6-chloro-7-(4-(2-(p-tolylthio)ethylcarbamoyl)phenoxy)chroman-4-carboxylic acid;
6-chloro-7-(4-(2-(4-chlorophenylthio)ethylcarbamoyl)phenoxy)chroman-4-carboxylic acid;
6-chloro-7-(4-(2-ethoxyphenethylcarbamoyl)phenoxy)chroman-4-carboxylic acid;
6-chloro-7-(4-(2-(2-chlorophenoxy)ethylcarbamoyl)phenoxy)chroman-4-carboxylic acid;
7-(4-(2-tert-butoxyphenethylcarbamoyl)phenoxy)-6-chlorochroman-4-carboxylic acid;
6-chloro-7-(4-(2-(methylthio)phenethylcarbamoyl)phenoxy)chroman-4-carboxylic acid;
6-chloro-7-(4-(4-(methylthio)phenethylcarbamoyl)phenoxy)chroman-4-carboxylic acid;
6-chloro-7-(4-(1-(3-chlorophenyl)pyrrolidin-3-ylcarbamoyl)phenoxy)chroman-4-carboxylic acid;
6-chloro-7-(4-(1-(3-chlorophenyl)piperidin-4-ylcarbamoyl)phenoxy)chroman-4-carboxylic acid;
6-chloro-7-(4-(1-(3-(trifluoromethyl)phenyl)azetidin-3-ylcarbamoyl)phenoxy)chroman-4-carboxylic acid;
6-chloro-7-(4-(1-(3-(trifluoromethyl)phenyl)pyrrolidin-3-ylcarbamoyl)phenoxy)chroman-4-carboxylic acid;
6-chloro-7-(4-(1-(3-(trifluoromethyl)phenyl)piperidin-4-ylcarbamoyl)phenoxy)chroman-4-carboxylic acid;
6-chloro-7-(4-(1-(2,4-dichlorophenyl)piperidin-4-ylcarbamoyl)phenoxy)chroman-4-carboxylic acid;
6-chloro-7-(4-((S)-1-(3-chlorophenyl)piperidin-3-ylcarbamoyl)phenoxy)chroman-4-carboxylic acid;
6-Cyano-7-(4-((2,3-dihydro-1H-inden-2-yl)methylcarbamoyl)phenoxy)chroman-4-carboxylic acid;
7-(4-(4-tert-Butylcyclohexylcarbamoyl)phenoxy)-6-cyanochroman-4-carboxylic acid;
7-(4-(4-Chlorophenylcarbamoyl)phenoxy)chroman-4-carboxylic acid;
7-(4-(4-Chlorophenethylcarbamoyl)-2-methylphenoxy)-6-cyanochroman-4-carboxylic acid;
6-Cyano-7-(4-((R)-2-phenylpropylcarbamoyl)phenoxy)chroman-4-carboxylic acid;
6-Cyano-7-(4-((S)-2-phenylpropylcarbamoyl)phenoxy)chroman-4-carboxylic acid;
7-(4-(1-(4-Chlorophenyl)propan-2-ylcarbamoyl)phenoxy)-6-cyanochroman-4-carboxylic acid;
7-(4-(4-Chloro-3-methoxyphenethylcarbamoyl)phenoxy)-6-cyanochroman-4-carboxylic acid;
7-(4-(3-tert-Butylphenylcarbamoyl)phenoxy)-6-cyanochroman-4-carboxylic acid;
6-Cyano-7-(4-(3-isopropoxyphenylcarbamoyl)phenoxy)chroman-4-carboxylic acid;
6-chloro-7-(4-(3,4-dichlorobenzylcarbamoyl)phenoxy)chroman-4-carboxylic acid;
6-chloro-7-(4-(4-(trifluoromethyl)phenethylcarbamoyl)phenoxy)chroman-4-carboxylic acid;
6-chloro-7-(4-(3,4-dichlorophenethylcarbamoyl)phenoxy)chroman-4-carboxylic acid;
6-chloro-7-(4-(2,3-dichlorophenethylcarbamoyl)phenoxy)chroman-4-carboxylic acid;
6-chloro-7-(4-(4-methoxyphenethylcarbamoyl)phenoxy)chroman-4-carboxylic acid;
6-chloro-7-(4-(3,4-dimethoxyphenethylcarbamoyl)phenoxy)chroman-4-carboxylic acid;
7-(4-(4-tert-butylphenethylcarbamoyl)phenoxy)-6-chlorochroman-4-carboxylic acid;
6-chloro-7-(4-(3-methoxyphenethylcarbamoyl)phenoxy)chroman-4-carboxylic acid;
6-chloro-7-(4-(2,4-dimethoxyphenethylcarbamoyl)phenoxy)chroman-4-carboxylic acid;
6-chloro-7-(4-(3-fluorophenethylcarbamoyl)phenoxy)chroman-4-carboxylic acid;
6-chloro-7-(4-(3-methylphenethylcarbamoyl)phenoxy)chroman-4-carboxylic acid;
6-chloro-7-(4-(4-(trifluoromethylthio)phenethylcarbamoyl)phenoxy)chroman-4-carboxylic acid;
6-chloro-7-(4-(3,5-dichlorophenethylcarbamoyl)phenoxy)chroman-4-carboxylic acid;
6-chloro-7-(4-(3-phenoxyphenethylcarbamoyl)phenoxy)chroman-4-carboxylic acid;
6-chloro-7-(4-(3-chlorophenethylcarbamoyl)phenoxy)chroman-4-carboxylic acid;
6-chloro-7-(4-(3-(trifluoromethyl)phenethylcarbamoyl)phenoxy)chroman-4-carboxylic acid;
6-chloro-7-(4-(2-(trifluoromethyl)phenethylcarbamoyl)phenoxy)chroman-4-carboxylic acid;
6-chloro-7-(4-(2-fluorophenethylcarbamoyl)phenoxy)chroman-4-carboxylic acid;
6-Cyano-7-(4-(3-(trifluoromethyl)phenylcarbamoyl)phenoxy)chroman-4-carboxylic acid;
Cis-6-Chloro-7-(4-(4-phenylcyclohexylcarbamoyl)phenoxy)chroman-4-carboxylic acid;
Trans-6-Chloro-7-(4-(4-phenylcyclohexylcarbamoyl)phenoxy)chroman-4-carboxylic acid;
7-(4-(4-tert-butylcyclohexylcarbamoyl)phenoxy)-6-chlorochroman-4-carboxylic acid;
6-Chloro-7-(4-(4,4-dimethylcyclohexylcarbamoyl)phenoxy)chroman-4-carboxylic acid;
6-Chloro-7-(4-(3-phenylcyclohexylcarbamoyl)phenoxy)chroman-4-carboxylic acid;
6-Chloro-7-(4-(3-(3-chlorophenyl)cyclohexylcarbamoyl)phenoxy)chroman-4-carboxylic acid;
6-Chloro-7-(4-(3-(4-methylphenyl)cyclohexylcarbamoyl)phenoxy)chroman-4-carboxylic acid;
6-Chloro-7-(4-(3-(4-methoxyphenyl)cyclohexylcarbamoyl)phenoxy)chroman-4-carboxylic acid;
6-Chloro-7-(4-(3-(4-(methylthio)phenyl)cyclohexylcarbamoyl)phenoxy)chroman-4-carboxylic acid;
6-Chloro-7-(4-(3-(3-methoxyphenyl)cyclohexylcarbamoyl)phenoxy)chroman-4-carboxylic acid;
6-chloro-7-(4-(3-(4-chlorophenyl)cyclohexylcarbamoyl)phenoxy)chroman-4-carboxylic acid;
6-chloro-7-(4-(3-phenylcyclopentylcarbamoyl)phenoxy)chroman-4-carboxylic acid;
6-Chloro-7-(4-(3-p-tolylcyclopentylcarbamoyl)phenoxy)chroman-4-carboxylic acid;
6-Chloro-7-(4-(3-(3-chlorophenyl)cyclopentylcarbamoyl)phenoxy)chroman-4-carboxylic acid;
6-chloro-7-(4-(3-(4-chlorophenyl)cyclopentylcarbamoyl)phenoxy)chroman-4-carboxylic acid;
6-chloro-7-(4-(3-(3-methylphenyl)cyclopentylcarbamoyl)phenoxy)chroman-4-carboxylic acid;
6-chloro-7-(4-(3-(3-(trifluoromethyl)phenyl)cyclopentylcarbamoyl)phenoxy)chroman-4-carboxylic acid;
6-chloro-7-(4-(3-(3-fluorophenyl)cyclopentylcarbamoyl)phenoxy)chroman-4-carboxylic acid;
6-chloro-7-(4-(3-(3-(methylthio)phenyl)cyclopentylcarbamoyl)phenoxy)chroman-4-carboxylic acid;

6-chloro-7-(4-(3-(3,4-dichlorophenyl)cyclopentylcarbamoyl)phenoxy)chroman-4-carboxylic acid;
6-chloro-7-(4-(3-(4-methoxyphenyl)cyclopentylcarbamoyl)phenoxy)chroman-4-carboxylic acid;
6-chloro-7-(4-(3-(4-(methylthio)phenyl)cyclopentylcarbamoyl)phenoxy)chroman-4-carboxylic acid;
6-chloro-7-(4-(4-(4-chlorophenyl)cyclohexylcarbamoyl)phenoxy)chroman-4-carboxylic acid;
6-chloro-7-(4-(3-phenylcyclobutylcarbamoyl)phenoxy)chroman-4-carboxylic acid;
6-chloro-7-(4-(1-(4-chlorophenyl)-3-hydroxypropan-2-ylcarbamoyl)phenoxy)chroman-4-carboxylic acid;
6-chloro-7-(4-(3,3-dimethylbutylcarbamoyl)phenoxy)chroman-4-carboxylic acid;
6-chloro-7-(4-(2-cyclohexylethylcarbamoyl)phenoxy)chroman-4-carboxylic acid;
6-chloro-7-(4-(4-chlorophenethylcarbamoyl)-2-methylphenoxy)chroman-4-carboxylic acid;
6-chloro-7-(4-(2,4-dichlorophenethylcarbamoyl)-2-methylphenoxy)chroman-4-carboxylic acid;
6-chloro-7-(4-(2,4-dichlorophenethylcarbamoyl)-3-methylphenoxy)chroman-4-carboxylic acid;
6-chloro-7-(4-(2-(4-chlorophenyl)-2-hydroxyethylcarbamoyl)phenoxy)chroman-4-carboxylic acid;
6-chloro-7-(4-(2-(2-chlorophenyl)-2-hydroxyethylcarbamoyl)phenoxy)chroman-4-carboxylic acid;
6-chloro-7-(4-(2-cyclopentylethylcarbamoyl)phenoxy)chroman-4-carboxylic acid;
7-(4-(1-oxaspiro[4.4]nonan-3-ylcarbamoyl)phenoxy)-6-chlorochroman-4-carboxylic acid;
6-chloro-7-(4-(2-(4-chlorophenyl)-2-methoxyethylcarbamoyl)phenoxy)chroman-4-carboxylic acid;
6-chloro-7-(4-(2-(4-chlorophenyl)-2-fluoroethylcarbamoyl)phenoxy)chroman-4-carboxylic acid;
6-chloro-7-(4-(3,5-dimethoxyphen-ethylcarbamoyl)phenoxy)chroman-4-carboxylic acid;
6-chloro-7-(4-(3-chloro-2-methoxyphen-ethylcarbamoyl)phenoxy)chroman-4-carboxylic acid;
6-chloro-7-(4-(4-chloro-2-(trifluoro-methyl)phenethyl-carbamoyl)phenoxy) chroman-4-carboxylic acid;
7-(4-(2-(benzo[d][1,3]dioxol-4-yl)ethylcarbamoyl)phenoxy)-6-chlorochroman-4-carboxylic acid;
6-chloro-7-(4-(2-(1-(4-(trifluoromethyl)phenyl)-1H-pyrrol-2-yl)ethylcarbamoyl)phenoxy)chroman-4-carboxylic acid;
6-chloro-7-(4-(2-(4-chlorophenyl)-2,2-difluoroethylcarbamoyl)phenoxy)chroman-4-carboxylic acid;
6-chloro-7-(4-(2-ethylphenethylcarbamoyl)phenoxy)chroman-4-carboxylic acid;
6-chloro-7-(4-(2-(2,4-dichlorophenyl)-2-hydroxyethylcarbamoyl)phenoxy)chroman-4-carboxylic acid;
6-chloro-7-(4-(4-chloro-2-ethoxyphen-ethylcarbamoyl)phenoxy)chroman-4-carboxylic acid;
6-chloro-7-(4-(4-chloro-2-(cyclopropyl-methoxy)phenethylcarbamoyl)phenoxy)chroman-4-carboxylic acid;
6-chloro-7-(4-(4-chloro-2-(2-methoxyethoxy)phenethylcarbamoyl)phenoxy)chroman-4-carboxylic acid;
6-chloro-7-(4-(4,5-dichloro-2-ethoxyphenethylcarbamoyl)phenoxy)chroman-4-carboxylic acid;
6-chloro-7-(4-(4-chloro-2-isopropoxy-phenethylcarbamoyl)phenoxy)chroman-4-carboxylic acid;
6-chloro-7-(4-(4-chloro-2-(trifluoromethoxy)phenethylcarbamoyl)phenoxy)chroman-4-carboxylic acid;
6-chloro-7-(4-(3,5-dichlorophen-ethylcarbamoyl)phenoxy) chroman-4-carboxylic acid;
6-chloro-7-(4-((1,2,3,4-tetrahydronaphthalen-1-yl)methylcarbamoyl)phenoxy)chroman-4-carboxylic acid;
6-chloro-7-(4-(2-(4-chlorophenoxy)phenethylcarbamoyl)phenoxy)chroman-4-carboxylic acid;
6-chloro-7-(4-(4-chloro-2-phenoxyphen-ethylcarbamoyl)phenoxy)chroman-4-carboxylic acid;
6-chloro-7-(4-(4-chloro-2-(4-chlorophenoxy)phenethylcarbamoyl)phenoxy)chroman-4-carboxylic acid;
6-chloro-7-(4-(2-(3-chlorophenoxy)phenethylcarbamoyl)phenoxy)chroman-4-carboxylic acid;
6-chloro-7-(4-(2-(2-chlorophenoxy)phenethylcarbamoyl)phenoxy)chroman-4-carboxylic acid;
6-chloro-7-(4-(4-chloro-2-(3-chlorophenoxy)phenethylcarbamoyl)phenoxy)chroman-4-carboxylic acid;
6-chloro-7-(4-(2-(3,4-dichlorophenoxy)-5-fluorophenethylcarbamoyl)phenoxy)chroman-4-carboxylic acid;
6-chloro-7-(4-(2-(2,4-dichlorophenoxy)-5-fluorophenethylcarbamoyl)phenoxy)chroman-4-carboxylic acid;
6-chloro-7-(4-(4-chloro-2-(2-fluoroethoxy)phenethylcarbamoyl)phenoxy)chroman-4-carboxylic acid;
6-chloro-7-(4-(4-chloro-2-(3-fluoropropoxy)phenethylcarbamoyl)phenoxy)chroman-4-carboxylic acid;
6-chloro-7-(4-(2-chloro-6-methoxyphen-ethylcarbamoyl)phenoxy)chroman-4-carboxylic acid;
6-chloro-7-(4-(2,6-dimethoxyphen-ethylcarbamoyl)phenoxy)chroman-4-carboxylic acid;
5-chloro-7-(4-(4-chlorophenethylcarbamoyl)phenoxy)chroman-4-carboxylic acid;
7-(4-((1-(4-chlorophenyl)cyclopropyl)methylcarbamoyl)phenoxy)-6-cyanochroman-4-carboxylic acid;
6-chloro-7-(4-(2-phenoxyethylcarbamoyl)phenoxy)chroman-4-carboxylic acid;
7-(4-(2,4-bis(trifluoromethyl)phenethylcarbamoyl)phenoxy)-6-chlorochroman-4-carboxylic acid;
6-chloro-7-(4-(2,4,6-trimethoxyphenethylcarbamoyl)phenoxy)chroman-4-carboxylic acid;
6-chloro-7-(4-(4-(difluoromethoxy)phenethylcarbamoyl)phenoxy)chroman-4-carboxylic acid;
6-chloro-7-(4-(2,6-dichloro-4-methoxyphenethylcarbamoyl)phenoxy)chroman-4-carboxylic acid;
6-chloro-7-(4-(2,4-diethoxyphenethylcarbamoyl)phenoxy)chroman-4-carboxylic acid;
6-chloro-7-(4-(2-chloro-4,6-dimethoxyphenethylcarbamoyl)phenoxy)chroman-4-carboxylic acid;
6-chloro-7-(4-(4-ethoxy-2-methoxyphenethylcarbamoyl)phenoxy)chroman-4-carboxylic acid;
6-chloro-7-(4-(2-ethoxy-4-methoxyphenethylcarbamoyl)phenoxy)chroman-4-carboxylic acid;
6-chloro-7-(4-(4-chloro-2-(methylthio)phenethylcarbamoyl)phenoxy)chroman-4-carboxylic acid;
6-chloro-7-(4-(4-chloro-2-fluorophenethylcarbamoyl)phenoxy)chroman-4-carboxylic acid;
6-chloro-7-(4-((5-chloro-2,3-dihydro-1H-inden-1-yl)methylcarbamoyl)phenoxy)chroman-4-carboxylic acid;
6-chloro-7-(4-(2-cyclopropyl-4-(trifluoromethyl)phenethylcarbamoyl)phenoxy)chroman-4-carboxylic acid;
6-Chloro-7-(4-(4-chloro-2-hydroxyphenethylcarbamoyl)phenoxy)chroman-4-carboxylic acid;
Enantiomer 2 of 6-chloro-7-(4-(4-chloro-2-cyclopropylphenethylcarbamoyl)phenoxy)chroman-4-carboxylic acid;
Enantiomer 2 of 6-chloro-7-(4-(4-cyclopropyl-2-methoxyphenethylcarbamoyl)phenoxy)chroman-4-carboxylic acid;
Enantiomer 2 of 6-chloro-7-(4-(2,4-dichloro-6-methoxyphenethylcarbamoyl)phenoxy)chroman-4-carboxylic acid;
Enantiomer 2 of 6-chloro-7-(4-(4-chloro-2-methoxyphenethylcarbamoyl)phenoxy)chroman-4-carboxylic acid;

6-chloro-7-(4-(2-methoxy-4-(trifluoromethyl)phenethylcarbamoyl)phenoxy)chroman-4-carboxylic acid;
Enantiomer 2 of 6-chloro-7-(4-(2-methoxy-4-(trifluoromethyl)phenethylcarbamoyl)phenoxy)chroman-4-carboxylic acid;
Enantiomer 2 of 6-chloro-7-(4-(2,4-dimethoxyphenethylcarbamoyl)phenoxy)chroman-4-carboxylic acid;
and salts thereof. Particular mention is made of the sodium salt of the aforementioned compounds.

Example A

DP-2 Binding Inhibition Assay

The coding sequence of human DP2 was introduced into the human Leukemic cell line K562 by electroporation and stable clones expressing DP2 were obtained by limiting dilution followed by cell surface staining with a rat monoclonal antibody specific for human DP2. Membranes were prepared from one of these DP2 expressing clones and used to determine the ability of compounds of the present invention to inhibit binding of prostaglandin D2 (PGD2) to its receptor DP2 in the presence of one or more of the following serum protein concentrations, 0.1% BSA, 1% HSA or 4% HSA, by the following procedure. Membranes (1.25 µg/well for 0.1% BSA and 6 µg/well for 1% or 4% HSA) were mixed with $^3$H-labeled PGD$_2$ and various concentrations of test compounds in 150 µL of binding buffer (50 mM Tris-HCl, pH 7.4, 40 mM MgCl$_2$, 0.1% bovine serum albumin, 0.1% NaN$_3$) in 96-well U-bottom polypropylene plates. After incubation for 60 minutes at room temperature, the assay was transferred to a filtration plate (#MAFB; Millipore Corporation, Bedford, Mass.), and washed three times with binding buffer. Radioactivity was measured by a scintillation counter (TopCount; PerkinElmer Life Sciences, Boston, Mass.). Nonspecific binding was determined by incubations in the presence of 1 µM unlabeled PGD$_2$ or 5 µM of a known DP2 antagonist. EC$_{50}$ values for inhibition of binding were determined for each compound tested from the inflexion point of a standard 4-parameter logistical curve fitted to the values obtained. Compounds of the invention had EC$_{50}$ values less than 5 micromolar in one or more of the binding assays. Certain compounds of the invention had EC$_{50}$ values less than 1 micromolar in one or more of the binding assays. Certain compounds of the invention had EC$_{50}$ values less than 0.5 micromolar in one or more of the binding assays. Certain compounds of the invention had EC$_{50}$ values less than 0.25 micromolar in one or more of the binding assays.

When certain compounds of the invention prepared as racemic mixtures were separated to isolate each enantiomer, it was found that one enantiomer was more potent than the other enantiomer when tested in a DP2 binding inhibition assay as described above.

EC$_{50}$ values for compounds of the invention when tested in a DP2 binding inhibition assay as described above are provided in Table A.

TABLE A

| Ex. # | EC$_{50}$ (nM) 4% HSA | EC$_{50}$ (Nm) 1% HSA | EC$_{50}$ (nM) 0.1% BSA |
|---|---|---|---|
| 1 | 400.1 | 16.6 | |
| 2 | | 70 | |
| 3 | 5000 | 129.4 | |
| 4 | | 10.7 | |
| 5 | | 37.4 | |
| 6 | | 77.3 | |
| 7 | | 19 | |
| 8 | | 16 | |
| 9 | | 203 | |
| 10 | 225 | 13.9 | |
| 11 Enantiomer 2 | 110.6 | 9.3 | |
| 12 | 794.3 | | |
| 13 | 404.6 | | |
| 14 | 824.1 | | |
| 15 | 746.4 | | |
| 16 | 318 | | |
| 17 | 395 | | |
| 18 | 502 | | |
| 19 | 638.3 | | |
| 20 | 758.6 | | |
| 21 | 169 | | |
| 22 | 438.5 | | |
| 23 | 326.6 | | |
| 24 | 481.9 | | |
| 25 | 3334 | | |
| 26 | 160.3 | | |
| 27 | 215.8 | | |
| 28 | 122.7 | | |
| 29 | 136.8 | | |
| 30 | 300.6 | | |
| 31 | 91.4 | | |
| 32 | 88 | | |
| 33 | 126 | | |
| 34 | 73.1 | 10.5 | |
| 35 | 64.3 | | |
| 36 | 93.05 | 17.3 | |
| 37 | 55 | 12 | |
| 38 | 365.6 | | |
| 39 | 68.2 | | |
| 40 | 42.2 | | |
| 41 | 150.3 | | |
| 42 | 73.8 | | |
| 43 | 51.5 | | |
| 44 | 3475.4 | | |
| 45 | | 1374 | |
| 46 | 176.2 | 15.8 | |
| 47 | | 12.1 | |
| 48 | | 30.7 | |
| 49 | | 22.5 | |
| 50 | | 11 | |
| 51 | 14.8 | 12.1 | |
| 52 | | 90.8 | |
| 53 | | 60.5 | |
| 54 | | 109.1 | |
| 55 | | 12.1 | |
| 56 | | 14.2 | |
| 57 | | 18.9 | |
| 58 | 434.5 | | |
| 59 | 157.8 | | |
| 60 | 131.2 | | |
| 61 | 920.4 | | |
| 62 | 88.5 | | |
| 63 | 304.8 | | |
| 64 | 153.1 | | |
| 65 | 80.4 | | |
| 66 | 68.2 | | |
| 67 | 172.6 | | |
| 68 | 206.1 | | |
| 69 | 239.9 | | |
| 70 | 995.4 | | |
| 71 | 119.1 | | |
| 72 | | 36.4 | |
| 73 | | 42.4 | |
| 74 | | 23.3 | |
| 75 | | 11.9 | |
| 76 | | 6.7 | |
| 77 | 356.5 | | |
| 78 | 680.8 | | |
| 79 | 98.9 | | |
| 80 | 165.2 | | |
| 81 | 191.4 | | |
| 82 | 473.2 | | |

TABLE A-continued

| Ex. # | EC$_{50}$ (nM) 4% HSA | EC$_{50}$ (Nm) 1% HSA | EC$_{50}$ (nM) 0.1% BSA |
|---|---|---|---|
| 83 | 568.9 | | |
| 84 | 1380.4 | | |
| 85 | 344.3 | | |
| 86 | 126.5 | | |
| 87 | 233.9 | | |
| 88 | 202.8 | | |
| 89 | 145.5 | | |
| 90 | 152.8 | | |
| 91 | 192.3 | | |
| 92 | 111.2 | | |
| 93 | 106.7 | | |
| 94 | 287.1 | | |
| 95 | 91.8 | | |
| 96 | 40.2 | | |
| 97 | 190.1 | | |
| 98 | 193.2 | | |
| 99 | 50.7 | 5.1 | |
| 100 | 619.4 | | |
| 101 | 292.4 | | |
| 102 | 48.9 | 7.7 | |
| 103 | 391.7 | | |
| 104 | 955 | | |
| 105 | 107.4 | | |
| 106 Enantiomer 2 | 62.7 | 2.65 | |
| 106 Enantiomer 1 | >5000 | | |
| 107 | 115.3 | | |
| 108 | 69.3 | | |
| 109 | 103.8 | | |
| 110 | 606.7 | | |
| 111 | 173.8 | | |
| 112 | 4187.9 | | |
| 113 | 2382.3 | | |
| 114 | 91 | | |
| 115 | 2437.8 | | |
| 116 | 304.1 | | |
| 117 | 246 | | |
| 118 | 425.6 | | |
| 119 | 206 | | |
| 120 | 371 | | |
| 121 | 4315 | | |
| 122 | 242 | | |
| 123 | 259 | | |
| 124 | 841 | | |
| 125 | 420.7 | | |
| 126 | 179.1 | | |
| 127 | 270.4 | | |
| 128 | 979.5 | 107.6 | |
| 129 | | 21.9 | |
| 130 | | 25.7 | |
| 131 | | 59.3 | |
| 132 | | 37.4 | |
| 133 | 625.2 | | |
| 134 | 112.5 | | |
| 135 | 204.6 | | |
| 136 | 4217 | | |
| 137 | 120.5 | | |
| 138 | 239.3 | | |
| 139 | 226.5 | | |
| 140 | 497.7 | | |
| 141 | 1000 | | |
| 142 | 139.6 | | |
| 143 | 1009.3 | | |
| 144 | 87.9 | 16.4 | |
| 145 | 654.6 | | |
| 146 | 608.1 | | |
| 147 | 239.9 | | |
| 148 | 196.3 | | |
| 149 | 280.5 | | |
| 150 | 341.2 | | |
| 151 | 342.8 | | |
| 152 | 159.6 | | |
| 153 | 521.2 | | |
| 154 | 485.3 | | |
| 155 peak 1 | 399 | | |
| 155 peak 2 | 1671.1 | | |
| 156 | 509.3 | | |
| 157 | 1584.9 | | |
| 158 | 1648.2 | | |
| 159 | 663.7 | | |
| 160 | 349.9 | | |
| 161 | 1116.9 | | |
| 162 | 429.5 | | |
| 163 | 509.3 | | |
| 164 | 183.2 | | |
| 165 | 400.9 | | |
| 166 | 272.3 | | |
| 167 | 179.1 | | |
| 168 | 302 | | |
| 169 | 204.2 | | |
| 170 | 297.9 | | |
| 171 | 332.7 | | |
| 172 | 281.8 | | |
| 173 | 327.3 | | |
| 174 | 722.8 | | |
| 175 | 571.5 | | |
| 176 | 338.8 | | |
| 177 | 163.3 | | |
| 178 | 1733.8 | | |
| 179 | 1112 | | |
| 180 | 407 | | |
| 181 | 331.1 | | |
| 182 | 151.4 | | |
| 183 | 968.3 | | |
| 184 | 824.1 | | |
| 185 | 857 | | |
| 186 | 538 | | |
| 187 | 649 | | |
| 188 | 758.6 | | |
| 189 | 196.8 | | |
| 190 | 922.6 | | |
| 191 | 164.1 | | |
| 192 | 191 | | |
| 193 | 639.7 | | |
| 194 | 3006 | | |
| 195 | 1145.5 | | |
| 196 | 269.2 | | |
| 197 | 688.7 | | |
| 198 | 68.1 | | |
| 199 | 110.7 | | |
| 200 | 331.1 | | |
| 201 | 137.7 | | |
| 202 | 71.6 | | |
| 203 | 103 | | |
| 204 | 196.3 | | |
| 205 | 94 | | |
| 206 | 64 | | |
| 207 | 26.4 | | |
| 208 | 41.4 | | |
| 209 | 57.7 | | |
| 210 | 54.1 | | |
| 211 | 37.2 | | |
| 212 | 81.5 | | |
| 213 | 45.1 | | |
| 214 | 94.2 | | |
| 215 | 58.2 | | |
| 216 | 493.2 | | |
| 217 | 180.3 | | |
| 218 | | 143.9 | |
| 219 | | 1039 | |
| 220 | >2000 | | |
| 221 | 45 | | |
| 222 | 118 | | |
| 223 | 209 | | |
| 224 | 373 | | |
| 225 | 56 | | |
| 226 | 88.5 | | |
| 227 | 74.5 | | |
| 228 | 88.9 | | |
| 229 | 67.5 | | |
| 230 | 243 | | |

TABLE A-continued

| Ex. # | EC$_{50}$ (nM) 4% HSA | EC$_{50}$ (Nm) 1% HSA | EC$_{50}$ (nM) 0.1% BSA |
|---|---|---|---|
| 231 | 225.4 | | |
| 232 | 46.5 | | |
| 233 | | | 11.1 |
| 234 | 21.7 | | |
| 234 Enantiomer 2 | >5000 | | |
| 234 Enantiomer 1 | | | |
| 235 | 17 | | |
| 235 Enantiomer 2 | >5000 | | |
| 235 Enantiomer 1 | | | |
| 236 | 34 | | |
| 236 Enantiomer 2 | | | 1361 |
| 236 Enantiomer 1 | | | |
| 237 | 25.6 | | |
| 237 Enantiomer 2 | >5000 | | |
| 237 Enantiomer 1 | | | |
| 238 | 16.2 | | |
| 238 Enantiomer 2 | | | |
| 239 | 48.1 | | |
| 239 Enantiomer 2 | | | 367 |
| 239 Enantiomer 1 | | | |

Example B

Mouse Allergic Rhinitis Model

Allergic rhinitis (AR) is the most common form of atopic disease with an estimated prevalence ranging from 5% to 22% (Naclerio, R. M., *N. Engl. J. Med.* 1991, 325:860-869), leading to enormous associated costs for treatment. The typical symptoms of AR in human subjects are well known, mainly sneezing and nasal blockage (Corrado O. J., et al., *Br. J. Clin. Pharmacol.* 1987, 24:283-292; Mygind N and Anggard A. *Clin. Rev. Allergy,* 1984, 2:173-188). The 3 major causes of the nasal blockage are thought to be dilatation of capacitance vessels in the nasal septum and turbinates, edematous swelling of nasal membranes, and the direct result of secretions (Sherwood J. E., et al. *J. Allergy Clin. Immunol.,* 1993, 92:435-441; Juliusson S. and Bende M., *Clin Allergy* 1987, 17:301-305; Mygind N. et al., *Eur J Respir Dis Suppl.* 1987, 153:26-33; Gawin A. Z., et al., *J Appl Physiol.* 1991, 71:2460-2468).

Nasal reactivity in AR has been shown to occur in 2 phases: early-phase and late-phase responses. Early-phase responses occur within minutes of exposure to the allergen and tend to produce sneezing, itching, and clear rhinorrhea; the late-phase response reaction occurs 6 to 24 hours after local allergen challenge of subjects with atopic rhinitis and is characterized by congestion, fatigue, malaise, and irritability (Naclerio, supra). Persistent tissue edema and eosinophils, mast cells, T$_H$2-type lymphocytes, and macrophages are thought to be involved (Naclerio, supra).

Methods

Ovalbumin (OVA) Sensitization and Nasal Challenge

Balb/c mice were obtained from Jackson Laboratories (Bar Harbor, Me.). Animals were housed under conventional conditions and maintained on an OVA-free diet. Female mice, 6-12 weeks of age, were used in all studies. All experimental animals used in these studies were under a protocol approved by the Institutional Animal Care and Use committee. Mice were sensitized by an intraperitoneal injection of 20 µg of OVA (Grade V; Sigma Chemical, St Louis, Mo.) emulsified in 2.25 mg of alum (AlumImuject; Pierce, Rockford, Ill.) in a total volume of 100 µL on days 0 and 14. Two weeks following sensitization, mice received daily challenges of OVA (10% in saline) by instillation in the nostril without anesthesia for 6 days. Animals were dosed either on day 4 or on each of days 1-6 with a compound of the invention at a dose between 0.1-10 mg/kg one hour before nasal challenge.

Measurement of Respiratory Parameters with Whole-Body Plethysmography

Respiratory frequency (RF), expiratory time, and inspiratory time were measured in unrestrained conscious animals by using single-chamber whole-body plethysmography (WBP; Buxco, Troy, N.Y.). Before the measurement, mice were left in the chambers for 20 minutes with constant airflow. For measurement of respiratory parameters during the early-phase reaction (4$^{th}$ nasal challenge), mice received OVA (20 µL of 25 mg/mL) through the nostril after measurement of baseline values and were then placed back into the box. RF, inspiratory time, and expiratory time were measured.

Measurement of Nasal Resistance

For resistance, measurements of piston volume displacement and cylinder pressure were used to calculate the impedance of the respiratory system, as described by Pillow et al. (*J Appl Physiol.* 2001, 91:2730-2734). Briefly, each muse was anesthetized with pentobarbital sodium (50 mg/kg administered intraperitoneally) and fixed in a supine position. Tracheostomized (18-gauge cannula) mice were mechanically ventilated (160 breaths/minute, tidal volume to 0.15 mL). The frontal and right lateral walls of the upper trachea and larynx were removed. After incision of the frontal wall of the pharynx, a blunt 19-gauge needle was carefully inserted into the nasopharynx through the pharynx. The needle was connected to a polyethylene tube (outer diameter, 0.165 cm) with a 2-mm overhang. The other end of the tube was connected to a custom-designed ventilator. The nasal cavity was ventilated with 8 mL/kg at a rate of 150 breaths/minute. Resistance was determined by measuring the piston volume displacement and cylinder pressure. Resistance of the late-phase response (persistent nasal obstruction) was measured 24 hours after the last OVA challenge. All data were analyzed with FlexiVent software (Scireq, Montreal, Quebec, Canada).

Compounds described herein were shown or will be shown to be effective in this model.

Preparation 1

4-(6-Chloro-4-(ethoxycarbonyl)chroman-7-yloxy) benzoic acid

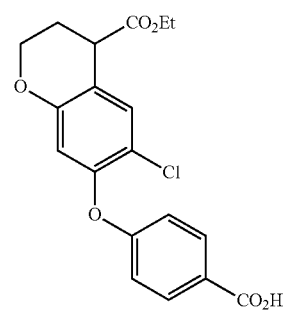 [SMILES: CCOC(=O)C1CCOc2cc(Oc3ccc(C(=O)O)cc3)c(Cl)cc21]

Step A: Preparation of 3-chloro-1-(5-chloro-2,4-dihydroxyphenyl)propan-1-one A 2-liter 4-neck round-bottom flask was charged with trifluoromethanesulfonic acid (500 g, 3.33 mol) and the flask contents were cooled below 10° C. 4-Chlororesorcinol (100 g, 0.69 mol) was added in portions over 20-30 minutes, maintaining the temperature at 4 to 8° C. The reaction mixture was stirred at or below 10° C. until a clear solution formed (40 minutes). 3-Chloropropanoic acid (78.8 g, 0.73 mol) was warmed until melted and then added in liquid form dropwise over 45 minutes to the flask, maintaining the temperature at or below 10° C. The reaction mixture was stirred for an additional 10 minutes at or below 10° C., then slowly heated to 50-55° C. and maintained there for 6 hours. The reaction mixture was cooled to ambient temperature and added dropwise to water (1.1 L) contained in a 3-liter 4-neck round-bottom flask. The resulting mixture was stirred at ambient temperature for 30 minutes. The resulting precipitate was collected by filtration, washed with water (3×540 mL), and dried in a fan dryer at 40° C. until the moisture content fell below 0.5%, to afford 3-chloro-1-(5-chloro-2,4-dihydroxyphenyl)propan-1-one as an orange solid (160 g, 98.4% yield).

Step B: Preparation of 6-chloro-7-hydroxychroman-4-one

A 20-liter 4-neck round-bottom flask was charged with water (10 L) and 3-chloro-1-(5-chloro-2,4-dihydroxyphenyl)propan-1-one (1.62 kg, 6.89 mol), and the resulting mixture was stirred and cooled to 10° C. A solution of sodium hydroxide (606.5 g, 15.16 mol) in water (2.96 L) was added dropwise over 40-60 minutes, maintaining the temperature at 10-15° C. The resulting mixture was stirred at ambient temperature for a further 30 minutes, then cooled to 5° C. Concentrated hydrochloric acid (1.31 L, 15.98 mol) was added dropwise over 30 minutes, maintaining the temperature at or below 10° C. The resulting mixture was stirred at ambient temperature for a further 30 minutes, and the resulting precipitate was collected by filtration, washed with water (3×5.5 L), and dried at 40° C. until the moisture content fell below 1%. This crude product (1.2 kg) was transferred to a 10-liter 4-neck round-bottom flask and stirred with acetonitrile (6.0 L) at ambient temperature for 2 hours, then cooled to 0-5° C. and stirred for an additional 2 hours. The resulting precipitate was collected by filtration, washed with 4:1 water:acetonitrile (1.5 L) and water (1.2 L), and dried in a fan dryer at 40° C. until the moisture content fell below 0.5%, to afford 6-chloro-7-hydroxychroman-4-one as an off-white solid (858 g, 62.7% yield).

Step C: Preparation of 6-chloro-4,7-bis(trimethylsilyloxy)chroman-4-carbonitrile (CAUTION: Hydrogen cyanide gas is produced in this reaction; take appropriate precautions). A 20-liter 4-neck round-bottom flask was charged with dichloromethane (12.5 L), iodine (32 g, 0.13 mol) and 6-chloro-7-hydroxychroman-4-one (1.25 kg, 6.30 mol). The resulting mixture was stirred under nitrogen and cooled to 10° C. Trimethylsilyl cyanide (2.36 L, 18.88 mol) was added dropwise over 30 minutes, maintaining the temperature at or below 10° C. The reaction mixture was stirred at ambient temperature for 10-11 hours, then cooled below 20° C. A solution of sodium thiosulfate (59.5 g, 0.38 mol) in water (500 mL) was added dropwise, maintaining the temperature below 20° C., and the resulting mixture was stirred for 20 minutes while maintaining the temperature below 20° C. Solid sodium sulfate anhydrous (3.75 kg) was added, and the resulting mixture was stirred for 30 minutes while maintaining the temperature below 20° C. The reaction mixture was filtered through a HyFlo™ bed, and the bed was washed with dichloromethane. The combined filtrate and washing were concentrated under reduced pressure at a temperature below 50° C. to afford 6-chloro-4,7-bis(trimethylsilyloxy)chroman-4-carbonitrile as a brown oil (2.2 kg, 94.5% yield).

Step D: Preparation of 6-chloro-7-hydroxychroman-4-carboxylic acid

A 20-liter 4-neck round-bottom flask was charged with glacial acetic acid (2.04 L), 6-chloro-4,7-bis(trimethylsilyloxy)chroman-4-carbonitrile (2.2 kg, 5.94 mol), and tin(II) chloride dihydrate (3.35 kg, 14.85 mol) and the resulting mixture was stirred at ambient temperature. Concentrated hydrochloric acid (5.0 L, 60 mol) was added, and the resulting mixture was stirred and heated to 80-85° C. for 12 hours. The reaction mixture was cooled to ambient temperature and water (3.6 L) was added, and stirring was continued at ambient temperature for 15 minutes. Isopropyl acetate (11.5 L) and water (5.8 L) were added, and stirring was continued at ambient temperature for 15 minutes. The layers were separated, and the aqueous layer was extracted with isopropyl acetate (2×2 L). The organic layers were combined and washed with brine (3×6 L), then dried over sodium sulfate and concentrated under reduced pressure at a temperature below 50° C. to afford crude 6-chloro-7-hydroxychroman-4-carboxylic acid as a brown semi-solid (1.70 kg, 125% yield).

Step E: Preparation of ethyl 6-chloro-7-hydroxychroman-4-carboxylate

A 20-liter 4-neck round-bottom flask was charged with ethanol (8.6 L) and crude 6-chloro-7-hydroxychroman-4-carboxylic acid (1.70 kg, 7.44 mol) and the resulting mixture was stirred at ambient temperature. Concentrated sulfuric acid (397 mL) was added over 10 minutes. The resulting mixture was stirred and heated to reflux for 16 hours. The reaction mixture was cooled to ambient temperature and diluted with ethyl acetate (9.0 mL). The resulting mixture was washed with brine (2×12 L). The brine washes were combined and extracted with ethyl acetate (4 L). The ethyl acetate layer was washed with brine (2 L). The organic layers were combined and dried over sodium sulfate, then concentrated under reduced pressure at a temperature below 50° C. The residue was purified by chromatography on silica gel (18 kg), eluting with 85:15 hexanes:ethyl acetate (235 L), to afford ethyl 6-chloro-7-hydroxychroman-4-carboxylate as a white powder (822 g, 43% yield). MS (apci) m/z=255.1 (M−H).

Step F: Preparation of ethyl 7-(4-(tert-butoxycarbonyl)phenoxy)-6-chlorochroman-4-carboxylate Tert-butyl 4-bromobenzoate (210.4 g, 818.2 mmol) was dissolved in 1 L of dioxane, which was previously degassed with argon, in a 4-neck 5 L round bottom flask equipped with a mechanical stirrer and a reflux condenser. Under argon flow and with stirring, ethyl 6-chloro-7-hydroxychroman-4-carboxylate (176.4 g, 687.2 mmol), N,N-dimethyl glycine hydrochloride (35.7 g, 346.2 mmol) and cuprous chloride (34.0 g, 342.9 mmol) were added via a funnel. Cesium carbonate then added and an additional 0.5 L of dioxane was added to the reaction mixture. The mixture was then heated at 95-97° C. for 20 hours. After cooling to ambient temperature, the reaction mixture was poured into 3 L of a 3:1 mixture of hexanes:ethyl acetate and activated charcoal (300 g) was added. After stirring periodically for 1 hour, the mixture was filtered thru GF/F paper, washing the filter cake with 2 L of a 3:1 mixture of hexanes:ethyl acetate. The resulting golden brown solution was concentrated to provide 304 g of crude ethyl 7-(4-(tert-butoxycarbonyl)-phenoxy)-6-chlorochroman-4-carboxylate. The crude product was dissolved in dichloromethane, concentrated onto silica gel and purified by flash column chromatography, eluting with a gradient of 10 to 25% ethyl acetate in hexanes to give ethyl 7-(4-(tert-butoxycarbonyl)phenoxy)-6-chlorochroman-4-carboxylate as a colorless, viscous oil (221 g, 74.3% yield). $^1$H NMR (400 MHz, CDCl$_3$) δ 7.96 (d, J=8.8 Hz, 2H), 7.37 (s, 1H), 6.94 (d, J=8.8 Hz, 2H), 6.54 (s, 1H), 4.21-4.29 (m, 4H), 3.74 (t, J=5.3 Hz, 1H), 2.30-2.36 (m, 1H), 2.05-2.14 (m, 1H), 1.58 (s, 9H), 1.31 (t, J=7.0 Hz, 3H).

Step G: Preparation of 4-(6-chloro-4-(ethoxycarbonyl)chroman-7-yloxy)benzoic acid Ethyl 7-(4-(tert-butoxycarbonyl)phenoxy)-6-chlorochroman-4-carboxylate (221 g, 0.511 mol) was dissolved in hydrogen chloride in ethyl acetate (2.4 N, 1.6 L, 3.84 mol) and the resulting solution was stirred at ambient temperature for 16 hours. The solution was concentrated to give 198 g of crude 4-(6-chloro-4-(ethoxycarbonyl)chroman-7-yloxy)-benzoic acid. The crude product was recrystallized by dissolving in hot isopropyl acetate (0.5 L) and diluting with hexanes (1.1 L). After 48 hours, the crystals were collected and wash with hexanes. The resulting white solids were dried under high vacuum to give 4-(6-chloro-4-(ethoxycarbonyl)chroman-7-yloxy)benzoic acid (169 g, 88% yield). $^1$H NMR (400 MHz, CDCl$_3$) δ 8.08 (d, J=8.9 Hz, 2H), 7.38 (s, 1H), 6.98 (d, J=8.8 Hz, 2H), 6.60 (s, 1H), 4.21-4.31 (m, 4H), 3.75 (t, J=5.4 Hz, 1H), 2.31-2.37 (m, 1H), 2.08-2.15 (m, 1H), 1.32 (t, J=7.0 Hz, 3H).

Preparation 2

4-(6-Cyano-4-(methoxycarbonyl)chroman-7-yloxy)benzoic acid

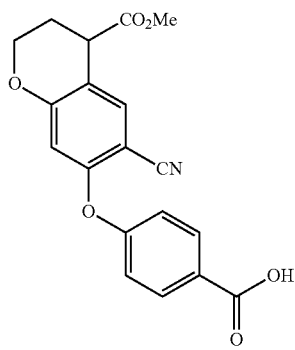 [SMILES: COC(=O)C1CCOc2cc(Oc3ccc(C(=O)O)cc3)c(C#N)cc21]

Step A: Preparation of methyl 7-(4-(tert-butoxycarbonyl)phenoxy)-6-cyanochroman-4-carboxylate A 500 ml flask equipped with a Claisen head and a condenser was charged with oven dried MS 4A powder (14.5 g), methyl 6-cyano-7-fluorochroman-4-carboxylate (14.11 g, 60.00 mmol), tert-butyl 4-hydroxybenzoate (14.57 g, 75.00 mmol), K$_2$CO$_3$ (20.73 g, 150.0 mmol), and 1-methyl-2-pyrrolidinone (120 mL). The mixture was degassed with Argon for 1 hour, then heated to 115° C. for 18 hours. The mixture was cooled to ambient temperature. The mixture was filtered through a CELITE pad and rinsed with EtOAc. The combined filtrates were washed with water. The EtOAc layer was dried over MgSO$_4$, filtered through GF paper, and concentrated to a crude oil. The crude oil was purified on silica gel (EtOAc in hexanes gradient) to provide 18.5 g of the desired compound as semisolid.

Step B: Preparation of 4-(6-cyano-4-(methoxycarbonyl)chroman-7-yloxy)benzoic acid Methyl 7-(4-(tert-Butoxycarbonyl)phenoxy)-6-cyanochroman-4-carboxylate (18.5 g, 45.185 mmol) was dissolved in dichloromethane (200 mL). Trifluoroacetic acid (50 mL) was added and the mixture was stirred at ambient temperature for 1.5 hours, and then concentrated under reduced pressure to provide a crude solid. The solid was dissolved in EtOAc (200 ml), and hexanes (600 ml) were added with stirring. White solid was crashed out and was collected by filtration to provide 13.11 g of the desired compound as white solid (81.9%). The mother liquor was concentrated and the residue was dissolved in EtOAc (25 ml). Hexanes (100 ml) were added with stirring and a white solid was crashed out and was collected by filtration to provide an additional 1.14 g of the desired compound.

Preparation 3

Methyl 6-cyano-7-(4-(3-iodophenylcarbamoyl)phenoxy)chroman-4-carboxylate

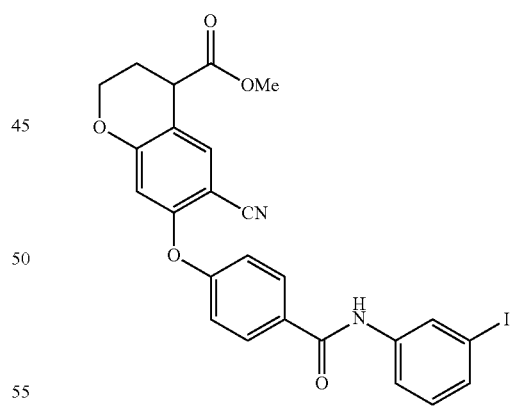

A 50 ml round bottomed flask was charged with 4-(6-cyano-4-(methoxycarbonyl)chroman-7-yloxy)benzoic acid (Preparation 2) (1.466 g, 4.15 mmol), a drop of DMF, and 1,2-dichloroethane (10 ml). Oxalyl chloride (2M in dichloromethane) (2.283 ml, 4.565 mmol) was slowly added and the mixture became a clear solution. Gas evolution was observed. The mixture was stirred for 17 hours at ambient temperature. Triethylamine (1.157 ml, 8.30 mmol) and 3-iodoaniline (0.524 ml, 4.358 mmol) were added to the acid chloride solution. The mixture was stirred for 1 hour at ambient temperature. The crude mixture was purified on silica gel (EtOAc in hexanes gradient) to provide 2.094 g of the title compound as light brown solid (91%).

Preparation 4

Ethyl 6-chloro-7-hydroxychroman-4-carboxylate

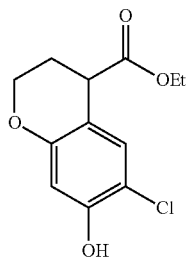 [SMILES: CCOC(=O)C1CCOc2cc(O)c(Cl)cc21]

Step A: Preparation of 6-chloro-7-hydroxychroman-4-one

A 50-liter reactor was charged with trifluoromethanesulfonic acid (8 kg) and the reactor cooled in an ice bath. To the reactor was added 4-chlororesorcinol (1.6 kg, 11.1 mol), in portions, at a rate such that the internal temperature did not exceed 10° C. To the reactor was then added 3-chloropropanoic acid (1.26 kg, 11.6 mol), and the resulting mixture was warmed to ambient temperature, then heated at 45-55° C. for 6 hours. The reaction mixture was then slowly added to ice-water (20 L). The resulting slurry was stirred for 2 hours, and the resulting precipitate was collected by filtration, washed with water (12 L), and air-dried. This material was added to a solution of sodium hydroxide (1.1 kg, 27.5 mol) in ice-water (24 L), at a rate such that the internal temperature did not exceed 20° C. The resulting solution was stirred below 20° C. for 1 hour, then cooled, and treated with concentrated hydrochloric acid (2.5 L), at a rate such that the temperature did not exceed 10° C. The resulting slurry was stirred below 10° C. for 1 hour, and the resulting precipitate was collected by filtration, washed with water (10 L), and partially air-dried. The crude solids from four such procedures were combined and added to a mixture of acetone (32 L) and water (40 L), and the resulting mixture was stirred and heated until a clear solution formed. This solution was then cooled to 5-10° C., and the resulting precipitate was collected by filtration, washed with water (12 L), and dried to afford 6-chloro-7-hydroxychroman-4-one as a white solid (4.6 kg, 52% yield).

Step B: Preparation of 6-chloro-7-hydroxychroman-4-carboxylic acid, dicyclohexylamine salt (CAUTION: Hydrogen cyanide gas is produced in this reaction; take appropriate precautions). A 10-liter 4-neck round-bottom flask equipped with a reflux condenser, mechanical stirrer, and thermometer was charged with 6-chloro-7-hydroxychroman-4-one (1.5 kg, 7.6 mol), zinc iodide (49.0 g, 0.154 mol), and trimethylsilyl cyanide (2.5 L, 20.0 mol), under an atmosphere of nitrogen. The resulting mixture was stirred at 45-50° C. for 2 hours, then cooled to ambient temperature and treated successively with a solution of sodium thiosulfate (2.5 kg) in water (6 L), saturated sodium bicarbonate solution (2 L), and ethyl acetate (5 L). The resulting mixture was stirred at ambient temperature for 30 minutes. The layers were separated, and the aqueous layer was extracted with ethyl acetate (2 L). The organic layers were combined and washed with saturated sodium bicarbonate solution (1 L) and brine (2×1 L), then concentrated under reduced pressure. To the resulting brown oil was added was added successively tin(II) chloride dihydrate (5.3 kg, 23.5 mol), concentrated hydrochloric acid (7.5 L) and glacial acetic acid (2.7 L). The resulting mixture was stirred and heated to reflux (100° C.) for 18 hours, then cooled to ambient temperature. The resulting orange precipitate was removed by filtration, and the filtrate was treated with dichloromethane (5 L). After stirring for 20 minutes, solid sodium chloride was added until the aqueous layer was saturated. The layers were separated, and the aqueous layer was extracted with dichloromethane (2×2 L). The organic layers were combined and washed with brine (1 L), then treated with 10% aqueous sodium hydroxide until the apparent pH of the organic layer was 10-11. The aqueous layer was acidified with concentrated hydrochloric acid to pH 3-4, then extracted with ethyl acetate (3×2 L). The organic layers were combined and stirred at ambient temperature, and dicyclohexylamine (1.5 L) was added dropwise. The resulting mixture was stirred at ambient temperature for 1 hour, and the resulting precipitate was collected by filtration, washed with ethyl acetate (2×1 L), and dried to afford 6-chloro-7-hydroxychroman-4-carboxylic acid, dicyclohexylamine salt as an off-white solid (2.0 kg, 64% yield).

Step C: Preparation of ethyl 6-chloro-7-hydroxychroman-4-carboxylate

A 10-liter 4-neck round-bottom flask equipped with a reflux condenser, mechanical stirrer, and thermometer was charged with 6-chloro-7-hydroxychroman-4-carboxylic acid, dicyclohexylamine salt (1.7 kg, 4.1 mol) and 10% aqueous sodium hydroxide (4 L). The resulting mixture was extracted with methyl tert-butyl ether (2×1 L). The aqueous layer was acidified to pH 2-3 with concentrated hydrochloric acid, then extracted with ethyl acetate (2×2 L). The organic layers were combined and dried over magnesium sulfate, then concentrated under reduced pressure. The residual free acid was dissolved in ethanol (4.5 L) and to the resulting solution was added concentrated sulfuric acid (240 mL), dropwise. The resulting solution was stirred and heated to reflux for 16 hours. After cooling to ambient temperature, the solution was diluted with water (1.5 L), followed by dropwise addition of saturated sodium bicarbonate solution (3 L), resulting in an apparent pH of about 3. The resulting mixture was stirred for 5 hours at ambient temperature, and the resulting precipitate was collected by filtration, washed with water 3 L), and dried to afford ethyl 6-chloro-7-hydroxychroman-4-carboxylate as a light pink powder (850 g, 81% yield). MS (apci) m/z=255.1 (M–H).

Preparation 5

2-(2-Bromo-4-chlorophenyl)ethanamine

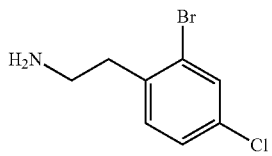 [SMILES: NCCc1ccc(Cl)cc1Br]

Step A: Preparation of 2-bromo-4-chloro-1-(dibromomethyl)benzene

To a stirred solution of 4-bromo-2-chlorotoluene (10.0 g; 48.7 mmol) and benzoyl peroxide (0.51 g; 2.09 mmol) in 80 mL of carbon tetrachloride was added N-bromosuccinimide (43.3 g; 243 mmol), and the resulting mixture was stirred and heated to reflux. After 15 hours, the mixture was cooled to ambient temperature, and the insoluble material was removed by filtration and washed twice with carbon tetrachloride. The filtrate and washings were combined and evaporated. The residue was purified by silica gel chromatography on a Biotage 65M column, eluting with hexanes to give 17.4 g of 2-bromo-4-chloro-1-(dibromomethyl)benzene as a colorless liquid.

Step B: Preparation of 2-bromo-4-chlorobenzaldehyde

A solution of 2-bromo-4-chloro-1-(dibromomethyl)benzene (17.4 g; 47.9 mmol) in 25 mL ethanol was stirred and heated to reflux, and a solution of silver(I) nitrate (76.1 g; 448 mmol) in 55 mL water was added dropwise over 20 minutes. The mixture turned yellow and a precipitate of AgBr formed immediately upon addition. Following completion of addition, the mixture was stirred at reflux for an additional hour. After reaching ambient temperature, the mixture was diluted with 200 mL water and filtered to remove insoluble material. The filtrate was extracted with 200 mL chloroform and the insoluble materials were washed with 2×200 mL chloroform. The chloroform layers were combined and washed with 250 mL water, then dried over sodium sulfate and evaporated to give 10.3 g of 2-bromo-4-chlorobenzaldehyde as a white solid.

Step C: Preparation of 2-bromo-4-chloro-1-(2-nitrovinyl)benzene

A suspension of 2-bromo-4-chlorobenzaldehyde (2.2 g; 10.0 mmol), methylamine hydrochloride (0.43 g; 6.4 mmol) and sodium acetate (0.53 g; 6.4 mmol) in 3.8 mL of nitromethane (70.1 mmol) was stirred at ambient temperature. After stirring for 19 hours the mixture was diluted with 20 mL water and 40 mL dichloromethane, and the mixture was transferred to a separatory funnel. After shaking, the organic layer was separated, dried over sodium sulfate and evaporated to give 2.56 g of a light brown solid. The crude material was purified by silica gel chromatography on a Biotage 40S column, eluting with 95/5 hexane/EtOAc to give 1.18 g of 2-bromo-4-chloro-1-(2-nitrovinyl)benzene as a light yellow solid. MS (apci, neg) m/z=261.

Step D: Preparation of 2-(2-bromo-4-chlorophenyl)ethanamine

To a stirred suspension of lithium borohydride (0.39 g; 18.0 mmol) in 25 mL THF at ambient temperature was added chlorotrimethylsilane (3.9 g; 36.0 mmol), dropwise over 2 minutes. Gas was evolved and the mixture warmed slightly. After stirring for 20 minutes, gas evolution had ceased, and argon gas was bubbled through the mixture for 2 minutes to try to remove the remaining trimethylsilane that had formed. A solution of 2-bromo-4-chloro-1-(2-nitrovinyl)benzene (1.18 g; 4.5 mmol) in 20 mL tetrahydrofuran was then added dropwise with stirring at ambient temperature over 4 minutes. The resulting mixture was stirred and heated to reflux. After 2 hours, the heat was removed, and after cooling to ambient temperature, the mixture was cooled in an ice bath and carefully quenched with 25 mL methanol. The solvent was evaporated, and the residue was partitioned between 50 mL of 20% KOH and 25 mL of dichloromethane. The organic layer was dried over sodium sulfate and evaporated to give 0.92 g of 2-(2-bromo-4-chlorophenyl)ethanamine as a cloudy yellow oil. MS (apci, pos) m/z=234.

Preparation 6

2-(2-Methoxy-4-bromophenyl)ethanamine

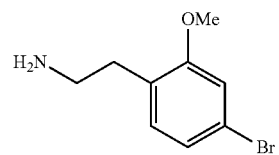 [SMILES: COc1cc(Br)ccc1CCN]

Step A: Preparation of 4-bromo-2-methoxybenzaldehyde

To a stirred solution of 4-bromo-2-fluorobenzaldehyde (3.38 g; 16 mmol) in 35 mL methanol at ambient temperature was added sodium methoxide solution (4.0 mL of 25% solution; 17.6 mmol), and the resulting solution was stirred and heated to reflux. After refluxing for 2 hours the solvent was evaporated. The residue was partitioned between 100 mL dichloromethane and 50 mL water. The organic layer was dried over sodium sulfate and evaporated. The residue was purified by silica gel chromatography to give 2.13 g of 4-bromo-2-methoxybenzaldehyde as a white solid. MS (apci, neg) m/z=199.

Step B: Preparation of 4-bromo-2-methoxy-1-(2-nitrovinyl)benzene

A suspension of 4-bromo-2-methoxybenzaldehyde (1.55 g; 7.2 mmol), methylamine hydrochloride (0.31 g; 50.4 mmol) and sodium acetate (0.38 g; 4.6 mmol) in 3 mL of nitromethane was stirred at ambient temperature. After stirring for 14.5 hours the mixture was diluted with 20 mL water and 40 mL dichloromethane, and the mixture was transferred to a separatory funnel. After shaking, the organic layer was dried over sodium sulfate and evaporated to give 1.74 g of 4-bromo-2-methoxy-1-(2-nitrovinyl)benzene as a light yellow solid. MS (apci, neg) m/z=257.

Step C: Preparation of 2-(4-bromo-2-methoxyphenyl)ethanamine

To a stirred suspension of lithium borohydride (0.57 g; 26.3 mmol) in 40 mL tetrahydrofuran at ambient temperature was added chlorotrimethylsilane (5.7 g; 52.7 mmol), dropwise over 2 minutes. Gas was evolved and the mixture warmed slightly. After stirring for 20 minutes, gas evolution had ceased, and argon gas was bubbled through the mixture for 2 minutes to try to remove the remaining trimethylsilane that had formed. A solution of 4-bromo-2-methoxybenzaldehyde (1.7 g; 6.6 mmol) in 30 mL tetrahydrofuran was then added dropwise with stirring at ambient temperature over 4 minutes. The resulting mixture was then stirred and heated to reflux. After 90 minutes, the heat was removed, and after cooling to ambient temperature, the mixture was cooled in an ice bath and carefully quenched with 40 mL methanol. The solvent was evaporated, and the residue was partitioned between 80 mL of 20% KOH and 40 mL of DCM. The organic layer was dried over sodium sulfate and evaporated to give 1.29 g of 2-(4-bromo-2-methoxyphenyl)ethanamine as a dark green oil. MS (apci, pos) m/z=230.

Preparation 7

2-(2,4-Dichloro-6-methoxyphenyl)ethanamine

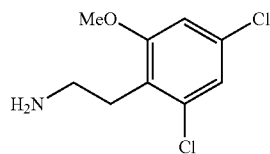 [SMILES: COc1cc(Cl)cc(Cl)c1CCN]

Step A: Preparation of 2,4-dichloro-6-methoxybenzaldehyde

To a stirred solution of 2,4-dichloro-6-hydroxybenzaldehyde (1.85 g; 9.7 mmol) in 20 mL DMF at ambient temperature was added solid potassium carbonate (1.47 g; 10.6 mmol), and the resulting yellow mixture was stirred at ambient temperature. After 30 minutes, iodomethane (5.5 g; 38.7 mmol) was added, and the resulting mixture was stirred in an oil bath set to 50° C. After 10 minutes, the reaction was determined to be complete by thin layer chromatography (90/10 hexane/EtOAc). After a total of 30 minutes the mixture was cooled to ambient temperature and diluted with 200 mL water. After stirring for a few minutes, the precipitate that formed was collected by filtration, washed with water, and dried under vacuum to give 1.93 g of 2,4-dichloro-6-methoxybenzaldehyde as an off-white powder.

Step B: Preparation of 1,5-dichloro-3-methoxy-2-(2-nitrovinyl)benzene

A suspension of 2,4-dichloro-6-methoxybenzaldehyde (0.51 g; 2.5 mmol), methylamine hydrochloride (0.11 g; 1.6 mmol) and sodium acetate (0.13 g; 1.6 mmol) in 3 mL of nitromethane was stirred at ambient temperature. After stirring for 15.5 hours the mixture was diluted with 20 mL water and 40 mL DCM, and then transferred to a separatory funnel. After shaking, the organic layer was dried over sodium sulfate and evaporated to give 0.57 g of 1,5-dichloro-3-methoxy-2-(2-nitrovinyl)benzene as a light yellow solid. MS (apci, neg) m/z=247

Step C: Preparation of 2-(2,4-dichloro-6-methoxyphenyl)ethanamine

To a stirred suspension of lithium borohydride (0.20 g; 9.0 mmol) in 15 mL tetrahydrofuran at ambient temperature was added chlorotrimethylsilane, dropwise over 2 minutes. Gas was evolved and the mixture warmed slightly. After stirring for 20 minutes, gas evolution had ceased, and argon gas was bubbled through the mixture for 2 minutes to remove the remaining trimethylsilane that had formed. A solution of 1,5-dichloro-3-methoxy-2-(2-nitrovinyl)benzene (0.56 g; 2.3 mmol) in 10 mL THF was then added dropwise with stirring at ambient temperature over 4 minutes. The resulting mixture was then stirred and heated to reflux. After 90 minutes, the heat was removed, and after cooling to ambient temperature, the mixture was cooled in an ice bath and carefully quenched with 15 mL of methanol. The solvent was evaporated, and the residue was partitioned between 30 mL of 20% KOH and 15 mL of dichloromethane. The organic layer was dried over sodium sulfate and evaporated to give 0.49 g of 2-(2,4-dichloro-6-methoxyphenyl)ethanamine as a cloudy yellow oil. MS (apci, pos) m/z=220.

Preparation 8

2-(4-Chloro-2-methoxyphenyl)ethanamine

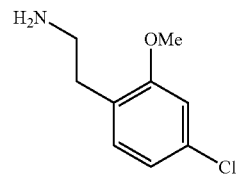 [SMILES: COc1cc(Cl)ccc1CCN]

Step A: Preparation of 2-bromo-4-chloro-1-(dibromomethyl)benzene

To a stirred solution of 4-bromo-2-chlorotoluene (100 g; 487 mmol) and benzoyl peroxide 5.07 g; 20.9 mmol) in 800 mL of carbon tetrachloride was added N-bromosuccinimide, and the resulting mixture was stirred and heated to reflux. After 16.5 hours, the mixture was cooled to ambient temperature, and the insoluble material was removed by filtration and washed twice with carbon tetrachloride. The filtrate and washings were combined and evaporated. The orange residual liquid contained some solid, and this material was taken up in 500 mL hexane. The resulting mixture was filtered to remove insoluble material, and the filtrate was itself filtered through a 1 inch pad of silica gel in a 150 mL fritted funnel. The filtrate was evaporated to give 161.5 g of 2-bromo-4-chloro-1-(dibromomethyl)benzene as a pale yellow liquid.

Step B: Preparation of 2-bromo-4-chlorobenzaldehyde

A solution of 2-bromo-4-chloro-1-(dibromomethyl)benzene (162 g; 446 mmol) in 250 mL ethanol was stirred and heated to reflux, and a solution of silver(I) nitrate (576 g; 3.39 mol) in 600 mL water was added dropwise over 40 minutes. The mixture turned yellow and a precipitate of AgBr formed immediately upon addition. Following completion of addition, the mixture was stirred at reflux for an additional hour. After reaching ambient temperature, the mixture was filtered through a sintered glass funnel to collect the precipitate, which was then washed with 200 mL water. The precipitate was washed with 500 mL chloroform. The washes were combined and transferred to a separatory funnel and the water contained was allowed to separate. The organic layer was dried over sodium sulfate and evaporated to give 93.3 g of 2-bromo-4-chlorobenzaldehyde as a white solid.

Step C: Preparation of (2-bromo-4-chlorophenyl)methanol

A solution of 2-bromo-4-chlorobenzaldehyde (21.95 g; 100.0 mmol) in 200 mL methanol was stirred and cooled in an ice bath for 15 minutes, and solid sodium borohydride (1.9 g; 50.0 mmol) was added. A yellow color formed and there was copious gas evolution. Stirring was continued in the bath for 1 hour. The solution was diluted with 200 mL water, and then the methanol was evaporated on a rotary evaporator. The residual mixture was extracted with 200 mL EtOAc. The organic layer was washed with 50 mL brine, then dried over sodium sulfate and evaporated. The residual solid was washed out of the flask with hexane and collected by filtration, ground with a mortar and pestle to break up the chunks, then washed with hexane and air-dried on the filter to give 17.8 g of (2-bromo-4-chlorophenyl)methanol as a white solid.

Step D: Preparation of 2-bromo-1-(bromomethyl)-4-chlorobenzene

A solution of (2-bromo-4-chlorophenyl)methanol (17.8 g; 80.4 mmol) in 250 mL of ether was stirred and cooled in an ice bath for 15 minutes. A solution of phosphorus tribromide (21.8 g; 80.4 mmol) in 75 mL ether was added, dropwise over 30 minutes. After stirring in the bath for an additional 30 minutes the solution was quenched by careful addition of saturated sodium bicarbonate solution until no more gas was evolved. The resulting mixture was transferred to a separatory funnel, and the organic layer was washed with 50 mL brine, then dried over sodium sulfate and evaporated to give 21.2 g of pale yellow oil. This material was dissolved in a mixture of 100 mL hexane and 25 mL EtOAc. This solution was poured over a 2 inch pad of silica gel in a 150 mL fritted funnel, and the pad was eluted with 2×150 mL hexane. The combined filtrates were evaporated to give 10.0 g of 2-bromo-1-(bromomethyl)-4-chlorobenzene as a pale yellow oil.

Step E: Preparation of 2-(2-bromo-4-chlorophenyl)acetonitrile

A mixture of 2-bromo-1-(bromomethyl)-4-chlorobenzene (9.8 g; 34.5 mmol) and sodium cyanide (2.0 g; 41.4 mmol) in 15 mL of 95% ethanol and 2.5 mL water was stirred and heated to reflux. After 30 minutes, the solvent was evaporated and the residue was partitioned between 100 mL ether and 50 mL water. The organic layer was dried over sodium sulfate and evaporated. The residual solid was washed out of the flask with hexane and collected by filtration, washed with hexane, and air-dried on the filter to give 4.82 g of 2-(2-bromo-4-chlorophenyl)acetonitrile as a light yellow solid.

Step F: Preparation of 2-(4-chloro-2-methoxyphenyl)ethanamine

A portion of 2-(2-bromo-4-chlorophenyl)acetonitrile (7.1 g; 39.1 mmol) was directly dissolved in borane solution (78.2 mL of a 1.0 M solution in tetrahydrofuran; 78.2 mmol), and the resulting solution was stirred and heated to reflux. After refluxing for a total of 90 minutes, the heat was removed and the solution was allowed to cool for a few minutes, and then 16 mL of methanol was carefully added to quench the solution. The resulting solution was again heated to reflux for 30 minutes. The solvent was then evaporated, and the residue was partitioned between 200 mL of 1M HCl (aq.) and 200 mL ether. The aqueous layer was filtered to remove a small amount of suspended insoluble material, and the pH of the filtrate was adjusted to pH>12 by the addition of 42% NaOH (aq.). The filtrate was then extracted with 200 mL dichloromethane. The organic layer was dried over sodium sulfate and evaporated to give 3.89 g of 2-(4-chloro-2-methoxyphenyl)ethanamine as a colorless liquid. MS (apci, pos) m/z=186.

Preparation 9

2-(2-Methoxy-4-(trifluoromethyl)phenyl)ethanamine

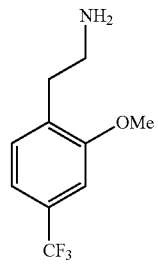 [SMILES: COc1cc(C(F)(F)F)ccc1CCN]

Step A: Preparation of 2-methoxy-4-(trifluoromethyl)benzaldehyde

2-Fluoro-4-(trifluoromethyl)benzaldehyde (5.0 g, 26 mmol) was diluted with sodium methoxide (57 ml of 0.5 M in methanol; 29 mmol), heated to 50° C. and stirred for 6 hours. The reaction was then partially concentrated, diluted with ethyl acetate and water. The layers were separated and the organic layer was dried over MgSO$_4$, filtered and concentrated to yield 2-methoxy-4-(trifluoromethyl)benzaldehyde (4.5 g, 22 mmol, 85% yield).

Step B: Preparation of (E)-2-methoxy-1-(2-nitrovinyl)-4-(trifluoromethyl)benzene A portion of 2-methoxy-4-(trifluoromethyl)benzaldehyde (3.78 g, 18.5 mmol) was diluted with nitromethane (7.02 ml, 130 mmol) followed by the addition of methylamine hydrochloride (0.750 g, 11.1 mmol) and sodium acetate (0.911 g, 11.1 mmol). After stirring for 12 hours, the reaction was loaded directly onto a biotage 40 cartridge and eluted with 5% ethyl acetate/hexanes to 20% ethyl acetate hexanes to yield (E)-2-methoxy-1-(2-nitrovinyl)-4-(trifluoromethyl)benzene (3.0 g, 12.1 mmol, 65.6% yield).

Step C: Preparation of 2-(2-methoxy-4-(trifluoromethyl)phenyl)ethanamine

A portion of lithium borohydride (0.458 g, 21.0 mmol) was diluted with THF (30 mL) followed by the dropwise addition of chlorotrimethylsilane (5.34 ml, 42.1 mmol). After stirring for 15 minutes, argon was bubbled through the reaction mixture for 2 minutes to eliminate trimethylsilane present in the reaction. (E)-2-methoxy-1-(2-nitrovinyl)-4-(trifluoromethyl)benzene (1.3 g, 5.26 mmol) was added portionwise (gas evolution occurred). The reaction was heated to reflux for 2 hours, cooled to 0° C. and carefully quenched with methanol (8 mL). The reaction mixture was concentrated, diluted with dichloromethane and 20% aqueous KOH. The layers were separated and the organic layer was dried over sodium sulfate, filtered and concentrated to yield 2-(2-methoxy-4-(trifluoromethyl)phenyl)ethanamine (1.1 g, 5.02 mmol, 95.4% yield).

Example 1

6-Cyano-7-(4-(4-chlorophenylcarbamoyl)phenoxy) chroman-4-carboxylic acid

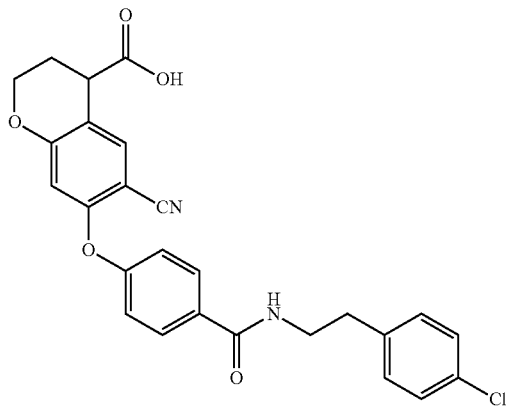 [SMILES: N#Cc1cc2c(cc1Oc1ccc(C(=O)NCCc3ccc(Cl)cc3)cc1)OCCC2C(=O)O]

Step A: Preparation of 7-fluoro-4-(trimethylsilyloxy) chroman-4-carbonitrile 7-Fluoro-2,3-dihydrochromen-4-one (470 mg, 2.829 mmol) and $ZnI_2$ (45.15 mg, 0.1414 mmol) was diluted with trimethylsilyl cyanide (1.413 mL, 11.32 mmol). The reaction was stirred for 4 hours at ambient temperature. The reaction was diluted with $CH_2Cl_2$ and washed with saturated sodium bicarbonate twice. The organic layer was dried over $MgSO_4$, filtered and concentrated to yield the title compound (750 mg, 99.92% yield).

Step B: Preparation of 7-fluoro-3,4-dihydro-2H-chromene-4-carboxylic acid

7-Fluoro-4-(trimethylsilyloxy)chroman-4-carbonitrile (750 mg, 2.83 mmol) and $SnCl_2$ dihydrate (2551 mg, 11.3 mmol) were diluted with glacial acetic acid (3 mL) and concentrated HCl (3 mL). The reaction was heated in an oil bath at 130° C. and stirred overnight. The reaction was allowed to cool, diluted with water and ethyl acetate. The layers were separated and the organic layer was dried over $MgSO_4$, filtered and concentrated to yield the title compound (465 mg, 83.9% yield).

Step C: Preparation of methyl 7-fluoro-3,4-dihydro-2H-chromene-4-carboxylate 7-Fluoro-3,4-dihydro-2H-chromene-4-carboxylic acid (346 mg, 1.76 mmol) was diluted with (THF) 2 mL, methanol (2 mL) and 4 drops of sulfuric acid. The reaction was heated at 55° C. and stirred for 12 hours. The reaction was cooled to ambient temperature, diluted with ethyl acetate and saturated sodium bicarbonate. The layers were separated and the organic layer was dried over $MgSO_4$, filtered and concentrated to yield the title compound (366 mg, 98.7% yield).

Step D: Preparation of methyl 6-bromo-7-fluoro-3,4-dihydro-2H-chromene-4-carboxylate Methyl 7-fluoro-3,4-dihydro-2H-chromene-4-carboxylate (336 mg, 1.60 mmol) was diluted with DMF (5 mL) followed by the addition of N-bromosuccinimide (313 mg, 1.76 mmol). The reaction was heated at 50° C. and stirred for 2.5 hours. The reaction was cooled, diluted with ethyl acetate and washed with water, saturated sodium bicarbonate, water, and brine. The organic layer was dried over $MgSO_4$, filtered and concentrated. The material was purified using a Biotage 40M cartridge, gradient 5% ethyl acetate/hexane to 50% to yield the title compound (415 mg, 89.8% yield).

Step E: Preparation of methyl 6-cyano-7-fluorochroman-4-carboxylate

Methyl 6-bromo-7-fluoro-3,4-dihydro-2H-chromene-4-carboxylate (415 mg, 1.44 mmol) was diluted with N-methylpyrrolidinone (5 mL) followed by the addition of Cu(I)CN (643 mg, 7.18 mmol). The reaction was bubbled with argon for 20 minutes, then heated at 160° C. under a slight argon bubble for 6 hours. The reaction was cooled to ambient temperature and loaded directly onto a Biotage 25 column eluting with 5% ethyl acetate/hexanes to 100% ethyl acetate to yield the title compound (260 mg, 77.0% yield).

Step F: Preparation of methyl 7-(4-((4-chlorophenethyl)carbamoyl)phenoxy)-6-cyanochroman-4-carboxylate Methyl 6-cyano-7-fluorochroman-4-carboxylate (50 mg, 0.21 mmol) was diluted with 1-methyl-2-pyrrolidinone (2 mL) followed by the addition of $K_2CO_3$ (147 mg, 1.1 mmol) and N-(4-chlorophenethyl)-4-hydroxybenzamide (59 mg, 0.21 mmol). The reaction was bubbled with argon for 10 minutes and then heated to 110° C. and stirred for 6 hours. After the reaction was allowed to cool, it was loaded directly onto a Biotage 25 column and eluted with 5% ethyl acetate/hexanes to 100% ethyl acetate to yield methyl 7-(4-((4-chlorophenethyl)carbamoyl)phenoxy)-6-cyanochroman-4-carboxylate (50 mg, 48% yield). MS (ESI)=490.9 (M+1).

Step G: Preparation of 7-(4-((4-chlorophenethyl) carbamoyl)phenoxy)-6-cyanochroman-4-carboxylic acid Methyl 7-(4-((4-chlorophenethyl)carbamoyl)phenoxy)-6-cyanochroman-4-carboxylate (100 mg, 0.204 mmol) was diluted with THF (1 mL) followed by the addition of NaOH (0.204 mL, 1.02 mmol) and 500 μL of water and methanol.

After stirring for 3 hours, the reaction was diluted with ethyl acetate and 2N HCl. The layers were separated and the organic layer was dried over MgSO$_4$, filtered and concentrated. The material was purified using the Horizon with a 25 cartridge and running a gradient 0.5% methanol/0.5% acetic acid/CH$_2$Cl$_2$ to 10% methanol/0.5% acetic acid/CH$_2$Cl$_2$ to yield the title compound (21 mg, 21.6% yield) as a white solid. MS (ESI)=476.9 (M+1).

Example 2

7-(4-(4-chlorophenylcarbamoyl)phenoxy)-6-cyano-4-methylchroman-4-carboxylic acid

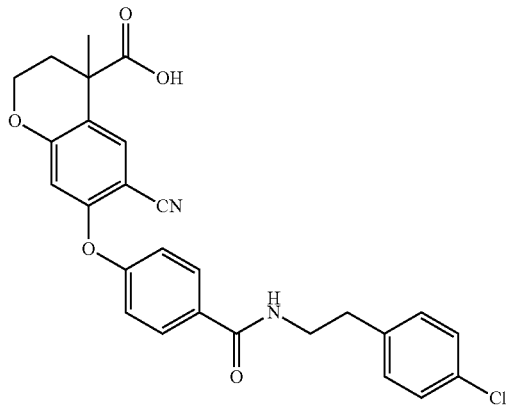 [SMILES: CC1(C(=O)O)CCOc2cc(Oc3ccc(C(=O)NCCc4ccc(Cl)cc4)cc3)c(C#N)cc21]

Step A: Preparation of methyl 6-cyano-7-fluoro-4-methylchroman-4-carboxylate

Methyl 6-cyano-7-fluoro-3,4-dihydro-2H-chromene-4-carboxylate (from Example 3, Step E; 28 mg, 0.12 mmol) was diluted with acetonitrile (1 mL) followed by the addition of K$_2$CO$_3$ (49 mg, 0.36 mmol) and iodomethane (0.023 mL, 0.36 mmol). The reaction was then heated at 60° C. for 1 hour, then cooled and NaH (8.6 mg, 0.36 mmol) was added. The reaction was deemed complete by LC. The reaction was loaded onto a Biotage 25 samplet and purified running a gradient 5% ethyl acetate/hexane to 100% ethyl acetate/hexane to yield the title compound (10 mg, 34% yield).

Step B: Preparation of methyl 7-(4-((4-chlorophenethyl)carbamoyl)phenoxy)-6-cyano-4-methylchroman-4-carboxylate Methyl 6-cyano-7-fluoro-4-methylchroman-4-carboxylate (10 mg, 0.040 mmol) was diluted with N-methylpyrrolidone (2 mL) followed by the addition of K$_2$CO$_3$ (28 mg, 0.20 mmol) and N-(4-chlorophenethyl)-4-hydroxybenzamide (11 mg, 0.040 mmol). The reaction was bubbled with argon for 10 minutes and then heated at 110° C. and stirred for 5 hours. The reaction was allowed to cool, loaded directly onto a 25 samplet and eluted on the horizon with 5% ethyl acetate/hexanes to 100% ethyl acetate/hexanes to yield the title compound (12 mg, 59% yield). MS (ESI)=504.9 (M+1).

Step C: Preparation of 7-(4-((4-chlorophenethyl)carbamoyl)phenoxy)-6-cyano-4-methylchroman-4-carboxylic acid Methyl 7-(4-((4-chlorophenethyl)carbamoyl)phenoxy)-6-cyano-4-methylchroman-4-carboxylate (12 mg, 0.0238 mmol) was diluted with THF (500 µL) followed by the addition of NaOH (0.0475 mL, 0.238 mmol) and 200 µL of water and methanol. After stirring for 3 hours, the reaction was diluted with ethyl acetate and 2N HCl. The layers were separated and the organic layer was dried over MgSO$_4$, filtered and concentrated. The material was purified using the Horizon with a 25 cartridge and running a gradient 0.5% methanol/0.5% acetic acid/CH$_2$Cl$_2$ to 10% methanol/0.5% acetic acid/CH$_2$Cl$_2$ to yield the title compound (4.0 mg, 34.3% yield) as a white solid. MS (ESI)=490.9 (M+1).

Example 3

7-(4-(4-Chlorophenylcarbamoyl)phenoxy)-6-cyano-2,2-dimethylchroman-4-carboxylic acid

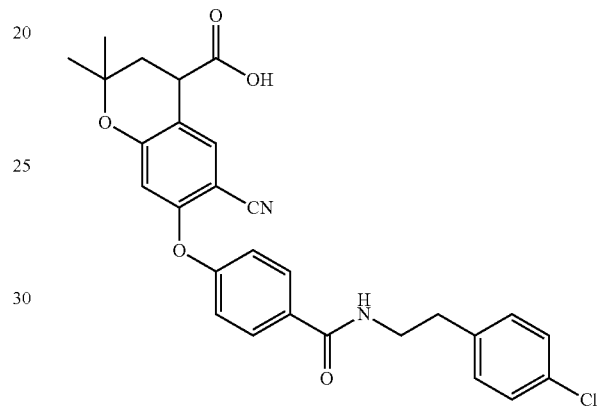

Step A: Preparation of 7-fluoro-2,2-dimethyl-2,3-dihydrochromen-4-one

To 1-(4-fluoro-2-hydroxyphenyl)ethanone (5.75 g, 37.3 mmol) and propan-2-one (12 mL, 37.3 mmol) in benzene (50 mL) was added pyrrolidine (3.11 mL, 37.3 mmol) and the reaction heated at 80° C. for 3 hours. The reaction was diluted with ethyl acetate (50 mL), washed with 1N HCl (50 mL), brine (50 mL), dried over magnesium sulfate and concentrated. The residue was purified by silica gel chromatography, eluting with a gradient of 5% ethyl acetate/hexanes to 50% ethyl acetate, to provide the title compound (5.12 g, 70.7% yield).

Step B: Preparation of 7-fluoro-2,2-dimethyl-3,4-dihydro-2H-chromene-4-carboxylic acid To 7-fluoro-2,2-dimethyl-2,3-dihydrochromen-4-one (1.000 g, 5.149 mmol) was added trimethylsilyl cyanide (3.215 mL, 25.75 mmol) followed by a spatula tip of zinc iodide. The reaction was heated at 50° C. for 1 hour. The reaction was cooled, diluted with ethyl acetate (40 mL) and washed with saturated sodium bicarbonate (2×25 mL), brine (25 mL), dried over magnesium sulfate and concentrated. The product was dissolved in 5 mL of acetic acid and 5 mL of HCl, and SnCl$_2$ dihydrate (4.648 g, 20.60 mmol) was added. The reaction heated at reflux (130° C. oil bath temperature) overnight. The reaction was cooled, diluted with ethyl acetate (50 mL), washed with water (50 mL) and brine (50 mL), dried over magnesium sulfate and concentrated. The residue was purified by silica gel chromatography over silica gel eluting with a gradient of 0.5% MeOH/CH$_2$Cl$_2$ containing 0.5% acetic acid to 10% MeOH/CH$_2$Cl$_2$ containing 0.5% acetic acid to provide the title compound (0.280 g, 24.25% yield).

Step C: Preparation of methyl 7-fluoro-2,2-dimethyl-3,4-dihydro-2H-chromene-4-carboxylate To 7-fluoro-2,2-dimethyl-3,4-dihydro-2H-chromene-4-carboxylic acid (0.280 g, 1.25 mmol) in CH$_2$Cl$_2$ (5 mL) and MeOH (1 mL) was added TMSCHN$_2$ (0.937 mL, 1.87 mmol) dropwise. After the addition, the reaction was concentrated, loaded onto silica gel, and the product eluted using a gradient of 5% ethyl acetate/hexanes to 40% ethyl acetate/hexanes to provide the title compound (0.225 g, 75.6% yield).

Step D: Preparation of methyl 6-bromo-7-fluoro-2,2-dimethyl-3,4-dihydro-2H-chromene-4-carboxylate Methyl 7-fluoro-2,2-dimethyl-3,4-dihydro-2H-chromene-4-carboxylate (187 mg, 0.785 mmol) was diluted with DMF (5 mL) followed by the addition of N-bromosuccinimide (154 mg, 0.863 mmol). The reaction was heated at 50° C. for 2.5 hours. The reaction was cooled, diluted with ethyl acetate and washed with water, saturated sodium bicarbonate, water, and brine. The organic layer was dried over MgSO$_4$, filtered and concentrated. The material was purified using a Biotage 40M cartridge, gradient 5% ethyl acetate/hexane to 50% to yield the title compound (232 mg, 93.2% yield).

Step E: Preparation of methyl 6-cyano-7-fluoro-2,2-dimethylchroman-4-carboxylate methyl 6-bromo-7-fluoro-2,2-dimethyl-3,4-dihydro-2H-chromene-4-carboxylate (232 mg, 0.732 mmol) was diluted with N-methylpyrrolidone (4 mL) followed by the addition of Cu(I)CN (328 mg, 3.66 mmol). The reaction was bubbled with Argon for 15 minutes and then heated at 160° C. The reaction was stirred for 5 hours and then allowed to cool. The reaction was loaded directly onto a Biotage 25 column eluting with 5% ethyl acetate/hexanes to 100% ethyl acetate to yield the title compound (120 mg, 62.3% yield).

Step F: Preparation of methyl 7-(4-((4-chlorophenethyl)carbamoyl)phenoxy)-6-cyano-2,2-dimethyl-chroman-4-carboxylate Methyl 6-cyano-7-fluoro-2,2-dimethylchroman-4-carboxylate (19 mg, 0.072 mmol) was diluted with N-methylpyrrolidone (2 mL) followed by the addition of K$_2$CO$_3$ (25 mg, 0.18 mmol) and N-(4-chlorophenethyl)-4-hydroxybenzamide (20 mg, 0.072 mmol). The reaction was bubbled with argon for 10 minutes and then heated at 110° C. for 6 hours. After cooling, the reaction mixture was loaded directly onto a Biotage 25 column and eluted with 5% ethyl acetate/hexanes to 100% ethyl acetate to yield the title compound (2.0 mg, 5.3% yield).

Step G: Preparation of 7-(4-((4-chlorophenethyl)carbamoyl)phenoxy)-6-cyano-2,2-dimethylchroman-4-carboxylic acid Methyl 7-(4-((4-chlorophenethyl)carbamoyl) phenoxy)-6-cyano-2,2-dimethylchroman-4-carboxylate (2.0 mg, 0.00385 mmol) was diluted with THF (500 µL) followed by the addition of NaOH (0.00771 mL, 0.0385 mmol) and 200 µL of water and methanol. After stirring for 3 hours, the reaction was diluted with ethyl acetate and 2N HCl. The layers were separated and the organic layer was dried over MgSO$_4$, filtered and concentrated. The material was purified using a 0.5 mm preparative TLC plate, eluting with 5% methanol/0.5% acetic acid/CH$_2$Cl$_2$ to yield the title compound (0.6 mg, 30.8% yield) as a white solid. MS (ESI)=504.9 (M+1).

Example 4

6-Cyano-7-(4-(2,4-dichlorophenylcarbamoyl)phenoxy)chroman-4-carboxylic acid

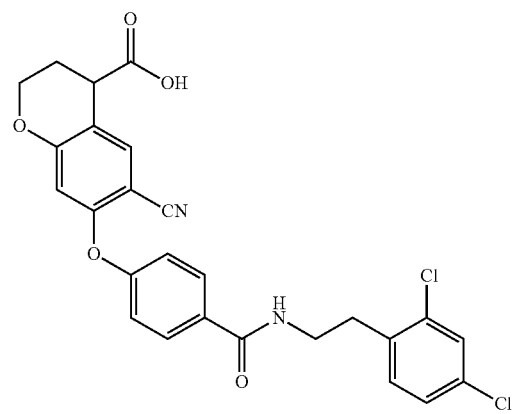 [SMILES: N#Cc1cc2c(cc1Oc1ccc(C(=O)NCCc3ccc(Cl)cc3Cl)cc1)OCCC2C(=O)O]

Step A: Preparation of 6-cyano-7-fluorochroman-4-carboxylic acid

Methyl 6-cyano-7-fluoro-3,4-dihydro-2H-chromene-4-carboxylate (45 mg, 0.19 mmol) was diluted with THF (1 mL) followed the addition of NaOH (0.19 mL, 0.96 mmol), 200 µL of water and methanol. After stirring for 3 hours, the reaction was diluted with ethyl acetate and 2N HCl. The layers were separated and the organic layer was dried over MgSO$_4$, filtered and concentrated to yield the title compound (40 mg, 95% yield).

Step B: Preparation of 7-(4-((2,4-dichlorophenethyl)carbamoyl)phenoxy)-6-cyanochroman-4-carboxylic acid 6-cyano-7-fluorochroman-4-carboxylic acid (40 mg, 0.18 mmol) was diluted with N-methylpyrrolidone (2 mL) followed by the addition of K$_2$CO$_3$ (100 mg, 0.72 mmol) and N-(2,4-dichlorophenethyl)-4-hydroxybenzamide (56 mg, 0.18 mmol). The reaction was bubbled with argon for 10 minutes and then heated at 140° C. After stirring for 5 hours, the reaction was loaded directly onto a Biotage 25 cartridge eluting with 0.5% acetic acid/0.5% methanol/CH$_2$Cl$_2$ to 0.5% acetic acid/10% methanol/CH$_2$Cl$_2$ to yield the title compound (4.8 mg, 5.2% yield). $^1$H NMR (400 MHz, CD$_3$OD) δ 8.57-8.59 (m, NH), 7.84 (d, J=8.7 Hz, 2H), 7.69 (s, 1H), 7.44 (d, J=2.4 Hz, 1H), 7.32 (d, J=8.4 Hz, 1H), 7.26 (dd, J=1.7, 8.0 Hz, 1H), 7.13 (d, J=8.7 Hz, 2H), 6.40 (s, 1H), 4.29-4.34 (m, 1H), 4.20-4.26 (m, 1H), 3.85 (t, J=5.1 Hz, 1H), 3.64 (q, J=6.1 Hz, 2H), 3.06 (t, J=7.0 Hz, 2H), 2.32-2.37 (m, 1H), 2.08-2.16 (m, 1H).

Example 5

6-Cyano-7-(4-(phenethylcarbamoyl)phenoxy)chroman-4-carboxylic acid

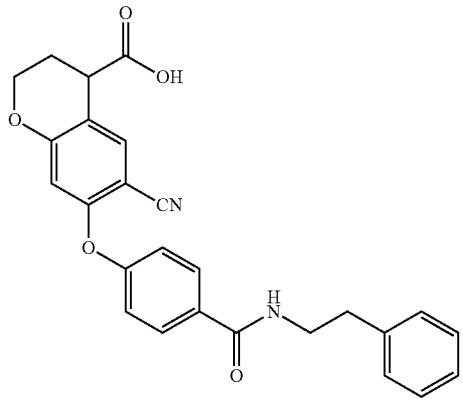 [SMILES: N#Cc1cc2c(cc1Oc1ccc(C(=O)NCCc3ccccc3)cc1)OCCC2C(=O)O]

Step A: Preparation of methyl 7-(4-(tert-butoxycarbonyl)phenoxy)-6-cyanochroman-4-carboxylate Methyl 6-cyano-7-fluorochroman-4-carboxylate (from Example 3, Step E) (700 mg, 2.98 mmol), tert-butyl 4-hydroxybenzoate (578 mg, 2.98 mmol) and $K_2CO_3$ (494 mg, 3.57 mmol) were diluted with N-methylpyrrolidone (6 mL) and bubbled with argon for 10 minutes. The reaction was heated to 110° C. and stirred for 5 hours. The reaction was loaded directly onto a Biotage 40M cartridge and eluted with 5% ethyl acetate/hexanes to 100% ethyl acetate to yield the title compound (400 mg, 32.8% yield).

Step B: Preparation of 4-(6-cyano-4-(methoxycarbonyl)chroman-7-yloxy)benzoic acid Methyl 7-(4-(tert-butoxycarbonyl)phenoxy)-6-cyanochroman-4-carboxylate (400 mg, 0.977 mmol) was diluted with $CH_2Cl_2$ followed by the addition of TFA (1 mL). After stirring for 2 hours, the reaction was concentrated to yield the title compound (240 mg, 69.5% yield).

Step C: Preparation of methyl 6-cyano-7-(4-(phenethylcarbamoyl)phenoxy)chroman-4-carboxylate 4-(6-cyano-4-(methoxycarbonyl)chroman-7-yloxy)benzoic acid (13 mg, 0.0368 mmol), HBTU (16.7 mg, 0.0442 mmol) were diluted with N-methylpyrrolidone (1 mL) followed by the addition of 2-phenylethanamine (0.00647 mL, 0.0515 mmol), N,N-diisopropylethylamine (0.0160 mL, 0.0920 mmol) and DMAP (1.35 mg, 0.0110 mmol). After stirring for 3 hours, the reaction was loaded directly onto a Biotage 12i cartridge eluting with 5% ethyl acetate/hexanes to 100% ethyl acetate to yield the title compound (16.1 mg, 95.9% yield).

Step D: Preparation of 6-cyano-7-(4-(phenethylcarbamoyl)phenoxy)chroman-4-carboxylic acid Methyl 6-cyano-7-(4-(phenethylcarbamoyl)phenoxy)chroman-4-carboxylate (16.1 mg, 0.0353 mmol) was diluted with THF (500 μL) followed by the addition of NaOH (0.0705 mL, 0.353 mmol) and water (100 μL) and methanol (100 μL). After stirring for 3 hours, the reaction was diluted with ethyl acetate and 2N HCl. The layers were separated and the organic layer was dried over $MgSO_4$, filtered and concentrated to yield the title compound (12.0 mg, 76.9% yield). $^1H$ NMR (400 MHz, $CD_3OD$) δ □7.85 (d, 2H), 7.66 (s, 1H), 7.20-7.30 (m, 5H), 7.15 (d, 2H), 6.40 (s, 1H), 4.20-4.35 (m, 2H), 3.85 (bt, 1H), 3.58 (t, 2H), 2.92 (t, 2H), 2.3-2.4 (m, 1H), 2.1-2.2 (m, 1H).

Example 6

6-Cyano-7-(4-(2,3-dihydro-1H-inden-2-ylcarbamoyl)phenoxy)chroman-4-carboxylic acid

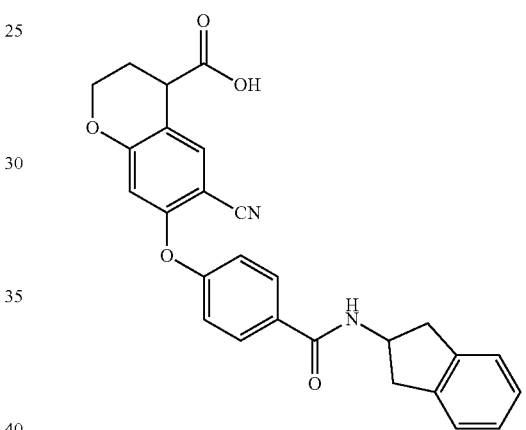

Step A: Preparation of Methyl 7-(4-((2,3-dihydro-1H-inden-2-yl)carbamoyl)phenoxy)-6-cyano-3,4-dihydro-2H-chromene-4-carboxylate 4-(6-Cyano-4-(methoxycarbonyl)chroman-7-yloxy)benzoic acid (from Example 7, Step B) (12 mg, 0.034 mmol), HBTU (15 mg, 0.041 mmol) were diluted with N-methylpyrrolidone (1 mL) followed by the addition of 2-aminoindan (4.5 mg, 0.034 mmol), N,N-diisopropylethylamine (0.015 mL, 0.085 mmol) and DMAP (1.2 mg, 0.010 mmol). After stirring for 3 hours, the reaction was loaded directly onto a Biotage 12i cartridge eluting with 5% ethyl acetate/hexanes to 100% ethyl acetate to yield the title compound (12 mg, 75% yield).

Step B: Preparation of 7-(4-((2,3-dihydro-1H-inden-2-yl)carbamoyl)phenoxy)-6-cyano-3,4-dihydro-2H-chromene-4-carboxylic acid Methyl 7-(4-((2,3-dihydro-1H-inden-2-yl)carbamoyl)phenoxy)-6-cyano-3,4-dihydro-2H-chromene-4-carboxylate (12 mg, 0.026 mmol) was diluted with THF (500 μL) followed by the addition of NaOH (1.0 mg, 0.026 mmol), water (200 μL) and methanol (200 μL). After stirring for 2 hours, the reaction was diluted with 2N HCl and ethyl acetate. The layers were separated and the organic layer was dried over MgSO$_4$, filtered and concentrated to yield the title compound (10 mg, 86% yield). $^1$H NMR (400 MHz, CD$_3$OD) δ 7.90 (d, 2H), 7.64 (s, 1H), 7.15-7.22 (m, 4H), 7.15 (d, 2H), 6.41 (s, 1H) 4.20-4.35 (m, 3H), 3.82 (bt, 1H), 3.3-3.4 (m, 2H), 2.95-3.05 (m, 2H), 2.35-2.40 (m, 1H), 2.10-2.15 (m, 1H).

Example 7

7-(4-(4-Chlorobenzyloxycarbamoyl)phenoxy)-6-cyanochroman-4-carboxylic acid

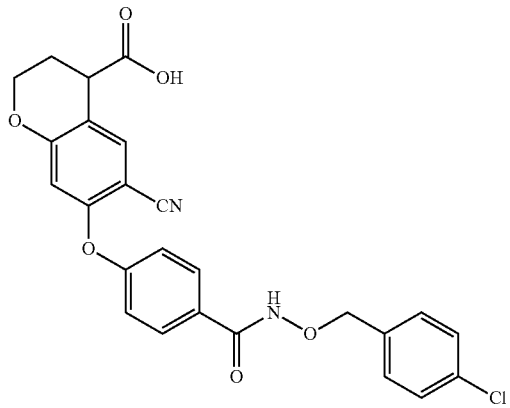 [SMILES: N#Cc1cc2c(cc1Oc1ccc(C(=O)NOCc3ccc(Cl)cc3)cc1)OCCC2C(=O)O]

Step A: Preparation of methyl 7-(4-((4-chlorobenzyloxy)carbamoyl)phenoxy)-6-cyano-3,4-dihydro-2H-chromene-4-carboxylate 4-(6-cyano-4-(methoxycarbonyl)-3,4-dihydro-2H-chromen-7-yloxy)benzoic acid (from Example 7, Step B) (17 mg, 0.0481 mmol) was diluted with CH$_2$Cl$_2$ (1 mL) followed by the addition of oxalyl chloride in CH$_2$Cl$_2$ (2M in CH$_2$Cl$_2$) (0.0289 mL, 0.0577 mmol) and 1 drop of DMF. This was stirred for 20 minutes followed by the addition of O-(4-chlorobenzyl)hydroxylamine (15.2 mg, 0.0962 mmol) and N,N-diisopropylethylamine (0.0335 mL, 0.192 mmol). After stirring for 30 minutes the reaction was loaded directly onto a Biotage 12i eluting with hexane:ethyl acetate (1:1) to yield the title compound (5 mg, 21.1% yield).

Step B: Preparation of 7-(4-((4-chlorobenzyloxy) carbamoyl)phenoxy)-6-cyano-3,4-dihydro-2H-chromene-4-carboxylic acid Methyl 7-(4-((4-chlorobenzyloxy) carbamoyl)phenoxy)-6-cyano-3,4-dihydro-2H-chromene-4-carboxylate (5 mg, 0.0101 mmol) was diluted with THF (500 μL) followed by the addition of NaOH (0.0203 mL, 0.101 mmol), water (200 μL) and methanol (200 μL). After stirring for 2 hours, the reaction was diluted with 2N HCl and ethyl acetate. The layers were separated and the organic layer was dried over MgSO$_4$, filtered and concentrated to yield the title compound (4.0 mg, 82.3% yield). $^1$H NMR (400 MHz, CD$_3$OD) δ 7.80 (d, 2H), 7.70 (s, 1H), 7.48 (d, 2H), 7.40 (d, 2H), 7.15 (d, 2H), 6.41 (s, 1H), 4.95 (s, 2H), 4.2-4.35 (m, 2H), 3.82 (bt, 1H), 2.35-2.40 (m, 1H), 2.10-2.15 (m, 1H).

Example 8

6-Cyano-7-(4-(3,4-dichlorophenylcarbamoyl)phenoxy)chroman-4-carboxylic acid

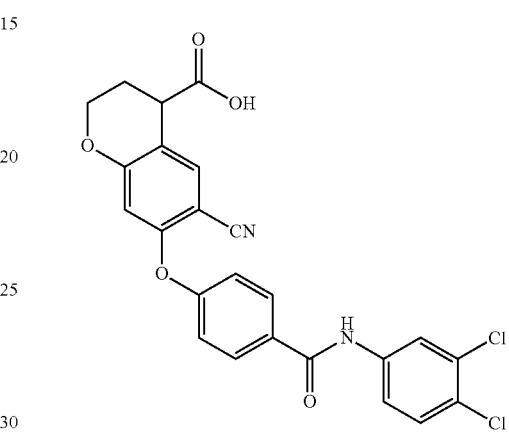

Step A: Preparation of methyl 7-(4-((3,4-dichlorophenyl)carbamoyl)phenoxy)-6-cyano-3,4-dihydro-2H-chromene-4-carboxylate 4-(6-Cyano-4-(methoxycarbonyl)-3,4-dihydro-2H-chromen-7-yloxy)benzoic acid (17 mg, 0.0481 mmol) was diluted with CH$_2$Cl$_2$ (1 mL) followed by the addition of oxalyl chloride in CH$_2$Cl$_2$ (2M in CH$_2$Cl$_2$) (0.0289 mL, 0.0577 mmol) and 1 drop of DMF. The reaction was stirred for 20 minutes, and then 3,4-dichlorobenzenamine (15.6 mg, 0.0962 mmol) and N,N-diisopropylethylamine (0.0210 mL, 0.120 mmol) were added. After stirring for 30 minutes the reaction was loaded directly onto a Biotage 12i eluting with hexane:ethyl acetate (1:1) to yield the title compound (17 mg, 71.0% yield) as a clear oil.

Step B: Preparation of 7-(4-((3,4-dichlorophenyl) carbamoyl)phenoxy)-6-cyano-3,4-dihydro-2H-chromene-4-carboxylic acid Methyl 7-(4-((3,4-dichlorophenyl) carbamoyl)phenoxy)-6-cyano-3,4-dihydro-2H-chromene-4-carboxylate (17 mg, 0.034 mmol) was diluted with THF (500 μL) followed by the addition of NaOH (0.041 mL, 0.21 mmol), water (200 μL) and methanol (200 μL). After stirring for 2 hours, the reaction was diluted with 2N HCl and ethyl acetate. The layers were separated and the organic layer was dried over MgSO$_4$, filtered and concentrated to yield the title compound (10 mg, 61% yield). $^1$H NMR (400 MHz, CD$_3$OD) δ 8.1 (d, 1H), 8.0

(d, 2H), 7.70 (s, 1H), 7.62 (dd, 1H), 7.48 (d, 1H), 7.20 (d, 2H), 6.41 (s, 1H), 4.2-4.35 (m, 2H), 3.82 (bt, 1H), 2.35-2.40 (m, 1H), 2.10-2.15 (m, 1H).

Example 9

6-Chloro-7-(4-(4-chlorophenethylcarbamoyl)-2-nitrophenoxy)chroman-4-carboxylic acid

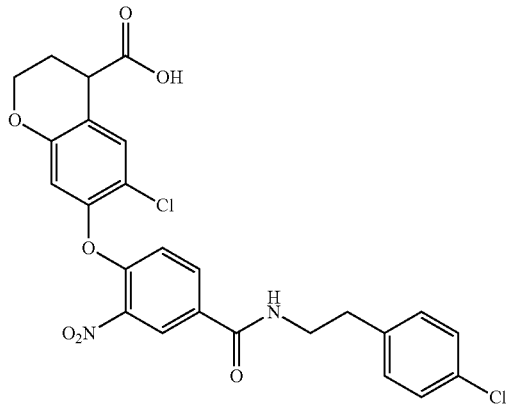 [SMILES: O=C(NCCc1ccc(Cl)cc1)c1ccc(Oc2cc3c(cc2Cl)C(C(=O)O)CCO3)c([N+](=O)[O-])c1]

Step A: Preparation of 4-chloro-N-(4-chlorophenethyl)-3-nitrobenzamide 2-(4-chlorophenyl)ethanamine (2.3 ml, 16 mmol) was diluted with DCM (40 mL) followed by the addition of DIEA (2.9 ml, 16 mmol) and 4-chloro-3-nitrobenzoyl chloride (3.0 g, 14 mmol) dropwise in 10 mL of DCM. After stirring for 30 minutes, the reaction was loaded onto silica gel and eluted with hexanes/ethyl acetate (2/1) to yield N-(4-chlorophenethyl)-4-chloro-3-nitrobenzamide (4.0 g, 86% yield) as a white solid.

Step B: Preparation of methyl 6-chloro-7-(4-(4-chlorophenethylcarbamoyl)-2-nitrophenoxy)chroman-4-carboxylate Methyl 6-chloro-7-hydroxychroman-4-carboxylate (100 mg, 0.412 mmol) (Preparation 4, substituting methanol for ethanol in Step C) was diluted with DMSO (1 mL) followed by the addition of $K_2CO_3$ (68.3 mg, 0.495 mmol) and N-(4-chlorophenethyl)-4-chloro-3-nitrobenzamide (140 mg, 0.412 mmol). The reaction was heated to 62° C. and stirred for 3 hours. The reaction was cooled, loaded directly onto silica gel and eluted with 5% ethyl acetate/hexanes to 100% ethyl acetate to yield methyl 7-(4-((4-chlorophenethyl)carbamoyl)-2-nitrophenoxy)-6-chlorochroman-4-carboxylate (60 mg, 26.7% yield).

Step C: Preparation of 6-chloro-7-(4-(4-chlorophenethylcarbamoyl)-2-nitrophenoxy)chroman-4-carboxylic acid To a stirred solution of methyl 7-(4-((4-chlorophenethyl)carbamoyl)-2-nitrophenoxy)-6-chlorochroman-4-carboxylate (5 mg, 0.00917 mmol) in THF (200 uL) was added NaOH (0.0183 ml, 0.0917 mmol) followed by water and methanol (100 uL each). After stirring for 2 hours, the reaction was diluted with ethyl acetate and 2N HCl. The layers were separated and the organic layer was dried over $MgSO_4$, filtered and concentrated to yield 7-(4-((4-chlorophenethyl)carbamoyl)-2-nitrophenoxy)-6-chlorochroman-4-carboxylic acid (1.8 mg, 37.0% yield). LCMS (apci/pos)=533.0 (M+H).

Example 10

6-Chloro-7-(4-(4-chlorophenethylcarbamoyl)phenoxy)chroman-4-carboxylic acid

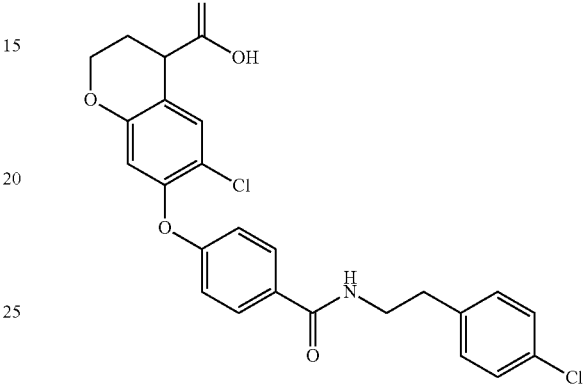

Step A: Preparation of ethyl 6-chloro-7-(4-(4-chlorophenethylcarbamoyl)phenoxy)chroman-4-carboxylate 4-(6-Chloro-4-(ethoxycarbonyl)chroman-7-yloxy)benzoic acid (Preparation 1) (100 g, 265.40 mmol) was dissolved in dry dichloromethane (750 ml) and few drops of DMF. Oxalyl Chloride (24.310 ml, 278.67 mmol) was slowly added to the mixture under nitrogen stream over a period of 0.5 hours at ambient temperature. Gas evolution was observed. The mixture was stirred for 5 hours at ambient temperature and cooled in an ice bath. 2-(4-Chlorophenyl)ethanamine (40.602 ml, 291.94 mmol) and diisopropylethylamine (55.624 ml, 318.48 mmol) were added. The mixture was warmed to ambient temperature and stirred for 16 hours. The crude mixture was transferred to a separatory funnel and washed with 1N HCl, water, and brine, dried over magnesium sulfate, filtered, and concentrated under reduced pressure. The resulting crude solid was further dried under high vacuum to provide 143.5 g of a pink solid. This solid was recrystallized from hot EtOAc/hexanes to provide 130.0 g of the title compound as a light purple solid.

Step B: Preparation of 6-chloro-7-(4-(4-chlorophenethylcarbamoyl)phenoxy)chroman-4-carboxylic acid Ethyl 6-chloro-7-(4-(4-chlorophenethylcarbamoyl)phenoxy)chroman-4-carboxylate (128.8 g, 250.4 mmol) was dissolved in EtOH (250 mL) and THF (500 mL). NaOH (6N) (62.60 ml, 375.6 mmol) was added and the mixture was stirred at ambient temperature for 1.5 hours. The mixture was transferred to a 2 L separatory funnel and 1N HCl (500.8 ml, 500.8 mmol) was added to the mixture. Additional EtOAc (250 ml) was added and the layers were separated. The organic layer was washed with water and brine, dried over magnesium sulfate, filtered, and concentrated under reduced pressure. The resulting crude solid was recrystallized from THF and hexanes to provide 122.0 g of the title compound as a faint pink solid (yield 95.0%). $^1$H NMR analysis showed that the solid contained THF. The THF content was 27 mol % (5.2% weight) and the desired product content by weight was 94.8%. MS (apci) m/z=486.1 (M+H).

Example 11

Separation of enantiomers of 6-Chloro-7-(4-(4-chlorophenethylcarbamoyl)phenoxy)chroman-4-carboxylic acid

Separation of enantiomers of 6-chloro-7-(4-(4-chlorophenethylcarbamoyl)phenoxy)chroman-4-carboxylic acid 6-Chloro-7-(4-(4-chlorophenethylcarbamoyl)phenoxy)chroman-4-carboxylic acid (Example 10; 140 g) was dissolved in methanol (50 mg/mL). The material was resolved via supercritical fluid chromatography employing a CHIRALCEL® OJ-H column (3×15 cm) eluting with 30% methanol/carbon dioxide at 100 bar, using 3 mL injections and a flow rate of 100 mL/min. Collection of fractions containing peak 2 and removal of volatiles provided the more potent DP2 binding enantiomer, Enantiomer 2 of 6-Chloro-7-(4-(4-chlorophenethylcarbamoyl)phenoxy)chroman-4-carboxylic acid (65 g, 46% yield). MS (apci) m/z=486.1 (M+H).

Example 12

Sodium 6-chloro-7-(4-(phenethylcarbamoyl)phenoxy)chroman-4-carboxylate

Step A: Preparation of ethyl 6-chloro-7-(4-(phenethylcarbamoyl)phenoxy)chroman-4-carboxylate To a stirred solution of 4-(6-chloro-4-(ethoxycarbonyl)chroman-7-yloxy)benzoic acid (Preparation 1) (75 mg, 0.20 mmol) and O-(7-azabenzotriazol-1-yl)-N,N,N',N'-tetramethyluronium hexafluorophosphate (84 mg, 0.22 mmol) in N,N-dimethylformamide (1 mL) at ambient temperature was added phenethylamine (28 μL, 0.22 mmol) and N,N-diisopropylethylamine (105 μL, 0.60 mmol). The resulting yellow solution was stirred at ambient temperature for 1 hour. The reaction mixture was diluted with water (10 mL) and extracted with ethyl acetate (10 mL). The organic layer was washed with brine (5 mL), then dried over sodium sulfate and concentrated to afford ethyl 6-chloro-7-(4-(phenethylcarbamoyl)phenoxy)chroman-4-carboxylate as an off-white solid (89 mg, 93% yield).

Step B: Preparation of sodium 6-chloro-7-(4-(phenethylcarbamoyl)phenoxy)chroman-4-carboxylate To a stirred solution of ethyl 6-chloro-7-(4-(phenethylcarbamoyl)phenoxy)chroman-4-carboxylate (88 mg, 0.18 mmol) in a mixture of tetrahydrofuran (0.6 mL) and ethanol (0.3 mL) at ambient temperature was added 1M sodium hydroxide (0.73 mL, 0.73 mmol). The resulting slightly cloudy mixture was vigorously stirred at ambient temperature for 1 hour. The reaction mixture was partitioned between ethyl acetate (10 mL) and 1M hydrochloric acid (5 mL). The organic layer was washed with brine (5 mL), then dried over sodium sulfate and concentrated to afford the carboxylic acid as a colorless oil (71 mg, 86% yield). To convert to the sodium salt, the oil was dissolved in methanol (1 mL) and treated with a 25% (w/v) solution of sodium methoxide in methanol (0.036 mL, 0.16 mmol). The resulting solution was concentrated, and the residue was concentrated twice from ether to afford sodium 6-chloro-7-(4-(phenethylcarbamoyl)phenoxy)chroman-4-carboxylate as an off-white glass (70 mg, 86% yield). MS (apci) m/z=452.1 (M+2H—Na).

Example 13

Sodium 6-chloro-7-(4-(4-phenylbutylcarbamoyl)phenoxy)chroman-4-carboxylate

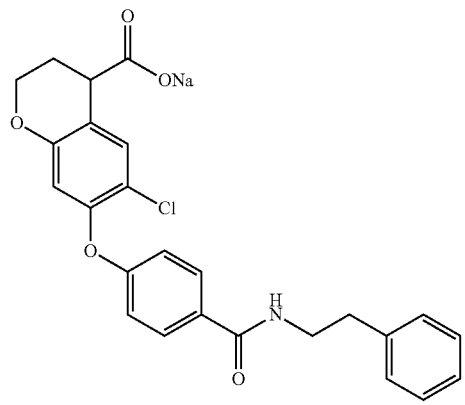

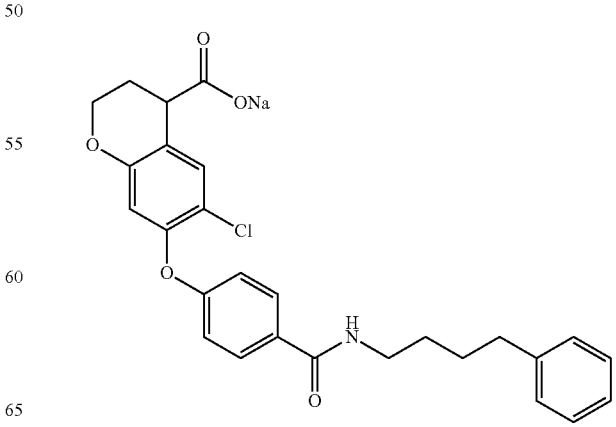

Prepared according to the method of Example 12, substituting 4-phenylbutylamine for phenethylamine. MS (apci) m/z=480.1 (M+2H—Na).

Example 14

Sodium 6-chloro-7-(4-(4-(3-chlorophenyl)butylcarbamoyl)phenoxy)chroman-4-carboxylate

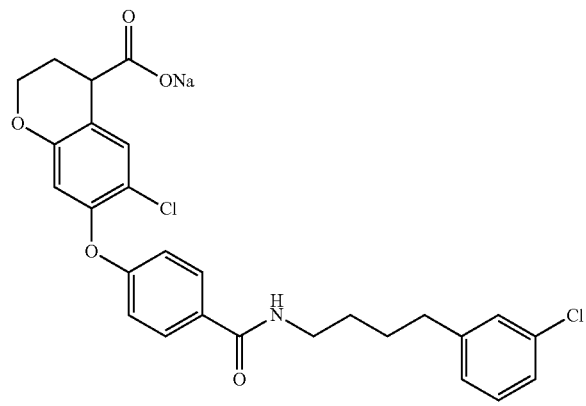

Step A: Preparation of (3-(1,3-dioxoisoindolin-2-yl)propyl)triphenylphosphonium bromide A solution of N-(3-bromopropyl)phthalimide (25.0 g, 93.2 mmol) and triphenylphosphine (24.5 g, 93.2 mmol) in toluene (200 mL) was stirred and heated to reflux for 15 hours. The reaction mixture was cooled to ambient temperature and the resulting precipitate was collected by filtration, washed with toluene, and dried under vacuum to afford (3-(1,3-dioxoisoindolin-2-yl)propyl)triphenylphosphonium bromide as a white powder (17.9 g, 36% yield).

Step B: Preparation of (Z)-2-(4-(3-chlorophenyl)but-3-enyl)isoindoline-1,3-dione To a stirred suspension of (3-(1,3-dioxoisoindolin-2-yl)propyl)triphenylphosphonium bromide (17.6 g, 33.2 mmol) in tetrahydrofuran (170 mL) at ambient temperature was added 3-chlorobenzaldehyde (3.76 mL, 33.2 mmol), and the resulting mixture was cooled with a dry-ice acetone bath to −75° C. Solid potassium t-butoxide (3.72 g, 33.2 mmol) was added, and stirring was continued in the bath for an additional 20 minutes; the temperature was −80° C. The cooling bath was removed, and when the internal temperature reached −30° C., the flask was placed in a water-ice bath. The temperature eventually settled at 10° C. and was maintained for 2 hours. The reaction mixture was poured into a separatory funnel containing water (250 mL), and this was extracted with ethyl acetate (250 mL). The organic layer was dried over sodium sulfate and concentrated. The residue was purified by chromatography on silica gel, eluting with 90/10 hexanes/ethyl acetate, to afford (Z)-2-(4-(3-chlorophenyl)but-3-enyl)isoindoline-1,3-dione as a white solid (8.46 g, 82% yield).

Step C: Preparation of (Z)-4-(3-chlorophenyl)but-3-en-1-amine

To a stirred suspension of (Z)-2-(4-(3-chlorophenyl)but-3-enyl)isoindoline-1,3-dione (8.4 g, 27 mmol) in ethanol (100 mL) at ambient temperature was added hydrazine monohydrate (65%, 2.6 mL, 54 mmol). The resulting mixture was stirred and heated to reflux, and a yellow solution formed upon attaining reflux. About 10 minutes after reflux began, a precipitate formed in the reaction mixture. After a total of 35 minutes at reflux, the precipitate nearly filled the flask, and the heat was removed. On reaching ambient temperature, the reaction mixture formed a solid mass. The mass was dissolved by adding of 2M sodium hydroxide (100 mL). The resulting solution was concentrated to remove most of the ethanol. The remaining cloudy mixture was extracted with ethyl acetate (100 mL). The aqueous layer turned into a gel and the organic layer was decanted away. The organic layer was washed with water (50 mL), then dried over sodium sulfate and concentrated to afford (Z)-4-(3-chlorophenyl)but-3-en-1-amine as a light brown oil (4.66 g, 95%).

Step D: Preparation of 4-(3-chlorophenyl)butan-1-amine

To a solution of (Z)-4-(3-chlorophenyl)but-3-en-1-amine (1.80 g, 9.91 mmol) in methanol (30 mL) was added platinum (IV) oxide (0.18 g, 0.79 mmol), and to the resulting stirred mixture at ambient temperature was fitted a balloon of hydrogen. The flask was purged and refilled five times with hydrogen, and the resulting mixture was stirred at ambient temperature under a balloon of hydrogen for 1 hour. The catalyst was removed by filtration through a glass microfibre filter, and the filtrate was concentrated to afford 4-(3-chlorophenyl)butan-1-amine as a light yellow oil (1.78 g, 98% yield).

Step E: Preparation of sodium 6-chloro-7-(4-(4-(3-chlorophenyl)butylcarbamoyl)phenoxy)chroman-4-carboxylate Prepared according to the method of Example 12, substituting 4-(3-chlorophenyl)butan-1-amine for phenethylamine. MS (apci) m/z=514.1 (M+2H—Na).

Example 15

Sodium 6-chloro-7-(4-(4-(4-chlorophenyl)butylcarbamoyl)phenoxy)chroman-4-carboxylate

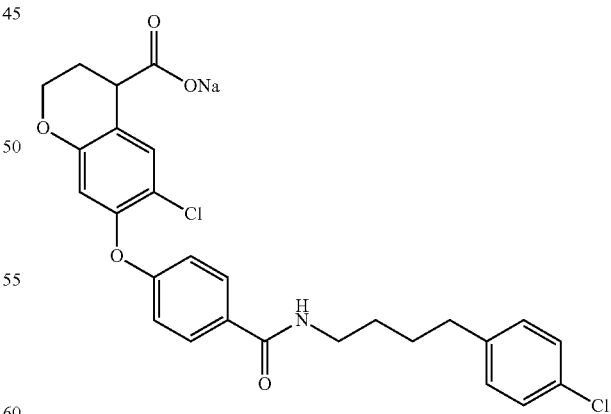

Step A: Preparation of 4-(4-chlorophenyl)butanamide

To a stirred solution of 4-(4-chlorophenyl)butanoic acid (3.97 g, 20.0 mmol) and 1-hydroxybenzotriazole hydrate (3.37 g, 22.0 mmol) in N,N-dimethylformamide (40 mL) at ambient temperature was added solid 1-ethyl-(3-dimethylaminopropyl)carbodiimide hydrochloride (4.21 g, 22 mmol). The resulting mixture was stirred at ambient temperature for 25 minutes, and a solution of ammonia in methanol (7M, 14.3 mL, 100 mmol) was added. After stirring at ambient temperature for a further 15 minutes, the reaction mixture was diluted with water (400 mL) and extracted with chloroform (100 mL). The organic layer was dried over sodium sulfate and concentrated. The residual oil was triturated with hexane to afford a solid, which was collected by filtration, washed with hexane, and dried under vacuum to afford 4-(4-chlorophenyl)butanamide as an off-white powder (2.40 g, 61% yield).

Step B: Preparation of 4-(4-chlorophenyl)butan-1-amine

To a stirred suspension of lithium aluminum hydride (1.84 g, 48.6 mmol) in diethyl ether (50 mL) at ambient temperature was added a solution of 4-(4-chlorophenyl)butanamide in tetrahydrofuran (25 mL), dropwise over 8 minutes. Stirring was continued at ambient temperature for a further 4 hours. The reaction mixture was carefully quenched by sequential slow addition of water (2 mL), 10M sodium hydroxide (0.75 mL), and water (7 mL). After stirring the mixture for 20 minutes, it was extracted with diethyl ether (50 mL). The organic layer was dried over sodium sulfate and concentrated to afford 4-(4-chlorophenyl)butan-1-amine as a light yellow oil (1.36 g, 61%).

Step C: Preparation of sodium 6-chloro-7-(4-(4-(4-chlorophenyl)butylcarbamoyl)phenoxy)chroman-4-carboxylate Prepared according to the method of Example 12, substituting 4-(4-chlorophenyl)butan-1-amine for phenethylamine. MS (apci) m/z=514.1 (M+2H—Na).

Example 16

Sodium (Z)-6-chloro-7-(4-(4-(2-chlorophenyl)but-3-enylcarbamoyl)phenoxy)chroman-4-carboxylate

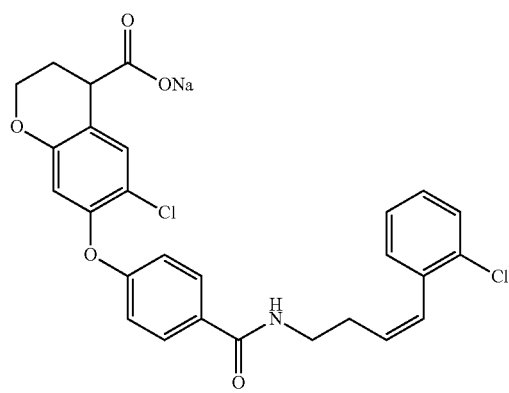

Step A: Preparation of (Z)-4-(2-chlorophenyl)but-3-en-1-amine

Prepared according to Steps A through C of Example 14, substituting 2-chlorobenzaldehyde for 3-chlorobenzaldehyde.

Step B: Preparation of Sodium (Z)-6-chloro-7-(4-(4-(2-chlorophenyl)but-3-enylcarbamoyl)phenoxy)chroman-4-carboxylate Prepared according to the method of Example 12, substituting (Z)-4-(2-chlorophenyl)but-3-en-1-amine for phenethylamine. MS (apci) m/z=512.0 (M+2H—Na).

Example 17

Sodium 6-chloro-7-(4-(4-(2-chlorophenyl)butylcarbamoyl)phenoxy)chroman-4-carboxylate

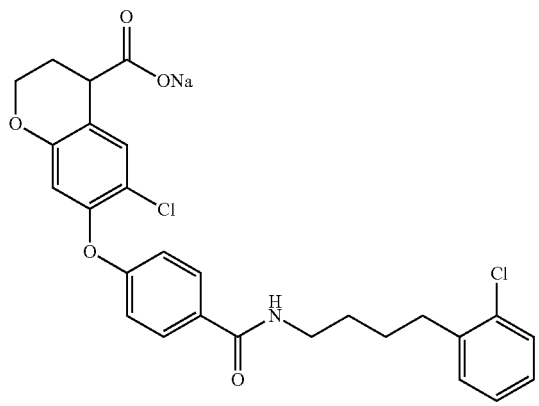

To a solution of sodium (Z)-6-chloro-7-(4-(4-(2-chlorophenyl)but-3-enylcarbamoyl)phenoxy)chroman-4-carboxylate (0.16 g, 0.31 mmol) in methanol (2 mL) was added platinum(IV) oxide (0.018 g, 0.079 mmol), and to the resulting stirred mixture at ambient temperature was fitted a balloon of hydrogen. The flask was purged and refilled five times with hydrogen, and the resulting mixture was stirred at ambient temperature under a balloon of hydrogen for 30 minutes, by which time the catalyst had clumped up. The methanol supernatant was decanted away from the catalyst with a pipet and concentrated, and the residue concentrated from diethyl ether to afford sodium 6-chloro-7-(4-(4-(2-chlorophenyl)butylcarbamoyl)phenoxy)chroman-4-carboxylate as a white glass (142 mg, 87% yield). MS (apci) m/z=514.1 (M+2H—Na).

Example 18

Sodium (Z)-6-chloro-7-(4-(4-(2,4-dichlorophenyl)but-3-enylcarbamoyl)phenoxy)chroman-4-carboxylate

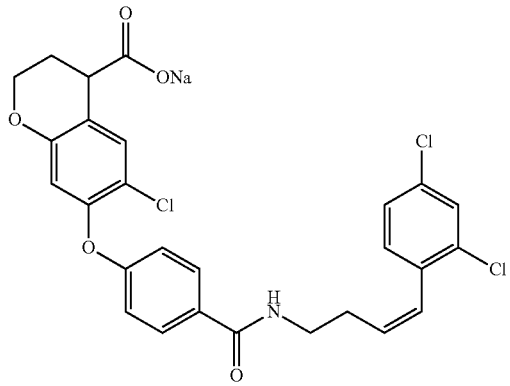

Step A: Preparation of (Z)-4-(2,4-dichlorophenyl)but-3-en-1-amine

Prepared according to Steps A through C of Example 14, substituting 2,4-dichlorobenzaldehyde for 3-chlorobenzaldehyde.

Step B: Preparation of sodium (Z)-6-chloro-7-(4-(4-(2,4-dichlorophenyl)but-3-enylcarbamoyl)phenoxy)chroman-4-carboxylate Prepared according to the method of Example 12, substituting (Z)-4-(2,4-dichlorophenyl)but-3-en-1-amine for phenethylamine. MS (apci) m/z=545.9 (M+2H—Na).

Example 19

Sodium 6-chloro-7-(4-(4-(2,4-dichlorophenyl)butylcarbamoyl)phenoxy)chroman-4-carboxylate

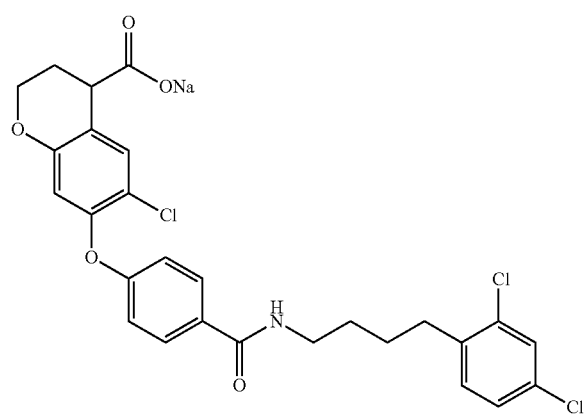

Prepared according to the method of Example 17, substituting sodium (Z)-6-chloro-7-(4-(4-(2,4-dichlorophenyl)but-3-enylcarbamoyl)phenoxy)chroman-4-carboxylate for sodium (Z)-6-chloro-7-(4-(4-(2-chlorophenyl)but-3-enylcarbamoyl)phenoxy)chroman-4-carboxylate. MS (apci) m/z=548.1 (M+2H—Na).

Example 20

Sodium 6-chloro-7-(4-(2-methylphenethylcarbamoyl)phenoxy)chroman-4-carboxylate

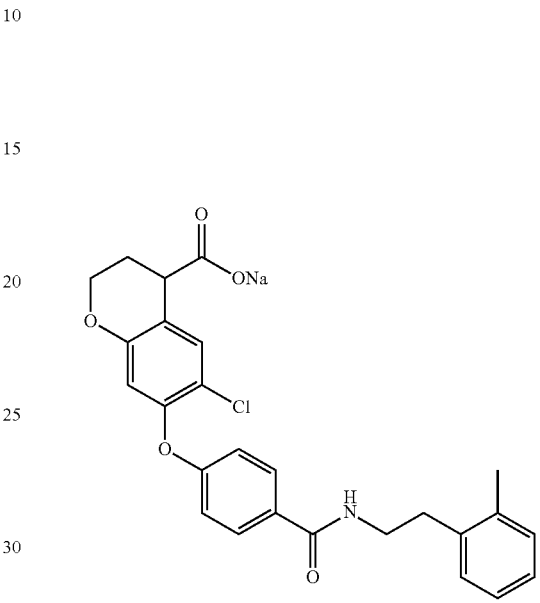

Prepared according to the method of Example 12, substituting 2-methylphenethylamine for phenethylamine. MS (apci) m/z=466.0 (M+2H—Na).

Example 21

Sodium 6-chloro-7-(4-(2,4-dimethylphenethylcarbamoyl)phenoxy)chroman-4-carboxylate

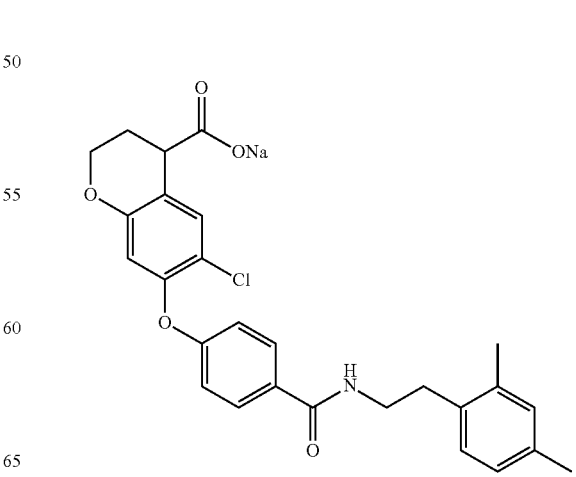

Prepared according to the method of Example 12, substituting 2,4-dimethylphenethylamine for phenethylamine. MS (apci) m/z=480.0 (M+2H—Na).

Example 22

Sodium 6-chloro-7-(4-(4-methylphenethylcarbamoyl)phenoxy)chroman-4-carboxylate

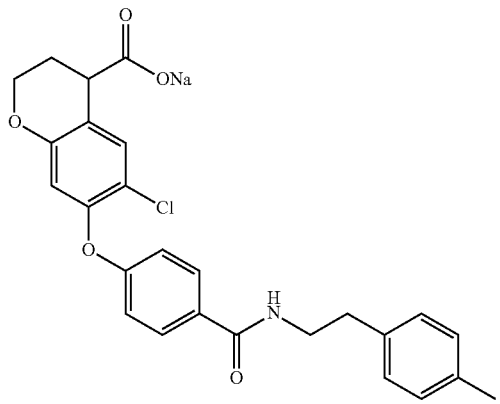

Step A: Preparation of ethyl 6-chloro-7-(4-(4-methylphenethylcarbamoyl)phenoxy)chroman-4-carboxylate To a stirred solution of 4-(6-chloro-4-(ethoxycarbonyl)chroman-7-yloxy)benzoic acid (Preparation 1) (75 mg, 0.20 mmol) and 1-hydroxybenzotriazole hydrate (34 mg, 0.22 mmol) in N,N-dimethylformamide (1 mL) at ambient temperature was added solid 1-ethyl-(3-dimethylaminopropyl)carbodiimide hydrochloride (47 mg, 0.24 mmol). The resulting solution was stirred at ambient temperature for 20 minutes, and 4-methylphenethylamine (30 mg, 0.23 mmol) was added. After stirring was at ambient temperature for a further 30 minutes, the mixture was diluted with water (10 mL) and extracted with ethyl acetate (5 mL). The organic layer was washed with brine (2 mL), then dried over sodium sulfate and concentrated to afford ethyl 6-chloro-7-(4-(4-methylphenethylcarbamoyl)phenoxy)chroman-4-carboxylate as a colorless oil (96 mg, 96% yield).

Step B: Preparation of sodium 6-chloro-7-(4-(4-methylphenethylcarbamoyl)phenoxy)chroman-4-carboxylate Prepared according to the method of Step B of Example 12, substituting afford ethyl 6-chloro-7-(4-(4-methylphenethylcarbamoyl)phenoxy)chroman-4-carboxylate for ethyl 6-chloro-7-(4-z(phenethylcarbamoyl)phenoxy)chroman-4-carboxylate. MS (apci) m/z=494.1 (M+2H—Na).

Example 23

Sodium 7-(4-(4-bromophenethylcarbamoyl)phenoxy)-6-chlorochroman-4-carboxylate

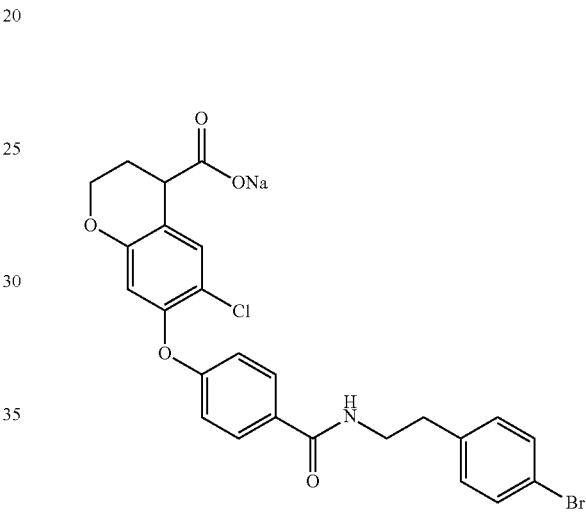

Step A: Preparation of ethyl 7-(4-(4-bromophenethylcarbamoyl)phenoxy)-6-chlorochroman-4-carboxylate Prepared according to Example 22, step A, substituting 4-bromophenethylamine for 4-methylphenethylamine (2.70 g, 95% yield).

Step B: Preparation of sodium 7-(4-(4-bromophenethylcarbamoyl)phenoxy)-6-chlorochroman-4-carboxylate Prepared according to the method of Step B of Example 12, substituting ethyl 7-(4-(4-bromophenethylcarbamoyl)phenoxy)-6-chlorochroman-4-carboxylate for ethyl 6-chloro-7-

(4-(phenethylcarbamoyl)phenoxy)chroman-4-carboxylate. MS (apci) m/z=530.0 (M+2H—Na).

Example 24

Sodium 6-chloro-7-(4-(4-cyclopropylphenethylcarbamoyl)phenoxy)chroman-4-carboxylate

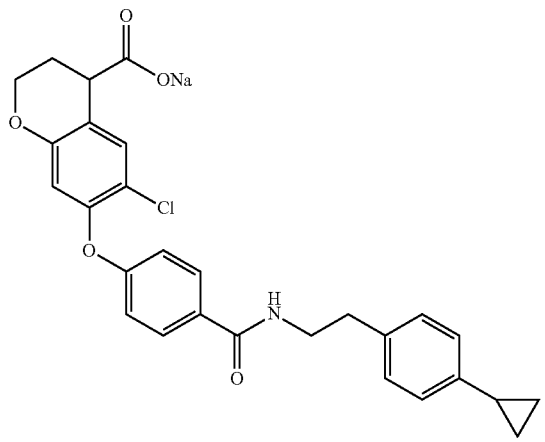

Step A: Preparation of ethyl 6-chloro-7-(4-(4-cyclopropylphenethylcarbamoyl)phenoxy)chroman-4-carboxylate To a stirred suspension of ethyl 7-(4-(4-bromophenethylcarbamoyl)phenoxy)-6-chlorochroman-4-carboxylate (0.56 g, 1.0 mmol) in toluene (6 mL) at ambient temperature was added successively water (0.3 mL), potassium phosphate (0.64 g, 3.0 mmol), tricyclohexylphosphine (0.11 g, 0.40 mmol), and cyclopropylboronic acid (0.17 g, 2.0 mmol). The resulting mixture was stirred and a balloon of nitrogen with a three-way purge valve was attached, and the flask was evacuated and refilled five times with nitrogen. Palladium(II) acetate (0.045 g, 0.20 mmol) was added, and again the flask was evacuated and refilled five times with nitrogen. The mixture was stirred in an oil bath set to 100° C. under the nitrogen balloon for 3 hours. The mixture was cooled to ambient temperature and diluted with ethyl acetate (25 mL) and water (15 mL). The organic layer was dried over sodium sulfate and concentrated. The residue was purified by chromatography on silica gel, eluting with 70/30 hexanes/ethyl acetate, to afford ethyl 6-chloro-7-(4-(4-cyclopropylphenethylcarbamoyl)phenoxy)chroman-4-carboxylate as a white solid (0.24 g, 46% yield).

Step B: Preparation of sodium 6-chloro-7-(4-(4-cyclopropylphenethyl carbamoyl)phenoxy)chroman-4-carboxylate Prepared according to the method of Step B of Example 12, substituting ethyl 6-chloro-7-(4-(4-cyclopropylphenethylcarbamoyl) phenoxy)chroman-4-carboxylate for ethyl 6-chloro-7-(4-(phenethylcarbamoyl)phenoxy)chroman-4-carboxylate. MS (apci) m/z=492.0 (M+2H—Na).

Example 25

Sodium 6-chloro-7-(4-(2-cyclopropylethylcarbamoyl)phenoxy)chroman-4-carboxylate

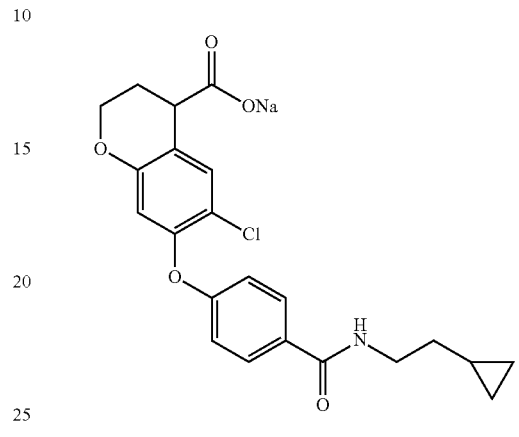

Prepared according to the method of Example 22, substituting 2-cyclopropylethylamine for 4-methylphenethylamine. MS (apci) m/z=416.0 (M+2H—Na).

Example 26

Sodium 6-chloro-7-(4-(2-(2'-chlorobiphenyl-4-yl)ethylcarbamoyl)phenoxy)chroman-4-carboxylate

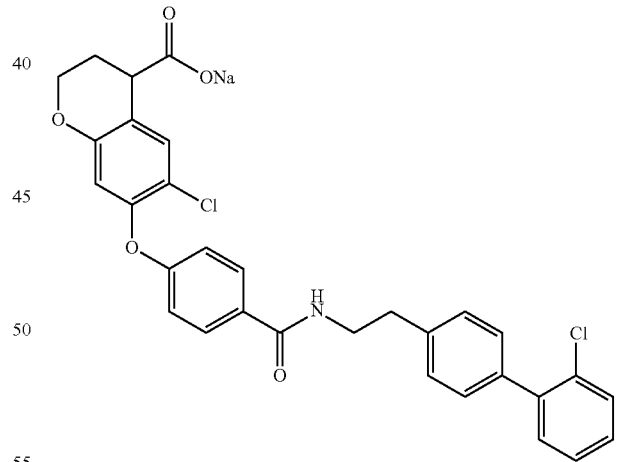

Step A: Preparation of ethyl 6-chloro-7-(4-(2-(2'-chlorobiphenyl-4-yl)ethylcarbamoyl)phenoxy)chroman-4-carboxylate To a stirred suspension of ethyl 7-(4-(4-bromophenethylcarbamoyl)phenoxy)-6-chlorochroman-4-carboxylate (0.56 g, 1.0 mmol) and 2-chlorophenylboronic acid (0.17 g, 1.1 mmol) in a mixture of 1,2-dimethoxyethane (4 mL) and methanol (2 mL) was added cesium fluoride (0.30 g, 2.0 mmol), followed by tetrakis(triphenylphosphine)palladium (0) (0.035 g, 0.03 mmol). The resulting mixture was stirred in an oil bath set to 80° C. for 1 hour. The mixture was cooled to ambient temperature and diluted with water (20 mL) and extracted with dichloromethane (2×20 mL). The organic layers were combined and dried over sodium sulfate, then concentrated. The residue was purified by chromatography on silica gel, eluting with 80/20 hexanes/ethyl acetate, to afford ethyl 6-chloro-7-(4-(2-(2'-chlorobiphenyl-4-yl)ethylcarbamoyl)phenoxy)chroman-4-carboxylate as a light brown oil (0.35 g, 59% yield).

Step B. Preparation of sodium 6-chloro-7-(4-(2-(2'-chlorobiphenyl-4-yl)ethylcarbamoyl)phenoxy)chroman-4-carboxylate Prepared according to the method of Step B of Example 12, substituting ethyl 6-chloro-7-(4-(2-(2'-chlorobiphenyl-4-yl)ethylcarbamoyl)phenoxy)chroman-4-carboxylate for ethyl 6-chloro-7-(4-(phenethylcarbamoyl)phenoxy)chroman-4-carboxylate. MS (apci) m/z=562.0 (M+2H—Na).

Example 27

Sodium 6-chloro-7-(4-(4-chloro-2-methylphenethylcarbamoyl)phenoxy)chroman-4-carboxylate

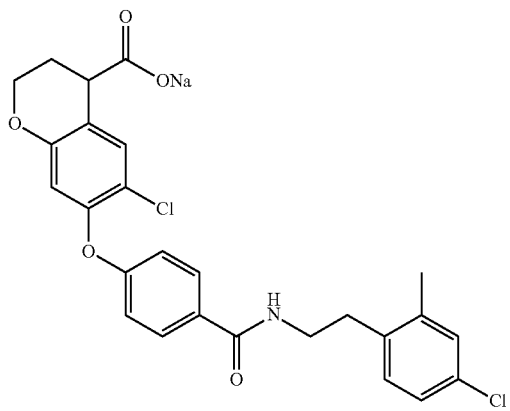

Step A: Preparation of 4-chloro-2-methyl-1-(2-nitrovinyl)benzene

A mixture of 4-chloro-2-methylbenzaldehyde (1.56 g, 10.1 mmol), methylamine hydrochloride (0.44 g, 6.5 mmol), and sodium acetate (0.53 g, 6.5 mmol) in nitromethane (4 mL) was vigorously stirred at ambient temperature for 24 hours. The reaction mixture was diluted with water (20 mL) and dichloromethane (40 mL). The organic layer was dried over sodium sulfate and evaporated to afford 4-chloro-2-methyl-1-(2-nitrovinyl)benzene as a light brown solid (1.87 g, 94% yield).

Step B: Preparation of 2-(4-chloro-2-methylphenyl)ethanamine

A solution of 4-chloro-2-methyl-1-(2-nitrovinyl)benzene (1.83 g, 9.26 mmol) in tetrahydrofuran (40 mL) was cooled to 0° C. in an ice bath, and a 1M solution of lithium aluminum hydride in tetrahydrofuran (37 mL, 37 mmol) was added, dropwise over 10 minutes. The resulting mixture was stirred in the ice bath for 2 hours 30 minutes, then quenched in the following manner: water (1.5 mL) was added dropwise, and after stirring for 5 minutes, 1M sodium hydroxide (1.5 mL) was added. After stirring for a further 15 minutes, water (5 mL) was added, and the resulting mixture was stirred at ambient temperature for 15 minutes, then filtered through a medium porosity sintered glass funnel. The collected precipitate was washed with ethyl acetate (60 mL). The combined filtrate and wash was dried over sodium sulfate and concentrated to afford 2-(4-chloro-2-methylphenyl)ethanamine as a brown oil (1.17 g, 75% yield).

Step C: Preparation of sodium 6-chloro-7-(4-(4-chloro-2-methylphenethylcarbamoyl)phenoxy)chroman-4-carboxylate Prepared according to the method of Example 22, substituting 2-(4-chloro-2-methylphenyl)ethanamine for 4-methylphenethylamine. MS (apci) m/z=500.1 (M+2+Na).

Example 28

Sodium 7-(4-(4-bromo-2-chlorophenethylcarbamoyl)phenoxy)-6-chlorochroman-4-carboxylate

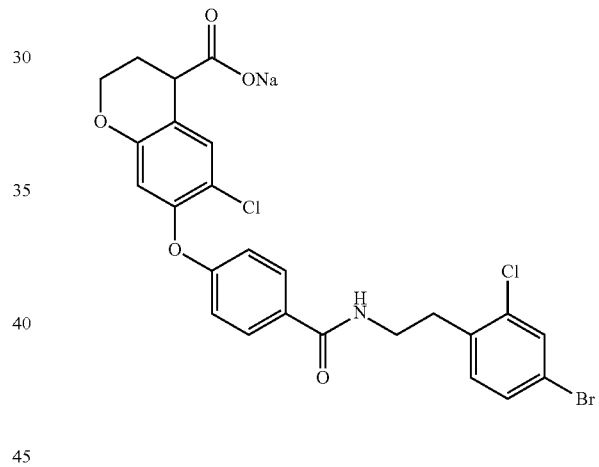

Step A: Preparation of 4-bromo-2-chloro-1-(dibromomethyl)benzene

To a stirred solution of 4-bromo-2-chlorotoluene (6.50 mL, 48.7 mmol) and benzoyl peroxide (0.51 g, 2.1 mmol) in carbon tetrachloride (80 mL) was added N-bromosuccinimide (43.3 g, 243 mmol), and the resulting mixture was stirred and heated to reflux for 15 hours. The mixture was cooled to ambient temperature and the insoluble material was removed by filtration, and washed twice with carbon tetrachloride. The filtrate and washings were combined and concentrated. The residue was purified by chromatography on silica gel, eluting with hexanes, to afford 4-bromo-2-chloro-1-(dibromomethyl)benzene as a colorless liquid (17.7 g, 100% yield).

Step B: Preparation of 4-bromo-2-chlorobenzaldehyde

A solution of 4-bromo-2-chloro-1-(dibromomethyl)benzene (17.7 g, 48.7 mmol) in ethanol (25 mL) was stirred and heated to reflux, and a solution of silver(I) nitrate (77.4 g, 456 mmol) in water (55 mL) was added dropwise over 20 minutes.

The mixture turned yellow and a precipitate of silver bromide formed immediately upon addition. Following completion of addition, the mixture was stirred at reflux for an additional hour. After cooling to ambient temperature, the mixture was diluted with water (200 mL) and filtered to remove insoluble material. The filtrate was extracted with chloroform (200 mL), and the insoluble material was washed with chloroform (2×200 mL). The three chloroform layers were combined and washed with water (250 mL), dried over sodium sulfate and concentrated to afford 4-bromo-2-chlorobenzaldehyde (10.6 g, 99% yield).

Step C: Preparation of 4-bromo-2-chloro-1-(2-nitrovinyl)benzene

Prepared according to the method of Step A of Example 27, substituting 4-bromo-2-chlorobenzaldehyde for 4-chloro-2-methylbenzaldehyde.

Step D: Preparation of 2-(4-bromo-2-chlorophenyl)ethanamine

To a stirred suspension of lithium borohydride (0.29 g, 13 mmol) in tetrahydrofuran (20 mL) at ambient temperature was added chlorotrimethylsilane (3.4 mL, 27 mmol), dropwise over 2 minutes. After stirring at ambient temperature for 20 minutes, argon gas was bubbled through the mixture for 2 minutes to remove the remaining trimethylsilane that had formed. A solution of 4-bromo-2-chloro-1-(2-nitrovinyl)benzene (0.88 g, 3.4 mmol) in tetrahydrofuran (15 mL) was added dropwise over 4 minutes with stirring at ambient temperature. The resulting mixture was stirred and heated to reflux for 1 hour. The mixture was cooled in an ice bath and carefully quenched with methanol (20 mL). The solvent was evaporated, and the residue was partitioned between 20% potassium hydroxide (40 mL) and dichloromethane (20 mL). The organic layer was dried over sodium sulfate and concentrated to afford 2-(4-bromo-2-chlorophenyl)ethanamine as a light yellow oil (0.75 g, 95% yield).

Step E: Preparation of ethyl 7-(4-(4-bromo-2-chlorophenethylcarbamoyl)phenoxy)-6-chlorochroman-4-carboxylate To a stirred solution of 4-(6-chloro-4-(ethoxycarbonyl)chroman-7-yloxy)benzoic acid (Preparation 1) (1.15 g, 3.05 mmol), 1-hydroxybenzotriazole hydrate (0.51 g, 3.4 mmol) and 2-(4-bromo-2-chlorophenyl)ethanamine (0.75 g, 3.2 mmol) in N,N-dimethylformamide (10 mL) at ambient temperature was added solid 1-ethyl-(3-dimethylaminopropyl)carbodiimide hydrochloride (0.70 g, 3.7 mmol). The resulting solution was stirred at ambient temperature for 17 hours, then diluted with water (100 mL) and extracted with ethyl acetate (100 mL). Addition of 1M hydrochloric acid (20 mL) enabled layer separation. The organic layer was dried over sodium sulfate and concentrated. The residue was purified by chromatography on silica gel, eluting with 75/25 hexanes/ethyl acetate, to afford ethyl 7-(4-(4-bromo-2-chlorophenethylcarbamoyl)phenoxy)-6-chlorochroman-4-carboxylate as an off-white solid (1.10 g, 60% yield).

Step F: Preparation of sodium 7-(4-(4-bromo-2-chlorophenethylcarbamoyl)phenoxy)-6-chlorochroman-4-carboxylate Prepared according to Step B of Example 12, substituting ethyl 7-(4-(4-bromo-2-chlorophenethylcarbamoyl)phenoxy)-6-chlorochroman-4-carboxylate for ethyl 6-chloro-7-(4-(phenethylcarbamoyl)phenoxy)chroman-4-carboxylate. MS (apci) m/z=564.0 (M+2H—Na).

Example 29

Sodium 6-chloro-7-(4-(2-(2',3-dichlorobiphenyl-4-yl)ethylcarbamoyl)phenoxy)chroman-4-carboxylate

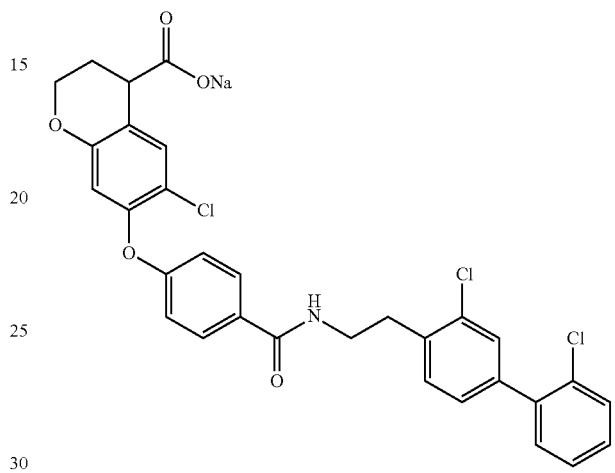

Prepared according to the method of Example 26, substituting ethyl 7-(4-(4-bromo-2-chlorophenethylcarbamoyl)phenoxy)-6-chlorochroman-4-carboxylate for ethyl 7-(4-(4-bromophenethylcarbamoyl)phenoxy)-6-chlorochroman-4-carboxylate. MS (apci) m/z=596.0 (M+2H—Na).

Example 30

Sodium 6-chloro-7-(4-(2-chloro-4-cyclopropylphenethylcarbamoyl)phenoxy)chroman-4-carboxylate

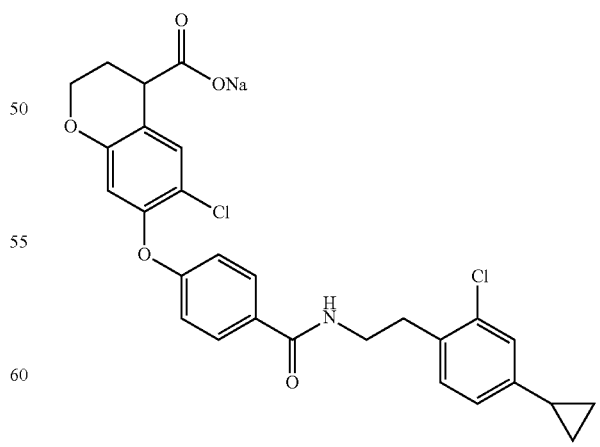

Prepared according to the method of Example 24, substituting ethyl 7-(4-(4-bromo-2-chlorophenethylcarbamoyl)phenoxy)-6-chlorochroman-4-carboxylate for ethyl 7-(4-(4- bromophenethylcarbamoyl)phenoxy)-6-chlorochroman-4-carboxylate. MS (apci)=526.0 (M+2+Na).

Example 31

Sodium 6-chloro-7-(4-(2-(3-chlorobiphenyl-4-yl)ethylcarbamoyl)phenoxy)chroman-4-carboxylate

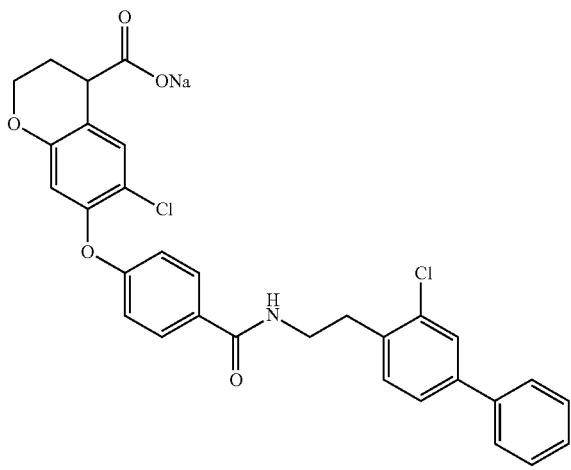

Prepared according to the method of Example 26, substituting ethyl 7-(4-(4-bromo-2-chlorophenethylcarbamoyl)phenoxy)-6-chlorochroman-4-carboxylate for ethyl 7-(4-(4-bromophenethylcarbamoyl)phenoxy)-6-chlorochroman-4-carboxylate, and substituting phenylboronic acid for 2-chlorophenylboronic acid. MS (apci)=562.1 (M+2H—Na).

Example 32

Sodium 7-(4-(2-bromo-4-chlorophenethylcarbamoyl)phenoxy)-6-chlorochroman-4-carboxylate

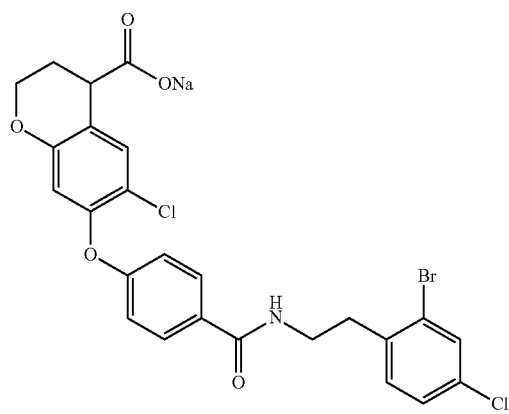

Prepared according to the method of Example 28, substituting 2-bromo-4-chlorotoluene for 4-bromo-2-chlorotoluene. MS (apci)=564.0 (M+2H—Na).

Example 33

Sodium 6-chloro-7-(4-(2-(2',5-dichlorobiphenyl-2-yl)ethylcarbamoyl)phenoxy)chroman-4-carboxylate

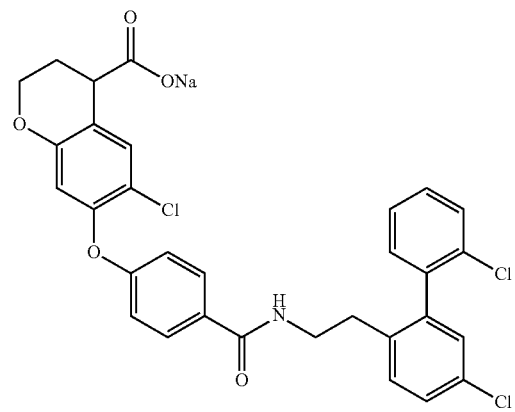

Prepared according to the method of Example 26, substituting ethyl 7-(4-(2-bromo-4-chlorophenethylcarbamoyl)phenoxy)-6-chlorochroman-4-carboxylate for ethyl 7-(4-(4-bromophenethylcarbamoyl)phenoxy)-6-chlorochroman-4-carboxylate. MS (apci) m/z=596.1 (M+2H—Na).

Example 34

Sodium 6-chloro-7-(4-(4-chloro-2-cyclopropylphenethylcarbamoyl)phenoxy)chroman-4-carboxylate

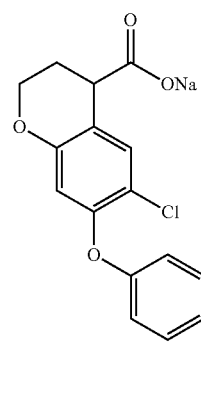

Prepared according to the method of Example 24, substituting ethyl 7-(4-(2-bromo-4-chlorophenethylcarbamoyl)phenoxy)-6-chlorochroman-4-carboxylate for ethyl 7-(4-(4-bromophenethylcarbamoyl)phenoxy)-6-chlorochroman-4-carboxylate. MS (apci) m/z=525.9 (M+2H—Na).

Example 35

Sodium 7-(4-(4-bromo-2-methoxyphenethylcarbamoyl)phenoxy)-6-chlorochroman-4-carboxylate

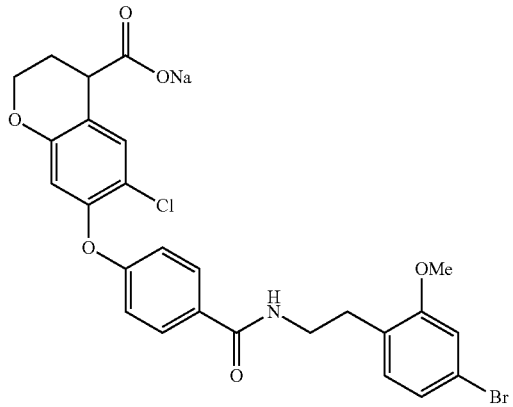

Step A: Preparation of 4-bromo-2-methoxybenzaldehyde

To a stirred solution of 4-bromo-2-fluorobenzaldehyde (96%, 3.38 g, 16.0 mmol) in methanol (35 mL) at ambient temperature was added a 25 wt % solution of sodium methoxide in methanol (4.02 mL, 17.6 mmol), and the resulting solution was stirred and heated to reflux for 2 hours. The solution was cooled to ambient temperature and concentrated, and the residue was partitioned between dichloromethane (100 mL) and water (50 mL). The organic layer was dried over sodium sulfate and concentrated. The residue was purified by chromatography on silica gel, eluting with 95/5 hexanes/ethyl acetate, to afford 4-bromo-2-methoxybenzaldehyde as a white solid (2.13 g, 62% yield).

Step B: Preparation of sodium 7-(4-(4-bromo-2-methoxyphenethylcarbamoyl)phenoxy)-6-chlorochroman-4-carboxylate Prepared according to the method of Steps C through F of Example 28, substituting 4-bromo-2-methoxybenzaldehyde for 4-chloro-2-methylbenzaldehyde. MS (apci) m/z=559.9 (M+2H—Na).

Example 36

Sodium 6-chloro-7-(4-(4-cyclopropyl-2-methoxyphenethylcarbamoyl)phenoxy)chroman-4-carboxylate

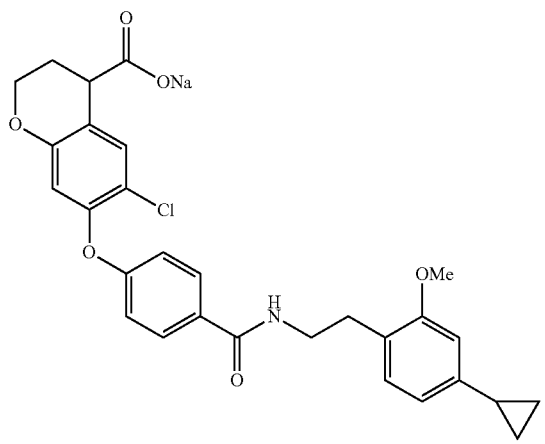

Prepared according to the method of Example 24, substituting ethyl 7-(4-(4-bromo-2-methoxyphenethylcarbamoyl)phenoxy)-6-chlorochroman-4-carboxylate for ethyl 7-(4-(4-bromophenethylcarbamoyl)phenoxy)-6-chlorochroman-4-carboxylate. MS (apci) m/z=522.0 (M+2H—Na).

Example 37

Sodium 6-chloro-7-(4-(2,4-dichloro-6-methoxyphenethylcarbamoyl)phenoxy)chroman-4-carboxylate

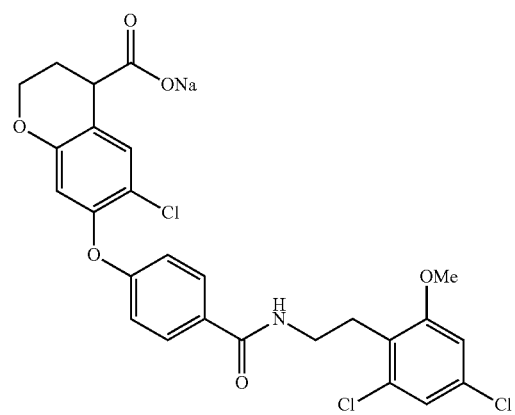

Step A: Preparation of 2,4-dichloro-6-methoxybenzaldehyde

To a stirred solution of 2,4-dichloro-6-hydroxybenzaldehyde (1.85 g, 9.69 mmol) in N,N-dimethylformamide (20 mL) at ambient temperature was added solid potassium carbonate (1.47 g, 10.7 mmol), and the resulting yellow mixture was stirred at ambient temperature for 30 minutes. Iodomethane (2.42 mL, 38.7 mmol) was added, and the resulting mixture was stirred in an oil bath set to 50° C. for 30 minutes. The mixture was cooled to ambient temperature and diluted with water (200 mL). After stirring for 10 minutes, the precipitate that formed was collected by filtration, washed with water, and dried under vacuum to afford 2,4-dichloro-6-methoxybenzaldehyde as an off-white powder (1.93 g, 97% yield).

Step B. Preparation of Sodium 6-chloro-7-(4-(2,4-dichloro-6-methoxyphenethylcarbamoyl)phenoxy)chroman-4-carboxylate Prepared according to the method of Steps C through F of Example 28, substituting 2,4-dichloro-6-methoxybenzaldehyde for 4-chloro-2-methylbenzaldehyde. MS (apci) m/z=549.9 (M+2H—Na).

Example 38

Sodium 8-bromo-6-chloro-7-(4-(4-chlorophenethyl-carbamoyl)phenoxy)chroman-4-carboxylate

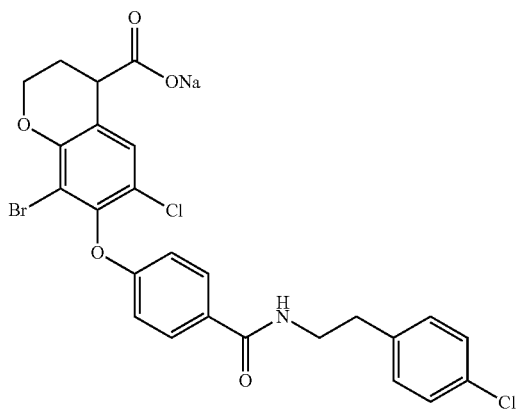

Step A: Preparation of ethyl 8-bromo-6-chloro-7-hydroxychroman-4-carboxylate To a stirred solution of ethyl 6-chloro-7-hydroxychroman-4-carboxylate (5.14 g, 20.0 mmol) in glacial acetic acid (50 mL) at ambient temperature was added bromine (1.2 mL, 24 mmol), in six equal portions, waiting 30-60 seconds between each addition for the bromine color to be discharged. Following completion of addition, the solution was concentrated and the residue concentrated from toluene, then partitioned between ethyl acetate (200 mL) and 5% sodium bisulfite (100 mL). The organic was layer dried over sodium sulfate, then stirred with activated charcoal (2 g) at ambient temperature for 20 minutes. The charcoal was removed by filtration through a glass microfibre filter and the filtrate was concentrated to afford ethyl 8-bromo-6-chloro-7-hydroxychroman-4-carboxylate as a light brown oil (6.05 g, 90% yield).

Step B: Preparation of ethyl 8-bromo-7-(4-(tert-butoxycarbonyl)-2-nitrophenoxy)-6-chlorochroman-4-carboxylate To a stirred solution of ethyl 8-bromo-6-chloro-7-hydroxychroman-4-carboxylate (4.00 g, 11.9 mmol) and tert-butyl 4-fluoro-3-nitrobenzoate (3.16 g, 13.1 mmol) in N,N-dimethylformamide (66 mL) at ambient temperature was added solid potassium carbonate (2.64 g, 19.1 mmol). The resulting mixture was stirred in an oil bath set to 90° C. for 30 minutes. The mixture was cooled to ambient temperature and poured into a separatory funnel containing water (600 mL). Chloroform (300 mL) was added, followed by 1M hydrochloric acid (100 mL). The organic layer was dried over sodium sulfate and concentrated. The residue was purified by chromatography on silica gel, eluting with 90/10 hexanes/ethyl acetate to afford ethyl 8-bromo-7-(4-(tert-butoxycarbonyl)-2-nitrophenoxy)-6-chlorochroman-4-carboxylate as a light yellow glass (4.33 g, 65% yield).

Step C: Preparation of ethyl 7-(2-amino-4-(tert-butoxycarbonyl)phenoxy)-8-bromo-6-chlorochroman-4-carboxylate To a stirred solution of ethyl 8-bromo-7-(4-(tert-butoxycarbonyl)-2-nitrophenoxy)-6-chlorochroman-4-carboxylate (2.00 g, 3.59 mmol) in tetrahydrofuran (15 mL) at ambient temperature was added zinc dust (4.70 g, 71.8 mmol), followed by saturated ammonium chloride solution (7.5 mL). The resulting mixture was stirred at ambient temperature for 1 hour. The mixture was filtered through a glass microfibre filter to remove the insoluble zinc solids, and the solids were washed twice with tetrahydrofuran. The combined filtrate and washings were concentrated to remove most of the tetrahydrofuran, and the residue was partitioned between ethyl acetate (100 mL) and water (50 mL). The organic layer was washed with brine (50 mL), then dried over sodium sulfate and concentrated to afford ethyl 7-(2-amino-4-(tert-butoxycarbonyl)phenoxy)-8-bromo-6-chlorochroman-4-carboxylate as a light brown glass (1.61 g, 85% yield).

Step D: Preparation of ethyl 8-bromo-7-(4-(tert-butoxycarbonyl)phenoxy)-6-chlorochroman-4-carboxylate N,N-dimethylformamide (20 mL) was heated in an oil bath set to 70° C. Isobutyl nitrite (0.90 mL, 7.6 mmol) was added, and to the resulting stirred solution at 68° C. was added a solution of ethyl 7-(2-amino-4-(tert-butoxycarbonyl)phenoxy)-8-bromo-6-chlorochroman-4-carboxylate (1.6 g, 6.0 mmol) in N,N-dimethylformamide (6 mL), dropwise over 5 minutes. The resulting solution was stirred at 70° C. for 30 minutes. The resulting red solution was cooled to ambient temperature and partitioned between water (600 mL) and ethyl acetate (50 mL). The organic layer was washed with 1M hydrochloric acid (10 mL) and brine (10 mL), then dried over sodium sulfate and concentrated. The residue was purified by chromatography on silica gel, eluting with 95/5 to 85/15 hexanes/ethyl acetate, to afford ethyl 8-bromo-7-(4-(tert-butoxycarbonyl)phenoxy)-6-chlorochroman-4-carboxylate as an orange oil (0.27 g, 17% yield).

Step E: Preparation of 4-(8-bromo-6-chloro-4-(ethoxycarbonyl)chroman-7-yloxy)benzoic acid To a stirred solution of ethyl 8-bromo-7-(4-(tert-butoxycarbonyl)phenoxy)-6-chlorochroman-4-carboxylate (0.26 g, 0.51 mmol) in dichloromethane (5 mL) at ambient temperature was added trifluoroacetic acid (5 mL). The resulting solution was stirred at ambient temperature for 30 minutes. The solution was concentrated and the residual glassy solid was redissolved in ethyl acetate (2 mL). Hexanes (10 mL) were added, and after mixing for a few minutes, the product solidified. The mixture was concentrated to afford 4-(8-bromo-6-chloro-4-(ethoxycarbonyl)chroman-7-yloxy)benzoic acid as a light brown powder (0.23 g, 99% yield).

Step F: Preparation of Sodium 8-bromo-6-chloro-7-(4-(4-chlorophenethylcarbamoyl)phenoxy)chroman-4-carboxylate Prepared according to the method of Example 12, substituting 4-(8-bromo-6-chloro-4-(ethoxycarbonyl)chroman-7-yloxy)benzoic acid for 4-(6-chloro-4-(ethoxycarbonyl)chroman-7-yloxy)benzoic acid and substituting 2-(4-chlorophenyl)ethanamine for phenethylamine. MS (apci) m/z=564.0 (M+2H—Na).

Example 39

Sodium 7-(4-(4-chlorophenethylcarbamoyl)phenoxy)-6,8-dicyclopropylchroman-4-carboxylate

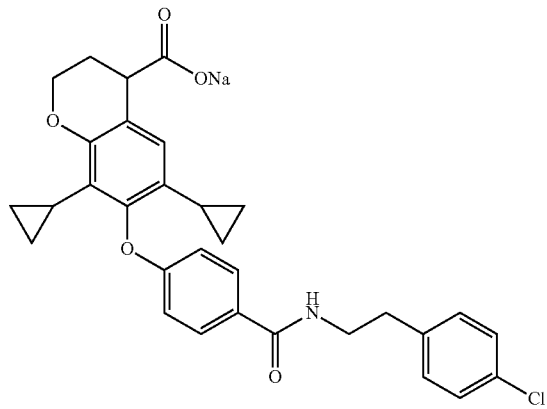

Step A: Preparation of ethyl 7-(4-(tert-butoxycarbonyl)-2-nitrophenoxy)-6,8-dicyclopropylchroman-4-carboxylate To a stirred solution of ethyl 8-bromo-7-(4-(tert-butoxycarbonyl)-2-nitrophenoxy)-6-chlorochroman-4-carboxylate (Example 38, Step B; 0.56 g, 1.0 mmol) in xylenes (6 mL) was added successively water (0.3 mL), potassium phosphate (1.27 g, 6.0 mmol), tricyclohexylphosphine (0.11 g, 0.40 mmol), and cyclopropylboronic acid (0.34 g, 4.0 mmol). The resulting mixture was stirred and a balloon of nitrogen with a three-way purge valve was attached, and the flask was evacuated and refilled five times with nitrogen. Palladium(II) acetate (0.045 g, 0.20 mmol) was added, and again the flask was evacuated and refilled five times with nitrogen. The mixture was stirred in an oil bath set to 140° C. under the nitrogen balloon for 2 hours. The mixture was cooled to ambient temperature, and diluted with ethyl acetate (25 mL) and water (15 mL). The organic layer was dried over sodium sulfate and concentrated. The residue was purified by chromatography on silica gel, eluting with 90/10 hexanes/ethyl acetate, to afford ethyl 7-(4-(tert-butoxycarbonyl)-2-nitrophenoxy)-6,8-dicyclopropylchroman-4-carboxylate as a light yellow glass (0.24 g, 46%).

Step B: Preparation of sodium 7-(4-(4-chlorophenethylcarbamoyl)phenoxy)-6,8-dicyclopropylchroman-4-carboxylate Prepared according to the method of Steps C through F of Example 38, substituting ethyl 7-(4-(tert-butoxycarbonyl)-2-nitrophenoxy)-6,8-dicyclopropylchroman-4-carboxylate for ethyl 8-bromo-7-(4-(tert-butoxycarbonyl)-2-nitrophenoxy)-6-chlorochroman-4-carboxylate. MS (apci) m/z=532.2 (M+2H—Na).

Example 40

Sodium 6,8-dicyclopropyl-7-(4-(2,4-dichlorophenethylcarbamoyl)phenoxy)chroman-4-carboxylate

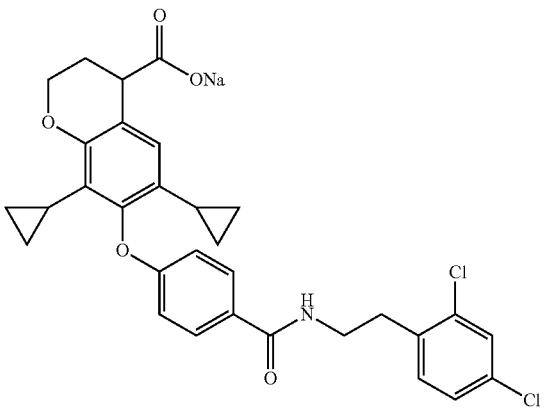

Prepared according to the method of Example 39, substituting 2-(2,4-dichlorophenyl)ethanamine for 2-(4-chlorophenyl)ethanamine. MS (apci) m/z=566.1 (M+2H—Na).

Example 41

Sodium 7-(4-(4-chlorophenethylcarbamoyl)phenoxy)-6-cyclopropylchroman-4-carboxylate

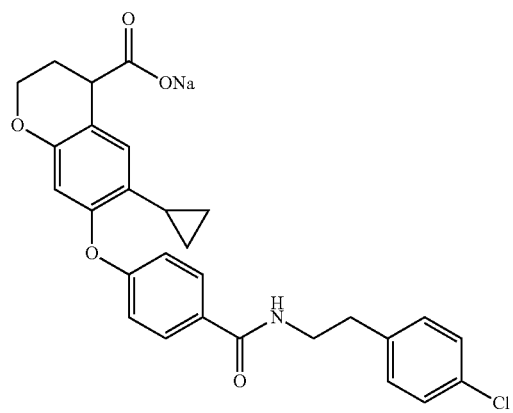

Step A: Preparation of ethyl 7-(4-(tert-butoxycarbonyl)-2-nitrophenoxy)-6-chlorochroman-4-carboxylate Prepared according to the method of Step B of Example 38, substituting ethyl 6-chloro-7-hydroxychroman-4-carboxylate for ethyl 8-bromo-6-chloro-7-hydroxychroman-4-carboxylate.

Step B: Preparation of ethyl 7-(4-(tert-butoxycarbonyl)-2-nitrophenoxy)-6-cyclopropylchroman-4-carboxylate To a stirred solution of ethyl 7-(4-(tert-butoxycarbonyl)-2-nitrophenoxy)-6-chlorochroman-4-carboxylate (1.38 g, 2.89 mmol) in toluene (15 mL) was added successively water (0.75 mL), potassium phosphate (3.06 g, 14.4 mmol), tricyclohexylphosphine (0.32 g, 1.16 mmol), and cyclopropylboronic acid (0.74 g, 8.7 mm3ol). The resulting mixture was stirred and a balloon of nitrogen with a three-way purge valve was attached, and the flask was evacuated and refilled five times with nitrogen. Palladium(II) acetate (0.13 g, 0.58 mmol) was added, and again the flask was evacuated and refilled five times with nitrogen. The mixture was stirred in an oil bath set to 110° C. under the nitrogen balloon for 16 hours. The mixture was cooled to ambient temperature, and diluted with ethyl acetate (100 mL) and water (50 mL). The organic layer was dried over sodium sulfate and concentrated. The residue was purified by chromatography on silica gel, eluting with 95/5 hexanes/ethyl acetate, to afford ethyl 7-(4-(tert-butoxycarbonyl)-2-nitrophenoxy)-6-cyclopropylchroman-4-carboxylate as a yellow oil (0.39 g, 28%).

Step C: Preparation of Sodium 7-(4-(4-chlorophenethylcarbamoyl)phenoxy)-6-cyclopropylchroman-4-carboxylate Prepared according to the method of Steps C through F of Example 38, substituting ethyl 7-(4-(tert-butoxycarbonyl)-2-nitrophenoxy)-6-cyclopropylchroman-4-carboxylate for ethyl 8-bromo-7-(4-(tert-butoxycarbonyl)-2-nitrophenoxy)-6-chlorochroman-4-carboxylate. MS (apci) m/z=492.1 (M+2H—Na).

Example 42

Sodium 6-cyclopropyl-7-(4-(2,4-dichlorophenethylcarbamoyl)phenoxy)chroman-4-carboxylate

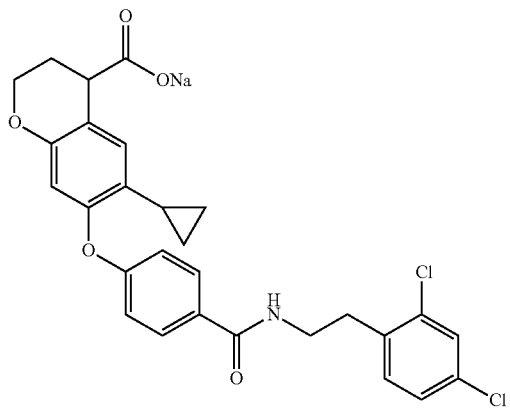

Prepared according to the method of Example 41, substituting 2-(2,4-dichlorophenyl)ethanamine for 2-(4-chlorophenyl)ethanamine. MS (apci) m/z=526.1 (M+2H—Na).

Example 43

Sodium 6-chloro-8-cyclopropyl-7-(4-(2,4-dichlorophenethylcarbamoyl)phenoxy)chroman-4-carboxylate

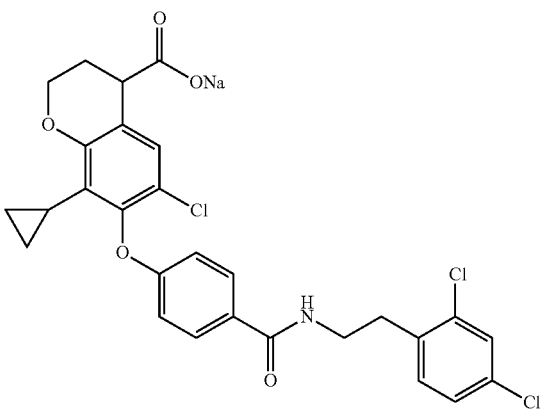

Step A: Preparation of ethyl 7-(4-(tert-butoxycarbonyl)-2-nitrophenoxy)-6-chloro-8-cyclopropylchroman-4-carboxylate To a stirred solution of ethyl 8-bromo-7-(4-(tert-butoxycarbonyl)-2-nitrophenoxy)-6-chlorochroman-4-carboxylate (0.59 g, 1.05 mmol) in toluene (6 mL) was added successively water (0.3 mL), potassium phosphate (0.67 g, 3.2 mmol), tricyclohexylphosphine (0.12 g, 0.42 mmol), and cyclopropylboronic acid (0.18 g, 2.1 mmol). The resulting mixture was stirred and a balloon of nitrogen with a three-way purge valve was attached, and the flask was evacuated and refilled five times with nitrogen. Palladium(II) acetate (0.047 g, 0.21 mmol) was added, and again the flask was evacuated and refilled five times with nitrogen. The mixture was stirred in an oil bath set to 100° C. under the nitrogen balloon for 1.5 hours. The mixture was cooled to ambient temperature, and diluted with ethyl acetate (25 mL) and water (15 mL). The organic layer was dried over sodium sulfate and concentrated. The residue was purified by chromatography on silica gel, eluting with 85/15 hexanes/ethyl acetate, to afford ethyl 7-(4-(tert-butoxycarbonyl)-2-nitrophenoxy)-6-chloro-8-cyclopropylchroman-4-carboxylate as a yellow oil (0.28 g, 51%).

Step B: Preparation of 4-(6-chloro-8-cyclopropyl-4-(ethoxycarbonyl)chroman-7-yloxy)benzoic acid Prepared according to Steps C through E of Example 38, substituting ethyl 7-(4-(tert-butoxycarbonyl)-2-nitrophenoxy)-6-chloro-8-cyclopropylchroman-4-carboxylate for ethyl 8-bromo-7-(4-(tert-butoxycarbonyl)-2-nitrophenoxy)-6-chlorochroman-4-carboxylate.

Step C: Preparation of sodium 6-chloro-8-cyclopropyl-7-(4-(2,4-dichlorophenethylcarbamoyl)phenoxy)chroman-4-carboxylate Prepared according to Steps E and F of Example 28, substituting 4-(6-chloro-8-cyclopropyl-4-(ethoxycarbonyl)

chroman-7-yloxy)benzoic acid for 4-(6-chloro-4-(ethoxycarbonyl)chroman-7-yloxy)benzoic acid, and substituting 2-(2,4-dichlorophenyl)ethanamine for 2-(4-bromo-2-chlorophenyl)ethanamine. MS (apci) m/z=560.1 (M+2H—Na).

Example 44

6-Cyano-7-(4-(4-((dimethylamino)methyl)phenethylcarbamoyl)phenoxy)chroman-4-carboxylic acid

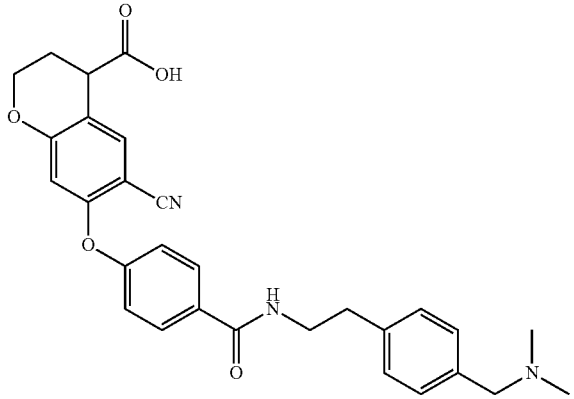 [SMILES: CN(C)Cc1ccc(CCNC(=O)c2ccc(Oc3cc4c(cc3C#N)C(C(=O)O)CCO4)cc2)cc1]

Step A: Preparation of 4-(2-(tert-butoxycarbonylamino)ethyl)benzoic acid

To a solution of 4-(2-aminoethyl)benzoic acid hydrochloride (10.0 g, 49.6 mmol) in a mixture of tert-butanol (liquefied, 7% water, 150 mL) and 1M sodium hydroxide (150 mL) at ambient temperature was added di-tert-butyl dicarbonate (13.0 g, 59.5 mmol). The resulting solution was stirred at ambient temperature for 16 hours. The reaction mixture was transferred to a separatory funnel containing water (250 mL), and was washed with hexanes (2×250 mL). The aqueous layer was acidified to pH<2 with concentrated hydrochloric acid. The precipitate that formed was allowed to stir for several minutes, collected by filtration, washed with a small amount of water, and dried under vacuum to afford 4-(2-(tert-butoxycarbonylamino)ethyl)benzoic acid as a white powder (12.5 g, 95% yield).

Step B: Preparation of tert-butyl 4-(hydroxymethyl)phenethylcarbamate

A 1M solution of borane-tetrahydrofuran complex in tetrahydrofuran (100 mL, 100 mmol) was added directly to solid (4-(2-(tert-butoxycarbonylamino)ethyl)benzoic acid (12.4 g, 46.7 mmol). The resulting solution was stirred at ambient temperature for 1 hour, carefully quenched with water (250 mL), and extracted with ethyl acetate (500 mL). The organic layer was washed with saturated sodium bicarbonate (200 mL) and brine (100 mL), dried over sodium sulfate and concentrated to afford tert-butyl 4-(hydroxymethyl)phenethylcarbamate as a pale yellow oil (10.0 g, 85% yield).

Step C: Preparation of 4-(2-(tert-butoxycarbonylamino)ethyl)benzyl methanesulfonate A solution of tert-butyl 4-(hydroxymethyl)phenethylcarbamate (2.51 g, 9.99 mmol) and N,N-diisopropylethylamine (1.9 mL, 11 mmol) in tetrahydrofuran (50 mL) was stirred and cooled in an ice bath. Methanesulfonyl chloride (0.85 mL, 11 mmol) was added in several portions, and stirring was continued in the bath for 50 minutes. The reaction mixture was transferred to a separatory funnel containing ethyl acetate (200 mL) and brine (200 mL). The organic layer was dried over sodium sulfate and concentrated to afford 4-(2-(tert-butoxycarbonylamino)ethyl)benzyl methanesulfonate as a soft white solid. (3.29 g, 100% yield).

Step D: Preparation of tert-butyl 4-((dimethylamino)methyl)phenethylcarbamate

To a stirred suspension of 4-(2-(tert-butoxycarbonylamino)ethyl)benzyl methanesulfonate (0.33 g, 1.0 mmol) and N,N-diisopropylethylamine (0.19 mL, 1.1 mmol) in tetrahydrofuran (50 mL) was added a 2M solution of dimethylamine in tetrahydrofuran (5.0 mL, 10 mmol). The resulting mixture was stirred in an oil bath set to 60° C. for 6 hours. The solution was cooled to ambient temperature and concentrated. The residue was partitioned between ethyl acetate (20 mL) and water (10 mL). The organic layer was dried over sodium sulfate and concentrated. The residue was purified by chromatography on silica gel, eluting with 99/1 to 98/2 chloroform/(90/10 methanol/concentrated ammonium hydroxide), to afford tert-butyl 4-((dimethylamino)methyl)phenethylcarbamate as a colorless oil (0.15 g, 54% yield).

Step E: Preparation of 2-(4-((dimethylamino)methyl)phenyl)ethanamine dihydrochloride To a stirred solution of tert-butyl 4-((dimethylamino)methyl)phenethylcarbamate (0.14 g, 0.50 mmol) in dioxane (1 mL) at ambient temperature was added a 4M solution of hydrogen chloride in dioxane (4 mL). The resulting solution was stirred at ambient temperature for 30 minutes, then concentrated to afford 2-(4-((dimethylamino)methyl)phenyl)ethanamine dihydrochloride as a white solid (0.12 g, 98% yield).

Step F: Preparation of methyl 6-cyano-7-(4-(4-((dimethylamino)methyl)phenethylcarbamoyl)phenoxy)chroman-4-carboxylate To a stirred suspension of 4-(6-cyano-4-(methoxycarbonyl)chroman-7-yloxy)benzoic acid (0.10 g, 0.28 mmol), 2-(4-((dimethylamino)methyl)phenyl)ethanamine dihydrochloride (0.056 g, 0.31 mmol), and O-(7-azabenzotriazol-1-yl)-N,N,N'-tetramethyluronium hexafluorophosphate (0.13 g, 0.34 mmol) in N,N-dimethylformamide (1.4 mL) at ambient temperature was added N,N-diisopropylethylamine (0.25 mL, 1.4 mmol). The resulting solution was stirred at ambient temperature for 60 minutes, then partitioned between water (15 mL) and ethyl acetate (10 mL). The organic layer was dried over sodium sulfate and concentrated. The residue was purified by chromatography on silica gel, eluting with 90/10 chloroform/(90/10 methanol/concentrated ammonium hydroxide), to afford methyl 6-cyano-7-(4-(4-((dimethylamino)methyl)phenethylcarbamoyl)phenoxy)chroman-4-carboxylate as a colorless film (0.083 g, 57% yield).

Step G: Preparation of 6-cyano-7-(4-(4-((dimethylamino)methyl)phenethylcarbamoyl)phenoxy)chroman-4-carboxylic acid To a stirred solution of methyl 6-cyano-7-(4-(4-((dimethylamino)methyl)phenethyl)carbamoyl)phenoxy)chroman-4- carboxylate (83 mg, 0.16 mmol) in methanol (1 mL) at ambient temperature was added a 2M solution of sodium hydroxide (0.40 mL, 0.80 mmol). After stirring at ambient temperature for 1 hour the solution was concentrated, and the residual solid was redissolved in water (5 mL). The pH was adjusted to 4.5 to precipitate the product, and chloroform (5 mL) was added. After stirring the multiphase mixture for a few minutes, the product separated as a thick oil on the side of the flask. The chloroform/water mixture was decanted away and the residue dried under vacuum to afford 6-cyano-7-(4-(4-((dimethylamino)methyl)phenethylcarbamoyl)phenoxy)chroman-4-carboxylic acid as a light yellow glass (23 mg, 28% yield). MS (apci) m/z=500.1 (M+H).

Example 45

6-Cyano-7-(4-(1,2,3,4-tetrahydroisoquinolin-7-ylcarbamoyl)phenoxy)chroman-4-carboxylic acid hydrochloride

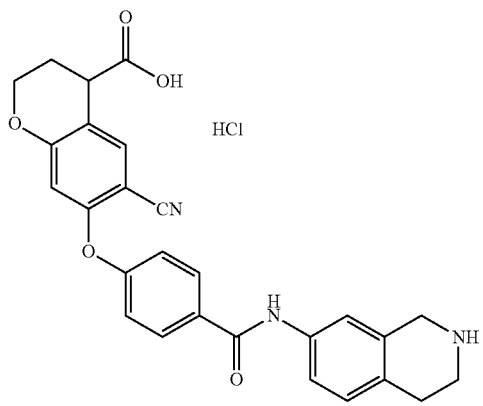 [SMILES: N#Cc1cc2c(cc1Oc1ccc(C(=O)Nc3ccc4c(c3)CNCC4)cc1)OCCC2C(=O)O ; Cl]

Step A: Preparation of 7-nitro-1,2,3,4-tetrahydroisoquinoline hydrochloride

Concentrated sulfuric acid (70 mL) was cooled in an ice-salt bath to 0° C. 1,2,3,4-Tetrahydroisoquinoline (96%, 19.6 g, 141 mmol) was added dropwise in portions over 35 minutes, with the temperature mostly staying below 20° C., but occasional brief excursions as high as 40° C. The resulting mixture was again cooled in an ice-salt bath to 0° C. and solid potassium nitrate (15.7 g, 155 mmol) was added in portions over 60 minutes, keeping the temperature mostly below 5° C. with occasional brief excursions as high as 7° C. Following completion of addition, the bath was removed and the resulting mixture was allowed to stir overnight at ambient temperature. The mixture was added carefully in small portions over 2 hours to concentrated ammonium hydroxide (200 mL), cooled initially in an ice-salt bath to −2° C. The resulting mixture was diluted with chloroform (400 mL) and the mixture stirred overnight at ambient temperature. Additional concentrated ammonium hydroxide was added to bring the pH to about 11. The mixture was transferred to a separatory funnel and the organic layer was dried over sodium sulfate and evaporated to give about 25 g of dark red oil. This oil was redissolved in ethanol (100 mL), and to the resulting stirred solution was added concentrated hydrochloric acid (10 mL). The mixture immediately formed a hard solid. Additional ethanol (100 mL) and concentrated hydrochloric acid (10 mL) were added, and after stirring for a few minutes, the resulting precipitate was collected by filtration, washed with ethanol, and air-dried. The precipitate was heated to boiling with methanol (200 mL), and the mixture was allowed to cool to ambient temperature and stand overnight. The precipitate was collected by filtration, washed with methanol, and dried under vacuum to afford 7-nitro-1,2,3,4-tetrahydroisoquinoline hydrochloride as an off-white solid (7.05 g, 23% yield).

Step B: Preparation of tert-butyl 7-nitro-3,4-dihydroisoquinoline-2(1H)-carboxylate To a stirred suspension of 7-nitro-1,2,3,4-tetrahydroisoquinoline hydrochloride (7.00 g, 32.6 mmol) in dichloromethane (150 mL) at ambient temperature was added triethylamine (9.55 mL, 68.5 mmol) To the resulting solution was added di-tert-butyl dicarbonate (7.83 g, 35.9 mmol). The resulting solution was stirred at ambient temperature for 90 minutes, then concentrated. The residue was partitioned between ethyl acetate (100 mL) and 1M citric acid (100 mL). The organic layer was washed with brine (50 mL), dried over sodium sulfate and concentrated to afford tert-butyl 7-nitro-3,4-dihydroisoquinoline-2(1H)-carboxylate as a brown oil (9.43 g, 104% yield).

Step C: Preparation of tert-butyl 7-amino-3,4-dihydroisoquinoline-2(1H)-carboxylate A solution of tert-butyl 7-nitro-3,4-dihydroisoquinoline-2(1H)-carboxylate (9.4 g, 34 mmol) in ethanol (150 mL) was treated with 10% palladium on carbon (0.5 g), and the resulting mixture was hydrogenated on a Parr shaker at an initial pressure of 40 psi for 30 minutes. The catalyst was removed by filtration through a glass microfibre filter, and the filtrate was concentrated. The residue was purified by chromatography on silica gel, eluting with 75/25 to 70/30 hexanes/ethyl acetate, to afford tert-butyl 7-amino-3,4-dihydroisoquinoline-2(1H)-carboxylate as a yellow oil (6.6 g, 79% yield).

Step D: Preparation of tert-butyl 7-(4-(6-cyano-4-(methoxycarbonyl)chroman-7-yloxy)benzamido)-3,4-dihydroisoquinoline-2(1H)-carboxylate To a stirred solution of 4-(6-cyano-4-(methoxycarbonyl)chroman-7-yloxy)benzoic acid (86 mg, 0.24 mmol) in N,N-dimethylformamide (0.5 mL) at ambient temperature was added a 0.6M solution of 7-aza-1-hydroxybenzotriazole in N,N-dimethylformamide (0.5 mL, 0.30 mmol), followed by solid 1-ethyl-(3-dimethylaminopropyl)carbodiimide hydrochloride (51 mg, 0.27 mmol). The resulting solution was stirred at ambient temperature for 1 hour. A solution of tert-butyl 7-amino-3,4-dihydroisoquinoline-2(1H)-carboxylate (66 mg, 0.27 mmol) in N,N-dimethylformamide (0.5 mL) was added. The resulting solution was stirred in an oil bath set to 50° C. for 21 hours. The solution was cooled to ambient temperature and diluted with water (15 mL). After stirring for a few minutes, the resulting precipitate was collected by filtration, washed with water, and dried under vacuum. This crude solid was purified by chromatography on silica gel, eluting with 50/50 hexanes/ethyl acetate, to afford tert-butyl 7-(4-(6-cyano-4-(methoxycarbonyl)chroman-7-yloxy)benzamido)-3,4-dihydroisoquinoline-2(1H)-carboxylate as an orange oil (84 mg, 59% yield).

Step E: Preparation of 7-(4-(2-(tert-butoxycarbonyl)-1,2,3,4-tetrahydroisoquinolin-7-ylcarbamoyl)phenoxy)-6-cyanochroman-4-carboxylic acid To a stirred solution of tert-butyl 7-(4-(6-cyano-4-(methoxycarbonyl)chroman-7-yloxy)benzamido)-3,4-dihydroisoquinoline-2(1H)-carboxylate (84 mg, 0.14 mmol) in a mixture of methanol (1 mL) and tetrahydrofuran (0.5 mL) was added 2M sodium hydroxide (0.36 mL, 0.72 mmol). The resulting solution was stirred at ambient temperature for 1 hour, then concentrated. The residue was partitioned between ethyl acetate (10 mL) and 1M hydrochloric acid (5 mL). The organic layer was dried over sodium sulfate and concentrated to afford 7-(4-(2-(tert-butoxycarbonyl)-1,2,3,4-tetrahydroisoquinolin-7-ylcarbamoyl)phenoxy)-6-cyanochroman-4-carboxylic acid as an orange oil (40 mg, 49% yield).

Step F: Preparation of 6-cyano-7-(4-(1,2,3,4-tetrahydroisoquinolin-7-ylcarbamoyl)phenoxy)chroman-4-carboxylic acid hydrochloride To a stirred solution of 7-(4-(2-(tert-butoxycarbonyl)-1,2,3,4-tetrahydroisoquinolin-7-ylcarbamoyl)phenoxy)-6-cyanochroman-4-carboxylic acid (40 mg, 0.070 mmol) in dioxane (1 mL) at ambient temperature was added a 4M solution of hydrogen chloride in dioxane (2 mL). The resulting solution was stirred at ambient temperature for 90 minutes. Some dark material had separated from the cloudy reaction mixture, and the supernatant was concentrated to afford 6-cyano-7-(4-(1,2,3,4-tetrahydroisoquinolin-7-ylcarbamoyl)phenoxy)chroman-4-carboxylic acid hydro-chloride as a light tan solid (30 mg, 84% yield). MS (apci) m/z=470.2 (M-Cl).

Example 46

Sodium 6,8-dichloro-7-(4-(4-chlorophenethylcarbamoyl)phenoxy)chroman-4-carboxylate

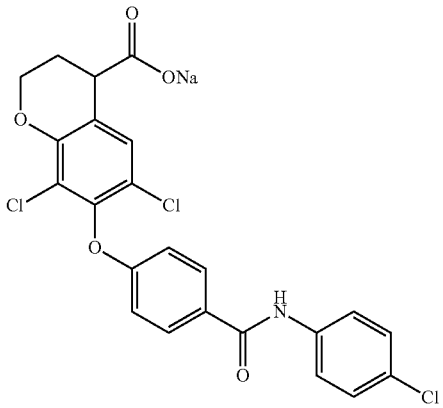

Step A: Preparation of ethyl 6,8-dichloro-7-hydroxychroman-4-carboxylate

To a mixture of ethyl 6-chloro-7-hydroxychroman-4-carboxylate (Preparation 1) (50 g, 194.79 mmol), diisobutylamine (2.72 ml, 15.58 mmol), and toluene (500 ml) was added $SO_2Cl_2$ (16.43 ml, 204.53 mmol) at ambient temperature. The mixture was heated to 70° C. for 1 hour. The mixture was washed with water and saturated aqueous $NaHCO_3$ solution (3×100 ml). The combined organic extracts were washed with brine (250 mL), dried over $MgSO_4$, filtered, and concentrated under reduced pressure to provide an oil. The crude oil (~60 g) was purified on silica gel (EtOAc in hexanes gradient) to provide 48.5 g of the title compound as a solid (86%).

Step B: Preparation of tert-butyl 4-fluoro-3-nitrobenzoate

To a 2 L high pressure vessel were added 4-fluoro-3-nitrobenzoic acid (25 g, 135 mmol), dimethylformamide di-t-butylacetal (162 ml, 675 mmol), and toluene (200 ml). The vessel was sealed and heated to 100° C. for 20 hours. The mixture was cooled to ambient temperature. The mixture was transferred to 100 mL of EtOAc and 100 ml of 1N HCl and the layers were separated. The organic layer was washed with 1N HCl, water, and brine, dried over $MgSO_4$, filtered through a medium frit filter, and concentrated. The crude was purified on silica gel (EtOAc in hexanes gradient) to provide 5.1 g of the title compound were obtained as light yellow solid (16%).

Step C: Preparation of ethyl 7-(4-(tert-butoxycarbonyl)-2-nitrophenoxy)-6,8-dichlorochroman-4-carboxylate A mixture of ethyl 6,8-dichloro-7-hydroxychroman-4-carboxylate (35 g, 120.22 mmol), tert-butyl 4-fluoro-3-nitrobenzoate (31.1 g, 128.93 mmol), $K_2CO_3$ (24.923 g, 180.33 mmol), and 1-methyl-2-pyrrolidinone (500 mL) was purged with Argon (bubbled through) for 15 minutes. The mixture was heated to 80° C. for 4 hours under Argon atmosphere. The mixture was cooled to ambient temperature and poured into 3 liters of water. The pH was adjusted to pH 2 by addition of concentrated HCl (4×10 ml). A solid precipitated out as HCl was added and gas evolution was observed. The crude mixture was filtered and the solid was dissolved in EtOAc (1 liter). The EtOAc solution was washed with 2N HCl solution (200 ml), water (2×200 ml), and brine (200 ml), dried over $MgSO_4$, filtered, and concentrated to provide 64.1 g of the title compound as a dark solid (104%).

Step D: Preparation of ethyl 7-(2-amino-4-(tert-butoxycarbonyl)phenoxy)-6,8-dichlorochroman-4-carboxylate A mixture of ethyl 7-(4-(tert-butoxycarbonyl)-2-nitrophenoxy)-6,8-dichlorochroman-4-carboxylate (61.593 g, 120.22 mmol), THF (500 ml), and saturated NH4Cl solution (500 ml) was purged with Argon for 10 minutes. Zn dust (78.612 g, 1202.2 mmol) was added and the mixture was stirred at ambient temperature for 1 hour under Argon atmosphere. The reaction was slightly exothermic. The mixture was diluted with EtOAc (500 ml) and filtered. The filtered solid was rinsed with EtOAc (250 ml). The filtrate was transferred to a 3 L separatory funnel. The layers were separated and the organic layer was washed with brine (250 ml). The organic layer was dried over $MgSO_4$, filtered, and concentrated. The crude residue was purified on silica gel (EtOAc in hexanes gradient) to provide 45.6 g of the title compound as an oil (79%).

Step E: Preparation of ethyl 7-(4-(tert-butoxycarbonyl)phenoxy)-6,8-dichlorochroman-4-carboxylate To a 2 L four neck round bottomed flask equipped with a thermocouple, a condenser, and an addition funnel were added DMF (200 ml) and isobutyl nitrite (30.8 ml, 260 mmol). The mixture was heated to 70° C. To the preheated mixture was added a solution of ethyl 7-(2-amino-4-(tert-butoxycarbonyl)phenoxy)-6,8-dichlorochroman-4-carboxylate (50.2 g, 104 mmol) in DMF (200 ml) over a period of 15 minutes. The reaction was slightly exothermic and gas evolution was observed. The mixture was stirred at 70° C. for 1.5 hours and cooled to ambient temperature. The mixture was transferred to a separatory funnel containing 2 liters of water. The mixture was extracted with EtOAc (500 ml, 2×250 ml). The combined extracts were washed with water (500 ml, 2×250 ml) and brine (250 ml), dried over MgSO$_4$, filtered, and concentrated. The residue was purified on silica gel (EtOAc in hexanes gradient) to provide 45.1 g of the title compound as a very viscous oil (93%).

Step F: Preparation of 4-(6,8-dichloro-4-(ethoxycarbonyl)chroman-7-yloxy)benzoic acid Ethyl 7-(4-(tert-butoxycarbonyl)phenoxy)-6,8-dichloro-chroman-4-carboxylate (45.1 g, 96.5 mmol) was dissolved in dichloromethane (500 ml). Trifluoroacetic acid (100 ml) was added slowly to the solution. The mixture was stirred for 2 hours at ambient temperature. The crude mixture was concentrated and the residue was dissolved in EtOAc (500 ml). The EtOAc solution was washed with saturated NaHCO$_3$ (3×100 ml) and brine (250 ml), dried over MgSO$_4$, filtered, and concentrated to provide 40.3 g of the title compound as a light brown solid (102%).

Step G: Preparation of ethyl 6,8-dichloro-7-(4-(4-chlorophenethylcarbamoyl)phenoxy)chroman-4-carboxylate 4-(6,8-Dichloro-4-(ethoxycarbonyl)chroman-7-yloxy)benzoic acid (22.96 g, 55.832 mmol) was dissolved in dichloromethane (200 ml) and DMF (0.2 ml). Oxalyl chloride (8.6 ml, 98.585 mmol) was added slowly over a period of 30 minutes at ambient temperature. The crude mixture was concentrated under reduced pressure. Dry dichloromethane (200 ml) was added and the mixture was cooled in an ice bath. 2-(4-Chlorophenyl)ethylamine (8.5413 ml, 61.415 mmol) and diisopropylethylamine (11.701 ml, 66.999 mmol) were added sequentially to the mixture. The mixture was stirred in an ice bath for 10 minutes and warmed to ambient temperature. The crude mixture was washed with 1N HCl (100 ml), water (2×50 ml), and brine (50 ml), dried over MgSO$_4$, filtered through GF paper, and concentrated to provide 30.1 g of a light brown solid after drying under high vacuum for 2 hours. The crude solid was recrystallized from hot EtOAc-hexanes to provide 26.8 g of the title compound as a light brown solid (87%).

Step H: Preparation of 6,8-dichloro-7-(4-(4-chlorophenethylcarbamoyl)phenoxy)chroman-4-carboxylic acid Ethyl 6,8-dichloro-7-(4-(4-chlorophenethylcarbamoyl)phenoxy)chroman-4-carboxylate (26.8 g, 48.83 mmol) was dissolved in 200 proof EtOH (50 ml)-THF (170 ml). 6N NaOH solution (12.21 ml, 73.25 mmol) was added to the mixture at ambient temperature. The mixture was stirred for 1 hour at ambient temperature. The mixture was transferred to a separatory funnel. 1N HCl solution (97.66 ml, 97.66 mmol) was added to the separatory funnel and EtOAc (100 ml) was added. The mixture was shaken and stood for layer separation. The layers were separated and the organic layer was washed with water and brine (100 ml), dried over MgSO$_4$, filtered, and concentrated to provide 28 g of foamy brown solid after drying under high vacuum. The crude solid was recrystallized from THF-hexanes to provide 22.8 g of the title compound as a white solid (89%).

Step I: Preparation of sodium 6,8-dichloro-7-(4-(4-chlorophenethylcarbamoyl)phenoxy)chroman-4-carboxylate 6,8-Dichloro-7-(4-(4-chlorophenethylcarbamoyl)phenoxy)chroman-4-carboxylic acid (22.78 g, 43.26 mmol) was dissolved in THF (100 ml) and 0.5M NaOMe solution in MeOH (86.52 ml, 43.26 mmol) was added at ambient temperature. The mixture was stirred for 1 hour and concentrated. A very thick light brown solid was obtained. The crude solid was treated with EtOH-hexanes and filtered to provide 23.4 g of the title compound as a white solid (99%). MS (apci) m/z=520.1 (M+2H—Na).

Example 47

7-(4-((2-Phenylcyclopropyl)carbamoyl)phenoxy)-6-cyano-3,4-dihydro-2H-chromene-4-carboxylic acid

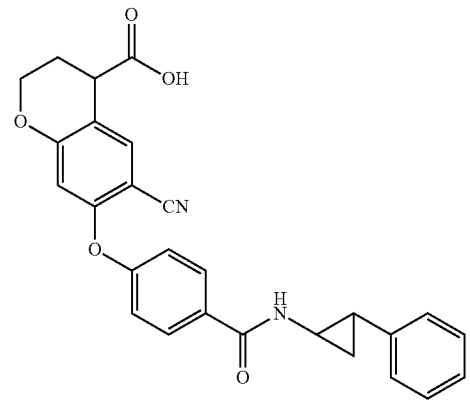 [SMILES: N#Cc1cc2c(cc1Oc1ccc(C(=O)NC3CC3c3ccccc3)cc1)OCCC2C(=O)O]

Step A: Preparation of methyl 7-(4-((2-phenylcyclopropyl)carbamoyl)phenoxy)-6-cyano-3,4-dihydro-2H-chromene-4-carboxylate To a solution of 4-(6-cyano-4-(methoxycarbonyl)chroman-7-yloxy)benzoic acid (Preparation 2) (21.8 mg, 0.0617 mmol) in dichloromethane (1 ml) with a drop of DMF was added oxalyl chloride (2M in dichloromethane) (0.0370 ml, 0.0740 mmol). Gas evolution was observed. The mixture was stirred for 0.5 hours at ambient temperature. Triethylamine (0.0430 ml, 0.3085 mmol) and 2-phenylcyclopropanamine, hemisulfate (28.11 mg, 0.1542 mmol) were added sequentially to the mixture. The mixture was stirred for 17 hours at ambient temperature. The crude mixture was purified on silica gel (MeOH in dichloromethane gradient) to provide 25.9 mg of the title compound as a thin film (90%).

Step B: Preparation of 7-(4-((2-phenylcyclopropyl)carbamoyl)phenoxy)-6-cyano-3,4-dihydro-2H-chromene-4-carboxylic acid Methyl 7-(4-((2-phenylcyclopropyl)carbamoyl)phenoxy)-6-cyano-3,4-dihydro-2H-chromene-4-carboxylate (25.9 mg, 0.0553 mmol) was dissolved in THF (1.5 ml) and 1M LiOH-monohydrate solution in water (0.111 ml, 0.111 mmol) was added. The mixture was stirred for 17 hours at ambient temperature. A few drops of trifluoroacetic acid were added to the mixture and the mixture was purified on silica gel (MeOH in

Example 48

7-(4-((3-Methoxyphenethyl)carbamoyl)phenoxy)-6-cyano-3,4-dihydro-2H-chromene-4-carboxylic acid dichloromethane gradient with 1% acetic acid) to provide 7.7 mg of the title compound as a thin film (30%). MS (apci) m/z=453.0 (M–H).

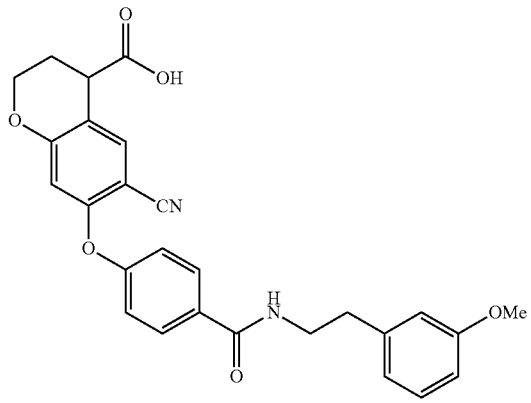 [SMILES: COc1cccc(CCNC(=O)c2ccc(Oc3cc4c(cc3C#N)C(C(=O)O)CCO4)cc2)c1]

Prepared according to Example 47, substituting 3-methoxyphenethylamine for 2-phenylcyclopropanamine in step A to provide 9.3 mg of the title compound (72%). MS (apci) m/z=470.9 (M–H).

Example 49

7-(4-((4-Fluorophenethyl)carbamoyl)phenoxy)-6-cyano-3,4-dihydro-2H-chromene-4-carboxylic acid

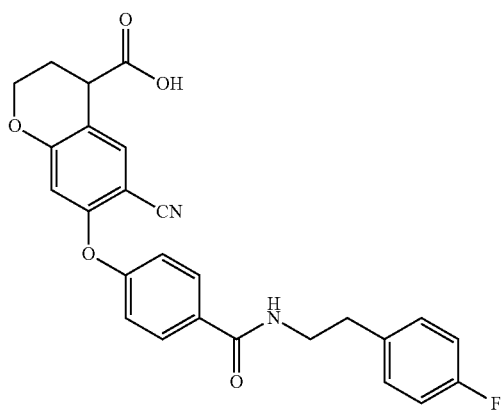 [SMILES: N#Cc1cc2c(cc1Oc1ccc(C(=O)NCCc3ccc(F)cc3)cc1)OCCC2C(=O)O]

Prepared according to Example 47, substituting 4-Fluorophenethylamine for 2-phenylcyclopropyanamine in Step A to provide 8.7 mg of the title compound (70%). MS (apci)= 458.7 (M–H).

Example 50

7-(4-((4-(Trifluoromethyl)phenethyl)carbamoyl) phenoxy)-6-cyano-3,4-dihydro-2H-chromene-4-carboxylic acid

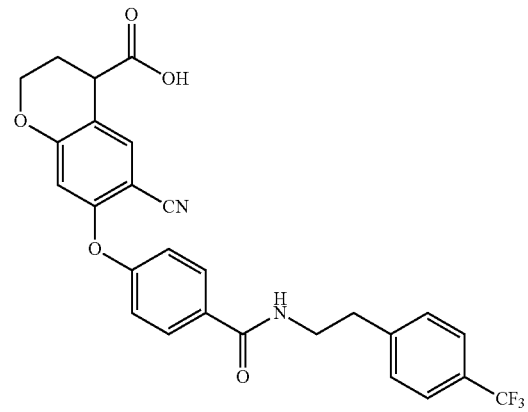 [SMILES: N#Cc1cc2c(cc1Oc1ccc(C(=O)NCCc3ccc(C(F)(F)F)cc3)cc1)OCCC2C(=O)O]

Prepared according to Example 47, substituting 4-Trifluoromethylphenethylamine for 2-phenylcyclopropyanamine in Step A to provide 5.0 mg of the title compound (47%).

Example 51

7-(4-((2-(4-Chlorophenyl)cyclopropyl)carbamoyl) phenoxy)-6-cyano-3,4-dihydro-2H-chromene-4-carboxylic acid

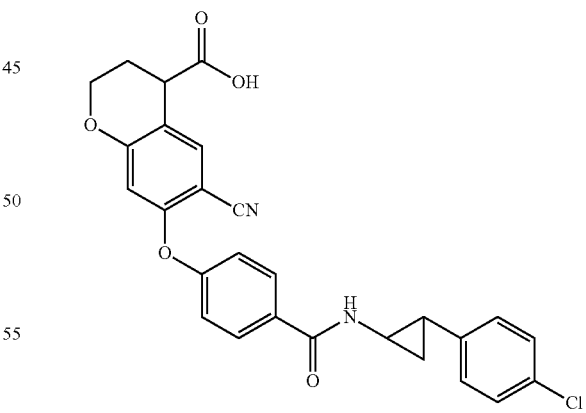

Step A: Preparation of ethyl 2-(4-chlorophenyl)cyclopropanecarboxylate

To a mixture of 4-chlorostyrene (1.20 ml, 10.0 mmol), Rh$_2$(OAc)$_4$ (0.221 g, 0.500 mmol), and toluene (20 ml) was added ethyl diazoacetate (1.09 ml, 10.50 mmol). Gas evolution was observed. The mixture was heated to 80° C. for 1 hour. The mixture was purified on silica gel (EtOAc in hexanes gradient) to provide 0.216 g of the title compound as an oil (9%).

Step B: Preparation of 2-(4-chlorophenyl)cyclopropanecarboxylic acid

Ethyl 2-(4-chlorophenyl)-cyclopropanecarboxylate (0.210 g, 0.935 mmol) was placed in a 50 ml flask and dissolved in EtOH (5 ml). NaOMe in MeOH (25%, 0.808 g, 3.74 mmol) was added to the mixture. The mixture was heated for 17 hours under reflux and then concentrated. The residue was dissolved in MeOH (10 ml), and 1M solution of LiOH—$H_2O$ (3.74 ml, 3.74 mmol) was added. The methanol was removed under reduced pressure. The residue was diluted with water (10 ml) and washed with EtOAc (10 ml). The aqueous layer was acidified by 1N HCl (10 ml) to pH 1 and a solid precipitated out of solution. The mixture was extracted with EtOAc (3×10 ml) and the combined extracts were dried over $MgSO_4$, filtered, and concentrated to provide 181 mg of the title compound as a solid (98%). The crude solid was used in the next step without further purification.

Step C: Preparation of tert-butyl 2-(4-chlorophenyl)cyclopropylcarbamate

A mixture of 2-(4-chlorophenyl)cyclopropanecarboxylic acid (100 mg, 0.509 mmol), diphenylphosphoryl azide (0.1209 ml, 0.559 mmol), triethylamine (0.106 ml, 0.763 mmol), and t-BuOH (2 ml) was heated at 90° C. under nitrogen atmosphere 17 hours. The mixture was concentrated, diluted with EtOAc (20 ml), and washed with saturated $K_2CO_3$ solution (10 ml). The EtOAc layer was dried over $MgSO_4$, filtered, concentrated, and dried under high vacuum for 17 hours to provide 300 mg of a light brown solid. The crude solid was purified on silica gel (EtOAc in hexanes gradient) to provide 64.7 mg of the title compound as a solid (47.5%).

Step D: Preparation of 2-(4-chlorophenyl)cyclopropanamine hydrochloride tert-Butyl 2-(4-chlorophenyl)cyclopropylcarbamate (51.9 mg, 0.1938 mmol) was dissolved in Dichloromethane (1 ml) and 4M HCl solution in dioxane (0.4846 ml, 1.938 mmol) was added. The mixture was stirred for 3 hours at ambient temperature, during which time a white solid precipitated out of solution. The crude mixture was concentrated and chased with EtOAc (2×10 ml). The residual fine solid was dried under high vacuum to provide 39.2 mg of the title compound as a solid (99%).

Step E: Preparation of methyl 7-(4-((2-(4-chlorophenyl)cyclopropyl)carbamoyl)phenoxy)-6-cyano-3,4-dihydro-2H-chromene-4-carboxylate A mixture of 4-(6-cyano-4-(methoxycarbonyl)chroman-7-yloxy)benzoic acid (Preparation 2) (0.041 g, 0.116 mmol), 1-(3-(dimethylamino)propyl)-3-ethyl-carbodiimide hydrochloride (0.0245 g, 0.128 mmol), 1-hydroxybenzotriazole monohydrate (0.0195 g, 0.128 mmol), and 1,2-dichloroethane (1 ml) was stirred at room temp for 0.5 hours. A mixture of 2-(4-chlorophenyl)cyclopropanamine hydrochloride (0.0261 g, 0.128 mmol) and triethylamine (0.0809 ml, 0.580 mmol) in 1,2-dichloroethane (1 ml) was added to the activated acid mixture. The mixture was stirred at ambient temperature for 1 hour. The crude mixture was directly purified on silica gel (EtOAc in hexanes gradient) to provide 50.7 mg of the title compound as a thin film (87%).

Step F: Preparation of 7-(4-((2-(4-chlorophenyl)cyclopropyl)carbamoyl)phenoxy)-6-cyano-3,4-dihydro-2H-chromene-4-carboxylic acid methyl 7-(4-((2-(4-chlorophenyl)cyclopropyl)carbamoyl)phenoxy)-6-cyano-3,4-dihydro-2H-chromene-4-carboxylate (50.7 mg, 0.101 mmol) was dissolved in THF (3 ml). A 1M solution of LiOH—$H_2O$ (0.202 ml, 0.202 mmol) was added and the mixture was stirred for 17 hours at ambient temperature. HCl (4M in dioxane) (0.0756 ml, 0.302 mmol) was added to the mixture. The solution was stirred additional 30 minutes and concentrated. The residue was purified on silica gel (MeOH in dichloromethane with 1% acetic acid gradient) to provide 47 mg of the title compound as a solid (95%). MS (apci) m/z=486.7 (M–H).

Example 52

7-(4-(chroman-3-ylcarbamoyl)phenoxy)-6-cyano-chroman-4-carboxylic acid

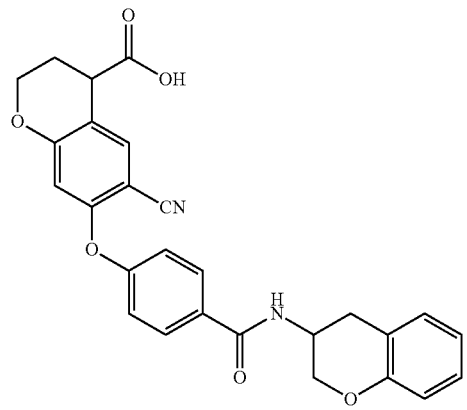 [SMILES: N#Cc1cc2c(cc1Oc1ccc(C(=O)NC3COc4ccccc4C3)cc1)OCCC2C(=O)O]

Step A: Preparation of methyl 7-(4-(chroman-3-ylcarbamoyl)phenoxy)-6-cyano-3,4-dihydro-2H-chromene-4-carboxylate A mixture of 4-(6-cyano-4-(methoxycarbonyl)chroman-7-yloxy)benzoic acid (Preparation 2) (0.0308 g, 0.0871 mmol), 1-(3-(dimethylamino)propyl)-3-ethyl-carbodiimide hydrochloride (0.01838 g, 0.0958 mmol), 1-hydroxybenzotriazole monohydrate (0.0146 g, 0.095 mmol), and 1,2-dichloroethane (1 ml) was stirred at ambient temperature for 20 minutes. A mixture of chroman-3-amine hydrochloride (0.01780 g, 0.09589 mmol), triethylamine (0.06075 ml, 0.435 mmol), and 1,2-dichloroethane (1 ml) was added to the activated acid and the mixture was stirred for 17 hours at ambient temperature. The crude mixture was purified on silica gel (MeOH in dichloromethane gradient) to provide 27.6 mg of the title compound as a foamy film (65%)

Step B: Preparation of 7-(4-(chroman-3-ylcarbamoyl)phenoxy)-6-cyanochroman-4-carboxylic acid Methyl 7-(4-(chroman-3-ylcarbamoyl)phenoxy)-6-cyano-3,4-dihydro-2H-chromene-4-carboxylate (27.6 mg, 0.0570 mmol) was dissolved in THF (3 ml) and 1M solution of LiOH—H₂O (114 µL, 0.114 mmol) was added. The mixture was stirred for 17 hours at ambient temperature. The mixture was quenched with 4M HCl dioxane (42.7 µL, 0.171 mmol). The crude mixture was purified on silica gel (MeOH in dichloromethane with 1% acetic acid gradient) to provide 21.2 mg of the title compound as white a solid (79%). MS (apci) m/z=471.0 (M+H).

Example 53

6-Cyano-7-(4-(6-methoxy-1,2,3,4-tetrahydronaphthalen-2-ylcarbamoyl)phenoxy)chroman-4-carboxylic acid

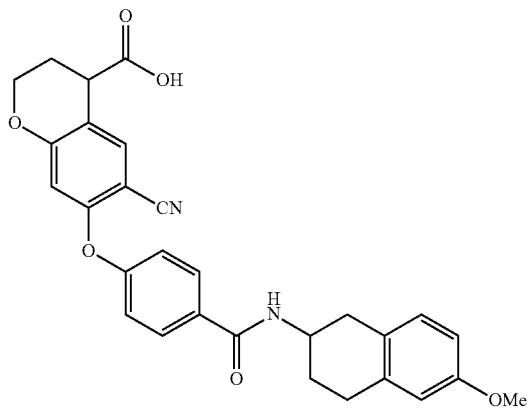 [SMILES: COc1ccc2c(c1)CCC(NC(=O)c1ccc(Oc3cc4c(cc3C#N)C(C(=O)O)CCO4)cc1)C2]

Step A: Preparation of methyl 7-(4-((6-methoxy-1,2,3,4-tetrahydronaphthalen-2-yl)carbamoyl)phenoxy)-6-cyano-3,4-dihydro-2H-chromene-4-carboxylate A mixture of 4-(6-cyano-4-(methoxycarbonyl)-chroman-7-yloxy)benzoic acid (Preparation 2) (0.0297 g, 0.0841 mmol), 1-(3-(dimethylamino)propyl)-3-ethyl-carbodiimide hydrochloride (0.0177 g, 0.0925 mmol), 1-hydroxybenzotriazole monohydrate (0.0142 g, 0.0925 mmol), and 1,2-dichloroethane (1 ml) was stirred at ambient temperature for 20 minutes. A mixture of chroman-6-methoxy-1,2,3,4-tetrahydronaphthalen-2-amine hydrochloride (0.0197 g, 0.0924 mmol), triethylamine (0.0585 ml, 0.4203 mmol)), and 1,2-dichloroethane (1 ml) was added to the activated acid and the mixture was stirred for 17 hours at ambient temperature. The crude mixture was purified on silica gel (MeOH in dichloromethane gradient) to provide 29.5 mg of the title compound as a foamy film (69%)

Step B: Preparation of 6-cyano-7-(4-(6-methoxy-1,2,3,4-tetrahydronaphthalen-2-ylcarbamoyl)phenoxy)-chroman-4-carboxylic acid 7-(4-((6-Methoxy-1,2,3,4-tetrahydronaphthalen-2-yl)carbamoyl)phenoxy)-6-cyano-3,4-dihydro-2H-chromene-4-carboxylate (29.5 mg, 0.0576 mmol) was dissolved in THF (3 ml) and 1M solution of LiOH—H₂O (115 µL, 0.115 mmol) was added. The mixture was stirred for 17 hours at ambient temperature. The mixture was quenched with 4M HCl dioxane (43.2 µL, 0.173 mmol). The crude mixture was purified on silica gel (MeOH in dichloromethane with 1% acetic acid gradient) to provide 28.9 mg of the title compound as a thin film (100%). MS (apci) m/z=499.1 (M+H).

Example 54

6-Cyano-7-(4-(naphthalen-1-ylmethylcarbamoyl)phenoxy)chroman-4-carboxylic acid

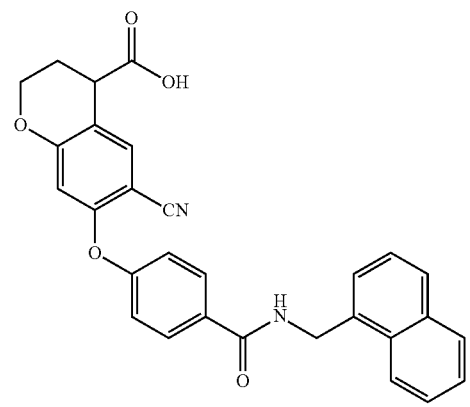 [SMILES: N#Cc1cc2c(cc1Oc1ccc(C(=O)NCc3cccc4ccccc34)cc1)OCCC2C(=O)O]

Prepared according to Example 53, substituting naphthalen-1-ylmethanamine for chroman-6-methoxy-1,2,3,4-tetrahydronaphthalen-2-amine hydrochloride in Step A to provide 22.9 mg of the title compound as a thin film (92%). MS (apci) m/z=476.8 (M−H).

Example 55

6-Cyano-7-(4-(2-(naphthalen-1-yl)ethylcarbamoyl)phenoxy)chroman-4-carboxylic acid

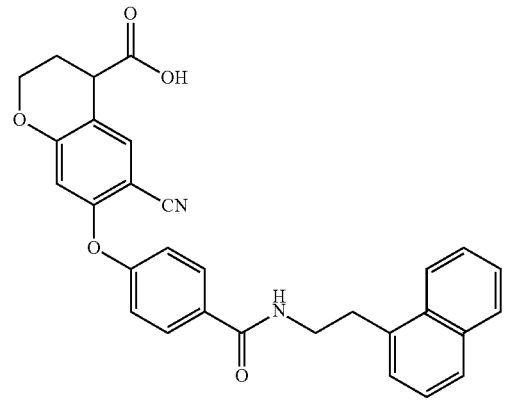 [SMILES: N#Cc1cc2c(cc1Oc1ccc(C(=O)NCCc3cccc4ccccc34)cc1)OCCC2C(=O)O]

Prepared according to Example 53, substituting 2-(naphthalen-1-yl)ethanamine for chroman-6-methoxy-1,2,3,4-tetrahydronaphthalen-2-amine hydrochloride in Step A to provide 24.1 mg of the title compound as a thin film (86%). MS (apci) m/z=490.9 (M−H).

Example 56

6-Cyano-7-(4-(2-(naphthalen-2-yl)ethylcarbamoyl)phenoxy)chroman-4-carboxylic acid

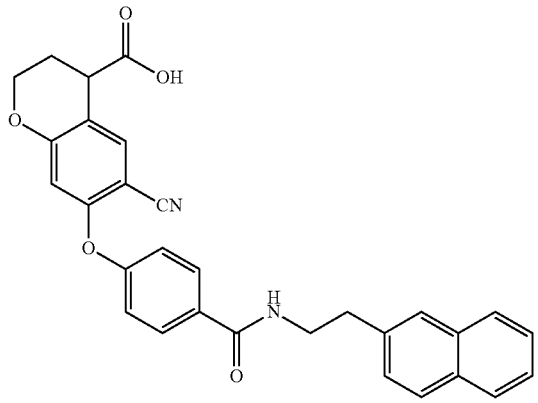 [SMILES: N#Cc1cc2c(cc1Oc1ccc(C(=O)NCCc3ccc4ccccc4c3)cc1)OCCC2C(=O)O]

Prepared according to Example 53, substituting 2-(naphthalen-2-yl)ethanamine for chroman-6-methoxy-1,2,3,4-tetrahydronaphthalen-2-amine hydrochloride in Step A to provide 8.4 mg of the title compound as a thin film (49%). MS (apci) m/z=490.9 (M−H).

Example 57

7-(4-(4-tert-Butylphenethylcarbamoyl)phenoxy)-6-cyanochroman-4-carboxylic acid

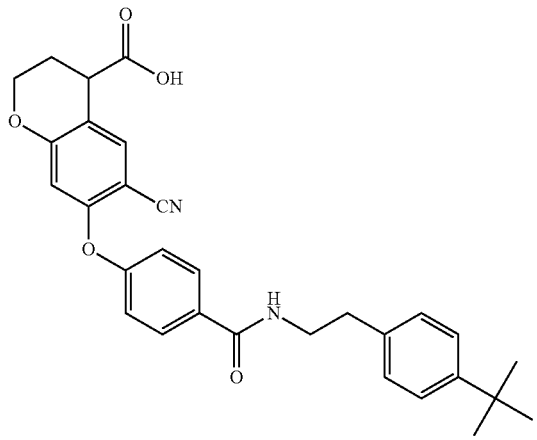 [SMILES: CC(C)(C)c1ccc(CCNC(=O)c2ccc(Oc3cc4c(cc3C#N)C(C(=O)O)CCO4)cc2)cc1]

Prepared according to Example 53, substituting 2-(4-tert-butylphenyl)ethanamine for chroman-6-methoxy-1,2,3,4- tetrahydronaphthalen-2-amine hydrochloride in Step A to provide 18 mg of the title compound as a thin film (77%). MS (apci) m/z=499.1 (M−H).

Example 58

7-(4-(2-(Biphenyl-4-yl)ethylcarbamoyl)phenoxy)-6-cyanochroman-4-carboxylic acid

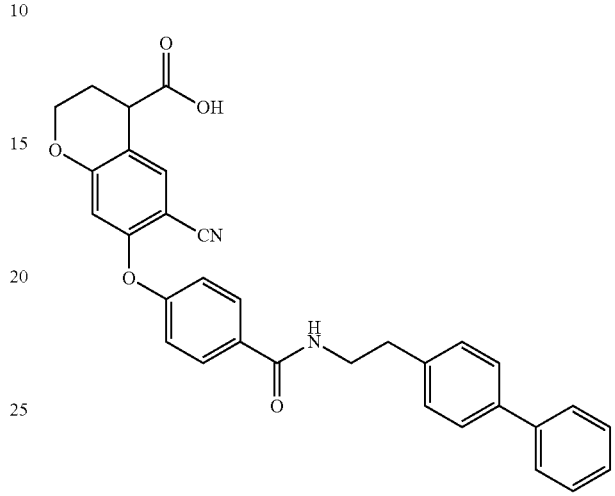

Prepared according to Example 53, substituting 2-(Biphenyl-4-yl)ethanamine for chroman-6-methoxy-1,2,3,4-tetrahydronaphthalen-2-amine hydrochloride in Step A to provide 32.5 mg of the title compound as a white solid (90%). MS (apci) m/z=519.1 (M+H).

Example 59

7-(4-(2-Biphenyl-4-yl)ethylcarbamoyl)phenoxy)-6-chlorochroman-4-carboxylic acid

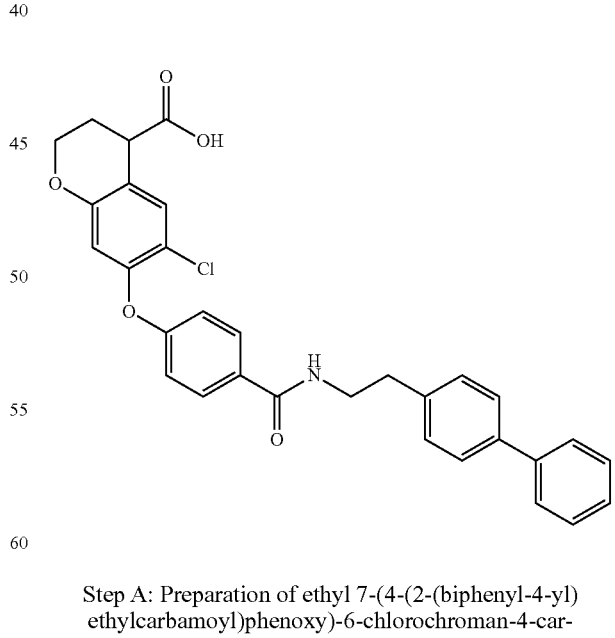

Step A: Preparation of ethyl 7-(4-(2-(biphenyl-4-yl)ethylcarbamoyl)phenoxy)-6-chlorochroman-4-carboxylate To a solution of 4-(6-chloro-4-(ethoxycarbonyl)chroman-7-yloxy)benzoic acid (Preparation 1) (50 mg, 0.133 mmol) in dichloromethane (1 ml) and a drop of DMF was added oxalyl chloride (2M in dichloromethane) (72.985 µL, 0.145 mmol) at ambient temperature. Gas evolution was observed. The mixture was stirred at ambient temperature for 30 minutes. 2-(Biphenyl-4-yl)ethanamine (27.488 mg, 0.139 mmol) and triethylamine (36.992 µL, 0.265 mmol) were added and the mixture was stirred for 1 hour at ambient temperature. The crude mixture was purified on silica gel (MeOH in dichloromethane gradient) to provide 62.5 mg of the title compound as a solid (85%).

Step B: Preparation of 7-(4-(2-(biphenyl-4-yl)ethylcarbamoyl)phenoxy)-6-chlorochroman-4-carboxylic acid Ethyl 7-(4-(2-(biphenyl-4-yl)ethylcarbamoyl)phenoxy)-6-cyanochroman-4-carboxylate (62.5 mg, 0.1124 mmol) was dissolved in THF (1 ml) and 1M solution of LiOH—H$_2$O (224.8 µL, 0.2248 mmol) was added. The mixture was stirred for 3 days at ambient temperature. The mixture was quenched with 1M HCl solution (400 µL, 0.400 mmol). The crude mixture was purified on silica gel (MeOH in dichloromethane with 1% acetic acid gradient) to provide 48.8 mg of the title compound as a white solid (82%).

Step C: Preparation of sodium 7-(4-(2-(biphenyl-4-yl)ethylcarbamoyl)phenoxy)-6-chlorochroman-4-carboxylate 7-(4-(2-(Biphenyl-4-yl)ethylcarbamoyl)phenoxy)-6-chlorochroman-4-carboxylic acid (42 mg, 0.07955 mmol) was dissolved in MeOH-THF (1 ml-1 ml). A 0.5 M solution of NaOMe in MeOH (159.1 µl, 0.0795 mmol) was added and the mixture was stirred for few minutes. The crude mixture was concentrated and chased with EtOAc and dichloromethane to provide 44.6 mg of the title compound as a white solid (102%). MS (apci) m/z=528.1 (M+2H—Na).

Example 60

Sodium 6-chloro-7-(4-((R)-2-phenylpropylcarbamoyl)phenoxy)chroman-4-carboxylate

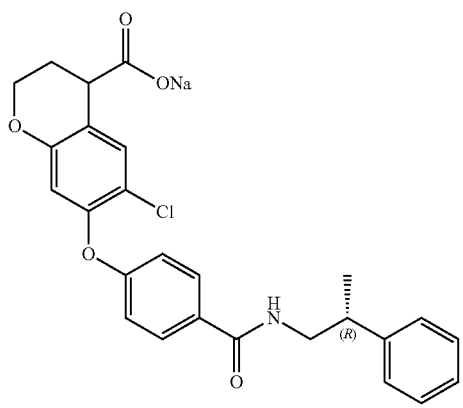

Prepared according to Example 59, substituting (R)-2-phenylpropan-1-amine for 2-(Biphenyl-4-yl)ethanamine in step A to provide 78.1 mg of the title compound as a white solid (99%). $^1$H NMR (400 MHz, DMSO-D$_6$) δ 8.42 (t, J=5.9 Hz, 1H), 7.79-7.76 (m, 2H), 7.54 (s, 1H), 7.32-7.23 (m, 4H), 7.21-7.17 (m, 1H), 6.92-6.88 (m, 2H), 6.50 (s, 1H), 4.23-4.17 (m, 1H), 4.12-4.07 (m, 1H), 3.44-3.33 (m, 2H), 3.20-3.16 (m, 1H), 3.08-3.03 (m, 1H), 2.23-2.15 (m, 1H), 1.79-1.70 (m, 1H), 1.21 (d, J=7.0 Hz, 3H).

Example 61

Sodium 6-chloro-7-(4-((S)-2-phenylpropylcarbamoyl)phenoxy)chroman-4-carboxylate

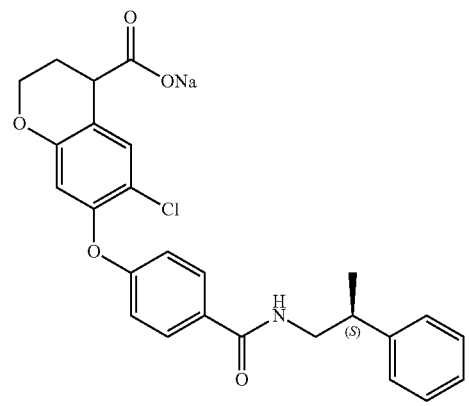

Prepared according to Example 59, substituting (S)-2-phenylpropan-1-amine for 2-(Biphenyl-4-yl)ethanamine in step A to provide 79.7 mg of the title compound as a white solid (97%). $^1$H NMR (400 MHz, DMSO-D$_6$) δ 8.42 (t, J=5.9 Hz, 1H), 7.79-7.76 (m, 2H), 7.54 (s, 1H), 7.32-7.23 (m, 4H), 7.21-7.17 (m, 1H), 6.92-6.88 (m, 2H), 6.50 (s, 1H), 4.23-4.17 (m, 1H), 4.12-4.07 (m, 1H), 3.44-3.33 (m, 2H), 3.20-3.16 (m, 1H), 3.08-3.03 (m, 1H), 2.23-2.15 (m, 1H), 1.79-1.70 (m, 1H), 1.21 (d, J=7.0 Hz, 3H).

Example 62

Sodium 6-chloro-7-(4-(2-(4-chlorophenyl)propylcarbamoyl)phenoxy)chroman-4-carboxylate

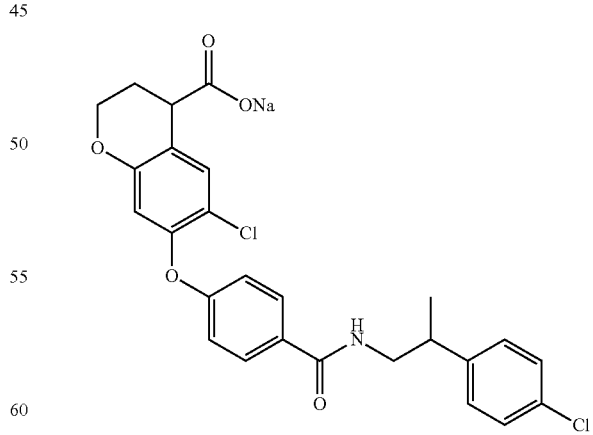

Prepared according to Example 59, substituting p-Chloro-β-methyl-phenethylamine-HCl salt for 2-(Biphenyl-4-yl)ethanamine in step A to provide 92.3 mg of the title compound as a white solid (101%). $^1$H NMR (400 MHz, DMSO-D$_6$) δ 8.41 (t, J=5.9 Hz, 1H), 7.78-7.74 (m, 2H), 7.54 (s, 1H), 7.36-7.33 (m, 2H), 7.29-7.25 (m, 2H), 6.92-6.88 (m, 2H), 6.50 (s, 1H), 4.23-4.16 (m, 1H), 4.13-4.06 (m, 1H), 3.42-3.33 (m, 2H), 3.21-3.16 (m, 1H), 3.09-3.03 (m, 1H), 2.22-2.15 (m, 1H), 1.79-1.70 (m, 1H), 1.21 (d, J=7.0 Hz, 3H).

Example 63

Sodium 6-chloro-7-(4-(2-methoxyphenethylcarbamoyl)phenoxy)chroman-4-carboxylate

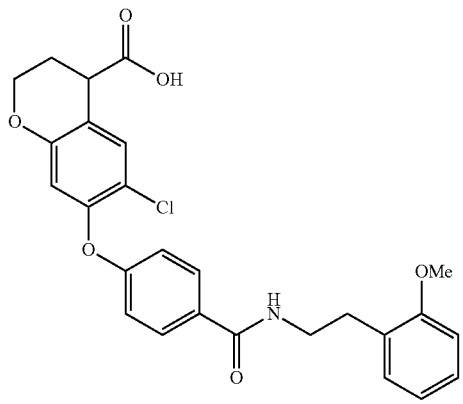 [SMILES: COc1ccccc1CCNC(=O)c1ccc(Oc2cc3c(cc2Cl)C(C(=O)O)CCO3)cc1]

Prepared according to Example 59, substituting 2-Methoxyphenethylamine for 2-(Biphenyl-4-yl)ethanamine in step A to provide 38.8 mg of the title compound as a white solid (107%). MS (apci) m/z=482.0 (M+2H—Na).

Example 64

Sodium 6-chloro-7-(4-(2-(trifluoromethoxy)phenethylcarbamoyl)phenoxy)chroman-4-carboxylate

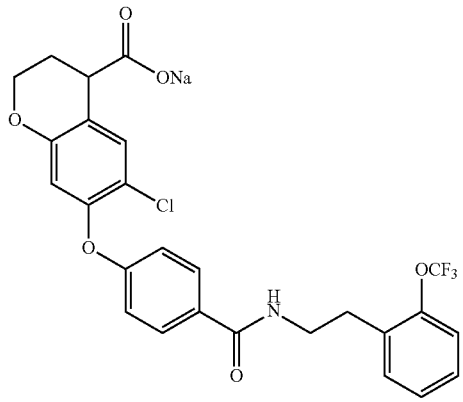

Prepared according to Example 59, substituting 2-(trifluoromethoxy)phenethylamine for 2-(Biphenyl-4-yl)ethanamine in step A to provide 46 mg of the title compound as a white solid (101%). MS (apci) m/z=536.1 (M+2H—Na).

Example 65

Sodium 6-chloro-7-(4-(2-phenoxyphenethylcarbamoyl)phenoxy)chroman-4-carboxylate

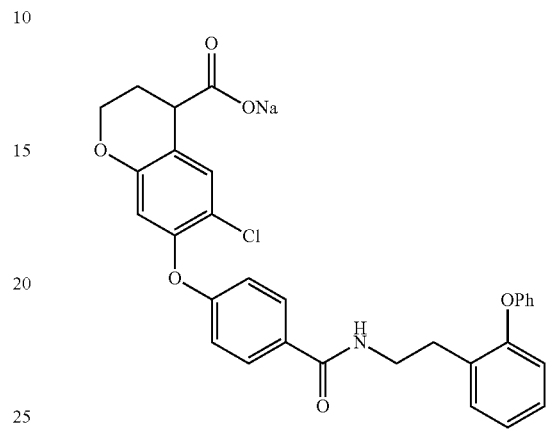

Prepared according to Example 59, substituting 2-phenoxyphenethylamine for 2-(Biphenyl-4-yl)ethanamine in step A to provide 48.3 mg of the title compound as a white solid (111%). MS (apci) m/z=544.0 (M+2H—Na).

Example 66

6-Cyano-7-(4-(3',4'-dimethylbiphenyl-3-ylcarbamoyl)phenoxy)chroman-4-carboxylic acid

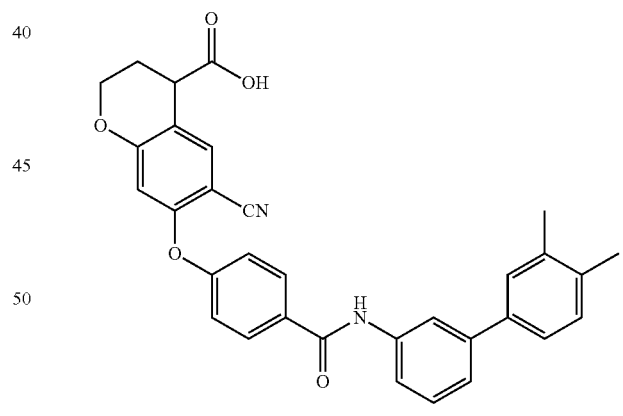

Step A: Preparation of methyl 6-cyano-7-(4-(3',4'-dimethylbiphenyl-3-ylcarbamoyl)phenoxy)chroman-4-carboxylate A mixture of 4-(6-cyano-4-(methoxycarbonyl)chroman-7-yloxy)benzoic acid (Preparation 2) (50 mg, 0.1415 mmol), 1-(3-(dimethylamino)propyl)-3-ethyl-carbodiimide hydrochloride (32.55 mg, 0.170 mmol), 1-hydroxybenzotriazole monohydrate (26.01 mg, 0.170 mmol), and 1,2-dichloroethane (2 ml) was stirred at ambient temperature for 30 minutes. To the mixture was added 3',4'-dimethylbiphenyl-3- amine hydrochloride (39.69 mg, 0.170 mmol) and triethylamine (98.62 μl, 0.707 mmol) and the mixture was stirred for 2 days at ambient temperature. The crude mixture was purified on silica gel (EtOAc in hexanes gradient) to provide 36 mg of the title compound as a thin film (48%).

Step B: Preparation of 6-cyano-7-(4-(3',4'-dimethyl-biphenyl-3-ylcarbamoyl)phenoxy)chroman-4-carboxylic acid Methyl 6-cyano-7-(4-(3',4'-dimethylbiphenyl-3-ylcarbamoyl)phenoxy)chroman-4-carboxylate (36 mg, 0.06759 mmol) was dissolved in THF (2 ml) and 1M solution of LiOH—H₂O (135.2 μL, 0.135 mmol) was added. The mixture was stirred for 17 hours at ambient temperature. The mixture was quenched with 4M HCl dioxane (50.70 μL, 0.203 mmol). The crude mixture was purified on silica gel (MeOH in dichloromethane with 1% acetic acid gradient) to provide 31 mg of the title compound as a thin film (90%). MS (apci)=519.1 (M+H).

Example 67

7-(4-(Biphenyl-3-ylcarbamoyl)phenoxy)-6-cyano-chroman-4-carboxylic acid

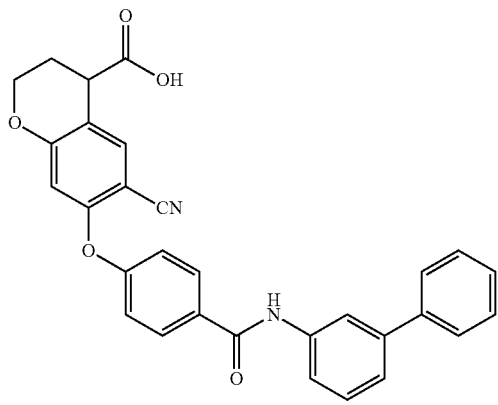 [SMILES: N#Cc1cc2c(cc1Oc1ccc(C(=O)Nc3cccc(-c4ccccc4)c3)cc1)OCCC2C(=O)O]

Step A: Preparation of methyl 7-(4-(biphenyl-3-yl-carbamoyl)phenoxy)-6-cyanochroman-4-carboxylate To a solution of 4-(6-cyano-4-(methoxycarbonyl)chroman-7-yloxy)benzoic acid (Preparation 2) (50 mg, 0.142 mmol) and a drop of DMF in dichloromethane (2 ml) was added oxalyl chloride (2M in dichloromethane) (84.91 μL, 0.170 mmol) at ambient temperature. Gas evolution was observed. The mixture was stirred for 1 hour at ambient temperature. Biphenyl-3-amine (28.74 mg, 0.170 mmol) in dichloromethane (1 ml) and triethylamine (59.172 μL, 0.424 mmol) were added to the activated acid. The mixture was stirred for 1 hour at ambient temperature. The crude mixture was purified on silica gel (EtOAc in hexanes gradient) to provide 55.6 mg of the title compound as a thin film (78%).

Step B: Preparation of 7-(4-(biphenyl-3-ylcarbamoyl)phenoxy)-6-cyanochroman-4-carboxylic acid To a solution of methyl 7-(4-(biphenyl-3-ylcarbamoyl)phenoxy)-6-cyanochroman-4-carboxylate (55.6 mg, 0.1102 mmol) in THF (2 ml) was added 1M solution of LiOH—H₂O (220.4 μl, 0.2204 mmol). The mixture was stirred for 1 hour at ambient temperature. The mixture was quenched with 4M HCl dioxane (82.65 μl, 0.331 mmol). The crude mixture was purified on silica gel (MeOH in dichloromethane with 1% acetic acid gradient) to provide 40.4 mg of the title compound as a thin film (75%). MS (apci) m/z=491.1 (M+H).

Example 68

7-(4-(Biphenyl-4-ylcarbamoyl)phenoxy)-6-cyano-chroman-4-carboxylic acid

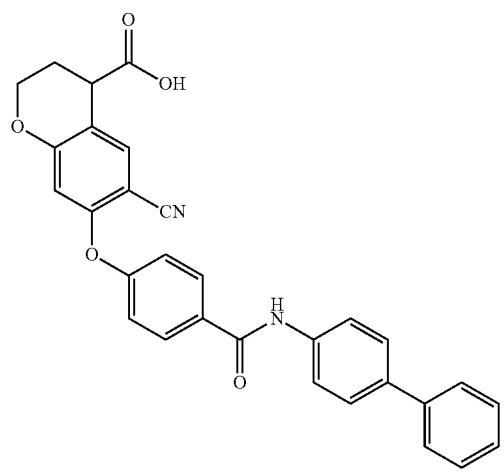 [SMILES: N#Cc1cc2c(cc1Oc1ccc(C(=O)Nc3ccc(-c4ccccc4)cc3)cc1)OCCC2C(=O)O]

Prepared according to Example 67, substituting biphenyl-4-amine for biphenyl-3-amine to provide 41.3 mg of the title compound as a white solid (88%). MS (apci) m/z=489.3 (M−H).

Example 69

7-(4-(4'-Chlorobiphenyl-4-ylcarbamoyl)phenoxy)-6-cyanochroman-4-carboxylic acid

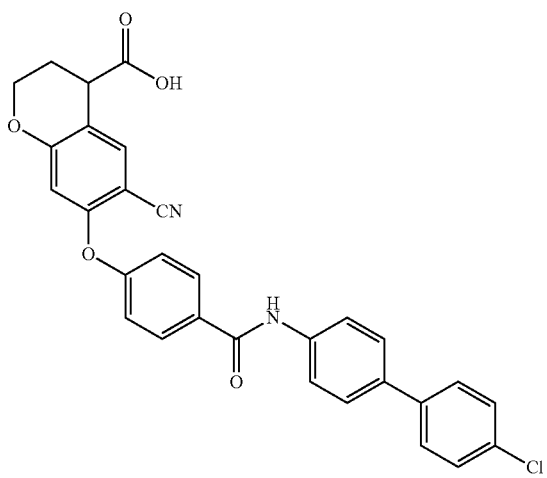 [SMILES: N#Cc1cc2c(cc1Oc1ccc(C(=O)Nc3ccc(-c4ccc(Cl)cc4)cc3)cc1)OCCC2C(=O)O]

Prepared according to Example 67, substituting 4'-Chlorobiphenyl-4-amine for biphenyl-3-amine to provide 40.1 mg of the title compound as a white solid (90%). MS (apci) =522.8 (M−H).

Example 70

6-Cyano-7-(4-(3-(2-methylpyrimidin-4-yl)phenylcarbamoyl)phenoxy)chroman-4-carboxylic acid

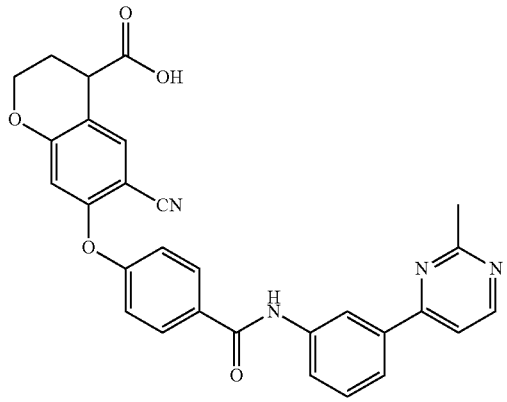 [SMILES: Cc1nccc(-c2cccc(NC(=O)c3ccc(Oc4cc5c(cc4C#N)C(C(=O)O)CCO5)cc3)c2)n1]

Prepared according to Example 67, substituting 3-(2-methylpyrimidin-4-yl)aniline for biphenyl-3-amine to provide 51.5 mg of the title compound as a white solid (90%). MS (apci)=507.3 (M+H).

Example 71

6-Chloro-7-(4-(4'-chloro-6-fluorobiphenyl-3-ylcarbamoyl)phenoxy)chroman-4-carboxylic acid

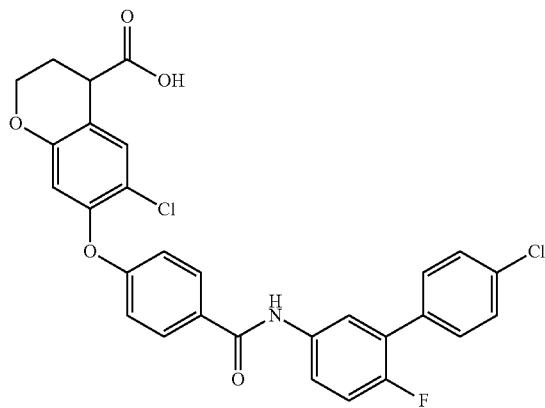 [SMILES: O=C(Nc1ccc(F)c(-c2ccc(Cl)cc2)c1)c1ccc(Oc2cc3c(cc2Cl)C(C(=O)O)CCO3)cc1]

Step A: Preparation of ethyl 7-(4-(3-bromo-4-fluorophenylcarbamoyl)phenoxy)-6-chlorochroman-4-carboxylate 4-(6-Chloro-4-(ethoxycarbonyl)chroman-7-yloxy)benzoic acid (Preparation 1) (0.214 g, 0.569 mmol) was dissolved in 1,2-dichloroethane (2 ml) and a drop of DMF was added. To the mixture was added oxalyl chloride (2M in dichloromethane) (0.313 ml, 0.626 mmol). Gas evolution was observed. The mixture was stirred for 2 hours at ambient temperature. A solution of 3-bromo-4-fluoroaniline (0.113 g, 0.597 mmol) and triethylamine (0.158 ml, 1.138 mmol) in dichloromethane (1 ml) was added to the acid chloride solution. The mixture was stirred for 0.5 hour and the crude mixture was purified on silica gel (EtOAc in hexanes gradient) to provide 0.2656 g of the title compound as a white solid (85%).

Step B: Preparation of ethyl 6-chloro-7-(4-(4'-chloro-6-fluorobiphenyl-3-ylcarbamoyl)phenoxy)chroman-4-carboxylate A mixture of ethyl 7-(4-(3-bromo-4-fluorophenylcarbamoyl)phenoxy)-6-chlorochroman-4-carboxylate (54.8 mg, 0.0998 mmol), 4-chlorophenylboronic acid (20.299 mg, 0.129 mmol), Na$_2$CO$_3$ (31.75 mg, 0.299 mmol), tetrakis(triphenylphosphine)palladium(0) (5.769 mg, 0.0049 mmol), water (0.1 ml), and toluene (1 ml) in a vial was purged with Argon for few minutes and heated for 17 hours at 125° C. The crude mixture was purified on silica gel (EtOAc in hexanes gradient) to provide 41.4 mg of the title compound as a foamy solid (71%).

Step C: Preparation of 6-cyano-7-(4-(2',3'-dimethylbiphenyl-3-ylcarbamoyl)phenoxy)chroman-4-carboxylic acid A mixture of ethyl 6-chloro-7-(4-(4'-chloro-6-fluorobiphenyl-3-ylcarbamoyl)phenoxy)-chroman-4-carboxylate (41.4 mg, 0.07133 mmol), 1M solution of LiOH—H$_2$O (142.7 μL, 0.1427 mmol), and THF (1 ml) was stirred for 17 hours at ambient temperature. The mixture was quenched with 1M HCl (214.0 μL, 0.2140 mmol). The crude mixture was purified on silica gel (MeOH in dichloromethane with 1% acetic acid gradient) to provide 32.9 mg of the title compound as a white solid (83%). MS (apci) m/z=552.1 (M+H).

Example 72

6-Cyano-7-(4-(1,2,3,4-tetrahydronaphthalen-2-ylcarbamoyl)phenoxy)chroman-4-carboxylic acid

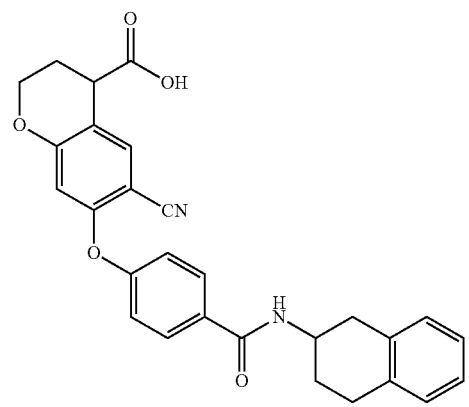 [SMILES: N#Cc1cc2c(cc1Oc1ccc(C(=O)NC3CCc4ccccc4C3)cc1)OCCC2C(=O)O]

Step A: Preparation of methyl 6-cyano-7-(4-(1,2,3,4-tetrahydronaphthalen-2-ylcarbamoyl)phenoxy)chroman-4-carboxylate 4-(6-Cyano-4-(methoxycarbonyl)chroman-7-yloxy)benzoic acid (Preparation 2) (10 mg, 0.028 mmol) was diluted with DCM (500 uL) followed by the addition of oxalyl chloride in DCM (2M) (0.017 ml, 0.034 mmol) and 1 drop of DMF. After stirring for 30 minutes, 1,2,3,4-tetrahydro-naphthalen-2-ylamine (8.3 mg, 0.057 mmol) and DIEA (0.020 mL, 0.11 mmol) were added. After stirring for 2 hours, the reaction was loaded directly onto a biotage 12i cartridge and eluted with 5% ethyl acetate/hexanes to 100% ethyl acetate to yield methyl 7-(4-((1,2,3,4-tetrahydronaphthalen-2-yl)carbamoyl)phenoxy)-6-cyanochroman-4-carboxylate (10 mg, 73% yield).

Step B: Preparation of 6-cyano-7-(4-(1,2,3,4-tetrahydronaphthalen-2-ylcarbamoyl)phenoxy)chroman-4-carboxylic acid Methyl 7-(4-((1,2,3,4-tetrahydronaphthalen-2-yl)carbamoyl)phenoxy)-6-cyanochroman-4-carboxylate (10 mg, 0.021 mmol) was diluted with THF (500 μL) followed by the addition of NaOH (0.12 ml, 0.12 mmol) and methanol (100 μL). After stirring for 1 hour, the reaction was diluted with ethyl acetate and 2N HCl. The layers were separated and the organic layer was dried over MgSO$_4$, filtered and concentrated to yield 7-(4-((1,2,3,4-tetrahydronaphthalen-2-yl)carbamoyl)phenoxy)-6-cyanochroman-4-carboxylic acid (3.0 mg, 31% yield). MS (ESI)=469.0 (M+H).

Example 73

7-(4-(5-Chloro-2,3-dihydro-1H-inden-2-ylcarbamoyl)phenoxy)-6-cyanochroman-4-carboxylic acid

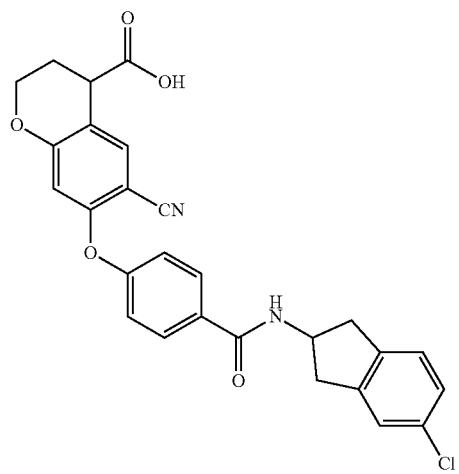 [SMILES: N#Cc1cc2c(cc1Oc1ccc(C(=O)NC3Cc4ccc(Cl)cc4C3)cc1)OCCC2C(=O)O]

Prepared according to the method of Example 72, substituting 5-chloro-2,3-dihydro-1H-inden-2-amine for 1,2,3,4-Tetrahydro-naphthalen-2-ylamine. MS (ESI)=489.0 (M+H).

Example 74

7-(4-(4-Chlorophenylcarbamoyl)phenoxy)-6-cyanochroman-4-carboxylic acid

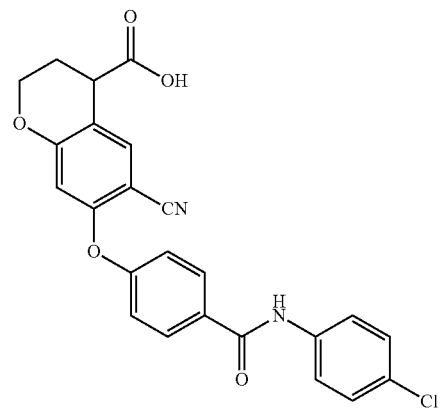 [SMILES: N#Cc1cc2c(cc1Oc1ccc(C(=O)Nc3ccc(Cl)cc3)cc1)OCCC2C(=O)O]

Prepared according to the method of Example 72, substituting 4-chloroaniline for 1,2,3,4-Tetrahydro-naphthalen-2-ylamine. MS (ESI)=448.9 (M+H).

Example 75

6-Cyano-7-(4-(4-(trifluoromethyl)phenylcarbamoyl)phenoxy)chroman-4-carboxylic acid

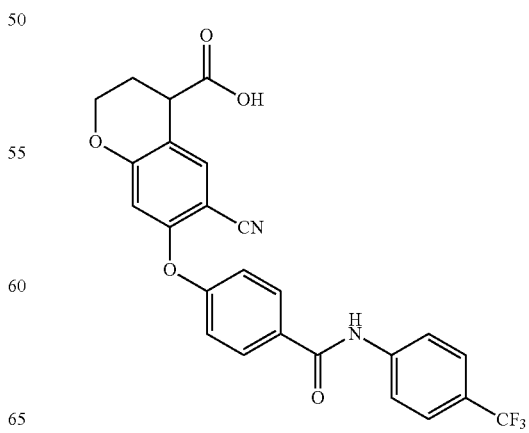

Prepared according to the method of Example 72, substituting 4-(trifluoromethyl)aniline for 1,2,3,4-Tetrahydro-naphthalen-2-ylamine. MS (ESI)=482.9 (M+H).

Example 76

6-Cyano-7-(4-(naphthalen-2-ylcarbamoyl)phenoxy) chroman-4-carboxylic acid

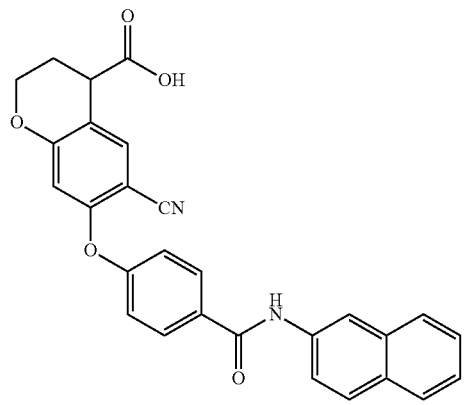 [SMILES: N#Cc1cc2c(cc1Oc1ccc(C(=O)Nc3ccc4ccccc4c3)cc1)OCCC2C(=O)O]

Prepared according to the method of Example 72, substituting naphthalen-2-amine for 1,2,3,4-Tetrahydro-naphthalen-2-ylamine. MS (ESI)=464.9 (M+H).

Example 77

Sodium 6-chloro-7-(4-(3-(4-chlorophenyl)propylcarbamoyl)phenoxy)chroman-4-carboxylate

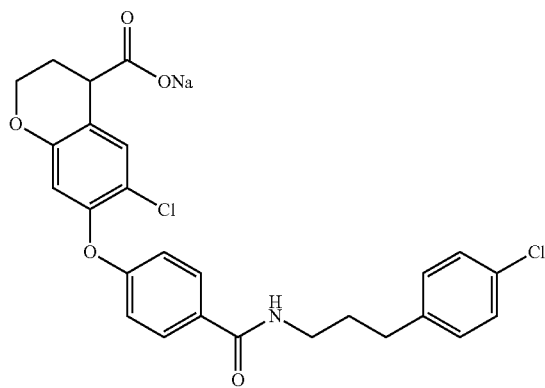

Step A: Preparation of ethyl 6-chloro-7-(4-(3-(4-chlorophenyl) propylcarbamoyl)phenoxy)chroman-4-carboxylate 4-(6-Chloro-4-(ethoxycarbonyl) chroman-7-yloxy)benzoic acid (Preparation 1) (67 mg, 0.18 mmol) was diluted with DCM (1 mL) followed by the addition of oxalyl chloride in DCM (2M) (98 µl, 0.20 mmol) and DMF (1 drop). After stirring for 10 minutes, 3-(4-chlorophenyl)propan-1-amine (33 mg, 0.20 mmol) and DIEA (68 µl, 0.39 mmol) were added and the reaction was stirred at ambient temperature for 2 hours. The reaction was loaded directly onto a biotage 25 cartridge and eluted with 5% ethyl acetate/hexanes to 75% ethyl acetate/hexanes to yield ethyl 6-chloro-7-(4-(3-(4-chlorophenyl)propylcarbamoyl)phenoxy)chroman-4-carboxylate (80 mg, 0.15 mmol, 85% yield).

Step B: Preparation of 6-chloro-7-(4-(3-(4-chlorophenyl)propylcarbamoyl)phenoxy)chroman-4-carboxylic acid Ethyl 6-chloro-7-(4-(3-(4-chlorophenyl) propylcarbamoyl)phenoxy)chroman-4-carboxylate (80 mg, 0.15 mmol) was diluted with THF (1 mL) followed by the addition of NaOH (757 µL, 0.76 mmol) and ethanol (500 µL). After stirring for 2 hours, the reaction was diluted with ethyl acetate and 2N HCl. The layers were separated and the organic layer was dried over MgSO$_4$, filtered and concentrated to yield 6-chloro-7-(4-(3-(4-chlorophenyl)propylcarbamoyl)phenoxy)chroman-4-carboxylic acid (76 mg, 0.15 mmol, 100% yield).

Step C: Preparation of sodium 6-chloro-7-(4-(3-(4-chlorophenyl) propylcarbamoyl)phenoxy)chroman-4-carboxylate 6-chloro-7-(4-(3-(4-chlorophenyl) propylcarbamoyl)phenoxy)chroman-4-carboxylic acid (76 mg, 0.15 mmol) was diluted with THF (500 µL) followed by the addition of NaOMe (304 µl, 0.15 mmol). After stirring for 2 hours, the reaction was concentrated under reduced pressure to yield 6-chloro-7-(4-(3-(4-chlorophenyl)propylcarbamoyl)phenoxy)chroman-4-carboxylic acid (50 mg, 0.100 mmol, 66% yield). MS (ESI)=500.2 (M-Na+2H).

Example 78

Sodium 6-chloro-7-(4-(3-phenylpropylcarbamoyl) phenoxy)chroman-4-carboxylate

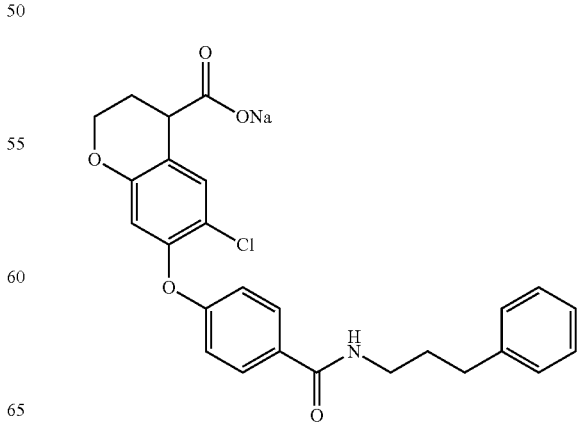

Prepared according to the method of Example 77, substituting 3-phenylpropan-1-amine for 3-(4-chlorophenyl)propan-1-amine. MS (ESI)=466.1 (M-Na+2H).

Example 79

Sodium 6-chloro-7-(4-(2-chlorophenethylcarbamoyl)phenoxy)chroman-4-carboxylate

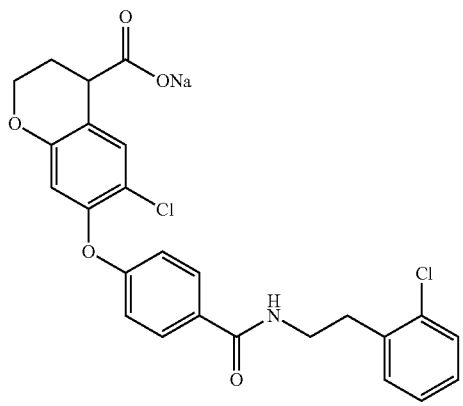

Prepared according to the method of Example 77, substituting 2-(2-chlorophenyl)ethanamine for 3-(4-chlorophenyl)propan-1-amine. MS (ESI)=486.1 (M-Na+2H).

Example 80

Sodium 6-chloro-7-(4-(2,6-dichlorophenethylcarbamoyl)phenoxy)chroman-4-carboxylate

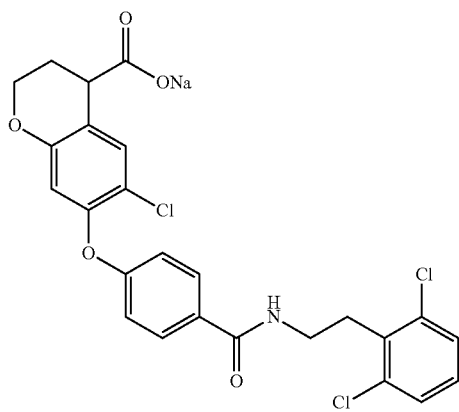

Prepared according to the method of Example 77, substituting 2-(2,6-dichlorophenyl)ethanamine for 3-(4-chlorophenyl)propan-1-amine. MS (ESI)=520.1 (M-Na+2H).

Example 81

Sodium 6-chloro-7-(4-(2,4-difluorophenethylcarbamoyl)phenoxy)chroman-4-carboxylate

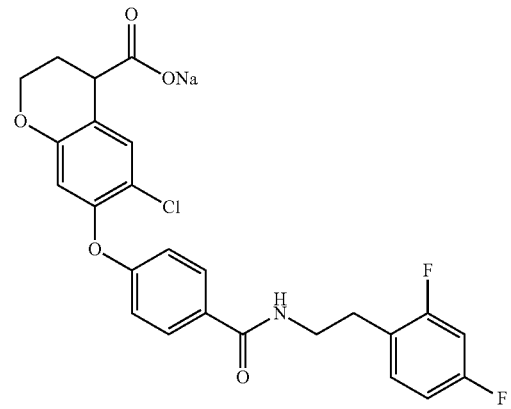

Prepared according to the method of Example 77, substituting 2-(2,4-difluorophenyl)ethanamine for 3-(4-chlorophenyl)propan-1-amine. MS (ESI)=488.1 (M-Na+2H).

Example 82

Sodium 6-chloro-7-(4-(2-chloro-6-fluorophenethylcarbamoyl)phenoxy)chroman-4-carboxylate

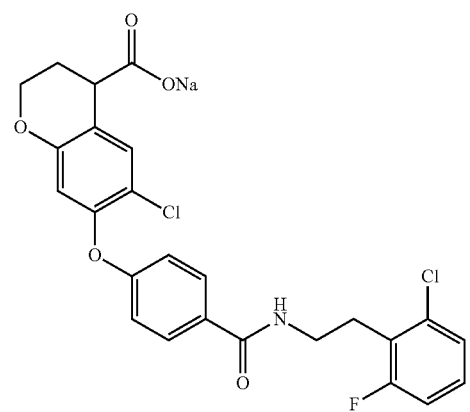

Prepared according to the method of Example 77, substituting 2-(2-chloro-6-fluorophenyl)ethanamine for 3-(4-chlorophenyl)propan-1-amine. MS (ESI)=504.2 (M-Na+2H).

Example 83

Sodium 6-chloro-7-(4-(3-hydroxyphenethylcarbamoyl)phenoxy)chroman-4-carboxylate

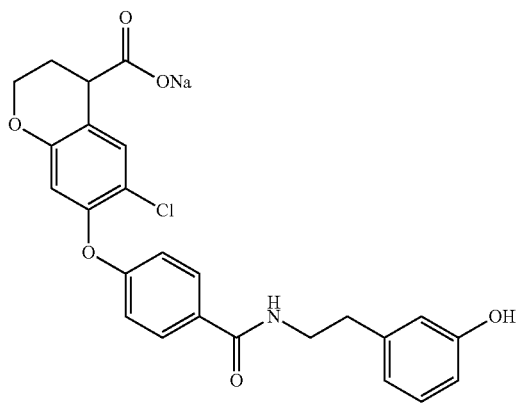

Prepared according to the method of Example 77, substituting 3-(2-aminoethyl)phenol for 3-(4-chlorophenyl)propan-1-amine. MS (ESI)=468.0 (M-Na+2H).

Example 84

Sodium 6-chloro-7-(4-(4-hydroxyphenethylcarbamoyl)phenoxy)chroman-4-carboxylate

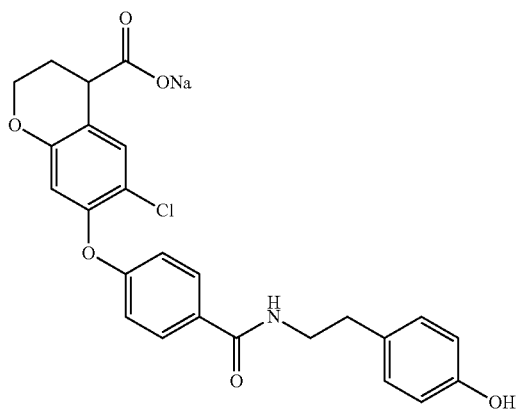

Prepared according to the method of Example 77, substituting 4-(2-aminoethyl)phenol for 3-(4-chlorophenyl)propan-1-amine. MS (ESI)=468.0 (M-Na+2H).

Example 85

Sodium 6-chloro-7-(4-(4-fluorophenethylcarbamoyl)phenoxy)chroman-4-carboxylate

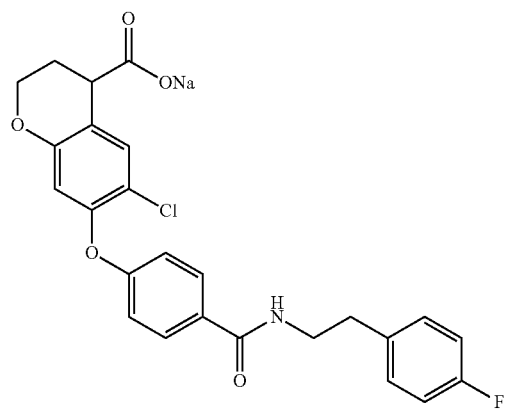

Prepared according to the method of Example 77, substituting 2-(4-fluorophenyl)ethanamine for 3-(4-chlorophenyl)propan-1-amine. MS (ESI)=470.1 (M-Na+2H).

Example 86

Sodium 6-chloro-7-(4-(2-(naphthalen-1-yl)ethylcarbamoyl)phenoxy)chroman-4-carboxylate

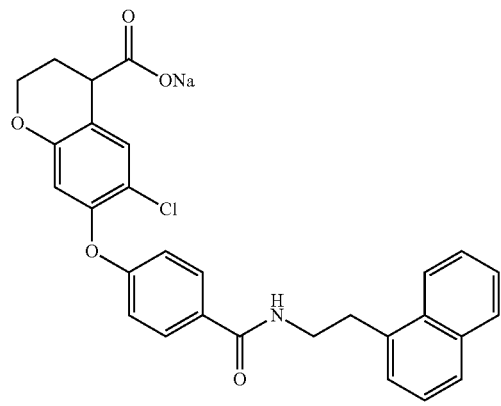

Prepared according to the method of Example 77, substituting 2-(naphthalen-1-yl)ethanamine for 3-(4-chlorophenyl)propan-1-amine. MS (ESI)=502.1 (M-Na+2H).

Example 87

Sodium 6-chloro-7-(4-(2-(naphthalen-2-yl)ethylcarbamoyl)phenoxy)chroman-4-carboxylate

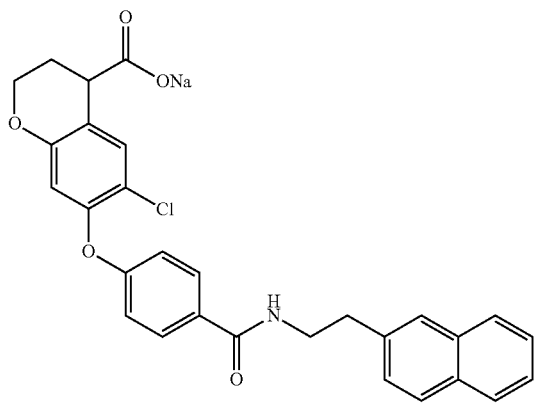

Prepared according to the method of Example 77, substituting 2-(naphthalen-2-yl)ethanamine for 3-(4-chlorophenyl)propan-1-amine. MS (ESI)=502.1 (M-Na+2H).

Example 88

Sodium 6-chloro-7-(4-(2,5-dimethoxyphenethylcarbamoyl)phenoxy)chroman-4-carboxylate

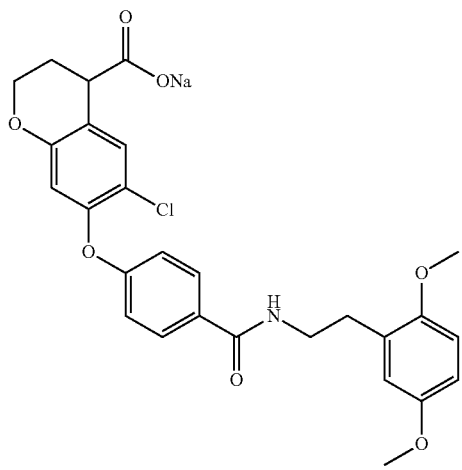

Prepared according to the method of Example 77, substituting 2-(2,5-dimethoxyphenyl)ethanamine for 3-(4-chlorophenyl)propan-1-amine. MS (ESI)=512.0 (M-Na+2H).

Example 89

Sodium 6-chloro-7-(4-(2,3-dimethoxyphenethylcarbamoyl)phenoxy)chroman-4-carboxylate

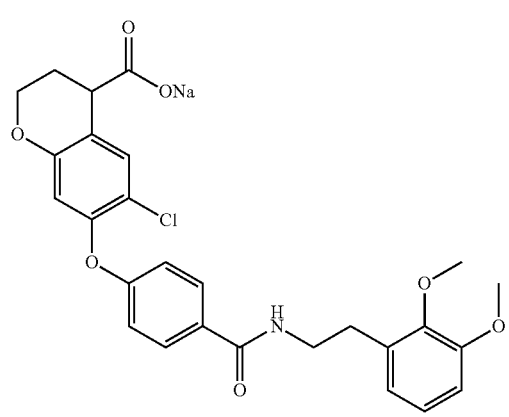

Prepared according to the method of Example 77, substituting 2-(2,3-dimethoxyphenyl)ethanamine for 3-(4-chlorophenyl)propan-1-amine. MS (ESI)=512.0 (M-Na+2H).

Example 90

Sodium 7-(4-(5-bromo-2-methoxyphenethylcarbamoyl)phenoxy)-6-chlorochroman-4-carboxylate

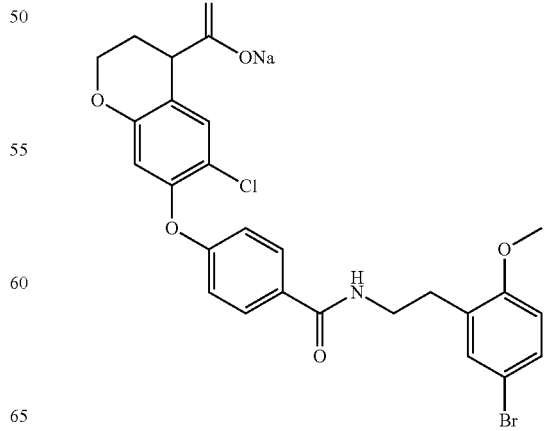

Prepared according to the method of Example 77, substituting 2-(5-bromo-2-methoxyphenyl)ethanamine for 3-(4-chlorophenyl)propan-1-amine. MS (ESI)=562.0 (M-Na+2H).

Example 91

Sodium 7-(4-(2-bromophenethylcarbamoyl)phenoxy)-6-chlorochroman-4-carboxylate

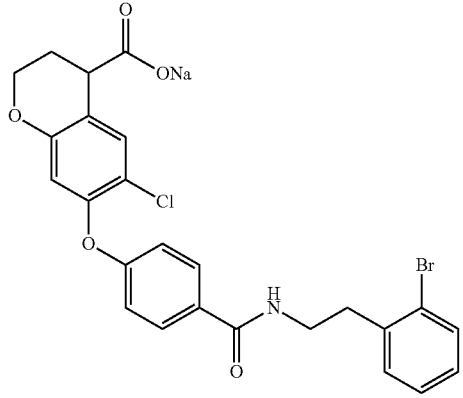

Prepared according to the method of Example 77, substituting 2-(2-bromophenyl)ethanamine for 3-(4-chlorophenyl)propan-1-amine. MS (ESI)=530.0 (M-Na+2H).

Example 92

Sodium 7-(4-(2-(biphenyl-2-yl)ethylcarbamoyl)phenoxy)-6-chlorochroman-4-carboxylate

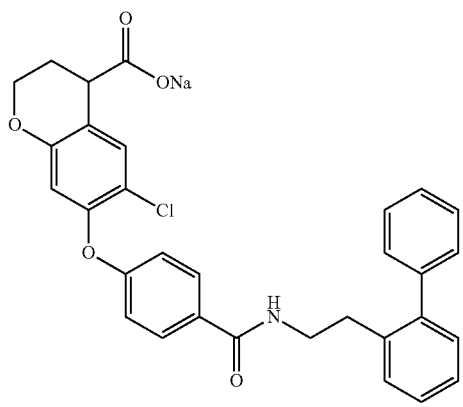

Step A: Preparation of ethyl 7-(4-(2-bromophenethylcarbamoyl)phenoxy)-6-chlorochroman-4-carboxylate 4-(6-Chloro-4-(ethoxycarbonyl)chroman-7-yloxy)benzoic acid (Preparation 1) (200 mg, 0.531 mmol) was diluted with DCM (3 mL) followed by the addition of oxalyl chloride in DCM (2M) (292 µl, 0.584 mmol) and DMF (1 drop). After stirring for 20 minutes, 2-(2-bromophenyl)ethanamine (117 mg, 0.584 mmol) and DIEA (203 µl, 1.17 mmol) were added and the reaction was stirred at ambient temperature for 12 hours. The reaction was loaded directly onto a biotage 25 cartridge and eluted with 5% ethyl acetate/hexanes to 75% ethyl acetate/hexanes to yield ethyl 7-(4-(2-bromophenethylcarbamoyl)phenoxy)-6-chlorochroman-4-carboxylate (268 mg, 0.480 mmol, 90.3% yield).

Step B: Preparation of ethyl 7-(4-(2-(biphenyl-2-yl)ethylcarbamoyl)phenoxy)-6-chlorochroman-4-carboxylate Ethyl 7-(4-(2-bromophenethylcarbamoyl)phenoxy)-6-chlorochroman-4-carboxylate (29 mg, 0.052 mmol, 79% yield), phenylboronic acid (10 mg, 0.086 mmol), $Na_2CO_3$ (21 mg, 0.20 mmol) and $Pd(PPh_3)_4$ (7.7 mg, 0.0066 mmol) were combined in a vial, diluted with dioxane (800 µL), purged with Argon, sealed and heated to 110° C. and stirred for 12 hours. The reaction was allowed to cool and loaded directly onto a biotage 25 cartridge eluting with 5% ethyl acetate/hexanes to 70% ethyl acetate/hexanes to yield ethyl 7-(4-(2-(biphenyl-2-yl)ethylcarbamoyl)phenoxy)-6-chlorochroman-4-carboxylate (29 mg, 0.052 mmol, 79% yield).

Step C: Preparation of 7-(4-(2-(biphenyl-2-yl)ethylcarbamoyl)phenoxy)-6-chlorochroman-4-carboxylic acid Ethyl 7-(4-(2-(biphenyl-2-yl)ethylcarbamoyl)phenoxy)-6-chlorochroman-4-carboxylate (29 mg, 0.052 mmol) was diluted with THF (1 mL) followed by the addition of NaOH (261 µL, 0.26 mmol) and ethanol (500 µL). After stirring for 2 hours, the reaction was diluted with ethyl acetate and 2N HCl. The layers were separated and the organic layer was dried over $MgSO_4$, filtered and concentrated to yield 7-(4-(2-(biphenyl-2-yl)ethylcarbamoyl)phenoxy)-6-chlorochroman-4-carboxylic acid (26 mg, 0.049 mmol, 94% yield).

Step D: Preparation of sodium 7-(4-(2-(biphenyl-2-yl)ethylcarbamoyl)phenoxy)-6-chlorochroman-4-carboxylate 7-(4-(2-(Biphenyl-2-yl)ethylcarbamoyl)phenoxy)-6-chlorochroman-4-carboxylic acid (26 mg, 0.049 mmol) was diluted with THF (500 µL) followed by the addition of NaOMe (98 µL, 0.049 mmol). After stirring for 2 hours, the reaction was concentrated and placed under high vacuum for 12 hours to yield sodium 7-(4-(2-(biphenyl-2-yl)ethylcarbamoyl)phenoxy)-6-chlorochroman-4-carboxylic acid (15 mg, 0.028 mmol, 58% yield) as a white foam. MS (ESI)=528.2 (M-Na+2H).

Example 93

Sodium 6-chloro-7-(4-(2-cyclopropylphenethylcarbamoyl)phenoxy)chroman-4-carboxylate

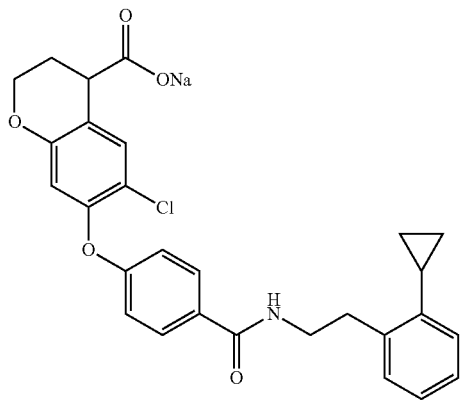

Prepared according to the method of Example 92, substituting phenylboronic acid in Step B with cyclopropylboronic acid. MS (ESI)=492.0 (M-Na+2H).

Example 94

Sodium 6-chloro-7-(4-(2-(4'-chlorobiphenyl-2-yl)ethylcarbamoyl)phenoxy)chroman-4-carboxylate

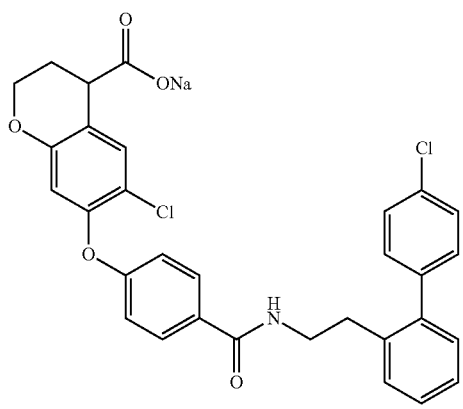

Prepared according to the method of Example 92, substituting phenylboronic acid in Step B with 4-chlorophenylboronic acid. MS (ESI)=562.1 (M-Na+2H).

Example 95

Sodium 6-chloro-7-(4-(2-(3'-chlorobiphenyl-2-yl)ethylcarbamoyl)phenoxy)chroman-4-carboxylate

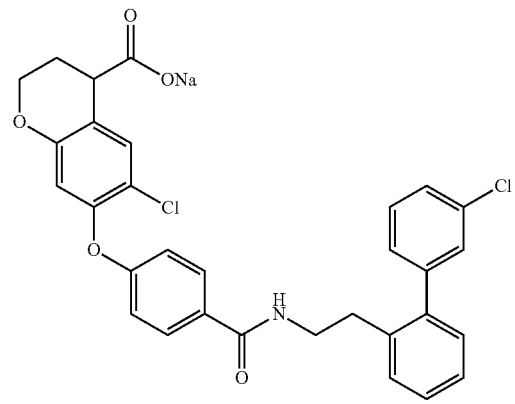

Prepared according to the method of Example 92, substituting phenylboronic acid in Step B with 3-chlorophenylboronic acid in Step B. MS (ESI)=562.1 (M-Na+2H).

Example 96

Sodium 6-chloro-7-(4-(2-(2'-chlorobiphenyl-2-yl)ethylcarbamoyl)phenoxy)chroman-4-carboxylate

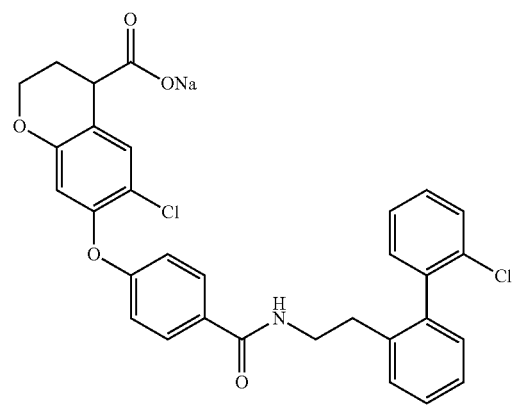

Prepared according to the method of Example 92, substituting phenylboronic acid in Step B with 2-chlorophenylboronic acid. MS (ESI)=562.1 (M-Na+2H).

Example 97

Sodium 6-chloro-7-(4-(2-chloro-4-fluorophenethylcarbamoyl)phenoxy)chroman-4-carboxylate

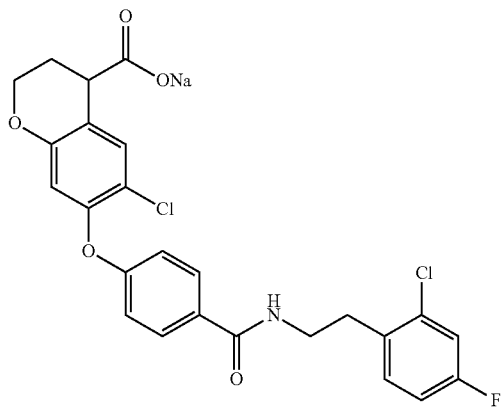

Step A: Preparation of 2-(2-chloro-4-fluorophenyl)ethanamine 2-(2-chloro-4-fluorophenyl)acetamide (400 mg, 2.13 mmol) was diluted with THF (2 mL), placed under nitrogen and cooled to 0° C. LAH (4264 µL, 4.26 mmol) was added dropwise and the reaction was refluxed for 3 hours. The reaction was cooled to 0° C. and quenched with 160 µL of water, 160 µL, of 15% NaOH, and 530 µL of water. After stirring for 30 minutes the reaction was filtered and concentrated. The material was purified using a biotage 25 column eluting with 2% NH₄OH/10% methanol/DCM to yield 2-(2-chloro-4-fluorophenyl)ethanamine (60 mg, 0.346 mmol, 16.2% yield).

Step B: Preparation of sodium 6-chloro-7-(4-(2-chloro-4-fluorophenethyl carbamoyl)phenoxy)chroman-4-carboxylate Prepared according to the method of Example 77, substituting 2-(2-chloro-4-fluorophenyl)ethanamine for 3-(4-chlorophenyl)propan-1-amine. MS (ESI)=504.1 (M-Na+2H).

Example 98

Sodium 6-chloro-7-(4-(2-chloro-4-(trifluoromethyl)phenethylcarbamoyl)phenoxy)chroman-4-carboxylate

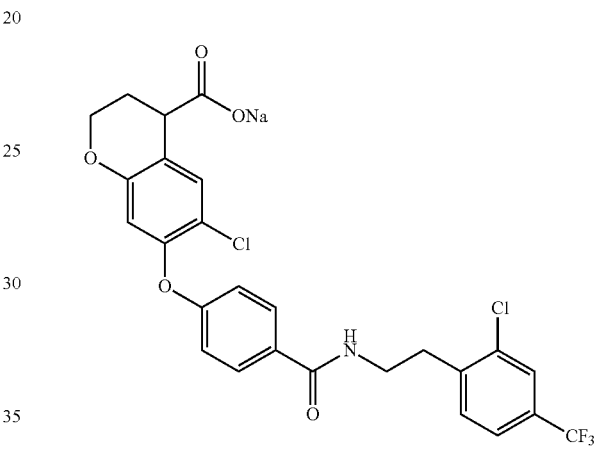

Step A: Preparation of 2-chloro-4-(trifluoromethyl)benzaldehyde

2-Chloro-4-(trifluoromethyl)benzonitrile (500 mg, 2.43 mmol) was diluted with toluene (3 mL), placed under nitrogen and cooled to −78° C. DIBAL-H (4865 µL, 4.86 mmol) was added dropwise and the reaction was stirred for 1 hour. The reaction was warmed to 0° C. and acetic acid (2 mL) was added followed by 10 mL of water. After stirring for 2 hours, the reaction was extracted twice with ethyl acetate, washed with Rochelle's salt, dried over MgSO₄, filtered and concentrated. The material was purified using a biotage 25 cartridge running a gradient, 100% hexanes to 20% DCM/hexanes to yield 2-chloro-4-(trifluoromethyl)benzaldehyde (400 mg, 1.92 mmol, 78.8% yield) as a clear oil.

Step B: Preparation of (E)-2-chloro-1-(2-nitrovinyl)-4-(trifluoromethyl)benzene 2-chloro-4-(trifluoromethyl)benzaldehyde (400 mg, 1.92 mmol) was diluted with nitromethane (727 µl, 13.4 mmol) followed by the addition of methylamine hydrochloride (77.7 mg, 1.15 mmol) and sodium acetate (94.4 mg, 1.15 mmol). After stirring for 12 hours, the reaction was loaded directly onto a biotage 25 cartridge and eluted with 5% ethyl acetate/hexanes to 50% ethyl acetate/hexanes to yield (E)-2-chloro-1-(2-nitrovinyl)-4-(trifluoromethyl)benzene (160 mg, 0.636 mmol, 33.2% yield).

Step C: Preparation of 2-(2-chloro-4-(trifluoromethyl)phenyl)ethanamine (E)-2-chloro-1-(2-nitrovinyl)-4-(trifluoromethyl)benzene (160 mg, 0.636 mmol) was diluted with THF (1 mL), placed under nitrogen and cooled to 0° C. LAH (2544 µL, 2.54 mmol) was added dropwise and the reaction was stirred for 5 hours warming to ambient temperature. The reaction was cooled to 0° C. and quenched with 100 µL of water, 100 µL of 15% NaOH and 300 µL water. After stirring for 1 hour, ethyl acetate and MgSO₄ was added. The reaction mixture was filtered and concentrated to yield 2-(2-chloro-4-(trifluoromethyl)phenyl)ethanamine (60 mg, 0.268 mmol, 42.2% yield).

Step D: Preparation of Sodium 6-chloro-7-(4-(2-chloro-4-(trifluoromethyl)phenethylcarbamoyl)phenoxy)chroman-4-carboxylate Prepared according to the method of Example 77, substituting 2-(2-chloro-4-(trifluoromethyl)phenyl)ethanamine for 3-(4-chlorophenyl)propan-1-amine. MS (ESI)=554.1 (M-Na+2H).

Example 99

Sodium 6-chloro-7-(4-(4-chloro-2-methoxyphenethylcarbamoyl)phenoxy)chroman-4-carboxylate

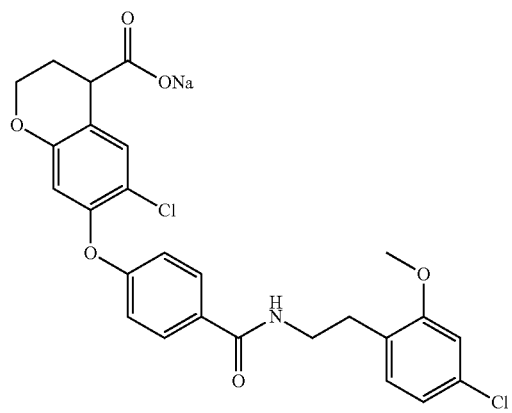

Step A: Preparation of 4-chloro-2-methoxybenzaldehyde

4-Chloro-2-Fluorobenzaldehyde (300 mg, 1.89 mmol) was diluted with NaOMe (3784 µL, 1.89 mmol) (solution in methanol), heated to 50° C. and stirred for 3 hours. The reaction was concentrated in half and loaded directly onto a biotage 25 cartridge eluting with 5% ethyl acetate/hexanes to yield 4-chloro-2-methoxybenzaldehyde (250 mg, 1.47 mmol, 77.5% yield).

Step B: Preparation of (E)-4-chloro-2-methoxy-1-(2-nitrovinyl)benzene

4-Chloro-2-methoxybenzaldehyde (250 mg, 1.47 mmol) was diluted with nitromethane (556 µL, 10.3 mmol) followed by the addition of methylamine hydrochloride (59.4 mg, 0.879 mmol) and sodium acetate (72.1 mg, 0.879 mmol). After stirring for 12 hours, the reaction was loaded directly onto a biotage 25 cartridge and eluted with 5% ethyl acetate/hexanes to yield (E)-4-chloro-2-methoxy-1-(2-nitrovinyl)benzene (245 mg, 1.15 mmol, 78.3% yield).

Step C: Preparation of 2-(4-chloro-2-methoxyphenyl)ethanamine (E)-4-chloro-2-methoxy-1-(2-nitrovinyl)benzene (245 mg, 1.15 mmol) was diluted with THF (1 mL), placed under nitrogen and cooled to 0° C. LAH (4588 µL, 4.59 mmol) was added dropwise and the reaction was stirred for 5 hours warming to ambient temperature. The reaction was cooled to 0° C. and quenched with 174 µL of water, 174 µL of 15% NaOH and 522 µL water. After stirring for 1 hour, ethyl acetate and MgSO₄ was added. The reaction mixture was filtered and concentrated to yield 2-(4-chloro-2-methoxyphenyl)ethanamine (160 mg, 0.862 mmol, 75.1% yield).

Step D: Preparation of sodium 6-chloro-7-(4-(4-chloro-2-methoxyphenethyl carbamoyl)phenoxy) chroman-4-carboxylate Prepared according to the method of Example 77, substituting 2-(4-chloro-2-methoxyphenyl)ethanamine for 3-(4-chlorophenyl)propan-1-amine. MS (ESI)=515.9 (M-Na+2H).

Example 100

Sodium 6-chloro-7-(4-(2-chloro-4-methoxyphenethylcarbamoyl)phenoxy)chroman-4-carboxylate

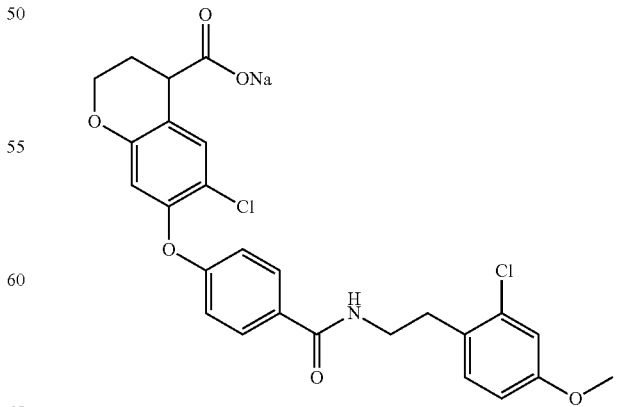

Prepared according to Example 99, substituting 2-Chloro-4-fluorobenzaldehyde for 4-chloro-2-fluorobenzaldehyde in Step A. MS (ESI)=515.9 (M-Na+2H).

Example 101

Sodium 6-chloro-7-(4-(4-fluoro-2-methoxyphenethylcarbamoyl)phenoxy)chroman-4-carboxylate

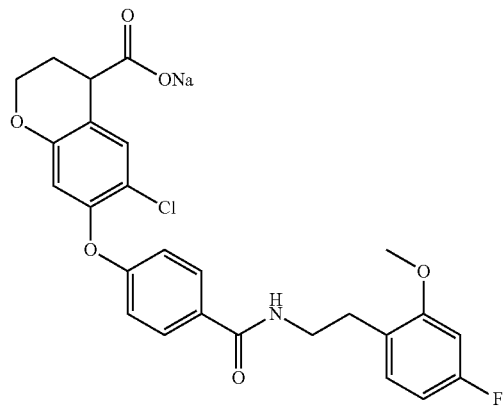

Prepared according to Example 99, substituting 2,4-difluorobenzaldehyde for 4-chloro-2-fluorobenzaldehyde in Step A. MS (ESI)=500.1 (M-Na+2H).

Example 102

Sodium 6-chloro-7-(4-(2-methoxy-4-(trifluoromethyl)phenethylcarbamoyl)phenoxy)chroman-4-carboxylate

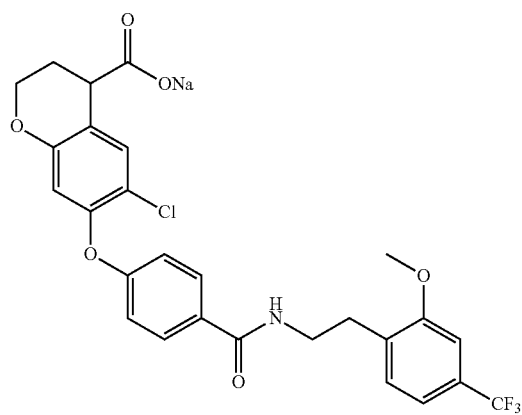

Prepared according to Example 99, substituting 2-Fluoro-4-(trifluoromethyl)benzaldehyde for 4-chloro-2-fluorobenzaldehyde in Step A. MS (ESI)=550.0 (M-Na+2H).

Example 103

Sodium 6-chloro-7-(4-(2,5-dichlorophenethylcarbamoyl)phenoxy)chroman-4-carboxylate

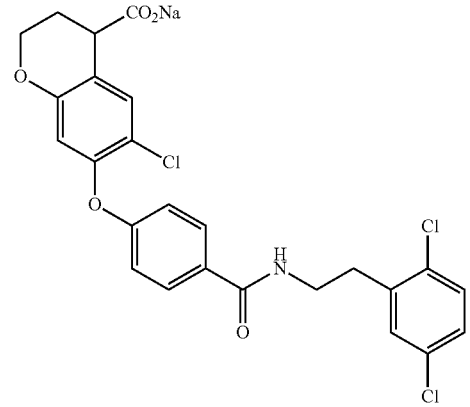

Prepared according to the method of Example 72, substituting 2,5-dichlorophenethyl amine for 1,2,3,4-tetrahydronaphthalen-2-amine. MS (apci) m/z=520 (M+2H—Na).

Example 104

Sodium 6-chloro-7-(4-(5-chloro-2-fluorophenethylcarbamoyl)phenoxy)chroman-4-carboxylate

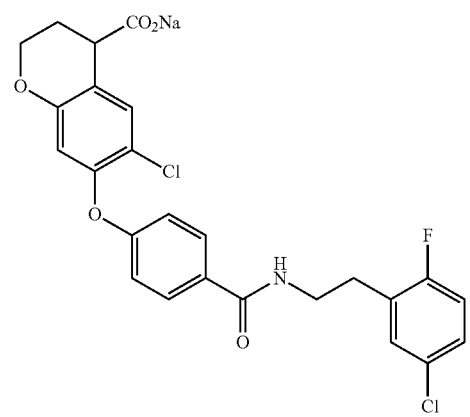

Prepared according to the method of Example 72, substituting 5-chloro-2-fluorophenethyl amine for 1,2,3,4-tetrahydronaphthalen-2-amine. MS (apci) m/z=502 (M+2H—Na).

Example 105

Sodium 6-chloro-7-(4-(2,4-dichlorophenethylcarbamoyl)-phenoxy)chroman-4-carboxylate

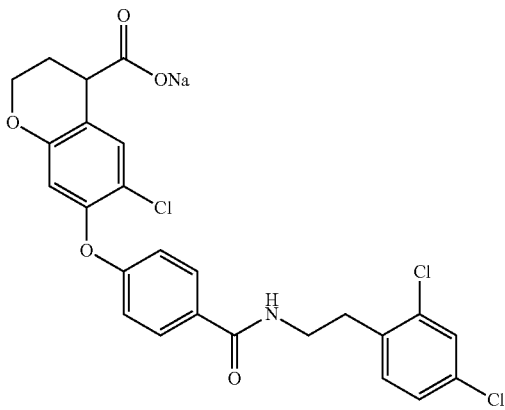

Step A: Preparation of ethyl 6-chloro-7-(4-(2,4-dichlorophenethylcarbamoyl)-phenoxy)chroman-4-carboxylate 4-(6-Chloro-4-(ethoxycarbonyl)chroman-7-yloxy)benzoic acid was dissolved in 700 mL of dichloromethane containing 8 drops of DMF and cooled to 5° C. Oxalyl chloride (31 mL, 355 mmol) was added as a solution in 10 mL of dichloromethane dropwise over 20 minutes keeping the reaction temperature between 8 and 11° C. After stirring at ambient temperature for 20 hours, the solution was cooled to 0° C. and 2,4-dichlorophenethyl amine (55 mL, 365 mmol) was added as a solution in 20 mL of dichloromethane dropwise over 20 minutes keeping the reaction temperature below 10° C. To the resulting thick, cream-colored slurry was added diisopropyl ethyl amine (70 mL, 402 mmol) dropwise over 20 minutes keeping the reaction temperature below 10° C. After 3 hours at ambient temperature, the reaction mixture was diluted with 2 L of dichloromethane and washed sequentially with three 500 mL portions of 1 N HCl, two 500 mL portions of water and two 500 mL portions of brine. The organic layer was dried over anhydrous sodium sulfate, filtered and concentrated to give 178 g of crude ethyl 6-chloro-7-(4-(2,4-dichlorophenethylcarbamoyl)phenoxy)chroman-4-carboxylate. The crude material was slurried in hot ethyl acetate, cooled to ambient temperature and the solids were collected, washing with 20% ethyl acetate in hexanes. The white solids were dried under high vacuum to give ethyl 6-chloro-7-(4-(2,4-dichlorophenethyl-carbamoyl)phenoxy)chroman-4-carboxylate (145 g, 80% yield). $^1$H NMR (400 MHz, CDCl$_3$) δ 7.68 (d, J=8.4 Hz, 2H), 7.40 (s, 1H), 7.36 (s, 1H), 7.20 (s, 2H), 6.96 (d, J=8.6 Hz, 2H), 6.53 (s, 1H), 6.12 (t, J=5.3 Hz, 1H), 4.21-4.29 (m, 4H), 3.67-3.75 (m, 3H), 3.05 (t, J=6.7 Hz, 2H), 2.30-2.35 (m, 1H), 2.05-2.14 (m, 1H), 1.31 (t, J=7.0 Hz, 3H).

Step B: Preparation of 6-chloro-7-(4-(2,4-dichlorophenethylcarbamoyl)phenoxy)-chroman-4-carboxylic acid Ethyl 6-chloro-7-(4-(2,4-dichlorophenethylcarbamoyl)phenoxy)-chroman-4-carboxylate (220 g, 401 mmol) was dissolved in 1.8 L of a 2:1 mixture of THF:EtOH. To the solution was added 4 N NaOH (150 mL, 600 mmol) and the reaction was stirred at ambient temperature for 2 hours. The mixture was concentrated to a solid residue, diluted with 1 L of water and 1 N HCl (700 mL, 700 mmol) was added. The resulting white solids were collected by filtration, washing with 2 L of water. The white solids were dried under high vacuum to give 6-chloro-7-(4-(2,4-dichlorophenethylcarbamoyl)-phenoxy)chroman-4-carboxylic acid (207 g, 99% yield). MS (apci)=520 (M−H).

Step C: Preparation of sodium 6-chloro-7-(4-(2,4-dichlorophenethylcarbamoyl)-phenoxy)chroman-4-carboxylate 6-Chloro-7-(4-(2,4-dichlorophenethylcarbamoyl)phenoxy)-chroman-4-carboxylic acid (4.50 g, 8.64 mmol) was dissolved in 25 mL of MeOH and cooled to 0° C. A 0.5 M solution of sodium methoxide in methanol (17.3 mL, 8.64 mmol) was then added and the cooling bath removed. After stirring at ambient temperature for 1 hour, the solution was concentrated to a residue. The residue was mixed with 50 mL of hexanes and stirred for 1 hour. The resulting precipitates were collected by filtration and dried under high vacuum to provide the title compound. The hexane treatment was repeated and the resulting white powder was dried under high vacuum at 65° C. to give sodium 6-chloro-7-(4-(2,4-dichlorophenethylcarbamoyl)-phenoxy)chroman-4-carboxylate (4.7 g, 100% yield). MS (apci) m/z=518 (M+2H—Na).

Example 106

Enantiomer 2 of 6-chloro-7-(4-(2,4-dichlorophenethylcarbamoyl)-phenoxy)chroman-4-carboxylic acid and preparation of sodium salt

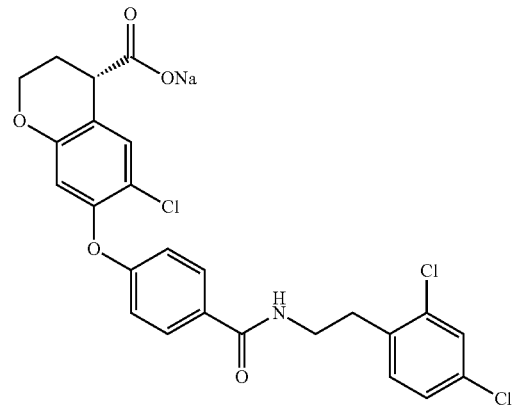

-continued

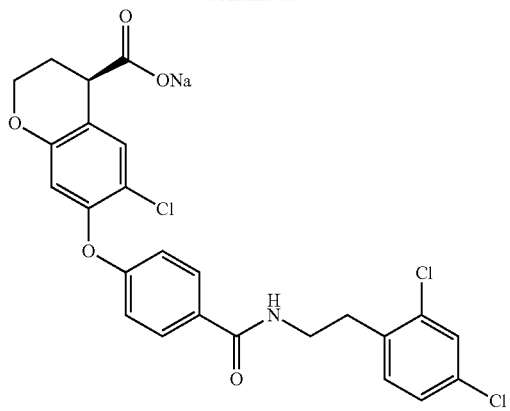

Step A: Separation of enantiomers of 6-chloro-7-(4-(2,4-dichlorophenethylcarbamoyl)phenoxy)-chroman-4-carboxylic acid 6-Chloro-7-(4-(2,4-dichlorophenethylcarbamoyl)phenoxy)-chroman-4-carboxylic acid (Example 105; 200 g) was dissolved in ethanol (21 mg/mL). The material was resolved via supercritical fluid chromatography employing a CHIRALCEL® OJ-H column (3×15 cm) eluting with 35% ethanol/carbon dioxide at 100 bar, using 3 mL injections and a flow rate of 140 mL/min. Collection of fractions containing peak 2 and removal of volatiles provided Enantiomer 2 of 6-chloro-7-(4-(2,4-dichlorophenethylcarbamoyl)-phenoxy)chroman-4-carboxylic acid (100 g, 50% yield). MS (apci) m/z=520 (M−H). Optical rotation: $[a]^{25}_D = -14°$ (c=1.00, MeOH).

Step B: Preparation of sodium salt of Enantiomer 2 of 6-chloro-7-(4-(2,4-dichlorophenethylcarbamoyl)-phenoxy)chroman-4-carboxylate 6-Chloro-7-(4-(2,4-dichlorophenethylcarbamoyl)-phenoxy)chroman-4-carboxylic acid (peak 2, 32.4 g, 57.9 mmol) was dissolved in 300 mL of MeOH, cooled to 0° C. and sodium methoxide (0.50 M in MeOH) (116 mL, 58 mmol) was added. The mixture was stirred at ambient temperature for 1 hour and concentrated to a solid residue. The residue was stirred with 800 mL of hexanes for 20 minutes and the solids were collected by filtration, washing with excess hexanes. The white solid was dried under high vacuum at 60 to 65° C. for 3 hours to give the sodium salt of peak 2, Enantiomer 2 of 6-chloro-7-(4-(2,4-dichlorophenethylcarbamoyl)-phenoxy)chroman-4-carboxylate (31.4 g, 99% yield). MS (apci) m/z=522 (M+2H—Na).

During the chiral separation described in Step A, peak 1 was isolated to provide Enantiomer 1 of 6-chloro-7-(4-(2,4-dichlorophenethylcarbamoyl)phenoxy)chroman-4-carboxylic acid. Chiral purity (ee) >98% as measured with a CHIRALPAK® QD-AX column in comparison to racemic material). The sodium salt of Enantiomer 1 was then prepared as described in Step B. MS (apci, neg) m/z 520 (M−H). The sodium salt of Enantiomer 1 was found to be less active than the sodium salt of Enantiomer 2 when tested in an assay described in Example A.

Example 107

6-Cyano-7-(4-(4'-methylbiphenyl-3-ylcarbamoyl)phenoxy)chroman-4-carboxylic acid

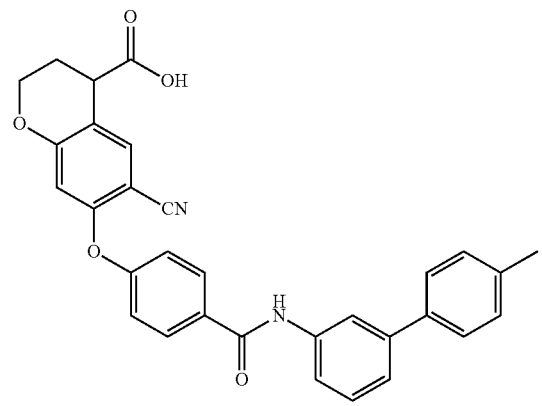 [SMILES: Cc1ccc(-c2cccc(NC(=O)c3ccc(Oc4cc5c(cc4C#N)C(C(=O)O)CCO5)cc3)c2)cc1]

Step A: Preparation of methyl 6-cyano-7-(4-(4'-methylbiphenyl-3-ylcarbamoyl)phenoxy)chroman-4-carboxylate In a vial were placed methyl 6-cyano-7-(4-(3-iodophenylcarbamoyl)phenoxy)chroman-4-carboxylate (Preparation 3) (56 mg, 0.1010 mmol), p-tolylboronic acid (17.855 mg, 0.1313 mmol), $Na_2CO_3$ (32.121 mg, 0.3030 mmol), toluene (1 ml), and water (0.1 ml). The mixture was degassed with Argon for few minutes. Tetrakis(triphenylphosphine)palladium(0) (5.836 mg, 0.005 mmol) was added and the vial was sealed. The mixture was stirred at 100° C. for 24 hours. The crude mixture was purified on silica gel (EtOAc in hexanes gradient) to provide 33.1 mg of the title compound as foamy solid (63%).

Step B: Preparation of 6-cyano-7-(4-(4'-methylbiphenyl-3-ylcarbamoyl)phenoxy)chroman-4-carboxylic acid A mixture of methyl 7-(4-(4'-methylbiphenyl-4-ylcarbamoyl)phenoxy)-6-cyanochroman-4-carboxylate (33 mg, 0.063 mmol), 1M solution of LiOH—$H_2O$ (127.3 μl, 0.127 mmol), and THF (1.5 ml) was stirred for 17 hours at ambient temperature. The mixture was quenched with 4M HCl dioxane (47.73 μL, 0.190 mmol). The crude mixture was purified on silica gel (MeOH in dichloromethane with 1% acetic acid gradient) to provide 29.8 mg of the title compound as a white solid (93%). MS (apci) m/z=505.1 (M+H).

Example 108

6-Cyano-7-(4-(3'-methylbiphenyl-3-ylcarbamoyl) phenoxy)chroman-4-carboxylic acid

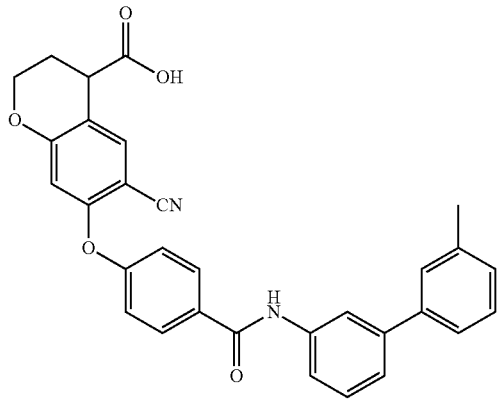 [SMILES: Cc1cccc(-c2cccc(NC(=O)c3ccc(Oc4cc5c(cc4C#N)C(C(=O)O)CCO5)cc3)c2)c1]

Prepared according to Example 107, substituting m-tolylboronic acid for p-tolylboronic acid to provide 26.9 mg of the title compound as a white solid (82%). MS (apci) m/z=505.1 (M+H).

Example 109

6-Cyano-7-(4-(2',3'-dimethylbiphenyl-3-ylcarbamoyl)phenoxy)chroman-4-carboxylic acid

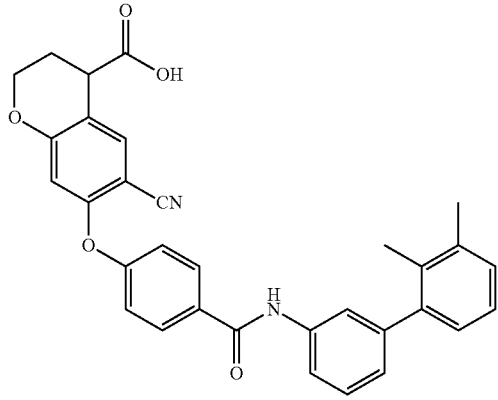 [SMILES: Cc1cccc(-c2cccc(NC(=O)c3ccc(Oc4cc5c(cc4C#N)C(C(=O)O)CCO5)cc3)c2)c1C]

Step A: Preparation of methyl 6-cyano-7-(4-(2',3'-dimethylbiphenyl-3-ylcarbamoyl)phenoxy)chroman-4-carboxylate In a vial were placed methyl 6-cyano-7-(4-(3-iodophenylcarbamoyl)phenoxy)chroman-4-carboxylate (Preparation 3) (56 mg, 0.101 mmol), 2,3-dimethylphenylboronic acid (19.70 mg, 0.131 mmol), $Na_2CO_3$ (32.12 mg, 0.303 mmol), toluene (1 ml), and water (0.1 ml). The mixture was degassed with Argon for few minutes. Tetrakis(triphenylphosphine)palladium(0) (5.836 mg, 0.0050 mmol) was added and the vial was sealed. The mixture was stirred for 17 hours at 100° C. The crude mixture was purified on silica gel (EtOAc in hexanes gradient) to provide 34.4 mg of the title compound as a thin film (64%).

Step B: Preparation of 6-cyano-7-(4-(2',3'-dimethylbiphenyl-3-ylcarbamoyl)phenoxy)chroman-4-carboxylic acid A mixture of methyl 7-(4-(2',3'-dimethylbiphenyl-4-ylcarbamoyl)phenoxy)-6-cyanochroman-4-carboxylate (34.4 mg, 0.0645 mmol), 1M solution of LiOH—$H_2O$ (129.7 μL, 0.129 mmol), and THF (1.5 ml) was stirred for 17 hours at ambient temperature. The mixture was quenched with 1M HCl (193.8 μL, 0.194 mmol). The crude mixture was purified on silica gel (MeOH in dichloromethane with 1% acetic acid gradient) to provide 25.2 mg of the title compound as a white solid (75%). MS (apci) m/z=519.1 (M+H).

Example 110

Sodium 7-(4-(2-(benzo[d][1,3]dioxol-5-yl)ethylcarbamoyl)phenoxy)-6-chlorochroman-4-carboxylate

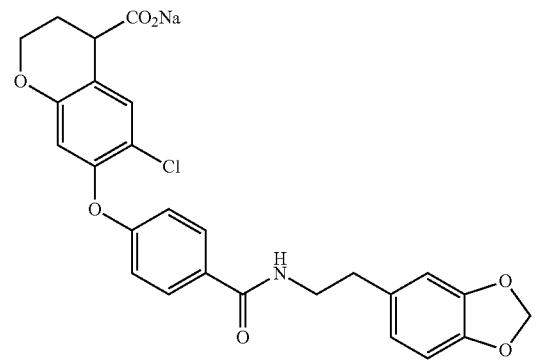

Step A: Preparation of ethyl 7-(4-(2-(benzo[d][1,3]dioxol-5-yl)ethylcarbamoyl)phenoxy)-6-chlorochroman-4-carboxylate 2-(Benzo[d][1,3]dioxol-5-yl)ethanamine (32.9 mg, 0.199 mmol) in DMF (0.1 M) was treated sequentially with 4-(6-chloro-4-(ethoxycarbonyl)chroman-7-yloxy)benzoic acid (Preparation 1) (1327 μL, 0.133 mmol), 1-(3-dimethylaminopropyl)-3-ethylcarbodiimide hydrochloride (30.5 mg, 0.159 mmol), and 1-hydroxy-7-azabenzotriazole (5.42 mg, 0.0398 mmol) at ambient temperature. After 16 hours, the reaction was applied directly to a silica gel column and eluted with a gradient (20% to 80%) of ethyl acetate-hexanes to provide the title compound (65 mg, 0.124 mmol, 93.5% yield) as a white solid.

Step B: Preparation of 7-(4-(2-(benzo[d][1,3]dioxol-5-yl)ethylcarbamoyl)phenoxy)-6-chlorochroman-4-carboxylic acid Ethyl 7-(4-(2-(benzo[d][1,3]dioxol-5-yl)ethylcarbamoyl)phenoxy)-6-chlorochroman-4-carboxylate (65 mg, 0.124 mmol) was dissolved in 2:1 tetrahydrofuran-ethanol and treated with 1.0 molar sodium hydroxide (496 μl, 0.496 mmol) at ambient temperature. After 3 hours, the reaction was diluted with ethyl acetate, neutralized with 1.0 molar hydrochloric acid (521 µl, 0.521 mmol), and partitioned between saturated sodium chloride aqueous solution. The organic layer was dried with sodium sulfate, filtered, concentrated, and dried under high vacuum to provide the title compound (61 mg, 0.123 mmol, 99.2% yield) as a solid.

Step C: Preparation of sodium 7-(4-(2-(benzo[d][1,3]dioxol-5-yl)ethylcarbamoyl)phenoxy)-6-chlorochroman-4-carboxylate 7-(4-(2-(benzo[d][1,3]dioxol-5-yl)ethylcarbamoyl)phenoxy)-6-chlorochroman-4-carboxylic acid (60 mg, 0.12 mmol), 0.1 molar in 4:1 tetrahydrofuran-methanol, was treated with sodium methanolate (242 µl, 0.12 mmol) at ambient temperature. After 15 minutes, the solvent was removed in vacuo. The resulting solid was taken up in ethyl acetate and concentrated in vacuo. The solid was then taken up in 4:1 dichloromethane-hexanes and concentrated in vacuo and dried under high vacuum to provide sodium 7-(4-(2-(benzo[d][1,3]dioxol-5-yl)ethylcarbamoyl)phenoxy)-6-chlorochroman-4-carboxylate (63 mg, 0.12 mmol, 101% yield) as a solid. MS (apci) m/z=495.9 (M+2H—Na).

Example 111

Sodium 6-chloro-7-(4-((2,3-dihydro-1H-inden-2-yl)methylcarbamoyl)phenoxy)chroman-4-carboxylate

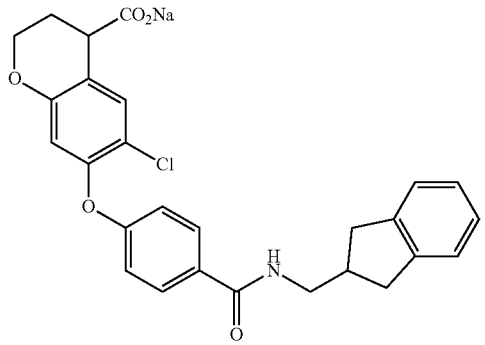

Step A: Preparation of ethyl 6-chloro-7-(4-((2,3-dihydro-1H-inden-2-yl)methylcarbamoyl)phenoxy)chroman-4-carboxylate 4-(6-chloro-4-(ethoxycarbonyl) chroman-7-yloxy)benzoic acid (Preparation 1) (50 mg, 0.133 mmol), suspended in 1.3 ml of dichloromethane, was treated sequentially with (2,3-dihydro-1H-inden-2-yl)methanamine hydrochloride (26.8 mg, 0.146 mmol), N-ethyl-N-isopropylpropan-2-amine (32.4 µl, 0.186 mmol), 1-(3-dimethylaminopropyl)-3-ethylcarbodiimide hydrochloride (30.5 mg, 0.159 mmol), and 1-hydroxy-7-azabenzotriazole (5.42 mg, 0.0398 mmol) at ambient temperature. After 16 hours, the reaction was applied directly to a silica gel column and eluted with a gradient (20% to 80%) of ethyl acetate-hexanes to provide the title compound (67 mg, 0.132 mmol, 99.8% yield) as a white solid.

Steps B and C

Prepared according to Example 110, Steps B and C to provide 63 mg (100%) of the title compound as a solid. MS (apci) m/z=478.1 (M+2H—Na).

Example 112

Sodium 6-chloro-7-(4-(2-(p-tolylthio)ethylcarbamoyl)phenoxy)chroman-4-carboxylate

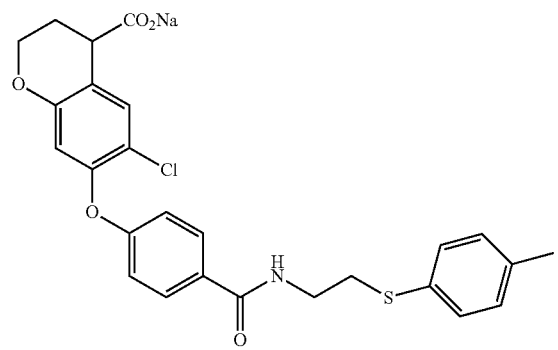

Prepared according to Example 110, replacing 1-(3-dimethylaminopropyl)-3-ethylcarbodiimide hydrochloride in Step A with 2-(p-tolylthio)ethanamine to provide the title compound (71 mg, 0.14 mmol, 99% yield) as a solid. MS (apci) m/z=497.9 (M+2H—Na).

Example 113

Sodium 6-chloro-7-(4-(2-(4-chlorophenylthio)ethylcarbamoyl)phenoxy)chroman-4-carboxylate

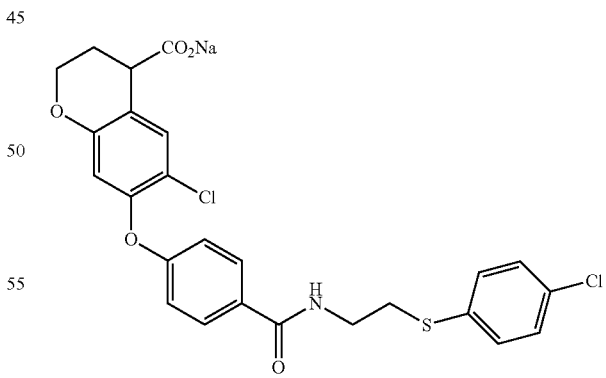

Step A: Preparation of ethyl 6-chloro-7-(4-(2-(4-chlorophenylthio)ethylcarbamoyl)phenoxy)chroman-4-carboxylate Prepared according to Example 111, Step A, replacing (2,3-dihydro-1H-inden-2-yl)methanamine hydrochloride with 2-(4-chlorophenylthio)ethanamine hydrochloride to provide the title compound (47 mg, 65% yield) as a solid.

Steps B and C

Followed the procedure of Example 110, Steps B and C, to provide the title compound (44 mg, 100% yield) as a solid. MS (apci) m/z=517.8 (M+2H—Na).

Example 114

Sodium 6-chloro-7-(4-(2-ethoxyphenethylcarbamoyl)phenoxy)chroman-4-carboxylate

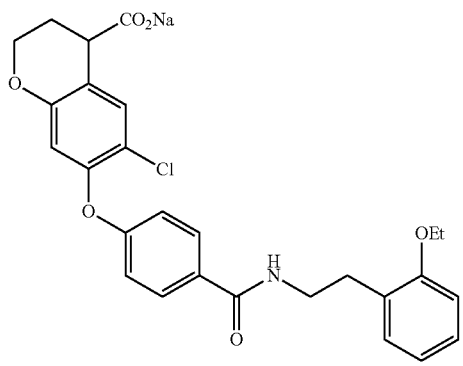

Prepared according to Example 110, replacing 2-(benzo[d][1,3]dioxol-5-yl)ethanamine in Step A with 2-(2-ethoxyphenyl)ethanamine to provide the title compound (66 mg, 100% yield) as a solid. MS (apci) m/z=495.9 (M+2H—Na).

Example 115

Sodium 6-chloro-7-(4-(2-(2-chlorophenoxy)ethylcarbamoyl)phenoxy)chroman-4-carboxylate

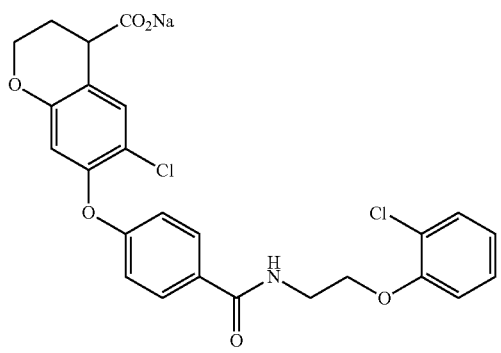

Prepared according to Example 110, replacing 2-(benzo[d][1,3]dioxol-5-yl)ethanamine in Step A with 2-(2-chlorophenoxy)ethylamine to provide the title compound (69 mg, 100% yield) as a solid. MS (apci) m/z=501.9 (M+2H—Na).

Example 116

Sodium 7-(4-(2-tert-butoxyphenethylcarbamoyl)phenoxy)-6-chlorochroman-4-carboxylate

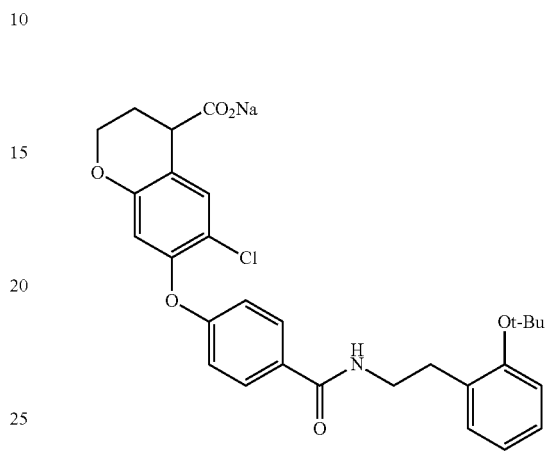

Step A: Preparation of tert-butoxy-2-(2-nitrovinyl)benzene 2-tert-Butoxybenzaldehyde (550 mg, 3.09 mmol) was treated with nitromethane (1167 µL, 21.6 mmol) at ambient temperature in a flask. Solid methylamine hydrochloride (133 mg, 1.98 mmol) and sodium acetate (162 mg, 1.98 mmol) were added and the colorless reaction mixture was stirred rapidly at ambient temperature. After 30 minutes, the reaction mixture started to turn yellow. After 16 hours, the reaction was very yellow and precipitate has formed. Water (20 ml) and dichloromethane (40 ml) were added and the layers partitioned. The dichloromethane layer was dried with sodium sulfate, filtered, and concentrated to provide the title compound (705 mg, 3.19 mmol, 103% yield) as a yellow oil.

Step B: Preparation of 2-(2-tert-butoxyphenyl)ethanamine 1-tert-Butoxy-2-(2-nitrovinyl)benzene (685 mg, 3.10 mmol) in tetrahydrofuran (10 ml) was cooled to 0° C. under an argon atmosphere (balloon). Lithium aluminum hydride (1 M in THF) (12384 µL, 12.4 mmol, equivalent to 470 mg) was added dropwise over 5 minutes. The reaction was stirred at 0° C. for 30 minutes and then at ambient temperature 4 hours. The reaction was quenched with 0.470 ml water at 0° C., followed by 0.470 ml 1 N aqueous NaOH at 0° C. After 15 minutes, an additional 1.45 ml water was added and the reaction mixture was warmed to ambient temperature and stirred rapidly for 1 hour, after which ethyl acetate (20 ml) and potassium were added. The reaction mixture was filtered and washed with ethyl acetate. The combined filtrate was concentrated in vacuo to afford the title compound (575 mg, 2.97 mmol, 96.1% yield) as a yellow oil.

145

Steps C-E

Followed the procedures of Example 110, Steps A-C to provide the title compound (59 mg, 99%) as a solid. MS (apci) m/z=523.7 (M+2H—Na).

Example 117

Sodium 6-chloro-7-(4-(2-(methylthio)phenethylcarbamoyl)phenoxy)chroman-4-carboxylate

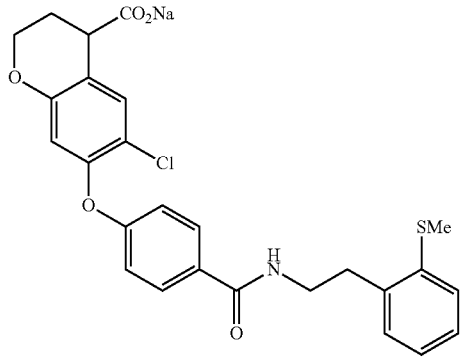

Step A: Preparation of (E)-methyl(2-(2-nitrovinyl)phenyl)sulfane

Prepared according to Example 116, Step A, replacing 2-tert-Butoxybenzaldehyde with 2-(methylthio)benzaldehyde. The crude reaction was purified on silica gel (elution with a gradient of 5-20% ethyl acetate-hexanes) to provide the title compound (319 mg, 48% yield) as a solid.

Step B: Preparation of 2-(2-(methylthio)phenyl)ethanamine

Prepared according to Example 116, Step B, replacing 1-tert-butoxy-2-(2-nitrovinyl)benzene with (E)-methyl(2-(2-nitrovinyl)phenyl)sulfane to afford the title compound (278 mg, 102% yield) as an oil.

Step C: Preparation of ethyl 6-chloro-7-(4-(2-(methylthio) phenethylcarbamoyl)phenoxy)chroman-4-carboxylate Prepared according to Example 110, Step A, replacing 2-(benzo[d][1,3]dioxol-5-yl)ethanamine with 2-(2-(methylthio)phenyl)ethanamine to provide the title compound (58 mg, 83%) as a solid.

Step D: Preparation of 6-chloro-7-(4-(2-(methylthio) phenethylcarbamoyl)phenoxy)chroman-4-carboxylic acid Prepared according to Example 110, Step B to provide the title compound (53 mg, 100%) as a solid.

Step E: Preparation sodium 6-chloro-7-(4-(2-(methylthio) phenethylcarbamoyl)phenoxy)chroman-4-carboxylate Prepared according to Example 110, Step C to provide the title compound (55 mg, 99%) as a solid. MS (apci) m/z=497.9 (M+2H—Na).

146

Example 118

Sodium 6-chloro-7-(4-(4-(methylthio)phenethylcarbamoyl)phenoxy)chroman-4-carboxylate

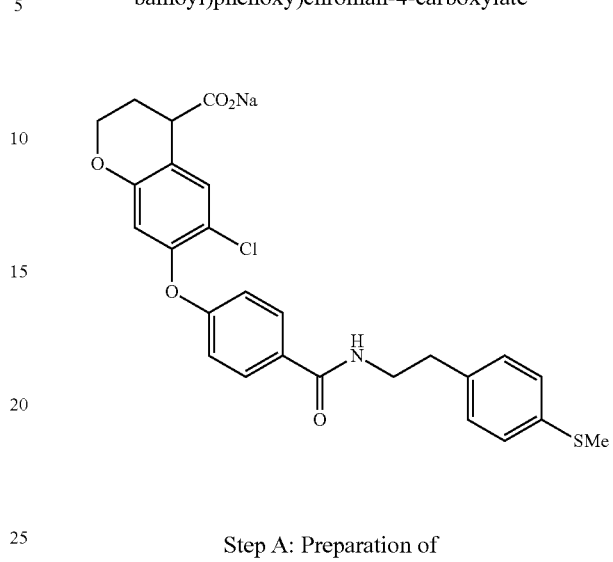

Step A: Preparation of methyl(4-(2-nitrovinyl)phenyl)sulfane

Prepared according to Example 116, Step A, replacing 2-tert-butoxybenzaldehyde with 4-(methylthio)benzaldehyde and the crude product was crystallized from methanol to provide the title compound (85 mg, 12% yield) as a solid.

Step B: Preparation of 2-(4-(methylthio)phenyl)ethanamine

Prepared according to Example 116, Step B, replacing 1-tert-Butoxy-2-(2-nitrovinyl)benzene with methyl(4-(2-nitrovinyl)phenyl)sulfane to afford the title compound (64 mg, 98% yield) as an oil.

Step C: Preparation of ethyl 6-chloro-7-(4-(4-(methylthio)phenethylcarbamoyl)phenoxy)chroman-4-carboxylate Prepared according to Example 110, Step A, replacing 2-(benzo[d][1,3]dioxol-5-yl)ethanamine with 2-(4-(methylthio)phenyl)ethanamine to provide the title compound (59 mg, 56%) as a solid.

Step D: Preparation of 6-chloro-7-(4-(4-(methylthio) phenethylcarbamoyl)phenoxy)chroman-4-carboxylic acid Prepared according to Example 110, Step B, to provide the title compound (59 mg, 100%) as a solid.

Step E: Preparation sodium sodium 6-chloro-7-(4-(4-(methylthio)phenethylcarbamoyl)phenoxy)chroman-4-carboxylate Prepared according to Example 110, Step C, to provide the title compound (57 mg, 99%) as a solid. MS (apci) m/z=497.9 (M+2H—Na).

Example 119

Sodium 6-chloro-7-(4-(1-(3-chlorophenyl)pyrrolidin-3-ylcarbamoyl)phenoxy)chroman-4-carboxylate

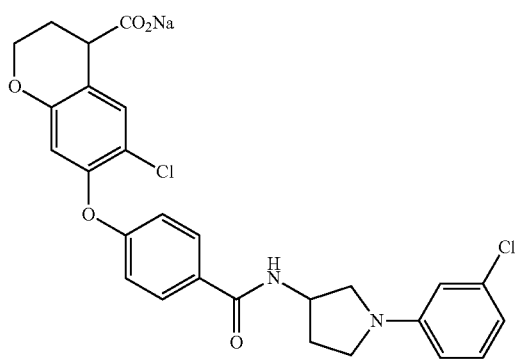

Step A: Preparation of tert-butyl 1-(3-chlorophenyl)pyrrolidin-3-ylcarbamate 3-N-Boc-amino pyrrolidine (120 mg, 0.644 mmol), cesium carbonate (252 mg, 0.773 mmol), and 3-bromochlorobenzene (75.7 µl, 0.644 mmol) were suspended in dry toluene. Argon was bubbled through the suspension for 2 minutes and then tris(dibenyzlideneacetone)dipalladium (35.4 mg, 0.0387 mmol) and rac-2,2-bis(diphenylphosphino)-1,1'-binaphthyl (60.4 mg, 0.0966 mmol) were added. The reaction vial was capped and heated to 110° C. with rapid stirring. After 15 hours, reaction was cooled to ambient temperature and applied directly to a silica gel column. Elution was a gradient of 5-70% ethyl acetate-hexanes provided the title compound (120 mg, 0.404 mmol, 62.8% yield) as an oil.

Step B: Preparation of 1-(3-chlorophenyl)pyrrolidin-3-amine dihydrochloride tert-Butyl 1-(3-chlorophenyl)pyrrolidin-3-ylcarbamate (120 mg, 0.404 mmol) in dichloromethane (0.5 ml) was treated with 4 molar hydrogen chloride in dioxane (1011 µL, 4.04 mmol) at ambient temperature in an open flask with rapid stirring. After 4 hours, the reaction was concentrated in vacuo to provide the di-hydrochloride salt of the title compound as a crude solid (122 mg, >100%).

Step C: Preparation of ethyl 6-chloro-7-(4-(1-(3-chlorophenyl)pyrrolidin-3-ylcarbamoyl)phenoxy)chroman-4-carboxylate Crude 1-(3-chlorophenyl)pyrrolidin-3-amine dihydrochloride (53.7 mg, 0.199 mmol) in dichloromethane was treated sequentially with N-ethyl-N-isopropylpropan-2-amine (78.6 µl, 0.451 mmol), 4-(6-chloro-4-(ethoxycarbonyl)chroman-7-yloxy)benzoic acid (Preparation 1) (50 mg, 0.133 mmol), 1-(3-dimethylaminopropyl)-3-ethylcarbodiimide hydrochloride (30.5 mg, 0.159 mmol), and 1-hydroxy-7-azabenzotriazole (5.42 mg, 0.0398 mmol) at ambient temperature. After 5 hours, the reaction was applied directly to a silica gel column. Elution with a gradient of 20-70% ethyl acetate-hexanes provided the title compound (70 mg, 0.126 mmol, 95.0% yield) as a solid.

Step D: Preparation of 6-chloro-7-(4-(1-(3-chlorophenyl)pyrrolidin-3-ylcarbamoyl)phenoxy)chroman-4-carboxylic acid Prepared according to Example 110, Step B to provide the title compound (65 mg, 99%) as a solid.

Step E: Preparation of sodium 6-chloro-7-(4-(1-(3-chlorophenyl)pyrrolidin-3-ylcarbamoyl)phenoxy)chroman-4-carboxylate Prepared according to Example 110, Step C to provide the title compound (66 mg, 97%) as a solid. MS (apci) m/z=526.9 (M+2H—Na).

Example 120

Sodium 6-chloro-7-(4-(1-(3-chlorophenyl)piperidin-4-ylcarbamoyl)phenoxy)chroman-4-carboxylate

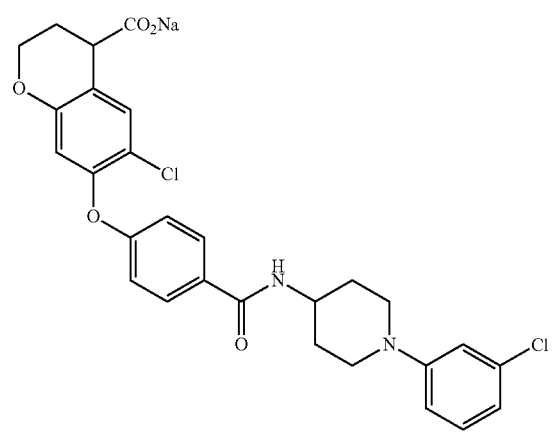

Prepared according to Example 119, replacing 3-N-Boc-amino pyrrolidine in Step A with 4-(N-Boc-amino)-piperidine to provide the title compound (59 mg, 99%) as a solid. MS (apci) m/z=541.0 (M+2H—Na).

Example 121

Sodium 6-chloro-7-(4-(1-(3-(trifluoromethyl)phenyl) azetidin-3-ylcarbamoyl)phenoxy)chroman-4-carboxylate

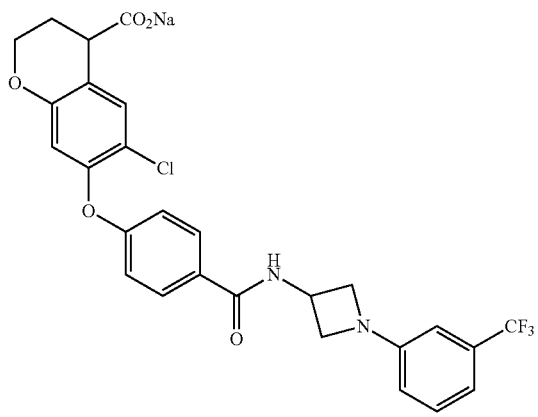

Prepared according to Example 119, replacing 3-N-Boc-amino pyrrolidine in Step A with azetidin-3-yl-carbamic acid to provide the title compound (28 mg, 96%) as a solid. MS (apci) m/z=547.0 (M+2H—Na).

Example 122

Sodium 6-chloro-7-(4-(1-(3-(trifluoromethyl)phenyl) pyrrolidin-3-ylcarbamoyl)phenoxy)chroman-4-carboxylate

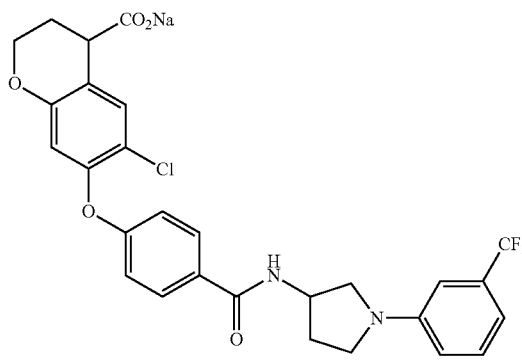

Prepared according to Example 119, replacing 3-bromochlorobenzene in Step A with 1-bromo-3-(trifluoromethyl) benzene to provide the title compound (70 mg, 99%) as a solid. MS (apci) m/z=560.9 (M+2H—Na).

Example 123

Sodium 6-chloro-7-(4-(1-(3-(trifluoromethyl)phenyl) piperidin-4-ylcarbamoyl)phenoxy)chroman-4-carboxylate

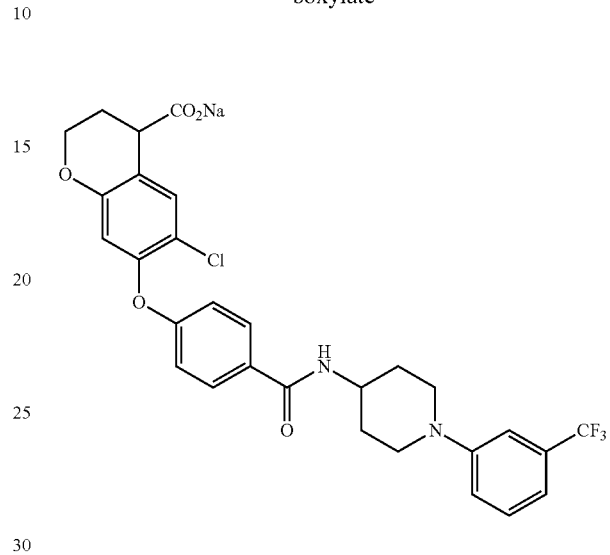

Prepared according to Example 119, replacing 3-N-Boc-amino pyrrolidine in Step A with 4-(N-Boc-amino)-piperidine and replacing 3-bromochlorobenzene with 1-bromo-3-(trifluoromethyl)benzene to provide the title compound (65 mg, 98%) as a solid. MS (apci) m/z=575.0 (M+2H—Na).

Example 124

Sodium 6-chloro-7-(4-(1-(2,4-dichlorophenyl)piperidin-4-ylcarbamoyl)phenoxy)chroman-4-carboxylate

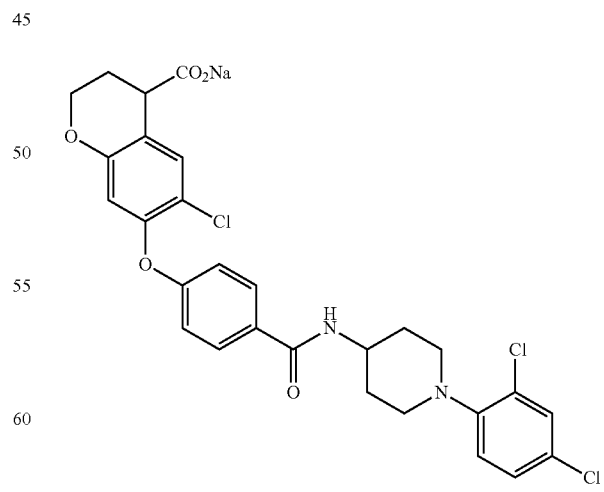

Prepared according to Example 119, replacing 3-N-Boc-amino pyrrolidine with 4-(N—BOC amino)-piperidine and replacing 3-bromochlorobenzene with 1-bromo-2,4-dichlorobenzene in Step A to provide the title compound (47 mg, 100%) as a solid. MS (apci) m/z=574.9 (M+2H—Na).

Example 125

Sodium 6-chloro-7-(4-((S)-1-(3-chlorophenyl)piperidin-3-ylcarbamoyl)phenoxy)chroman-4-carboxylate

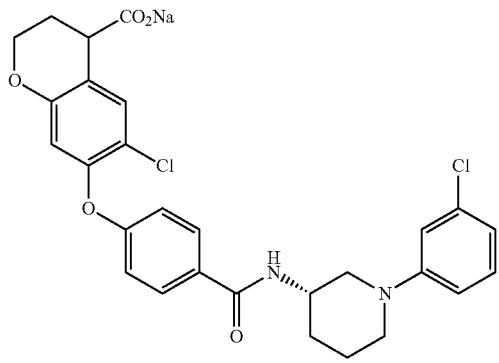

Prepared according to Example 119, replacing 3-N-Boc-amino pyrrolidine in Step A with (S)-tert-butyl piperidin-3-ylcarbamate to provide the title compound (70 mg, 100%) as a solid. MS (apci) m/z=541.0 (M+2H—Na).

Example 126

6-Cyano-7-(4-((2,3-dihydro-1H-inden-2-yl)methylcarbamoyl)phenoxy)chroman-4-carboxylic acid

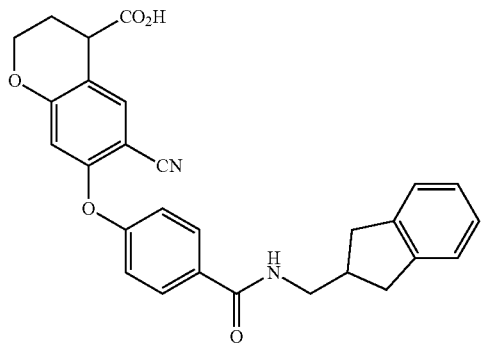 [SMILES: N#Cc1cc2c(cc1Oc1ccc(C(=O)NCC3Cc4ccccc4C3)cc1)OCCC2C(=O)O]

Step A: Preparation methyl 6-cyano-7-(4-((2,3-dihydro-1H-inden-2-yl)methylcarbamoyl)phenoxy)chroman-4-carboxylate Prepared according to Example 111, Step A replacing 4-(6-chloro-4-(ethoxycarbonyl)chroman-7-yloxy)benzoic acid with 4-(6-cyano-4-(methoxycarbonyl)chroman-7-yloxy) benzoic acid to provide the title compound (74 mg, 99% yield) as a solid.

Step B: Preparation of 6-cyano-7-(4-((2,3-dihydro-1H-inden-2-yl)methylcarbamoyl)phenoxy)chroman-4-carboxylate Prepared according to Example 110, Step B to provide the title compound (61 mg, 85%) as a solid. MS (apci) m/z=469.1 (M+H).

Example 127

7-(4-(4-tert-Butylcyclohexylcarbamoyl)phenoxy)-6-cyanochroman-4-carboxylic acid

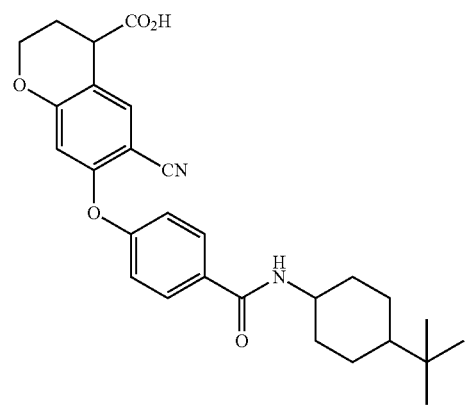 [SMILES: CC(C)(C)C1CCC(NC(=O)c2ccc(Oc3cc4c(cc3C#N)C(C(=O)O)CCO4)cc2)CC1]

Step A: Preparation methyl 7-(4-(4-tert-butylcyclohexylcarbamoyl)phenoxy)-6-cyanochroman-4-carboxylate Prepared according to Example 110, Step A where the reacting carboxylic acid replacing 4-(6-chloro-4-(ethoxycarbonyl)chroman-7-yloxy)benzoic acid with 4-(6-cyano-4-(methoxycarbonyl)chroman-7-yloxy)benzoic acid and replacing 2-(benzo[d][1,3]dioxol-5-yl)ethanamine with 4-tert-Butylcyclohexylamine to provide the title compound (73 mg, 97% yield) as a solid.

Step B: Preparation of 7-(4-(4-tert-butylcyclohexyl-carbamoyl)phenoxy)-6-cyanochroman-4-carboxylic acid Prepared according to Example 110, Step B to provide the title compound (68 mg, 91%) as a solid. MS (apci) m/z=477.2 (M+H).

Example 128

7-(4-(4-chlorophenyethylcarbamoyl)phenoxy)chroman-4-carboxylic acid

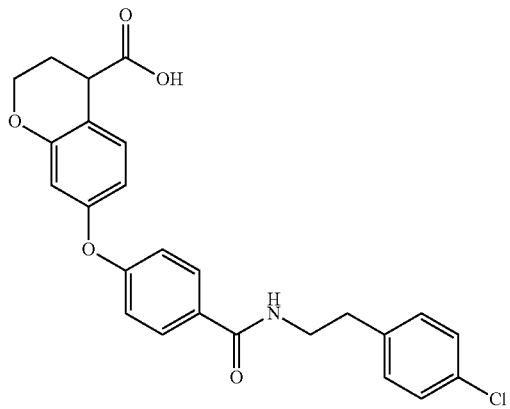 [SMILES: O=C(NCCc1ccc(Cl)cc1)c1ccc(Oc2ccc3c(c2)OCCC3C(=O)O)cc1]

Step A: Preparation of 7-methoxy-2,3-dihydrochromen-4-one

7-Hydroxy-2,3-dihydrochromen-4-one (4.47 g, 27.2 mmol) was diluted with tetrahydrofuran (40 mL) followed by the addition of $K_2CO_3$ (5.64 g, 40.8 mmol) and MeI (2.55 mL, 40.8 mmol). The reaction was heated at 70° C. for 5 hours. The reaction was allowed to cool and loaded onto a Biotage 40M cartridge running a gradient 5% ethyl acetate/hexanes to 75% to yield the title compound (3.5 g, 72.1% yield).

Step B: Preparation of 7-methoxy-4-(trimethylsilyloxy)-3,4-dihydro-2H-chromene-4-carbonitrile To a thick suspension of 7-methoxy-2,3-dihydrochromen-4-one (1.04 g, 5.84 mmol) in tetrahydrofuran (5 mL) was added zinc(II) iodide (0.0932 g, 0.292 mmol) followed by the dropwise addition of (trimethylsilyl)formonitrile (2.35 mL, 17.5 mmol). The reaction was stirred at ambient temperature for 4 hours, then diluted with ethyl acetate (50 mL) and washed with water (50 mL) and brine (50 mL). The combined organic layers were dried over magnesium sulfate and concentrated to give the title compound (1.62 g, 100% yield) which was used directly in the next step without further purification.

Step C: Preparation of 7-methoxy-3,4-dihydro-2H-chromene-4-carboxylic acid

To 7-methoxy-4-(trimethylsilyloxy)-3,4-dihydro-2H-chromene-4-carbonitrile (1.62 g, 5.84 mmol) in acetic acid (15 mL) and HCl (15 mL) was added $SnCl_2$ dihydrate (5.27 g, 23.4 mmol). The reaction was heated at 130° C. for 1 day. The reaction was cooled, diluted with dichloromethane (50 mL) and washed with water (50 mL) and brine (50 mL). The combined organic layers were dried over magnesium sulfate and concentrated. The residue was chromatographed over silica gel using a gradient of 0.5% $MeOH/CH_2Cl_2$ containing 0.5% acetic acid to 10% $MeOH/CH_2Cl_2$ containing 0.5% acetic acid to provide the title compound (0.95 g, 78.1% yield).

Step D: Preparation of methyl 7-hydroxy-3,4-dihydro-2H-chromene-4-carboxylate

To 7-methoxy-3,4-dihydro-2H-chromene-4-carboxylic acid (0.71 g, 3.41 mmol) was added HBr (0.276 g, 3.41 mmol) and the reaction was heated at 130° C. for 3 hours. The reaction was cooled and concentrated, and the residue was loaded onto a silica gel samplet. The product was eluted using a gradient of 0.5% $MeOH/CH_2Cl_2$ containing 0.5% acetic acid to 10% acetic acid/$CH_2Cl_2$ containing 0.5% acetic acid. The isolated product was dissolved in MeOH (5 mL) and concentrated sulfuric acid (1 mL) was added and the reaction heated at 75° C. After 2 hours, reaction was cooled, diluted with ethyl acetate (25 mL) and washed with water (25 mL) and brine (25 mL). The organic layer was dried over magnesium sulfate and concentrated. The residue was purified by silica gel chromatography, eluting with a gradient of 0.5% $MeOH/CH_2Cl_2$ to 10% $MeOH/CH_2Cl_2$, to provide the title compound (0.312 g, 43.9% yield).

Step E: Preparation of Methyl 7-(4-((4-chlorophenethyl)carbamoyl)phenoxy)-3,4-dihydro-2H-chromene-4-carboxylate Methyl 7-hydroxy-3,4-dihydro-2H-chromene-4-carboxylate (0.075 g, 0.360 mmol), N-(4-chlorophenethyl)-4-iodobenzamide (0.126 g, 0.327 mmol), 2,2,6,6-tetramethyl-3,5-heptanedione (0.00603 g, 0.0327 mmol), CuCl (0.0162 g, 0.164 mmol) and $Cs_2CO_3$ (0.213 g, 0.655 mmol) were stirred together in N-methylpyrrolidone (2 mL) at 120° C. for 3 hours. The reaction was cooled and loaded onto a silica gel samplet. The product was a eluted over using a gradient of 5% ethyl acetate/hexanes to 75% ethyl acetate/hexanes to provide the title compound (0.056 g, 37.8% yield).

Step F: Preparation of 7-(4-((4-chlorophenethyl)carbamoyl)phenoxy)-3,4-dihydro-2H-chromene-4-carboxylic acid Methyl 7-(4-((4-chlorophenethyl)carbamoyl)phenoxy)-3,4-dihydro-2H-chromene-4-carboxylate was dissolved in THF (3 mL) and methanol (3 mL) and treated with 1N NaOH (3 mL), and the reaction was stirred for 1 hour. The reaction was diluted with $CH_2Cl_2$ (25 mL) and washed with 2N HCl (25 mL), dried over magnesium sulfate and concentrated. The residue was purified by silica gel chromatography, eluting with a gradient of 0.5% $MeOH/CH_2Cl_2$ containing 0.5% acetic acid to 7.5% $MeOH/CH_2Cl_2$ containing 0.5% acetic acid to provide the title compound (0.056 g, 37.8% yield) as a white solid. MS (ESI)=452.1 (M+1).

Example 129

7-(4-(4-Chlorophenethylcarbamoyl)-2-methylphenoxy)-6-cyanochroman-4-carboxylic acid

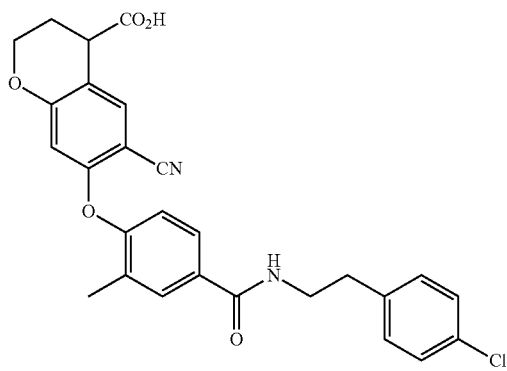 [SMILES: Cc1cc(C(=O)NCCc2ccc(Cl)cc2)ccc1Oc1cc2c(cc1C#N)C(C(=O)O)CCO2]

Step A: Preparation of 7-fluoro-4-(trimethylsilyloxy)chroman-4-carbonitrile

7-Fluoro-2,3-dihydrochromen-4-one (470 mg, 2.829 mmol) and $ZnI_2$ (45.15 mg, 0.1414 mmol) was diluted with trimethylsilyl cyanide (1.413 mL, 11.32 mmol). The reaction was stirred for 4 hours at ambient temperature. The reaction was diluted with $CH_2Cl_2$ and washed with saturated sodium bicarbonate twice. The organic layer was dried over $MgSO_4$, filtered and concentrated to yield the title compound (750 mg, 99.92% yield).

Step B: Preparation of 7-fluoro-3,4-dihydro-2H-chromene-4-carboxylic acid

7-Fluoro-4-(trimethylsilyloxy)chroman-4-carbonitrile (750 mg, 2.83 mmol) and $SnCl_2$ dihydrate (2551 mg, 11.3 mmol) were diluted with glacial acetic acid (3 mL) and concentrated HCl (3 mL). The reaction was heated in an oil bath at 130° C. and stirred overnight. The reaction was allowed to cool, diluted with water and ethyl acetate. The layers were separated and the organic layer was dried over $MgSO_4$, filtered and concentrated to yield the title compound (465 mg, 83.9% yield).

Step C: Preparation of methyl 7-fluoro-3,4-dihydro-2H-chromene-4-carboxylate

7-Fluoro-3,4-dihydro-2H-chromene-4-carboxylic acid (346 mg, 1.76 mmol) was diluted with (THF) 2 mL, methanol (2 mL) and 4 drops of sulfuric acid. The reaction was heated at 55° C. and stirred for 12 hours. The reaction was cooled to ambient temperature, diluted with ethyl acetate and saturated sodium bicarbonate. The layers were separated and the organic layer was dried over $MgSO_4$, filtered and concentrated to yield the title compound (366 mg, 98.7% yield).

Step D: Preparation of methyl 6-bromo-7-fluoro-3,4-dihydro-2H-chromene-4-carboxylate Methyl 7-fluoro-3,4-dihydro-2H-chromene-4-carboxylate (336 mg, 1.60 mmol) was diluted with DMF (5 mL) followed by the addition of N-bromosuccinimide (313 mg, 1.76 mmol). The reaction was heated at 50° C. and stirred for 2.5 hours. The reaction was cooled, diluted with ethyl acetate and washed with water, saturated sodium bicarbonate, water, and brine. The organic layer was dried over $MgSO_4$, filtered and concentrated. The material was purified using a Biotage 40M cartridge, gradient 5% ethyl acetate/hexane to 50% to yield the title compound (415 mg, 89.8% yield).

Step E: Preparation of methyl 6-cyano-7-fluoro-3,4-dihydro-2H-chromene-4-carboxylate Methyl 6-bromo-7-fluoro-3,4-dihydro-2H-chromene-4-carboxylate (415 mg, 1.44 mmol) was diluted with N-methylpyrrolidone (5 mL) followed by the addition of Cu(I)CN (643 mg, 7.18 mmol). The reaction was bubbled with argon for 20 minutes, then heated at 160° C. under a slight argon bubble for 6 hours. The reaction was cooled to ambient temperature and loaded directly onto a Biotage 25 column eluting with 5% ethyl acetate/hexanes to 100% ethyl acetate to yield the title compound (260 mg, 77.0% yield).

Step F: Preparation of 4-(6-cyano-4-(methoxycarbonyl)chroman-7-yloxy)-3-methylbenzoic acid A mixture of $K_2CO_3$ (0.026 g, 0.19 mmol), methyl 6-cyano-7-fluoro-3,4-dihydro-2H-chromene-4-carboxylate (0.040 g, 0.17 mmol), and tert-butyl 4-hydroxy-3-methylbenzoate (0.039 g, 0.19 mmol) in 0.5 ml NMP was heated under argon at 120° C. for 24 hours. The reaction was cooled, poured into 10% aqueous HCl, and extracted with ethyl acetate. The organic extracts were dried with sodium sulfate and purified on silica gel. Elution with 25% ethyl acetate-hexanes provided material that still contained impurities. The mixture was deprotected with to 1:1 trifluoracetic acid-dichloromethane to provide the title compound (13 mg, still impure) which was used directly in the next step.

Step G: Preparation of methyl 7-(4-(4-chlorophenethylcarbamoyl)-2-methylphenoxy)-6-cyanochroman-4-carboxylate 4-(6-Cyano-4-(methoxycarbonyl)-3,4-dihydro-2H-chromen-7-yloxy)-3-methylbenzoic acid (0.013 g, 0.03539 mmol) in 1 ml dry DMF was treated with N-ethyl-N-isopropylpropan-2-amine (0.01233 ml, 0.07078 mmol), HBTU (0.01610 g, 0.04247 mmol) and 2-(4-chlorophenyl)ethanamine (0.009843 ml, 0.07078 mmol) at ambient temperature. After 48 h, the reaction was poured into 10% aqueous HCl, extracted with ethyl acetate, dried over sodium sulfate, filtered, and concentrated to provide the crude material as a yellow film. Purification of the crude material on silica gel, eluting with 1% MeOH/DCM, provided the title compound (6 mg, 34%)

Step H: Preparation of 7-(4-(4-chlorophenethylcarbamoyl)-2-methylphenoxy)-6-cyanochroman-4-carboxylic acid Methyl 7-(4-((4-chlorophenethyl)carbamoyl)-2-methylphenoxy)-6-cyanochroman-4-carboxylate (0.0063 g, 0.0125 mmol) was taken up in 0.5 ml THF and treated with aqueous 1.0 molar LiOH (0.0250 ml, 0.0250 mmol) at ambient temperature. After 48 hours, the reaction was neutralized with acetic acid and concentrated in vacuo. Purification of the crude material by preparative thin layer chromatography using 5% MeOH/DCM with 1% HOAc as the mobile phase provided the title compound (2 mg, 38%). MS (apci) m/z=491.1 (M+H).

Example 130

6-Cyano-7-(4-((R)-2-phenylpropylcarbamoyl)phenoxy)chroman-4-carboxylic acid

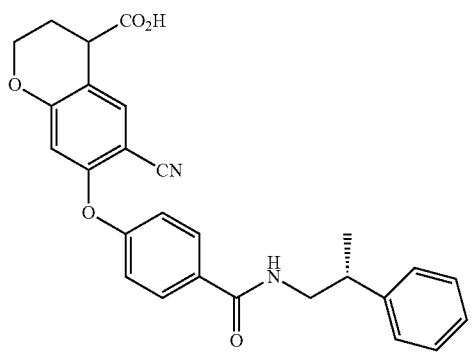 [SMILES: C[C@@H](CNC(=O)c1ccc(Oc2cc3c(cc2C#N)C(C(=O)O)CCO3)cc1)c1ccccc1]

Step A: Methyl 6-cyano-7-(4-((R)-2-phenylpropylcarbamoyl)phenoxy)chroman-4-carboxylate 4-(6-Cyano-4-(methoxycarbonyl)chroman-7-yloxy)benzoic acid (0.030 g, 0.0849 mmol) in 2 ml dry dichloromethane was treated with oxalyl chloride (0.0296 ml, 0.340 mmol) followed by 1 drop DMF at ambient temperature. After 45 minutes, the solution was concentrated under vacuum and the residue re-suspended in 2 ml DCM and treated with (R)-2-phenylpropan-1-amine (0.0182 ml, 0.127 mmol), 4-dimethylaminopyridine (0.00104 g, 0.00849 mmol), and pyridine (0.0137 ml, 0.170 mmol). After 12 hours, the reaction was diluted with dichloromethane and washed with 10% aqueous HCl. The dichloromethane layer was dried over sodium sulfate, filtered, concentrated, and purified on silica gel. Elution with a gradient of 30-50% ethyl acetate-hexanes provided the title compound (39 mg, 98%) as a solid.

Step B: 6-Cyano-7-(4-((R)-2-phenylpropylcarbamoyl)phenoxy)chroman-4-carboxylic acid Prepared according to Example 129, Step H to provide the title compound (13 mg, 27%) as an oil. MS (ESI) m/z=457.1 (M+H).

Example 131

6-Cyano-7-(4-((S)-2-phenylpropylcarbamoyl)phenoxy)chroman-4-carboxylic acid

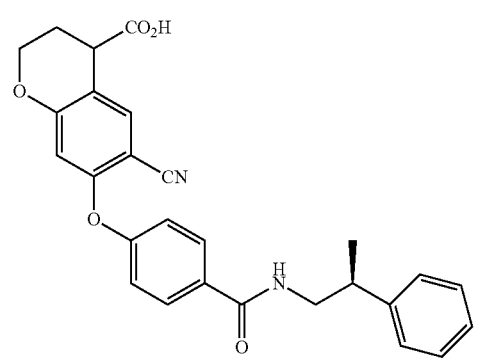 [SMILES: C[C@H](CNC(=O)c1ccc(Oc2cc3c(cc2C#N)C(C(=O)O)CCO3)cc1)c1ccccc1]

Prepared according to Example 130 step A replacing (R)-2-phenylpropan-1-amine with (S)-2-phenylpropan-1-amine to provide the title compound (12 mg, 35%) as a solid. MS (ESI) m/z=457.1 (M+H).

Example 132

7-(4-(1-(4-Chlorophenyl)propan-2-ylcarbamoyl)phenoxy)-6-cyanochroman-4-carboxylic acid

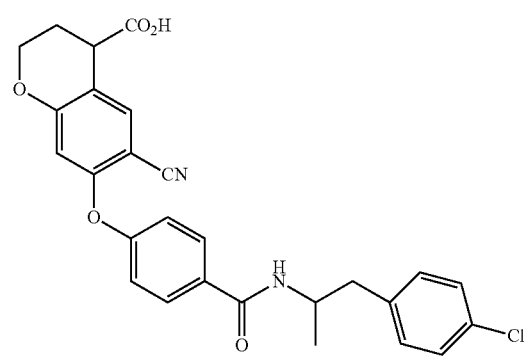 [SMILES: CC(Cc1ccc(Cl)cc1)NC(=O)c1ccc(Oc2cc3c(cc2C#N)C(C(=O)O)CCO3)cc1]

Prepared according to Example 130, step A, replacing (R)-2-phenylpropan-1-amine with 1-(4-chlorophenyl)propan-2-

Example 133

7-(4-(4-Chloro-3-methoxyphenethylcarbamoyl)phenoxy)-6-cyanochroman-4-carboxylic acid

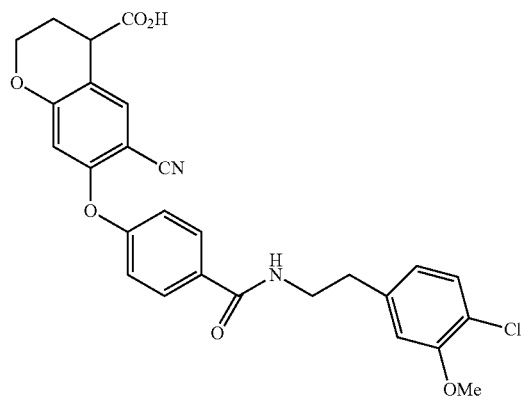 [SMILES: COc1cc(CCNC(=O)c2ccc(Oc3cc4c(cc3C#N)C(C(=O)O)CCO4)cc2)ccc1Cl]

Prepared according to Example 130, step A replacing (R)-2-phenylpropan-1-amine with 2-(4-chloro-3-methoxyphenyl)ethanamine to provide the title compound (12 mg, 50%). MS (ESI) m/z=507.0 (M+H).

Example 134

7-(4-(3-tert-Butylphenylcarbamoyl)phenoxy)-6-cyanochroman-4-carboxylic acid

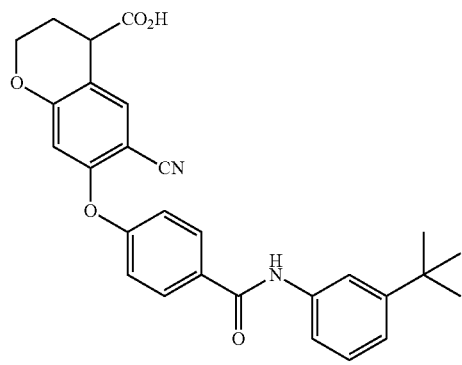 [SMILES: CC(C)(C)c1cccc(NC(=O)c2ccc(Oc3cc4c(cc3C#N)C(C(=O)O)CCO4)cc2)c1]

Step A: Methyl 7-(4-(3-tert-butylphenylcarbamoyl)phenoxy)-6-cyanochroman-4-carboxylate 4-(6-Cyano-4-(methoxycarbonyl)chroman-7-yloxy)benzoic acid (90 mg, 0.255 mmol), 3-tert-butylaniline (38 mg, 0.255 mmol), 1-(3-dimethylaminopropyl)-3-ethylcarbodiimide hydrochloride (43 mg, 0.280 mmol), and 1-hydroxy-7-azabenzotriazole (25 mg, 0.255 mmol) were combined in a round bottom flask and taken up in 5 ml dry of DMF. The reaction was stirred at ambient temperature for 12 hours and then poured into 10% HCl and extracted with ethyl acetate. The organic layer was dried over sodium sulfate, filtered, concentrated, and purified on silica gel. Elution with a gradient of 2-5% methanol-dichloromethane provided the title compound (100 mg, 81%).

Step B: 7-(4-(3-tert-butylphenylcarbamoyl)phenoxy)-6-cyanochroman-4-carboxylic acid Prepared according to Example 129, Step H to provide the title compound (46 mg, 47%) as solid. MS (apci) m/z=468.8 (M−H).

Example 135

6-Cyano-7-(4-(3-isopropoxyphenylcarbamoyl)phenoxy)chroman-4-carboxylic acid

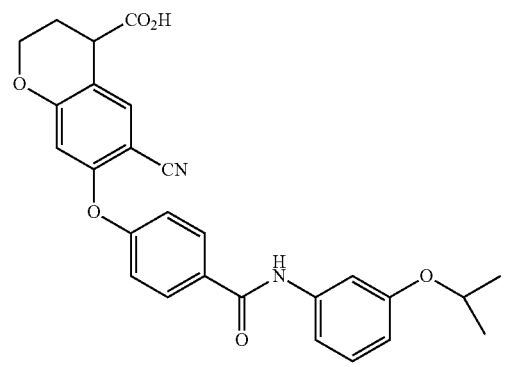 [SMILES: CC(C)Oc1cccc(NC(=O)c2ccc(Oc3cc4c(cc3C#N)C(C(=O)O)CCO4)cc2)c1]

Prepared according to Example 134, step A replacing 3-tert-butylaniline with 3-isopropoxyaniline to provide the title compound (53 mg, 56%) as a solid. MS (apci) m/z=473.1 (M+H).

Example 136

Sodium 6-chloro-7-(4-(3,4-dichlorobenzylcarbamoyl)phenoxy)chroman-4-carboxylate

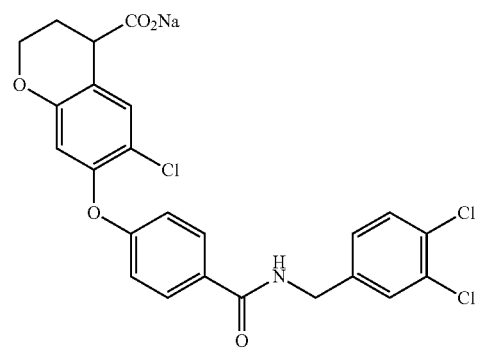

Step A: Preparation of ethyl 6-chloro-7-(4-(3,4-dichlorobenzylcarbamoyl)phenoxy)chroman-4-carboxylate 4-(6-chloro-4-(ethoxycarbonyl)chroman-7-yloxy)benzoic acid (Preparation 1) (51.5 mg, 0.137 mmol), in 1:1 DMF:DCM (0.1 M) was sequentially treated with 3,4-dichlorobenzylamine (26.5 mg, 0.150 mmol), 1-(3-dimethylaminopropyl)-3-ethylcarbodiimide hydrochloride (31.4 mg, 0.164 mmol), and 1-Hydroxy-7-azabenzotriazole (5.58 mg, 0.0410 mmol) at ambient temperature. After 16 hours the reaction was applied directly to a silica gel column and eluted with a gradient (15% to 60%) of ethyl acetate-hexanes to provide the title compound (69.0 mg, 0.129 mmol, 94.4% yield) as a white solid.

Step B: Preparation of 6-chloro-7-(4-(3,4-dichlorobenzylcarbamoyl)phenoxy)chroman-4-carboxylic acid ethyl 6-chloro-7-(4-(3,4-dichlorobenzylcarbamoyl)phenoxy)chroman-4-carboxylate (69.0 mg, 0.129 mmol) was reacted with 1.0 molar sodium hydroxide (516 µL, 0.516 mmol) in a 3:1 THF:Ethanol solution (0.05 M). After 2 hours the reaction was diluted with ethyl acetate, neutralized with 1.0 molar hydrochloric acid (542 µL, 0.542 mmol) and partitioned between saturated aqueous sodium chloride The organic layer was dried with sodium sulfate, filtered, concentrated, and dried under high vacuum to provide the title compound (49.4 mg, 0.0975 mmol, 75.6% yield) as a solid.

Step C: Preparation of sodium 6-chloro-7-(4-(3,4-dichlorobenzylcarbamoyl)phenoxy)chroman-4-carboxylate 6-chloro-7-(4-(3,4-dichlorobenzylcarbamoyl)phenoxy)chroman-4-carboxylic acid (49.4 mg, 0.0975 mmol), 0.1 molar in tetrahydrofuran, was treated with sodium methanolate (195 µL, 0.0975 mmol) at ambient temperature. After 20 minutes, the solvent was removed in vacuo. The resulting solid was taken up in ethyl acetate and concentrated in vacuo. The solid was taken up in 4:1 dichloromethane-hexanes and concentrated in vacuo and dried under high vacuum to provide sodium 6-chloro-7-(4-(3,4-dichlorobenzylcarbamoyl)phenoxy)chroman-4-carboxylate (51.5 mg, 0.0974 mmol, 99.9% yield) as a solid. MS (apci) m/z=507.6 (M+2H—Na).

Example 137

Sodium 6-chloro-7-(4-(4-(trifluoromethyl)phenethylcarbamoyl)phenoxy)chroman-4-carboxylate

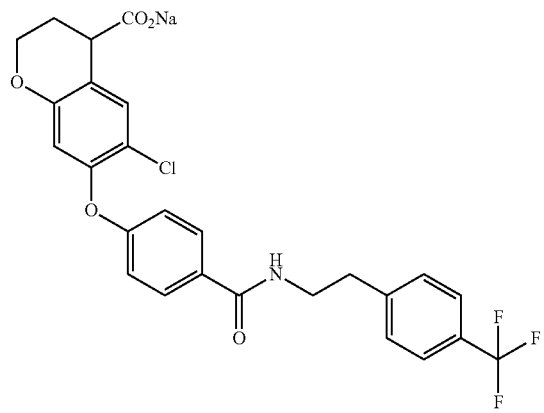

Prepared according to Example 136, substituting 2-(4-Trifluoromethyl-phenyl)-ethylamine for 3,4-dichlorobenzylamine to provide sodium 6-chloro-7-(4-(4-(trifluoromethyl) phenethylcarbamoyl)phenoxy)chroman-4-carboxylate (45.0 mg, 0.0830 mmol, 94.5% yield) as a solid. MS (apci) m/z=518.9 (M+2H—Na).

Example 138

Sodium 6-chloro-7-(4-(3,4-dichlorophenethylcarbamoyl)phenoxy)chroman-4-carboxylate

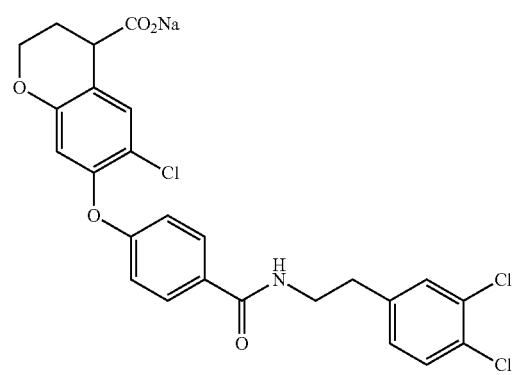

Prepared according to Example 136, substituting 3,4-Dichlorophenethylamine for 3,4-dichlorobenzylamine to provide sodium 6-chloro-7-(4-(3,4-dichlorophenethylcarbamoyl)phenoxy)chroman-4-carboxylate (81.1 mg, 0.149 mmol, 99.6% yield) as a solid. MS (apci) m/z=522.0 (M+2H—Na).

Example 139

Sodium 6-chloro-7-(4-(2,3-dichlorophenethylcarbamoyl)phenoxy)chroman-4-carboxylate

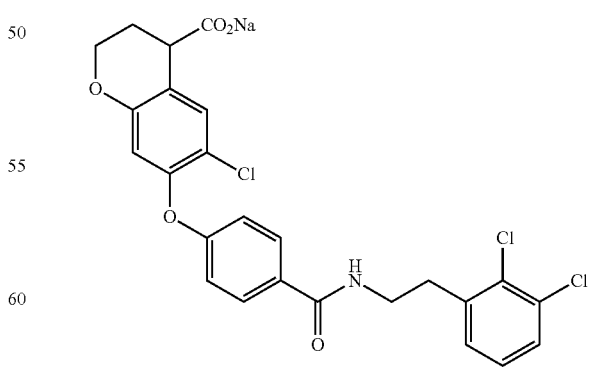

Prepared according to Example 136, substituting 2-(2,3-dichlorophenyl)ethanamine for 3,4-dichlorobenzylamine to provide sodium 6-chloro-7-(4-(2,3-dichlorophenethylcarbamoyl)phenoxy)chroman-4-carboxylate (43.0 mg, 0.0792 mmol, 100% yield) as a solid. MS (apci) m/z=520.0 (M+2H—Na).

Example 140

Sodium 6-chloro-7-(4-(4-methoxyphenethylcarbamoyl)phenoxy)chroman-4-carboxylate

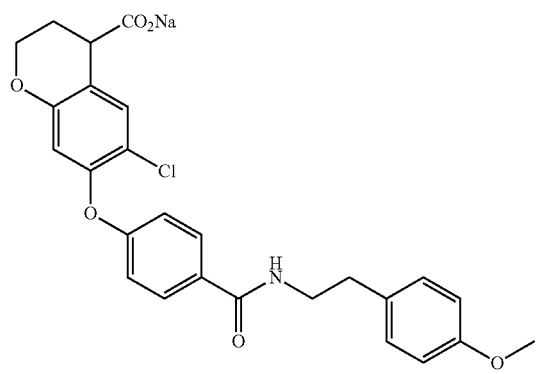

Prepared according to Example 136, substituting 4-methoxyphenethylamine for 3,4-dichlorobenzylamine to provide sodium 6-chloro-7-(4-(4-methoxyphenethylcarbamoyl)phenoxy)chroman-4-carboxylate (49.0 mg, 0.0972 mmol, 99.3% yield) as a solid. MS (apci) m/z=482.0 (M+2H—Na).

Example 141

Sodium 6-chloro-7-(4-(3,4-dimethoxyphenethylcarbamoyl)phenoxy)chroman-4-carboxylate

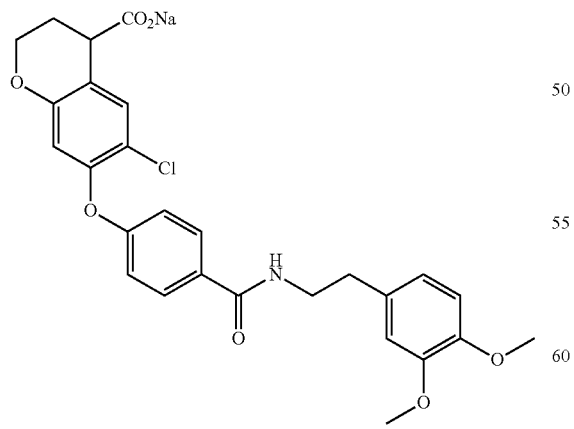

Prepared according to Example 136, substituting 3,4-dimethoxyphenethylamine for 3,4-dichlorobenzylamine to provide sodium 6-chloro-7-(4-(3,4-dimethoxyphenethylcarbamoyl)phenoxy)chroman-4-carboxylate (52.0 mg, 0.0974 mmol, 99.1% yield) as a solid. MS (apci) m/z=511.9 (M+2H—Na).

Example 142

Sodium 7-(4-(4-tert-butylphenethylcarbamoyl)phenoxy)-6-chlorochroman-4-carboxylate

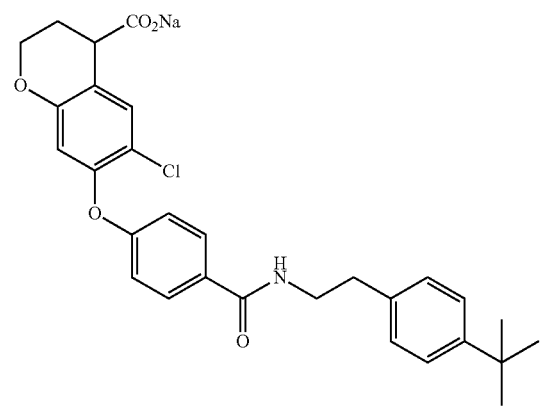

Prepared according to Example 136, substituting 2(-4-tert-butylphenyl)ethylamine for 3,4-dichlorobenzylamine to provide sodium 7-(4-(4-tert-butylphenethylcarbamoyl)phenoxy)-6-chlorochroman-4-carboxylate (36.0 mg, 0.0679 mmol, 97.5% yield) as a solid. MS (apci) m/z=508.0 (M+2H—Na).

Example 143

Sodium 6-chloro-7-(4-(3-methoxyphenethylcarbamoyl)phenoxy)chroman-4-carboxylate

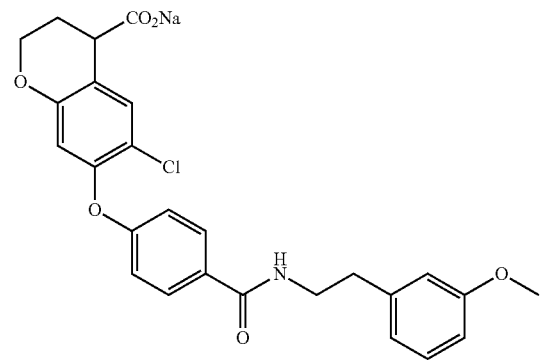

Prepared according to Example 136, substituting 3-methoxyphenethylamine for 3,4-dichlorobenzylamine to provide sodium 6-chloro-7-(4-(3-methoxyphenethylcarbamoyl)phenoxy)chroman-4-carboxylate (54.0 mg, 0.107 mmol, 98.9% yield) as a solid. MS (apci) m/z=481.9 (M+2H—Na).

Example 144

Sodium 6-chloro-7-(4-(2,4-dimethoxyphenethylcarbamoyl)phenoxy)chroman-4-carboxylate

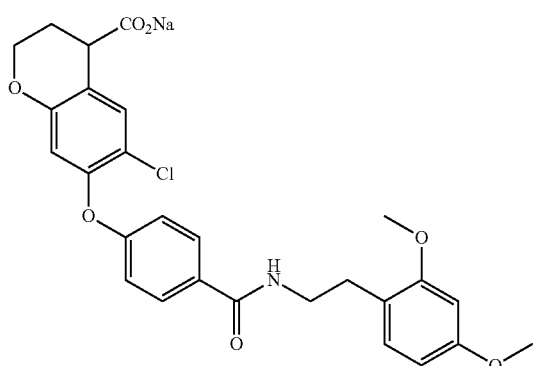

Prepared according to Example 136, substituting 2-(2,4-dimethoxyphenyl)ethanamine for 3,4-dichlorobenzylamine to provide sodium 6-chloro-7-(4-(2,4-dimethoxyphenethylcarbamoyl)phenoxy)chroman-4-carboxylate (34.0 mg, 0.0637 mmol, 99.1% yield) as a solid. MS (apci) m/z=511.9 (M+2H—Na).

Example 145

Sodium 6-chloro-7-(4-(3-fluorophenethylcarbamoyl)phenoxy)chroman-4-carboxylate

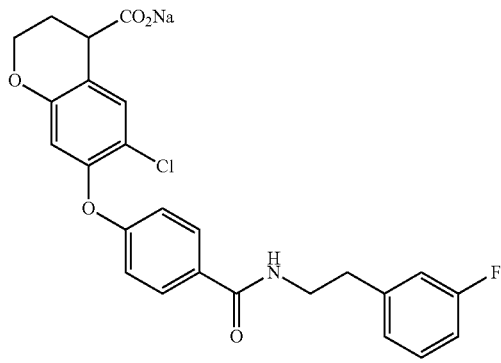

Prepared according to Example 136, substituting 3-fluorophenethylamine for 3,4-dichlorobenzylamine to provide sodium 6-chloro-7-(4-(3-fluorophenethylcarbamoyl)phenoxy)chroman-4-carboxylate (49.7 mg, 0.0996 mmol, 98.5% yield) as a solid. MS (apci) m/z=470.0 (M+2H—Na).

Example 146

Sodium 6-chloro-7-(4-(3-methylphenethylcarbamoyl)phenoxy)chroman-4-carboxylate

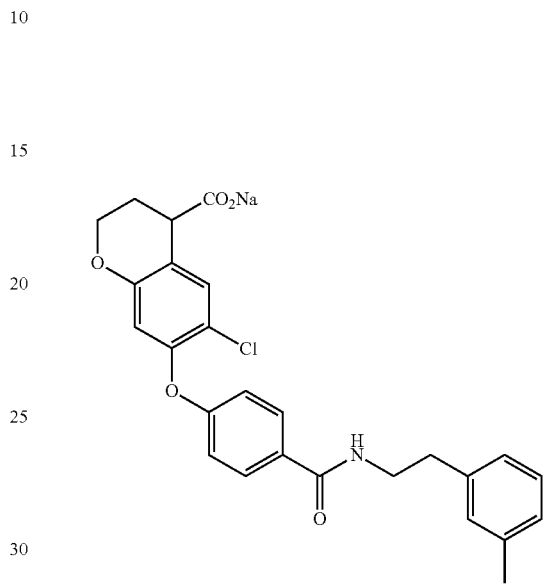

Prepared according to Example 136, substituting 3-Methylphenethylamine for 3,4-dichlorobenzylamine to provide sodium 6-chloro-7-(4-(3-methylphenethylcarbamoyl)phenoxy)chroman-4-carboxylate (49.0 mg, 0.100 mmol, 99.8% yield) as a solid. MS (apci) m/z=466.0 (M+2H—Na).

Example 147

Sodium 6-chloro-7-(4-(4-(trifluoromethylthio)phenethylcarbamoyl)phenoxy)chroman-4-carboxylate

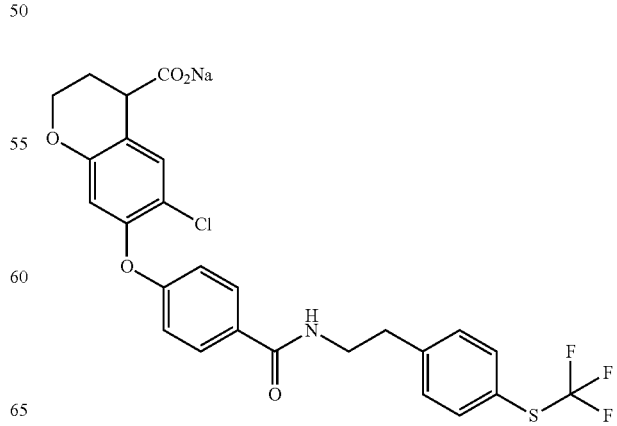

Step A: Preparation of 2-(4-(trifluoromethylthio)phenyl)ethanamine 4-(Trifluoromethylthio)phenylacetonitrile (183.4 mg, 0.844 mmol), 0.3 molar in THF, was heated to reflux and then treated with Borane-methyl sulfide complex (88.09 µL, 0.929 mmol). After 1 hour of refluxing, the reaction mixture was cooled to ambient temperature and then treated dropwise with 5.0 molar hydrochloric acid (607.9 µL, 3.040 mmol). The reaction mixture was then heated to reflux for an additional 30 minutes. After 30 minutes the reaction mixture was cooled to 0° C. and then treated with 1.0 molar sodium hydroxide (4644 µL, 4.644 mmol). The reaction mixture was diluted with diethyl ether and partitioned with deionized water. The organic layer was dried with potassium carbonate 98% powder, filtered, concentrated, and dried for one minute under high vacuum to provide the title compound (170.7 mg, 0.772 mmol, 91.2% yield) as a light yellow oil.

Step B: Preparation of ethyl 6-chloro-7-(4-(4-(trifluoromethylthio) phenethylcarbamoyl)phenoxy)chroman-4-carboxylate 4-(6-Chloro-4-(ethoxycarbonyl) chroman-7-yloxy)benzoic acid (Preparation 1) (50.7 mg, 0.137 mmol), in 1:1 DCM: DMF (0.1 M) was sequentially treated with 2-(4-(trifluoromethylthio)phenyl)ethanamine (32.7 mg, 0.148 mmol), 1-(3-dimethylaminopropyl)-3-ethylcarbodiimide hydrochloride (31.0 mg, 0.161 mmol), 1-hydroxy-7-azabenzotriazole (5.49 mg, 0.0404 mmol), and N,N-Diisopropylethylamine (26.1 mg, 0.202 mmol) at ambient temperature. After 16 hours the reaction was applied directly to a silica gel column and eluted with a gradient (15% to 60%) of ethyl acetate-hexanes to provide the title compound (73.3 mg, 0.126 mmol, 93.9% yield) as a white solid.

Step C: Preparation of 6-chloro-7-(4-(4-(trifluoromethylthio) phenethylcarbamoyl)phenoxy)chroman-4-carboxylic acid ethyl 6-chloro-7-(4-(4-(trifluoromethylthio)phenethylcarbamoyl)phenoxy)chroman-4-carboxylate (73.3 mg, 0.126 mmol) was reacted with 1.0 molar sodium hydroxide (506 µL, 0.506 mmol) in a 3:1 THF:Ethanol solution (0.05 M). After 2 hours the reaction was diluted with ethyl acetate, neutralized with 1.0 molar hydrochloric acid (531 µL, 0.531 mmol) and partitioned between saturated aqueous sodium chloride. The organic layer was dried with sodium sulfate, filtered, concentrated, and dried under high vacuum to provide the title compound (58.7 mg, 0.106 mmol, 84.2% yield) as a solid.

Step D: Preparation of sodium 6-chloro-7-(4-(4-(trifluoromethylthio) phenethylcarbamoyl)phenoxy)chroman-4-carboxylate 6-Chloro-7-(4-(4-(trifluoromethylthio) phenethylcarbamoyl)phenoxy)chroman-4-carboxylic acid (58.7 mg, 0.106 mmol), 0.1 molar in tetrahydrofuran, was treated with sodium methanolate (213 µL, 0.106 mmol) at ambient temperature. After 20 minutes, the solvent was removed in vacuo. The resulting solid was taken up in ethyl acetate and concentrated in vacuo. The solid was taken up in 4:1 dichloromethane-hexanes and concentrated in vacuo and dried under high vacuum to provide sodium 6-chloro-7-(4-(4-(trifluoromethylthio)phenethylcarbamoyl)phenoxy)chroman-4-carboxylate (60.0 mg, 0.105 mmol, 98.3% yield) as a solid. MS (apci) m/z=552.0 (M+2H—Na).

Example 148

Sodium 6-chloro-7-(4-(3,5-dichlorophenethylcarbamoyl)phenoxy)chroman-4-carboxylate

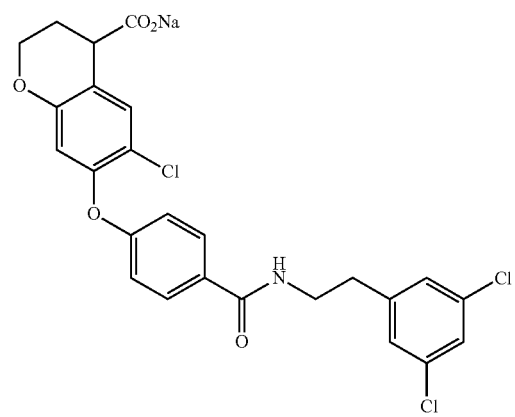

Step A: Preparation of 2-(3,5-dichlorophenyl)acetonitrile 3,5-Dichlorobenzyl chloride (315.6 mg, 1.615 mmol), 0.2 molar in DMSO, was treated with sodium cyanide (158.2 mg, 3.229 mmol) and allowed to stir at ambient temperature for 24 hours. After 24 hours the reaction mixture was diluted with diethyl ether and partitioned between saturated aqueous sodium chloride. The organic layer was dried with magnesium sulfate, filtered, and concentrated to provide the title compound (155.5 mg, 0.836 mmol, 51.8% yield) as a dark red oil.

Step B: Preparation of 2-(3,5-dichlorophenyl)ethanamine 2-(3,5-dichlorophenyl)acetonitrile (155.5 mg, 0.836 mmol), 0.3 molar in THF, was heated to reflux and then treated with Borane-methyl sulfide complex (87.20 µL, 0.919 mmol). After 1 hour of refluxing, the reaction mixture was cooled to ambient temperature and then treated dropwise with 5.0 molar hydrochloric acid (601.8 µl, 3.009 mmol). The reaction mixture was heated to reflux for an additional 30 minutes. After 30 minutes the reaction mixture was cooled to 0° C. and treated with 1.0 molar sodium hydroxide (4597 µL, 4.597 mmol). The reaction mixture was diluted with diethyl ether and partitioned with deionized water. The organic layer was dried with potassium carbonate 98% powder, filtered, concentrated, and dried for one minute under high vacuum to provide the title compound (135.2 mg, 0.7113 mmol, 85.1% yield) as a light yellow oil.

Step C: Preparation of ethyl 6-chloro-7-(4-(3,5-dichlorophenethylcarbamoyl)phenoxy)chroman-4-carboxylate 4-(6-Chloro-4-(ethoxycarbonyl)chroman-7-yloxy)benzoic acid (Preparation 1) (54.2 mg, 0.144 mmol), in 1:1 DCM:

DMF (0.1 M) was sequentially treated with 2-(3,5-dichlorophenyl)ethanamine (30.1 mg, 0.158 mmol), 1-(3-dimethylaminopropyl)-3-ethylcarbodiimide hydrochloride (33.1 mg, 0.173 mmol), 1-Hydroxy-7-azabenzotriazole (5.87 mg, 0.0432 mmol), and N,N-diisopropylethylamine (27.9 mg, 0.216 mmol) at ambient temperature. After 24 hours the reaction was applied directly to a silica gel column and eluted with a gradient (15% to 60%) of ethyl acetate-hexanes to provide the title compound (76.4 mg, 0.139 mmol, 96.8% yield) as a white solid.

Step D: Preparation of 6-chloro-7-(4-(3,5-dichlorophenethylcarbamoyl)phenoxy)chroman-4-carboxylic acid ethyl 6-chloro-7-(4-(3,5-dichlorophenethylcarbamoyl)phenoxy)chroman-4-carboxylate (76.4 mg, 0.139 mmol) was reacted with 1.0 molar sodium hydroxide (557 µl, 0.557 mmol) in a 3:1 THF:Ethanol solution (0.05 M). After 2 hours the reaction was diluted with ethyl acetate, neutralized with 1.0 molar hydrochloric acid (585 µl, 0.585 mmol) and partitioned between saturated aqueous sodium chloride. The organic layer was dried with sodium sulfate, filtered, concentrated, and dried under high vacuum to provide the title compound (72.5 mg, 0.115 mmol, 82.8% yield) as a solid.

Step E: Preparation of sodium 6-chloro-7-(4-(3,5-dichlorophenethyl-carbamoyl)phenoxy)chroman-4-carboxylate 6-chloro-7-(4-(3,5-dichlorophenethylcarbamoyl)phenoxy)chroman-4-carboxylic acid (60.0 mg, 0.115 mmol), 0.1 molar in tetrahydrofuran, was treated with sodium methanolate (230 µl, 0.115 mmol) at ambient temperature. After 20 minutes, the solvent was removed in vacuo. The resulting solid was taken up in ethyl acetate and concentrated in vacuo. The solid was taken up in 4:1 dichloromethane-hexanes and concentrated in vacuo and dried under high vacuum to provide sodium 6-chloro-7-(4-(3,5-dichlorophenethylcarbamoyl)phenoxy)chroman-4-carboxylate (62.0 mg, 0.114 mmol, 99.1% yield) as a solid. MS (apci) m/z=521.9 (M+2H—Na)

Example 149

Sodium 6-chloro-7-(4-(3-phenoxyphenethylcarbamoyl)phenoxy)chroman-4-carboxylate

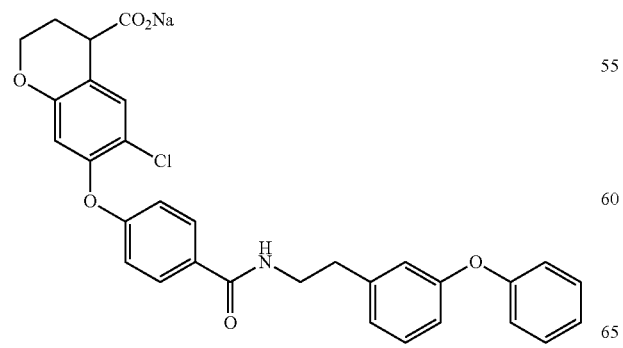

Step A: Preparation of ethyl 6-chloro-7-(4-(3-phenoxyphenethylcarbamoyl)phenoxy)chroman-4-carboxylate 4-(6-Chloro-4-(ethoxycarbonyl)chroman-7-yloxy)benzoic acid (Preparation 1) (51.6 mg, 0.137 mmol), in 1:1 DCM:DMF (0.1 M) was sequentially treated with 3-phenoxyphenethylamine (32.1 mg, 0.151 mmol), 1-(3-dimethylaminopropyl)-3-ethylcarbodiimide hydrochloride (31.5 mg, 0.164 mmol), and 1-hydroxy-7-azabenzotriazole (5.59 mg, 0.0411 mmol) at ambient temperature. After 24 hours the reaction was applied directly to a silica gel column and eluted with a gradient (15% to 60%) of ethyl acetate-hexanes to provide the title compound (71.6 mg, 0.125 mmol, 91.4% yield) as a white solid.

Step B: Preparation of 6-chloro-7-(4-(3-phenoxyphenethylcarbamoyl)phenoxy)chroman-4-carboxylic acid Ethyl 6-chloro-7-(4-(3-phenoxyphenethylcarbamoyl)phenoxy)chroman-4-carboxylate (71.6 mg, 0.125 mmol) was reacted with 1.0 molar sodium hydroxide (501 µl, 0.501 mmol) in a 3:1 THF:Ethanol solution (0.05 M). After 2 hours the reaction was diluted with ethyl acetate, neutralized with 1.0 molar hydrochloric acid (526 µl, 0.526 mmol) and partitioned between saturated aqueous sodium chloride. The organic layer was dried with sodium sulfate, filtered, concentrated, and dried under high vacuum to provide the title compound (56.4 mg, 0.104 mmol, 82.8% yield) as a solid.

Step C: Preparation of sodium 6-chloro-7-(4-(3-phenoxyphenethyl-carbamoyl)phenoxy)chroman-4-carboxylate 6-Chloro-7-(4-(3-phenoxyphenethylcarbamoyl)phenoxy)chroman-4-carboxylic acid (56.4 mg, 0.104 mmol), 0.1 molar in tetrahydrofuran, was treated with sodium methanolate (207 µl, 0.104 mmol) at ambient temperature. After 20 minutes, the solvent was removed in vacuo. The resulting solid was taken up in ethyl acetate and concentrated in vacuo. The solid was taken up in 4:1 dichloromethane-hexanes and concentrated in vacuo and dried under high vacuum to provide sodium 6-chloro-7-(4-(3-phenoxyphenethylcarbamoyl)phenoxy)chroman-4-carboxylate (58.0 mg, 0.102 mmol, 98.8% yield) as a solid. MS (apci) m/z=543.9 (M+2H—Na).

Example 150

Sodium 6-chloro-7-(4-(3-chlorophenethylcarbamoyl)phenoxy)chroman-4-carboxylate

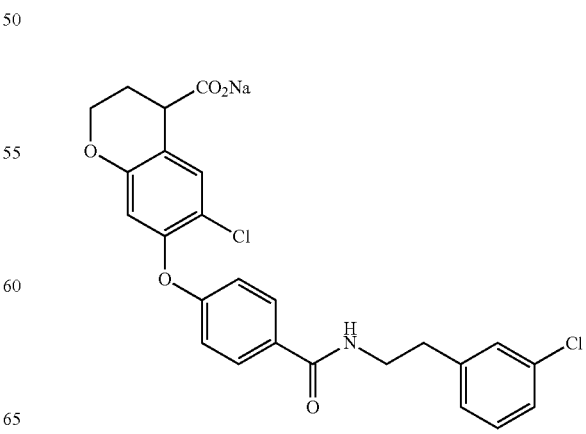

Step A: Preparation of ethyl 6-chloro-7-(4-(3-chlorophenethylcarbamoyl)phenoxy)chroman-4-carboxylate 4-(6-Chloro-4-(ethoxycarbonyl)chroman-7-yloxy)benzoic acid (Preparation 1) (48.8 mg, 0.130 mmol), in 1:1 DCM:DMF (0.1 M) was sequentially treated with 2-(3-chlorophenyl)ethylamine (22.2 mg, 0.143 mmol), 1-(3-dimethylaminopropyl)-3-ethylcarbodiimide hydrochloride (29.8 mg, 0.155 mmol), and 1-hydroxy-7-azabenzotriazole (5.29 mg, 0.0389 mmol) at ambient temperature. After 48 hours the reaction was applied directly to a silica gel column and eluted with a gradient (15% to 60%) of ethyl acetate-hexanes to provide the title compound (61.1 mg, 0.119 mmol, 91.7% yield) as a white solid.

Step B: Preparation of 6-Chloro-7-(4-(3-chlorophenethylcarbamoyl)phenoxy) chroman-4-carboxylic acid ethyl 6-chloro-7-(4-(3-chlorophenethylcarbamoyl)phenoxy) chroman-4-carboxylate (61.1 mg, 0.119 mmol) was reacted with 1.0 molar sodium hydroxide (475 µl, 0.475 mmol) in a 3:1 THF:Ethanol solution (0.05 M). After 2 hours the reaction was diluted with ethyl acetate, neutralized with 1.0 molar hydrochloric acid (499 µL, 0.499 mmol) and partitioned between saturated aqueous sodium chloride. The organic layer was dried with sodium sulfate, filtered, concentrated, and dried under high vacuum to provide the title compound (40.2 mg, 0.0827 mmol, 69.6% yield) as a solid.

Step C: Preparation of sodium 6-chloro-7-(4-(3-chlorophenethylcarbamoyl)phenoxy)chroman-4-carboxylate 6-Chloro-7-(4-(3-chlorophenethylcarbamoyl)phenoxy) chroman-4-carboxylic acid (40.2 mg, 0.0827 mmol), 0.1 molar in tetrahydrofuran, was treated with sodium methanolate (165 µL, 0.0827 mmol) at ambient temperature. After 20 minutes, the solvent was removed in vacuo. The resulting solid was taken up in ethyl acetate and concentrated in vacuo. The solid was taken up in 4:1 dichloromethane-hexanes and concentrated in vacuo and dried under high vacuum to provide sodium 6-chloro-7-(4-(3-chlorophenethylcarbamoyl) phenoxy)chroman-4-carboxylate (42.0 mg, 0.0826 mmol, 100% yield) as a solid. MS (apci) m/z=486.0 (M+2H—Na).

Example 151

Sodium 6-chloro-7-(4-(3-(trifluoromethyl)phenethylcarbamoyl)phenoxy)chroman-4-carboxylate

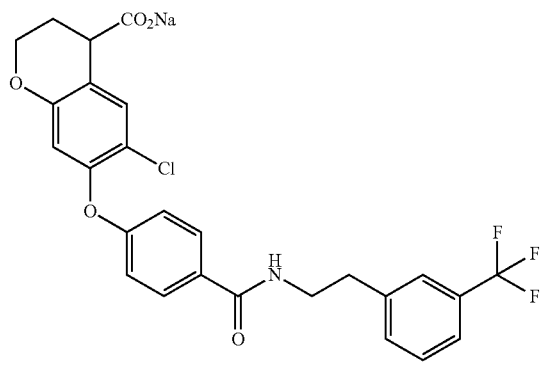

Prepared according to Example 150, substituting 2-(3-Trifluoromethylphenyl)-ethylamine for 2-(3-chlorophenyl)ethylamine to provide sodium 6-chloro-7-(4-(3-(trifluoromethyl)phenethylcarbamoyl)phenoxy)chroman-4-carboxylate (54.0 mg, 0.0997 mmol, 99.0% yield) as a solid. MS (apci) m/z=517.8 (M+2H—Na).

Example 152

Sodium 6-chloro-7-(4-(2-(trifluoromethyl)phenethylcarbamoyl)phenoxy)chroman-4-carboxylate

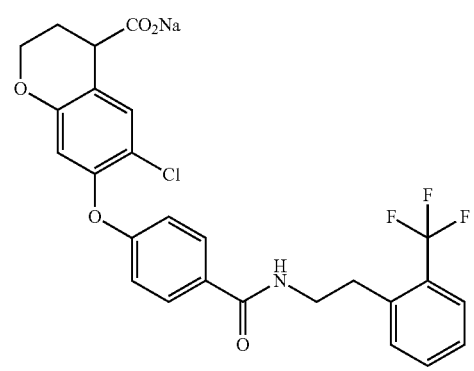

Prepared according to Example 150, substituting 2-(2-trifluoromethylphenyl)ethylamine for 2-(3-chlorophenyl)ethylamine to provide sodium 6-chloro-7-(4-(2-(trifluoromethyl) phenethylcarbamoyl)phenoxy)chroman-4-carboxylate (55.0 mg, 0.101 mmol, 101% yield) as a solid. MS (apci) m/z=520.0 (M+2H—Na).

Example 153

Sodium 6-chloro-7-(4-(2-fluorophenethylcarbamoyl) phenoxy)chroman-4-carboxylate

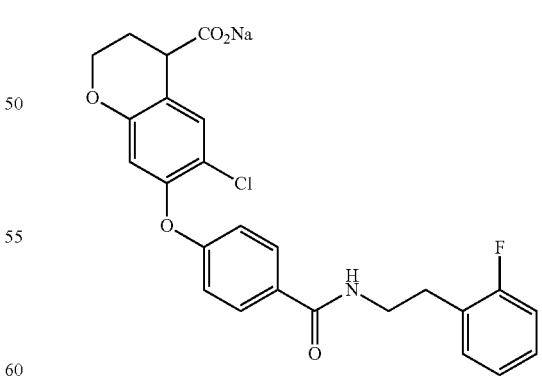

Prepared according to Example 150, substituting 2-fluorophenethylamine for 2-(3-chlorophenyl)ethylamine to provide sodium 6-chloro-7-(4-(2-fluorophenethylcarbamoyl) phenoxy)chroman-4-carboxylate (47.0 mg, 0.0956 mmol, 100% yield) as a solid. MS (apci) m/z=470.1 (M+2H—Na).

Example 154

6-Cyano-7-(4-(3-(trifluoromethyl)phenylcarbamoyl)phenoxy)chroman-4-carboxylic acid

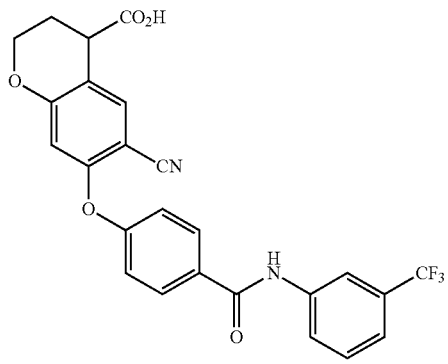 [SMILES: N#Cc1cc2c(cc1Oc1ccc(C(=O)Nc3cccc(C(F)(F)F)c3)cc1)OCCC2C(=O)O]

Step A: Preparation of methyl 6-cyano-7-(4-(3-(trifluoromethyl)phenylcarbamoyl)phenoxy)chroman-4-carboxylate To a solution of 4-(6-cyano-4-(methoxycarbonyl)chroman-7-yloxy)benzoic acid (0.050 g, 0.1415 mmol) in dichloromethane (0.7 ml) and N,N-dimethylformamide (1 drop) was added oxalyl dichloride (0.01358 ml, 0.1557 mmol), and the reaction was stirred at ambient temperature for 30 minutes. 3-(Trifluoromethyl)aniline (0.01944 ml, 0.1557 mmol) and triethylamine (0.04339 ml, 0.3113 mmol) were added, and the reaction was stirred at ambient temperature for 3 days. The reaction mixture was diluted with ethyl acetate and washed with 1M hydrochloric acid, saturated sodium bicarbonate, and saturated sodium chloride, dried over anhydrous sodium sulfate, filtered, and concentrated. The residue was diluted with dichloromethane and stirred with excess amine-3 functionalized silica gel for 30 minutes, then filtered and concentrated. The crude material was purified by preparative thin layer chromatography eluting with 25% EtOAc in hexanes to yield 19 mg of the title compound (27% yield).

Step B: Preparation of 6-cyano-7-(4-(3-(trifluoromethyl)phenylcarbamoyl)phenoxy)chroman-4-carboxylic acid To a solution of methyl 6-cyano-7-(4-(3-(trifluoromethyl)phenylcarbamoyl)phenoxy)chroman-4-carboxylate (0.019 g, 0.0383 mmol) in 3:1 THF/methanol (2 ml) was added 1M sodium hydroxide (0.0459 ml, 0.0459 mmol), and the reaction was stirred at ambient temperature overnight. The reaction was concentrated and partitioned between EtOAc and diluted HCl in water. The aqueous was extracted once with EtOAc, and the combined organic layers were dried over sodium sulfate, filtered and concentrated. The crude material was purified by preparative thin layer chromatography eluting with 95:5:1 dichloromethane/methanol/acetic acid to yield 10 mg of the title compound (54.2% yield). MS (apci) m/z=480.8 (M+H).

Example 155

6-Chloro-7-(4-(4-phenylcyclohexylcarbamoyl)phenoxy)chroman-4-carboxylic acid (Mixture of cis and trans isomers)

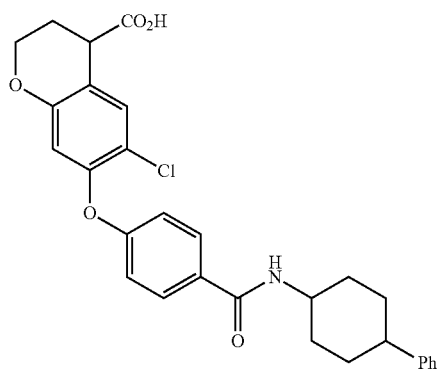 [SMILES: O=C(NC1CCC(c2ccccc2)CC1)c1ccc(Oc2cc3c(cc2Cl)C(C(=O)O)CCO3)cc1]

Step A: Preparation of 4-phenylcyclohexanone oxime

To a solution of 4-phenylcyclohexanone (1.50 g, 8.609 mmol) in 95% ethanol (20 ml) was added 50% hydroxylamine in water (5.276 ml, 86.09 mmol), and the reaction was heated to reflux for 1 hour. The reaction was allowed to cool to ambient temperature, and the product was precipitated by the slow addition of water. The solids were collected via filtration to yield 1.0 g of the title compound (61.38% yield).

Step B: Preparation of 4-phenylcyclohexanamine

To a solution of 4-phenylcyclohexanone oxime (0.310 g, 1.64 mmol) in THF (3 ml) was added 1M lithium aluminum hydride in THF (3.44 ml, 3.44 mmol), and the reaction was heated to reflux for 4 hours. The reaction was allowed to cool to ambient temperature, and water (0.131 ml), 1M NaOH (0.131 ml) and additional water (0.393 ml) were added, and the reaction was stirred for 30 minutes. The reaction was diluted with EtOAc and filtered. The filtrate was concentrated to yield 100 mg of the title compound (34.8% yield) as a 1:1 mixture of cis and trans isomers.

Step C: Preparation of ethyl 6-chloro-7-(4-(4-phenylcyclohexylcarbamoyl)phenoxy)chroman-4-carboxylate (2 isomers)

To a solution of 4-(6-chloro-4-(ethoxycarbonyl)chroman-7-yloxy)benzoic acid (0.0899 g, 0.238 mmol), N,N-dimethylpyridin-4-amine (0.00291 g, 0.0238 mmol), and (1R,4R)-4-phenylcyclohexanamine (0.0627 g, 0.358 mmol) in DMF (1.25 ml) was added N1-((ethylimino)methylene)-N3,N3-dimethylpropane-1,3-diamine hydrochloride (0.0549 g, 0.286 mmol), and the reaction was stirred overnight. The reaction was diluted with EtOAc and washed with 1M hydrochloric acid, saturated sodium bicarbonate, and saturated sodium chloride. The organic layer was separated and dried over anhydrous sodium sulfate, filtered, and concentrated.

The crude material was purified on a Biotage SP1 system eluting with a linear gradient of 5% to 50% EtOAc in hexanes to yield two isomers of the product. The first eluting isomer was collected and called isomer 1 (27 mg). The second eluting isomer was called isomer 2 (32 mg). The relative configurations of each of these isomers were not determined.

Step D(1): Preparation of 6-chloro-7-(4-(4-phenylcyclohexylcarbamoyl)phenoxy)chroman-4-carboxylic acid, isomer 1

To a solution of ethyl 6-chloro-7-(4-(4-phenylcyclohexylcarbamoyl)phenoxy)chroman-4-carboxylate, isomer 1 (0.027 g, 0.051 mmol) in 3:1 THF/methanol (1 ml) was added 1M sodium hydroxide (0.11 ml; 0.11 mmol), and the reaction was stirred for 16 hours at ambient temperature. The reaction was concentrated, and diluted with water and 1M hydrochloric acid, and extracted twice with EtOAc. The combined organic layers were washed with saturated sodium chloride, dried over anhydrous sodium sulfate, filtered, and concentrated to yield 26 mg of the title compound (100% yield). MS (apci) m/z=506.1 (M+H).

Step D(2): Preparation of 6-chloro-7-(4-(4-phenylcyclohexylcarbamoyl)phenoxy)chroman-4-carboxylic acid, isomer 2

To a solution of ethyl 6-chloro-7-(4-(4-phenylcyclohexylcarbamoyl)phenoxy)chroman-4-carboxylate, isomer 2 (0.032 g, 0.060 mmol) in 3:1 THF/methanol (1 ml) was added 1M sodium hydroxide (0.13 ml, 0.13 mmol), and the reaction was stirred for 16 hours at ambient temperature. The reaction was concentrated, and diluted with water and 1M hydrochloric acid, and extracted twice with EtOAc. The combined organic layers were washed with saturated sodium chloride, dried over anhydrous sodium sulfate, filtered, and concentrated to yield 30 mg of the title compound (100% yield). MS (apci) m/z=506.1 (M+H).

Example 156

7-(4-(4-tert-butylcyclohexylcarbamoyl)phenoxy)-6-chlorochroman-4-carboxylic acid

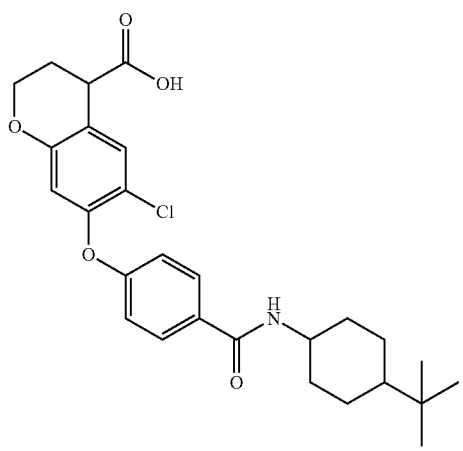 [SMILES: CC(C)(C)C1CCC(NC(=O)c2ccc(Oc3cc4c(cc3Cl)C(C(=O)O)CCO4)cc2)CC1]

Step A: Preparation of ethyl 7-(4-(4-tert-butylcyclohexylcarbamoyl)phenoxy)-6-chlorochroman-4-carboxylate To a solution of 4-(6-chloro-4-(ethoxycarbonyl)chroman-7-yloxy)benzoic acid (0.154 g, 0.409 mmol), N,N-dimethylpyridin-4-amine (0.00499 g, 0.0409 mmol), and 4-tert-butylcyclohexanamine (0.0875 ml, 0.490 mmol) in DMF (2 ml) was added N1-((ethylimino)methylene)-N3,N3-dimethylpropane-1,3-diamine hydrochloride (0.0940 g, 0.490 mmol), and the reaction was stirred at ambient temperature for 16 hours. The reaction was diluted with EtOAc and washed with 1M hydrochloric acid, saturated sodium bicarbonate, and saturated sodium chloride. The organic layer was dried over anhydrous sodium sulfate, filtered, and concentrated. The crude material was purified on a Biotage SP1 system eluting with a linear gradient of 5-70% EtOAc in hexanes to yield 37 mg of the title compound (18% yield).

Step B: Preparation of 7-(4-(4-tert-butylcyclohexylcarbamoyl)phenoxy)-6-chlorochroman-4-carboxylic acid To a solution of ethyl 7-(4-(4-tert-butylcyclohexylcarbamoyl)phenoxy)-6-chlorochroman-4-carboxylate (0.037 g, 0.072 mmol) in 3:1 THF/methanol (1 ml) was added 1M sodium hydroxide (0.15 ml, 0.15 mmol), and the reaction was stirred for 16 hours at ambient temperature. The reaction was concentrated and the residue was diluted with dilute hydrochloric acid and extracted twice with EtOAc. The combined organic layers were washed with saturated sodium chloride, dried over anhydrous sodium sulfate, filtered, and concentrated to yield 32 mg of the title compound (91% yield). MS (apci) m/z=486.1 (M+H).

Example 157

6-Chloro-7-(4-(4,4-dimethylcyclohexylcarbamoyl)phenoxy)chroman-4-carboxylic acid

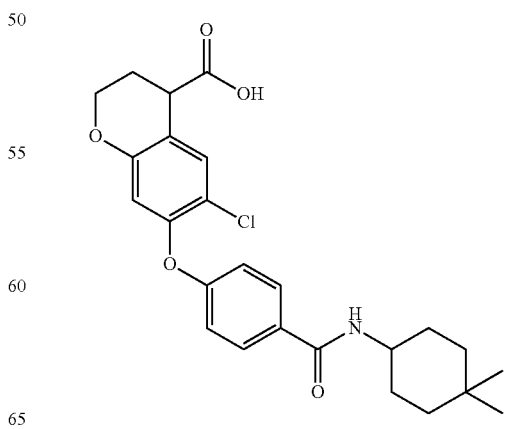

Step A: Preparation of 4,4-dimethylcyclohexanone oxime

To a solution of 4,4-dimethylcyclohexanone (0.511 g, 4.049 mmol) in 95% ethanol (20 ml) was added 50% hydroxylamine in water (2.481 ml, 40.49 mmol), and the reaction was heated to reflux for 2 hours. The reaction was cooled to ambient temperature, and the product was precipitated by the addition of water. The solids were collected by vacuum filtration to yield 202 mg of the title compound (35% yield).

Step B: Preparation of 4,4-dimethylcyclohexanamine hydrochloride

To a solution of 4,4-dimethylcyclohexanone oxime (0.204 g, 1.44 mmol) in THF (3 ml) was added 1M lithium aluminum hydride in THF (3.03 ml, 3.03 mmol), and the reaction was heated to reflux for 4 hours. The reaction was allowed to cool to ambient temperature, and water (0.115 ml), 1M sodium hydroxide (115 ml), and additional water (0.345 ml) were added. The reaction was stirred for 15 minutes and filtered. The filtrate was washed with EtOAc, and The combined organic layers were concentrated. The crude product was treated with 5M hydrogen chloride in dioxane, allowed to stir for 10 minutes, and was concentrated to yield 60 mg of the title compound (25.4% yield).

Step C: Preparation of ethyl 6-chloro-7-(4-(4,4-dimethylcyclohexylcarbamoyl)phenoxy)chroman-4-carboxylate To a solution of 4-(6-chloro-4-(ethoxycarbonyl)chroman-7-yloxy)benzoic acid (0.0921 g, 0.244 mmol), N,N-dimethylpyridin-4-amine (0.00299 g, 0.0244 mmol), triethylamine (0.0511 ml, 0.367 mmol), and 4,4-dimethylcyclohexanamine hydrochloride (0.060 g, 0.367 mmol) in DMF (1.5 ml) was added N1-((ethylimino)methylene)-N3,N3-dimethylpropane-1,3-diamine hydrochloride (0.0562 g, 0.293 mmol), and the reaction was stirred for 16 hours. The reaction was diluted with EtOAc and washed with 1M hydrochloric acid, saturated sodium bicarbonate, and saturated sodium chloride. The organic layer was dried over anhydrous sodium sulfate, filtered, and concentrated. The crude material was purified on a Biotage SP1 system eluting with a linear gradient of 5-70% EtOAc in hexanes to yield 56 mg of the title compound (47.2% yield).

Step D: Preparation of 6-chloro-7-(4-(4,4-dimethylcyclohexylcarbamoyl)phenoxy)chroman-4-carboxylic acid To a solution of ethyl 6-chloro-7-(4-(4,4-dimethylcyclohexylcarbamoyl)phenoxy)chroman-4-carboxylate (0.056 g, 0.12 mmol) in 3:1 THF/EtOH (1 ml) was added 1M sodium hydroxide (0.24 ml, 0.24 mmol), and the reaction was stirred at ambient temperature overnight. The reaction was concentrated and the residue was diluted with water and 1M hydrochloric acid. The reaction was extracted twice with EtOAc, and the combined organic layers were washed with saturated sodium chloride. The organic layer was dried over anhydrous sodium sulfate, filtered, and concentrated to yield 42 mg of the title compound (80% yield). MS (apci) m/z=458.1 (M+H).

Example 158

6-Chloro-7-(4-(3-phenylcyclohexylcarbamoyl)phenoxy)chroman-4-carboxylic acid

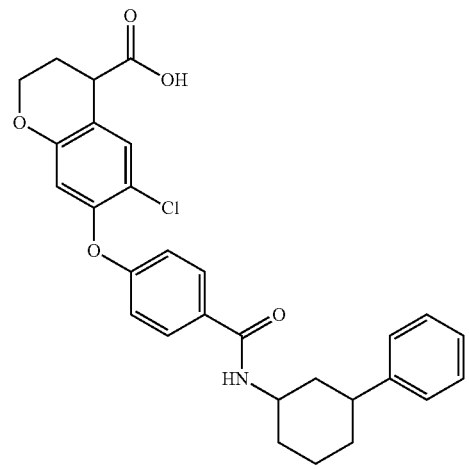 [SMILES: O=C(NC1CCCC(c2ccccc2)C1)c1ccc(Oc2cc3c(cc2Cl)C(C(=O)O)CCO3)cc1]

Step A: Preparation of 3-phenylcyclohexanone

To a solution of phenylboronic acid (0.630 g, 5.17 mmol) and 2,2'-bis(diphenylphosphino)-1,1'-binaphthyl (0.0193 g, 0.0310 mmol) in 10:1 dioxane/water (2.5 ml) was added acetylacetonatobis(ethylene)rhodium(I) (0.00800 g, 0.0310 mmol), and the reaction was degassed with argon. To this was added cyclohex-2-enone (0.100 ml, 1.03 mmol), and the reaction was heated to 120° C. for 16 hours in a screw-top vial. The reaction was allowed to cool to ambient temperature, diluted with EtOAc, and washed with twice with saturated sodium bicarbonate and once with saturated sodium chloride. The organic layer was dried over anhydrous sodium sulfate, filtered, and concentrated. The crude material was purified on a Biotage SP1 system eluting with a linear gradient of 5-50% EtOAc in hexanes to yield 60 mg of the title compound (33.3% yield).

Step B: Preparation of 3-phenylcyclohexanone oxime

To a solution of 3-phenylcyclohexanone (0.060 g, 0.3444 mmol) in 95% ethanol (2 ml) was added 50% hydroxylamine in water (0.2110 ml, 3.444 mmol), and the reaction was stirred at ambient temperature overnight. The reaction was diluted with EtOAc and washed with water and saturated sodium chloride. The organic layer was dried over anhydrous sodium sulfate, filtered, and concentrated to yield 60 mg of the title compound (92.07% yield).

Step C: Preparation of 3-phenylcyclohexanamine

To a solution of 3-phenylcyclohexanone oxime (0.060 g, 0.32 mmol) in THF (2 ml) was added 1M lithium aluminum hydride in THF (0.67 ml, 0.67 mmol), and the reaction was heated to reflux for 3 hours. The reaction was cooled to ambient temperature and water (0.0254 ml), 1M sodium hydroxide (0.0254 ml), and additional water (0.0762 ml) were added sequentially, and the reaction was stirred for 15 minutes. The reaction was diluted with EtOAc and filtered. The filtrate was concentrated to yield 41 mg of the title compound (74% yield).

Step D: Preparation of ethyl 6-chloro-7-(4-(3-phenylcyclohexylcarbamoyl)phenoxy)chroman-4-carboxylate To a solution of 4-(6-chloro-4-(ethoxycarbonyl)chroman-7-yloxy)benzoic acid (83.9 mg, 0.223 mmol), N,N-dimethylpyridin-4-amine (2.72 mg, 0.0223 mmol), and 3-phenylcyclohexanamine (41 mg, 0.234 mmol) in DMF (1.2 ml) was added N1-((ethylimino)methylene)-N3,N3-dimethylpropane-1,3-diamine hydrochloride (47.0 mg, 0.245 mmol), and the reaction was stirred overnight at ambient temperature. The reaction was diluted with EtOAc and washed with 1M hydrochloric acid, saturated sodium bicarbonate, and saturated sodium chloride. The organic layer was dried over anhydrous sodium sulfate, filtered, and concentrated. The crude material was purified on a Biotage SP1 system to yield 58 mg of the title compound (48.7% yield).

Step E: Preparation of 6-chloro-7-(4-(3-phenylcyclohexylcarbamoyl)phenoxy)chroman-4-carboxylic acid To a solution of ethyl 6-chloro-7-(4-(3-phenylcyclohexylcarbamoyl)phenoxy)chroman-4-carboxylate (58 mg, 0.11 mmol) in 3:1 THF/ethanol (1 ml) was added 1M sodium hydroxide (228 µl, 0.23 mmol), and the reaction was stirred for 16 hours at ambient temperature. The reaction was concentrated and then acidified with 1M HCl and extracted twice with EtOAc. The combined organic layers were washed with saturated sodium chloride, dried over anhydrous sodium sulfate, filtered, and concentrated to yield 55 mg of the title compound (100% yield). MS (apci) m/z=506.1 (M+H).

Example 159

6-Chloro-7-(4-(3-(3-chlorophenyl)cyclohexylcarbamoyl)phenoxy)chroman-4-carboxylic acid

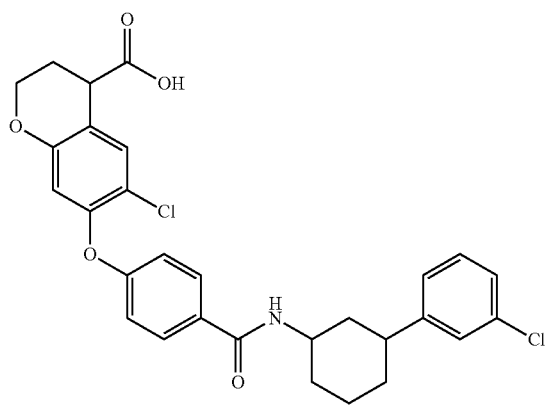 [SMILES: O=C(NC1CCCC(c2cccc(Cl)c2)C1)c1ccc(Oc2cc3c(cc2Cl)C(C(=O)O)CCO3)cc1]

Prepared according to the method of Example 158, substituting 3-chlorophenylboronic acid for phenylboronic acid. MS (apci) m/z=537.8 (M+H).

Example 160

6-Chloro-7-(4-(3-(4-methylphenyl)cyclohexylcarbamoyl)phenoxy)chroman-4-carboxylic acid

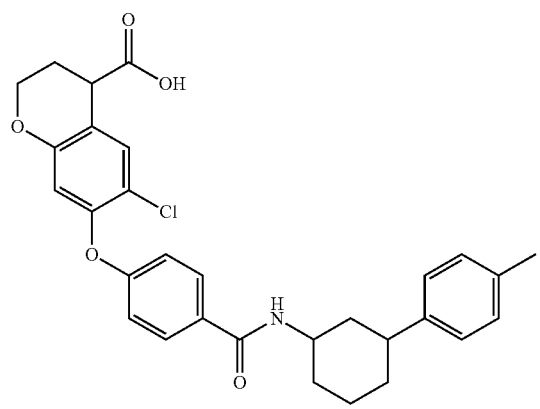 [SMILES: Cc1ccc(C2CCCC(NC(=O)c3ccc(Oc4cc5c(cc4Cl)C(C(=O)O)CCO5)cc3)C2)cc1]

Prepared according to the method of Example 158, substituting 4-methylphenylboronic acid for phenylboronic acid. MS (apci) m/z=520.1 (M+H).

Example 161

6-Chloro-7-(4-(3-(4-methoxyphenyl)cyclohexylcarbamoyl)phenoxy)chroman-4-carboxylic acid Prepared according to the method of Example 158, substituting 4-methoxyphenylboronic acid for phenylboronic acid. MS (apci) m/z=536.1 (M+H).

Example 162

6-Chloro-7-(4-(3-(4-(methylthio)phenyl)cyclohexylcarbamoyl)phenoxy)chroman-4-carboxylic acid

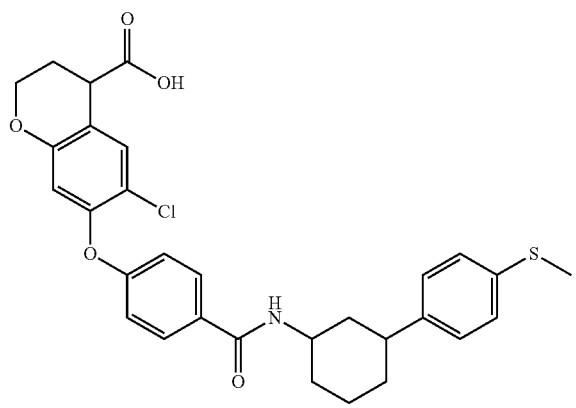 [SMILES: COc1ccc(C2CCCC(NC(=O)c3ccc(Oc4cc5c(cc4Cl)C(C(=O)O)CCO5)cc3)C2)cc1]

Prepared according to the method of Example 158, substituting 4-(methylthio)phenylboronic acid for phenylboronic acid. MS (apci) m/z=552.0 (M+H).

Example 163

6-Chloro-7-(4-(3-(3-methoxyphenyl)cyclohexylcarbamoyl)phenoxy)chroman-4-carboxylic acid

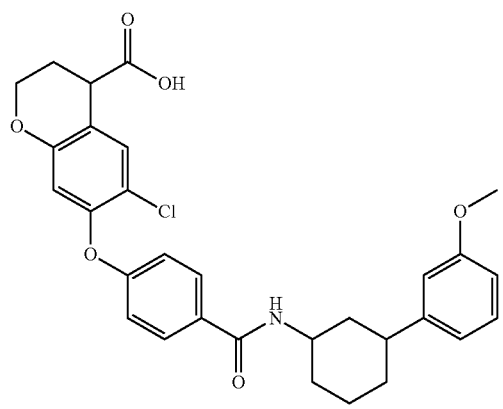 [SMILES: COc1cccc(C2CCCC(NC(=O)c3ccc(Oc4cc5c(cc4Cl)C(C(=O)O)CCO5)cc3)C2)c1]

Prepared according to the method of 158, substituting 3-methoxyphenylboronic acid for phenylboronic acid. MS (apci) m/z=536.0 (M+H).

Example 164

Sodium 6-chloro-7-(4-(3-(4-chlorophenyl)cyclohexylcarbamoyl)phenoxy)chroman-4-carboxylate

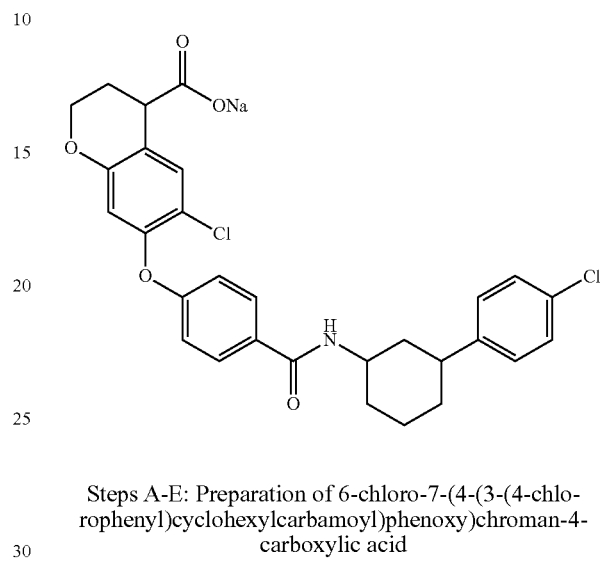

Steps A-E: Preparation of 6-chloro-7-(4-(3-(4-chlorophenyl)cyclohexylcarbamoyl)phenoxy)chroman-4-carboxylic acid Prepared according to the method of Example 158, substituting 4-chlorophenylboronic acid for phenylboronic acid.

Step F: Preparation of sodium 6-chloro-7-(4-(3-(4-chlorophenyl)cyclohexylcarbamoyl)phenoxy)chroman-4-carboxylate To a solution of 6-chloro-7-(4-(3-(4-chlorophenyl)cyclohexylcarbamoyl)phenoxy)chroman-4-carboxylic acid (0.032 g, 0.0592 mmol) in methanol (2 ml) was added 0.5M sodium methanolate in methanol (0.121 ml, 0.0604 mmol), and the reaction was stirred overnight. The reaction was concentrated to yield 33 mg of the title compound (99.1% yield). MS (apci) m/z=540.0 (M-Na+2H).

Example 165

6-chloro-7-(4-(3-phenylcyclopentylcarbamoyl)phenoxy)chroman-4-carboxylic acid

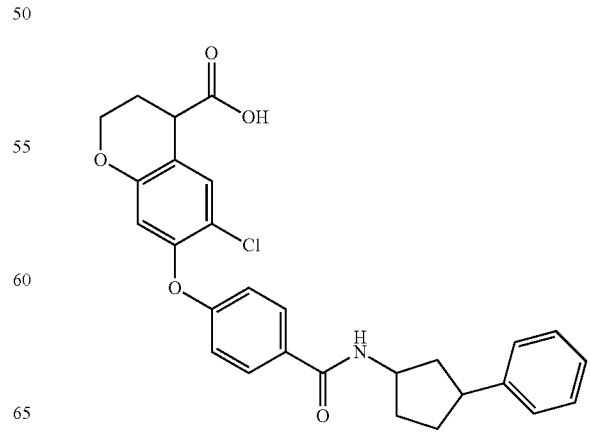

Prepared according to the method of Example 158, substituting cyclopenten-2-one for cyclohexen-2-one. MS (apci) m/z=492.1 (M+H).

Example 166

6-Chloro-7-(4-(3-p-tolylcyclopentylcarbamoyl)phenoxy)chroman-4-carboxylic acid

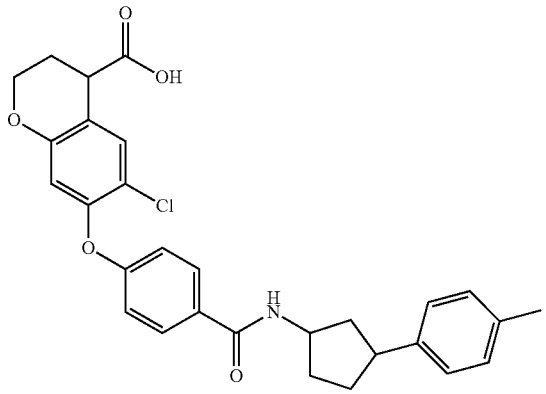 [SMILES: Cc1ccc(C2CCC(NC(=O)c3ccc(Oc4cc5c(cc4Cl)C(C(=O)O)CCO5)cc3)C2)cc1]

Prepared according to the method of Example 158, substituting 4-methylphenylboronic acid for phenylboronic acid and substituting cyclopenten-2-one for cyclohexen-2-one. MS (apci) m/z=506.1 (M+H).

Example 167

6-Chloro-7-(4-(3-(3-chlorophenyl)cyclopentylcarbamoyl)phenoxy)chroman-4-carboxylic acid

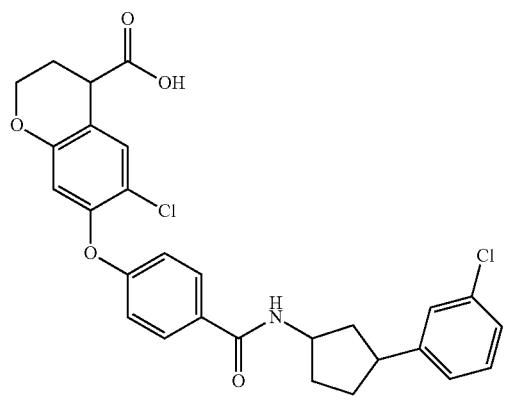 [SMILES: O=C(NC1CCC(c2cccc(Cl)c2)C1)c1ccc(Oc2cc3c(cc2Cl)C(C(=O)O)CCO3)cc1]

Prepared according to the method of Example 158, substituting 3-chlorophenylboronic acid for phenylboronic acid and substituting cyclopenten-2-one for cyclohexen-2-one. MS (apci)=526.1 (M+H).

Example 168

Sodium 6-chloro-7-(4-(3-(4-chlorophenyl)cyclopentylcarbamoyl)phenoxy)chroman-4-carboxylate

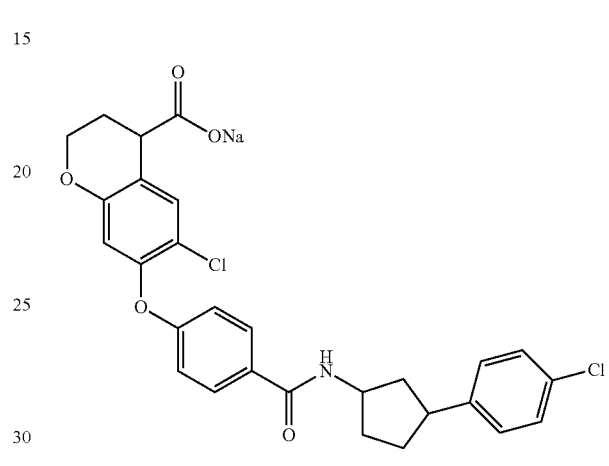

Prepared according to the method of Example 158, substituting 4-chlorophenylboronic acid for phenylboronic acid substituting cyclopenten-2-one for cyclohexen-2-one. MS (apci) m/z=526.1 (M-Na+2H).

Example 169

Sodium 6-chloro-7-(4-(3-(3-methylphenyl)cyclopentylcarbamoyl)phenoxy)chroman-4-carboxylate

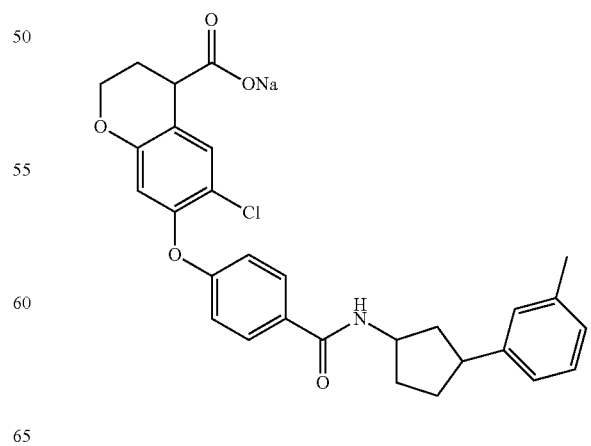

Prepared according to the method of Example 158, substituting 3-methylphenylboronic acid for phenylboronic acid and substituting cyclopenten-2-one for cyclohexen-2-one. MS (apci) m/z=506.1 (M-Na+2H).

Example 170

Sodium 6-chloro-7-(4-(3-(3-(trifluoromethyl)phenyl)cyclopentylcarbamoyl)phenoxy)chroman-4-carboxylate

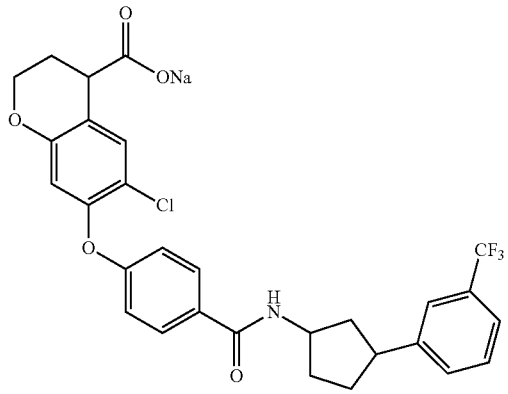

Prepared according to the method of Example 158, substituting reagent 3-(trifluoromethyl)phenylboronic acid for phenylboronic acid and substituting cyclopenten-2-one for cyclohexen-2-one. MS (apci) m/z=560.1 (M-Na+2H).

Example 171

Sodium 6-chloro-7-(4-(3-(3-fluorophenyl)cyclopentylcarbamoyl)phenoxy)chroman-4-carboxylate

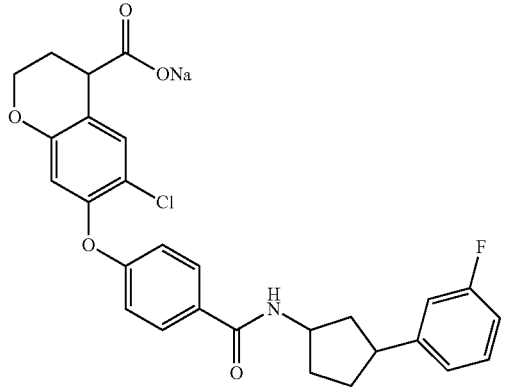

Prepared according to the method of Example 158, substituting 3-fluorophenylboronic acid for phenylboronic acid and substituting cyclopenten-2-one for cyclohexen-2-one. MS (apci) m/z=510.1 (M-Na+2H).

Example 172

Sodium 6-chloro-7-(4-(3-(3-(methylthio)phenyl)cyclopentylcarbamoyl)phenoxy)chroman-4-carboxylate

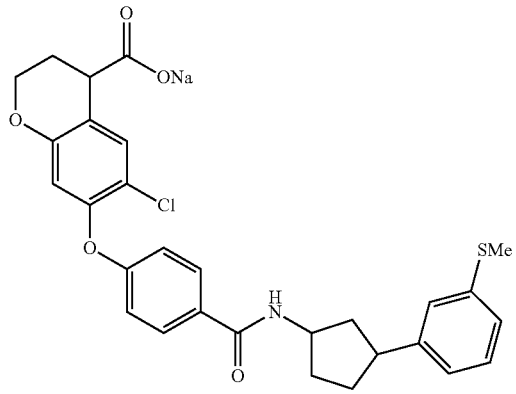

Prepared according to the method of Example 158, substituting 3-(methylthio)phenylboronic acid for phenylboronic acid and substituting cyclopenten-2-one for cyclohexen-2-one. MS (apci) m/z=538.0 (M-Na+2H).

Example 173

Sodium 6-chloro-7-(4-(3-(3,4-dichlorophenyl)cyclopentylcarbamoyl)phenoxy)chroman-4-carboxylate

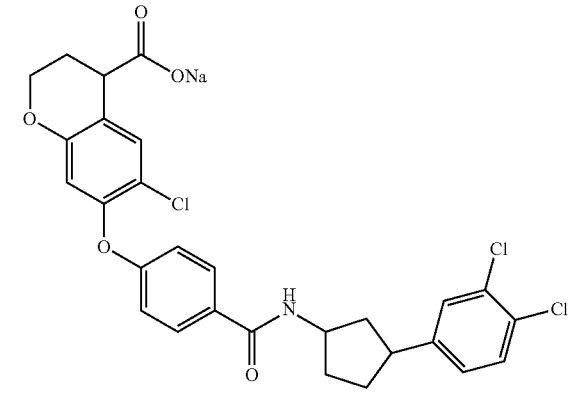

Prepared according to the method of Example 158, substituting 3,4-dichlorophenylboronic acid for phenylboronic acid and substituting cyclopenten-2-one for cyclohexen-2-one. MS (apci) m/z=560.0 (M-Na+2H).

Example 174

Sodium 6-chloro-7-(4-(3-(4-methoxyphenyl)cyclopentylcarbamoyl)phenoxy)chroman-4-carboxylate

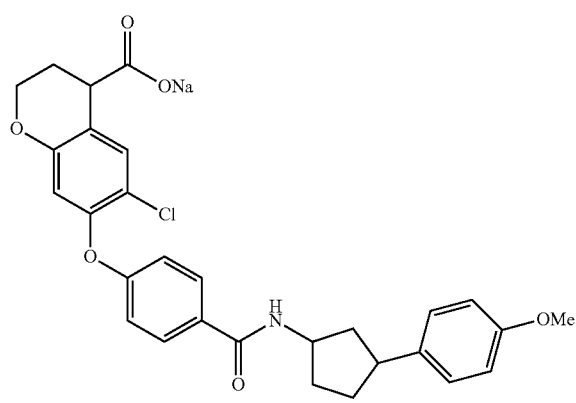

Prepared according to the method of Example 158, substituting 4-methoxyphenylboronic acid for phenylboronic acid and substituting cyclopenten-2-one for cyclohexen-2-one. MS (apci) m/z=522.1 (M-Na+2H).

Example 175

Sodium 6-chloro-7-(4-(3-(4-(methylthio)phenyl)cyclopentylcarbamoyl)phenoxy)chroman-4-carboxylate

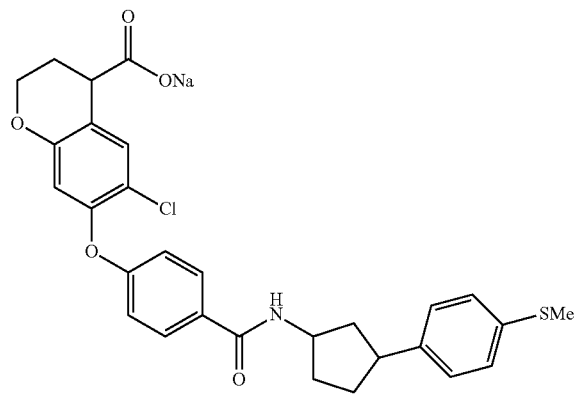

Prepared according to the method of Example 158, substituting 4-(methylthio)phenylboronic acid for phenylboronic acid and substituting cyclopenten-2-one for cyclohexen-2-one. MS (apci) m/z=538.1 (M-Na+2H).

Example 176

Sodium 6-chloro-7-(4-(4-(4-chlorophenyl)cyclohexylcarbamoyl)phenoxy)chroman-4-carboxylate

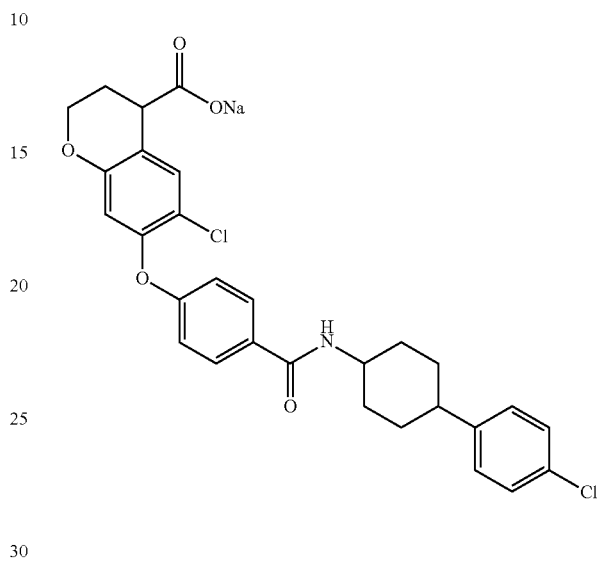

Step A: Preparation of tert-butyl 4-(4-chlorophenyl)cyclohexylcarbamate

To a solution of 4-(4-chlorophenyl)cyclohexanecarboxylic acid (1.01 g, 4.231 mmol) and triethylamine (0.5897 ml, 4.231 mmol) in tert-butanol (22 ml) was added diphenyl phosphorazidate (0.9147 ml, 4.231 mmol), and the reaction was heated to reflux for 16 hours. The reaction was diluted with EtOAc and washed with 1M hydrochloric acid, saturated sodium bicarbonate, and saturated sodium chloride. The organic layer was dried over anhydrous sodium sulfate, filtered, and concentrated. The crude material was on a Biotage SP1 system eluting with a linear gradient of 5-50% EtOAc in hexanes to yield 760 mg of the title compound (57% yield).

Step B: Preparation of 4-(4-chlorophenyl)cyclohexanamine

To a solution of tert-butyl 4-(4-chlorophenyl)cyclohexylcarbamate (0.760 g, 2.45 mmol) in dichloromethane (5 ml) was added trifluoroacetic acid (5 ml), and the reaction was stirred at ambient temperature for 2 hours. The reaction was concentrated, taken up in water, and 1M NaOH was added until the pH was >13. The aqueous layer was extracted twice with dichloromethane, and the combined organic layers were dried over anhydrous sodium sulfate, filtered, and concentrated to yield 371 mg of the title compound (72.1% yield).

Step C: Preparation of ethyl 6-chloro-7-(4-(4-(4-chlorophenyl)cyclohexylcarbamoyl)phenoxy)chroman-4-carboxylate To a solution of 4-(6-chloro-4-(ethoxycarbonyl)chroman-7-yloxy)benzoic acid (0.050 g, 0.13 mmol), N,N-dimethylpyridin-4-amine (0.0016 g, 0.013 mmol), and 4-(4-chlorophenyl)cyclohexanamine (0.042 g, 0.20 mmol) in DMF (1 ml) was added N1-((ethylimino)methylene)-N3,N3-dimethylpropane-1,3-diamine hydrochloride (0.031 g, 0.16 mmol), and the reaction was stirred overnight at ambient temperature. The reaction was diluted with EtOAc and washed with 1M hydrochloric acid, saturated sodium bicarbonate, and saturated sodium chloride. The organic layer was dried over anhydrous sodium sulfate, filtered, and concentrated to yield 65 mg of the title compound (86% yield).

Step D: Preparation of 6-chloro-7-(4-(4-(4-chlorophenyl)cyclohexylcarbamoyl)phenoxy)chroman-4-carboxylic acid To a suspension of ethyl 6-chloro-7-(4-(4-(4-chlorophenyl)cyclohexylcarbamoyl)phenoxy)chroman-4-carboxylate (0.065 g, 0.11 mmol) in 3:1 THF/ethanol (1 ml) was added 1M sodium hydroxide (0.24 ml, 0.24 mmol), and the reaction was stirred for 16 hours at ambient temperature. The reaction was concentrated, taken up in water, acidified with 1M hydrochloric acid, and extracted twice with EtOAc. The combined organic layers were dried over anhydrous sodium sulfate, filtered, and concentrated to yield 45 mg of the title compound (73% yield).

Step E: Preparation of sodium 6-chloro-7-(4-(4-(4-chlorophenyl)cyclohexylcarbamoyl)phenoxy)chroman-4-carboxylate To a suspension of 6-chloro-7-(4-(4-(4-chlorophenyl)cyclohexylcarbamoyl)phenoxy)chroman-4-carboxylic acid (0.045 g, 0.0833 mmol) in 1:1 THF/methanol (5 ml) was added 0.5M sodium methanolate in methanol (0.170 ml, 0.0849 mmol), and the reaction was stirred for 3 weeks, then concentrated to yield 47 mg of the title compound (100% yield). MS (apci) m/z=562.1 (M-Na+2H).

Example 177

Sodium 6-chloro-7-(4-(3-phenylcyclobutylcarbamoyl)phenoxy)chroman-4-carboxylate

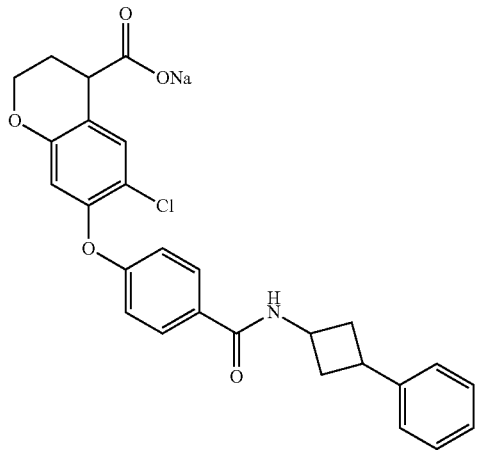

Step A: Preparation of 3-phenylcyclobutanone oxime

To a solution of 3-phenylcyclobutanone (0.198 g, 1.354 mmol) in 95% ethanol (7 ml) was added 50% hydroxylamine in water (0.8300 ml, 13.54 mmol), and the reaction was stirred for 16 hours at ambient temperature. The reaction was diluted with EtOAc and washed with water and saturated sodium chloride. The organic layer was dried over anhydrous sodium sulfate, filtered, and concentrated to yield 167 mg of the title compound (76.49% yield).

Step B: Preparation of 3-phenylcyclobutylamine

To a solution of 3-phenylcyclobutanone oxime (0.167 g, 1.04 mmol) in THF (5 ml) was added 1M lithium aluminum hydride in THF (2.18 ml, 2.18 mmol) dropwise over 3 minutes. The reaction was heated to reflux for 4 hours, then cooled to ambient temperature. Water (0.083 ml), 1M sodium hydroxide (0.083 ml), and additional water (0.248 ml) were added, and the reaction was stirred an additional 30 minutes. The reaction was filtered, and the solids were washed with THF. The filtrates were combined and concentrated to yield 101 mg of the title compound (66.2% yield).

Step C: Preparation of ethyl 6-chloro-7-(4-(3-phenylcyclobutylcarbamoyl)phenoxy)chroman-4-carboxylate To a solution of 3-phenylcyclobutanamine (0.101 g, 0.686 mmol) in DMF (2 ml) was added 4-(6-chloro-4-(ethoxycarbonyl)chroman-7-yloxy)benzoic acid (0.129 g, 0.343 mmol), N,N-dimethylpyridin-4-amine (0.00838 g, 0.0686 mmol), and N1-((ethylimino)methylene)-N3,N3-dimethylpropane-1,3-diamine hydrochloride (0.0789 g, 0.412 mmol), and the reaction was stirred for 16 hours at ambient temperature. The reaction was diluted with EtOAc and washed with 1M hydrochloric acid, saturated sodium bicarbonate, and saturated sodium chloride. The organic layer was dried over anhydrous sodium sulfate, filtered, and concentrated. The crude material was on a Biotage SP1 system eluting with a 5-70% EtOAc in hexanes linear gradient to yield 86 mg of the title compound (49.5% yield).

Step D: Preparation of 6-chloro-7-(4-(3-phenylcyclobutylcarbamoyl)phenoxy)chroman-4-carboxylic acid To a solution of ethyl 6-chloro-7-(4-(3-phenylcyclobutylcarbamoyl)phenoxy)chroman-4-carboxylate (0.086 g, 0.17 mmol) in 3:1 THF/ethanol (4 ml) was added 1M sodium hydroxide (0.36 ml, 0.36 mmol), and the reaction was stirred overnight. The reaction was concentrated, taken up in water, acidified with 1M hydrochloric acid, and extracted twice with EtOAc. The combined organic layers were washed with saturated sodium chloride, dried over Na$_2$SO$_4$, filtered, and concentrated to yield 67 mg of the title compound (82% yield).

Step E: Preparation of sodium 6-chloro-7-(4-(3-phenylcyclobutylcarbamoyl)phenoxy)chroman-4-carboxylate To a solution of 6-chloro-7-(4-(3-phenylcyclobutylcarbamoyl)phenoxy)chroman-4-carboxylic acid (0.067 g, 0.140 mmol) in methanol (2 ml) was added 0.5M sodium methanolate in methanol (0.294 ml, 0.147 mmol), and the reaction was

Example 178

Sodium 6-chloro-7-(4-(1-(4-chlorophenyl)-3-hydroxypropan-2-ylcarbamoyl)phenoxy)chroman-4-carboxylate

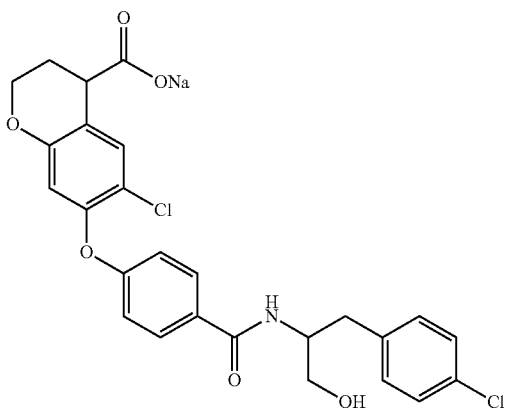

Step A: Preparation of ethyl 6-chloro-7-(4-(1-(4-chlorophenyl)-3-hydroxypropan-2-ylcarbamoyl)phenoxy)chroman-4-carboxylate To a solution of 4-(6-chloro-4-(ethoxycarbonyl)chroman-7-yloxy)benzoic acid (0.100 g, 0.2654 mmol) in dichloromethane (1.5 ml) and DMF (1 drop) was added oxalyl dichloride (0.02778 ml, 0.3185 mmol), and the reaction was stirred for 30 minutes. N-ethyl-N-isopropylpropan-2-amine (0.1112 ml, 0.6370 mmol) and 2-amino-3-(4-chlorophenyl)propan-1-ol (0.06405 g, 0.3450 mmol) were added, and the reaction was stirred for 16 hours. The reaction was diluted with EtOAc and washed with 1M hydrochloric acid, saturated sodium bicarbonate, and saturated sodium chloride. The organic layer was dried over anhydrous sodium sulfate, filtered, and concentrated. The crude material was purified on a Biotage SP1 system eluting with 25-100% EtOAc in hexanes to yield 111 mg of the title compound (76.82% yield).

Step B: Preparation of 6-chloro-7-(4-(1-(4-chlorophenyl)-3-hydroxypropan-2-ylcarbamoyl)phenoxy)chroman-4-carboxylic acid To a solution of ethyl 6-chloro-7-(4-(1-(4-chlorophenyl)-3-hydroxypropan-2-ylcarbamoyl)phenoxy)chroman-4-carboxylate (0.111 g, 0.204 mmol) in 3:1 THF/ethanol (2 ml) was added 1M sodium hydroxide (0.428 ml, 0.428 mmol), and the reaction was stirred overnight. It was concentrated and then taken up in water. It was then acidified with 1M hydrochloric acid and extracted twice with EtOAc. The combined organic layers were washed with saturated sodium chloride, dried over anhydrous sodium sulfate, filtered, and concentrated to yield 87 mg of the title compound (82.6% yield).

Step C: Preparation of sodium 6-chloro-7-(4-(1-(4-chlorophenyl)-3-hydroxypropan-2-ylcarbamoyl)phenoxy)chroman-4-carboxylate To a solution of 6-chloro-7-(4-(1-(4-chlorophenyl)-3-hydroxypropan-2-ylcarbamoyl)phenoxy)chroman-4-carboxylic acid (0.087 g, 0.168 mmol) in methanol (2 ml) was added 0.5M sodium methanolate in methanol (0.354 ml, 0.177 mmol), and the reaction was stirred for 2 hours. It was concentrated, taken up in dichloromethane and hexanes, and concentrated again to yield 87 mg of the title compound (95.9% yield). MS (apci) m/z=515.9 (M-Na+2H).

Example 179

Sodium 6-chloro-7-(4-(3,3-dimethylbutylcarbamoyl)phenoxy)chroman-4-carboxylate

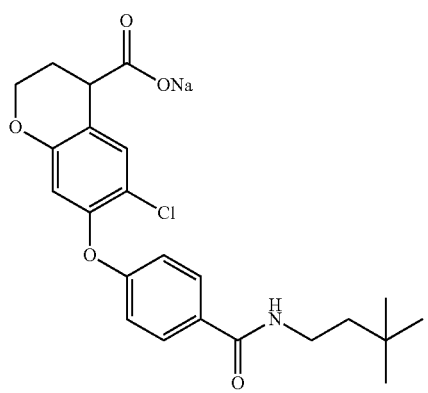

Prepared according to the method of Example 178, substituting 3,3-dimethylbutan-1-amine for 2-amino-3-(4-chlorophenyl)propan-1-ol. MS (apci) m/z=432.2 (M-Na+2H).

Example 180

Sodium 6-chloro-7-(4-(2-cyclohexylethylcarbamoyl)phenoxy)chroman-4-carboxylate

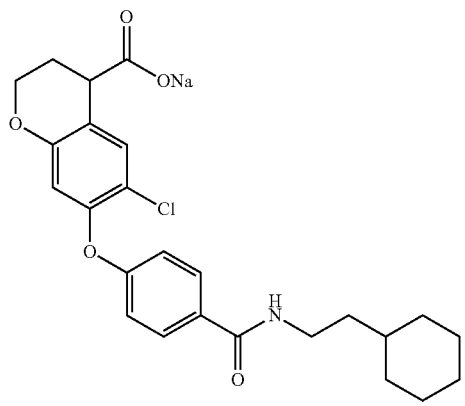

Prepared according to the method of Example 178, substituting 2-cyclohexanamine hydrochloride for 2-amino-3-(4-chlorophenyl)propan-1-ol and increasing the amount of (stirred for 16 hours. The reaction was concentrated to yield 70 mg of the title compound (99.9% yield). MS (apci) m/z=471.1 (M-Na+2H).)

N-ethyl-N-isopropylpropan-2-amine used in Step A from 2.2 equivalents to 3.5 equivalents. MS (apci) m/z=458.2 (M-Na+2H).

Example 181

Sodium 6-chloro-7-(4-(4-chlorophenethylcarbamoyl)-2-methylphenoxy)chroman-4-carboxylate

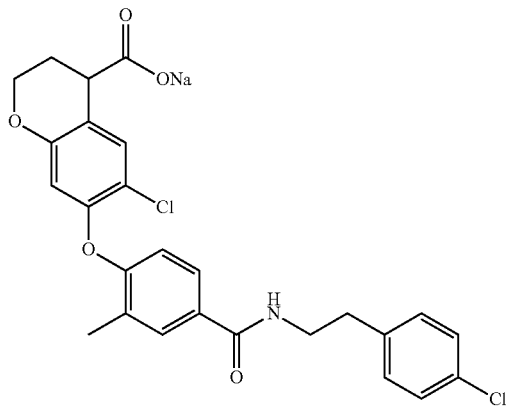

Step A: Preparation of 4-bromo-N-(4-chlorophenethyl)-3-methylbenzamide

To a suspension of 4-bromo-3-methylbenzoic acid (0.500 g, 2.325 mmol) in dichloromethane (10 ml) and DMF (1 drop) was added oxalyl dichloride (0.2231 ml, 2.558 mmol), and the reaction was stirred for 30 minutes. N-ethyl-N-isopropylpropan-2-amine (0.8934 ml, 5.115 mmol) and 2-(4-chlorophenyl)ethanamine (0.3557 ml, 2.558 mmol) were added, and the reaction was stirred for 1 hour at ambient temperature. The reaction was diluted with EtOAc and washed with 1M hydrochloric acid, saturated sodium bicarbonate, and saturated sodium chloride. The organic layer was dried over anhydrous sodium sulfate, filtered, and concentrated. The crude material was purified by recrystallization from EtOAc and hexanes to yield 400 mg of the title compound (48.78% yield).

Step B: Preparation of ethyl 6-chloro-7-(4-(4-chlorophenethylcarbamoyl)-2-methylphenoxy)chroman-4-carboxylate To a solution of 4-bromo-N-(4-chlorophenethyl)-3-methylbenzamide (0.0831 g, 0.236 mmol), ethyl 6-chloro-7-hydroxychroman-4-carboxylate (0.050 g, 0.195 mmol), and 2-(dimethylamino)acetic acid (0.0104 g, 0.101 mmol) in dioxane (1 ml) degassed with argon was added cesium carbonate (0.133 g, 0.409 mmol) and copper(I) chloride (0.0100 g, 0.101 mmol). The reaction was sealed in a screw-cap vial and heated to 100° C. for 16 hours. The reaction was cooled to ambient temperature, then loaded directly onto a Biotage SP1 system, eluting with a linear gradient of 5-70% EtOAc in hexanes to yield 22 mg of the title compound (21% yield).

Step C: Preparation of 6-chloro-7-(4-(4-chlorophenethylcarbamoyl)-2-methylphenoxy)chroman-4-carboxylic acid To a solution of ethyl 6-chloro-7-(4-(4-chlorophenethylcarbamoyl)-2-methylphenoxy)chroman-4-carboxylate (0.022 g, 0.042 mmol) in 3:1 THF/ethanol (2 ml) was added 1M sodium hydroxide (0.087 ml, 0.087 mmol). The reaction was stirred overnight and then concentrated. The residue was taken up in water and acidified with 1M hydrochloric acid and extracted twice with EtOAc. The combined organic layers were washed with saturated sodium chloride, dried over anhydrous sodium sulfate, filtered, and concentrated. The crude material was purified by preparatory thin layer chromatography eluting with 95:5:1 dichloromethane/methanol/glacial acetic acid to yield 11 mg of the title compound (53% yield).

Step D: Preparation of sodium 6-chloro-7-(4-(4-chlorophenethylcarbamoyl)-2-methylphenoxy)chroman-4-carboxylate To a solution of 6-chloro-7-(4-(4-chlorophenethylcarbamoyl)-2-methylphenoxy)chroman-4-carboxylic acid (0.011 g, 0.0220 mmol) in methanol (2 ml) was added 0.5 M sodium methanolate in methanol (0.0462 ml, 0.0231 mmol), and the reaction was stirred at ambient temperature for 3 hours. The reaction was concentrated, and the residue was diluted with dichloromethane and hexanes, and concentrated again to yield 11 mg of the title compound (95.8% yield). MS (apci) m/z=500.0 (M-Na+2H).

Example 182

Sodium 6-chloro-7-(4-(2,4-dichlorophenethylcarbamoyl)-2-methylphenoxy)chroman-4-carboxylate

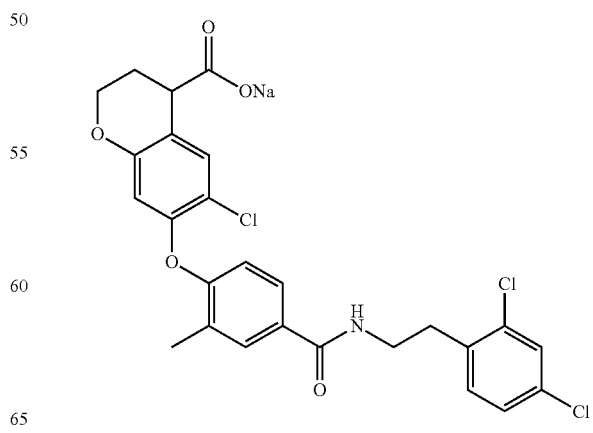

Prepared according to the method of Example 181, substituting 2-(2,4-dichlorophenyl)ethanamine for 2-(4-chlorophenyl)ethanamine. MS (apci) m/z=534.0 (M-Na+2H).

Example 183

Sodium 6-chloro-7-(4-(2,4-dichlorophenethylcarbamoyl)-3-methylphenoxy)chroman-4-carboxylate

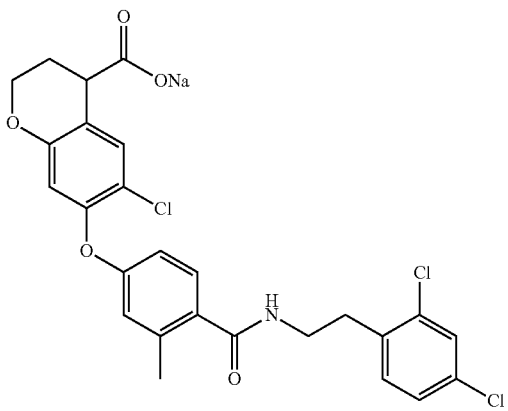

Prepared according to the method of Example 181, substituting 4-bromo-2-methylbenzoic acid for 4-bromo-3-methylbenzoic acid. MS (apci) m/z=534.0 (M-Na+2H).

Example 184

Sodium 6-chloro-7-(4-(2-(4-chlorophenyl)-2-hydroxyethylcarbamoyl)phenoxy)chroman-4-carboxylate

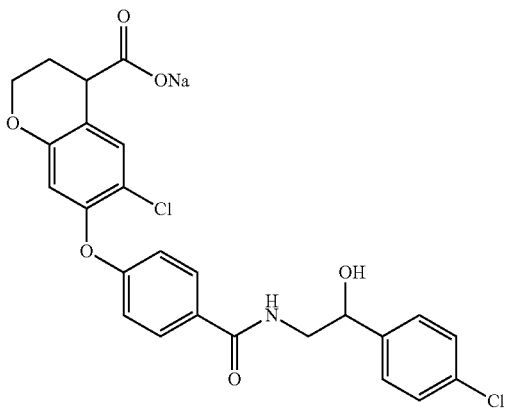

Step A: Preparation of ethyl 6-chloro-7-(4-(2-(4-chlorophenyl)-2-hydroxyethylcarbamoyl)phenoxy)chroman-4-carboxylate To a solution of 4-(6-chloro-4-(ethoxycarbonyl)chroman-7-yloxy)benzoic acid (0.050 g, 0.13 mmol), 2-amino-1-(4-chlorophenyl)ethanol hydrochloride (0.033 g, 0.16 mmol), N-ethyl-N-isopropylpropan-2-amine (0.030 ml, 0.17 mmol), and 3H-[1,2,3]triazolo[4,5-b]pyridin-3-ol (0.018 g, 0.13 mmol) in DMF (1 ml) was added N1-((ethylimino)methylene)-N3,N3-dimethylpropane-1,3-diamine hydrochloride (0.031 g, 0.16 mmol), and the reaction was stirred at ambient temperature for 16 hours. It was diluted with EtOAc and washed with 10% citric acid, saturated sodium bicarbonate, and saturated sodium chloride. It was dried over anhydrous sodium sulfate, filtered, and concentrated. The crude material was on a Biotage SP1 system using a 25-100% EtOAc/hexanes linear gradient to yield 56 mg of the title compound (80% yield).

Step B: Preparation of 6-chloro-7-(4-(2-(4-chlorophenyl)-2-hydroxyethylcarbamoyl)phenoxy)chroman-4-carboxylic acid To a solution of ethyl 6-chloro-7-(4-(2-(4-chlorophenyl)-2-hydroxyethylcarbamoyl)phenoxy)chroman-4-carboxylate (0.056 g, 0.11 mmol) in a solution of 3:1 THF/ethanol (2 ml) was added 1M sodium hydroxide (0.22 ml, 0.22 mmol), and the reaction was stirred for 16 hours. The reaction was concentrated, taken up in water, acidified with 1M hydrochloric acid, and extracted twice with EtOAc. The combined organic layers were washed with saturated sodium chloride, dried over anhydrous sodium sulfate, filtered, and concentrated to yield 46 mg of the title compound (87% yield).

Step C: Preparation of sodium 6-chloro-7-(4-(2-(4-chlorophenyl)-2-hydroxyethylcarbamoyl)phenoxy)chroman-4-carboxylate To a solution of 6-chloro-7-(4-(2-(4-chlorophenyl)-2-hydroxyethylcarbamoyl)phenoxy)chroman-4-carboxylic acid (0.046 g, 0.092 mmol) in methanol (1 ml) was added 0.5M sodium methanolate in methanol (0.18 ml, 0.092 mmol), and the reaction was stirred at ambient temperature for 16 hours. It was concentrated, taken up in dichloromethane and hexanes, and concentrated again to yield 46 mg of the title compound (96% yield). MS (apci) m/z=501.8 (M-Na+2H).

Example 185

Sodium 6-chloro-7-(4-(2-(2-chlorophenyl)-2-hydroxyethylcarbamoyl)phenoxy)chroman-4-carboxylate

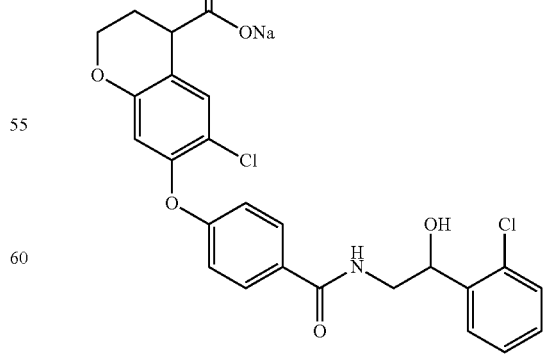

Prepared according to the method of Example 184, replacing 2-amino-1-(4-chlorophenyl)ethanol hydrochloride with 2-amino-1-(2-chlorophenyl)ethanol hydrochloride. MS (apci) m/z=501.8 (M-Na+2H).

Example 186

Sodium 6-chloro-7-(4-(2-cyclopentylethylcarbamoyl)phenoxy)chroman-4-carboxylate

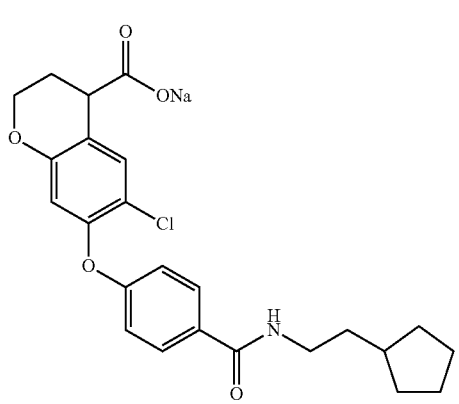

Prepared according to the method of Example 184, substituting 2-amino-1-(4-chlorophenyl)ethanol hydrochloride with 2-cyclopentylethanamine and omitting N-ethyl-N-isopropylpropan-2-amine. MS (apci) m/z=444.2 (M-Na+2H).

Example 187

Sodium 7-(4-(1-oxaspiro[4.4]nonan-3-ylcarbamoyl)phenoxy)-6-chlorochroman-4-carboxylate

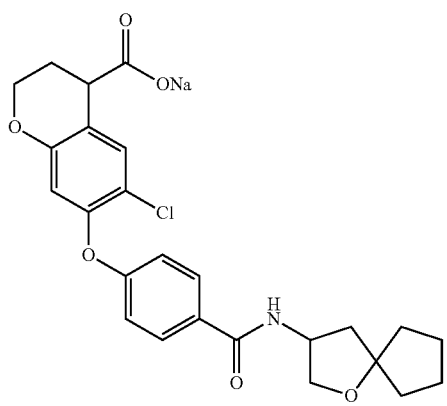

Prepared according to the method of Example 184, substituting 2-amino-1-(4-chlorophenyl)ethanol hydrochloride with 1-oxaspiro[4.4]nonan-3-amine and omitting N-ethyl-N-isopropylpropan-2-amine. MS (apci) m/z=472.0 (M-Na+2H).

Example 188

Sodium 6-chloro-7-(4-(2-(4-chlorophenyl)-2-methoxyethylcarbamoyl)phenoxy)chroman-4-carboxylate

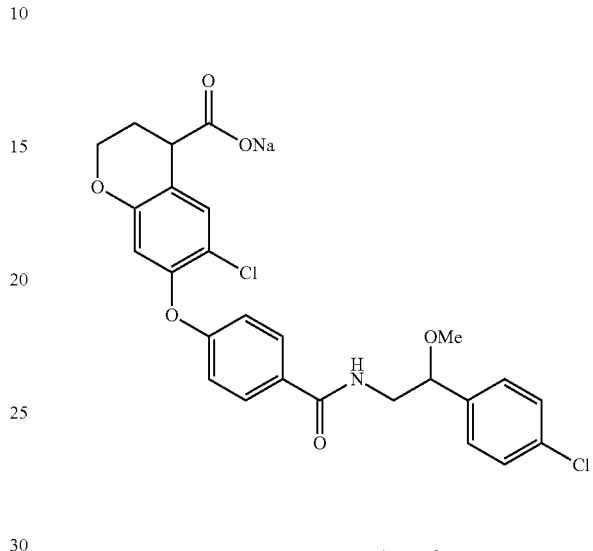

Step A: Preparation of [N-[(p-nitrophenyl)sulfonyl]imino]phenyliodinane

To a solution of 4-nitrobenzenesulfonamide (0.628 g, 3.10 mmol) and potassium hydroxide (0.410 g, 6.21 mmol) in MeOH (10 ml) at 0° C. was added iodobenzene diacetate (1.00 g, 3.10 mmol), and the reaction was allowed to warm to ambient temperature and stir for 4 hours. The reaction was filtered, and the solids were washed with water and dried under reduced pressure to yield 980 mg of the title compound (78.1% yield).

Step B: Preparation of 2-(4-chlorophenyl)-1-(4-nitrophenylsulfonyl)aziridine

To a suspension of 1-chloro-4-vinylbenzene (0.1195 ml, 0.9957 mmol), tetrakis(acetonitrile)copper(I) hexafluorophosphate (0.01856 g, 0.04979 mmol), and 4 angstrom molecular sieves (300 mg) in dry acetonitrile (2.5 ml) degassed with argon was added [N-[(p-nitrophenyl)sulfonyl]imino]phenyliodinane (0.6037 g, 1.494 mmol) portion-wise over 2 hours as a solid. It was stirred overnight under argon, then was loaded directly onto a Biotage SP1 system eluting with a 2-30% linear gradient of EtOAc in hexanes to yield 276 mg of the title compound (81.8% yield).

Step C: Preparation of N-(2-(4-chlorophenyl)-2-methoxyethyl)-4-nitrobenzenesulfonamide 2-(4-Chlorophenyl)-1-(4-nitrophenylsulfonyl)aziridine (0.276 g, 0.815 mmol) was dissolved in 8 ml of methanol and 4 ml of dichloromethane. The reaction was stirred at ambient temperature for 5 days, and then concentrated. The crude material was on a Biotage SP1 system eluting with a 5-50% linear gradient of EtOAc in hexanes to yield 231 mg of the title compound (76.5% yield).

Step D: Preparation of tert-butyl 2-(4-chlorophenyl)-2-methoxyethylcarbamate A solution of N-(2-(4-chlorophenyl)-2-methoxyethyl)-4-nitrobenzenesulfonamide (0.231 g, 0.6230 mmol), benzenethiol (0.1910 ml, 1.869 mmol), and potassium carbonate (0.3444 g, 2.492 mmol) in 49:1 acetonitrile/DMSO (15 ml) was heated to 50° C. for 3 hours. The reaction was cooled to ambient temperature and di-tert-butyl dicarbonate (0.6798 g, 3.115 mmol) was added. The reaction was stirred for 1 hour. The reaction was concentrated and the crude material was loaded directly onto a Biotage SP1 system, eluting with a 5-40% linear gradient of EtOAc in hexanes to yield 129 mg of the title compound (72.46% yield).

Step E: Preparation of 2-(4-chlorophenyl)-2-methoxyethanamine

To a solution of tert-butyl 2-(4-chlorophenyl)-2-methoxyethylcarbamate (0.129 g, 0.451 mmol) in dichloromethane (5 ml) was added trifluoroacetic acid (5 ml), and the reaction was stirred at ambient temperature for 16 hours. The reaction was concentrated and taken up in water. Sodium hydroxide (1M) was added until the pH was >13. The mixture was extracted twice with dichloromethane, and the combined organic layers were dried over anhydrous sodium sulfate, filtered, and concentrated to yield 71 mg of the title compound (84.7% yield).

Step F: Preparation of ethyl 6-chloro-7-(4-(2-(4-chlorophenyl)-2-methoxyethylcarbamoyl)phenoxy)chroman-4-carboxylate To a solution of 2-(4-chlorophenyl)-2-methoxyethanamine (0.071 g, 0.38 mmol), 4-(6-chloro-4-(ethoxycarbonyl)chroman-7-yloxy)benzoic acid (0.060 g, 0.16 mmol), and 3H-[1,2,3]triazolo[4,5-b]pyridin-3-ol (0.022 g, 0.16 mmol) in DMF (1 ml) was added N1-((ethylimino)methylene)-N3,N3-dimethylpropane-1,3-diamine hydrochloride (0.037 g, 0.19 mmol), and the reaction was stirred at ambient temperature overnight. The reaction was diluted with EtOAc and washed with 1M hydrochloric acid, saturated sodium bicarbonate, and saturated sodium chloride. The organic layer was dried over anhydrous sodium sulfate, filtered, and concentrated. The crude material was loaded onto a Biotage SP1 system, eluting with a linear gradient of 5-70% EtOAc in hexanes to yield 67 mg of the title compound (77% yield).

Step G: Preparation of 6-chloro-7-(4-(2-(4-chlorophenyl)-2-methoxyethylcarbamoyl)phenoxy)chroman-4-carboxylic acid To a solution of ethyl 6-chloro-7-(4-(2-(4-chlorophenyl)-2-methoxyethylcarbamoyl)phenoxy)chroman-4-carboxylate (0.067 g, 0.12 mmol) in 3:1 THF/ethanol (2 ml) was added 1M sodium hydroxide (0.26 ml, 0.26 mmol). The reaction was stirred for 16 hours, and then concentrated, diluted with water, and acidified with 1M hydrochloric acid. The mixture was extracted twice with EtOAc, and the combined organic layers were washed with saturated sodium chloride, dried over anhydrous sodium sulfate, filtered, and concentrated to yield 56 mg of the title compound (88% yield).

Step F: Preparation of sodium 6-chloro-7-(4-(2-(4-chlorophenyl)-2-methoxyethylcarbamoyl)phenoxy)chroman-4-carboxylate To a solution of 6-chloro-7-(4-(2-(4-chlorophenyl)-2-methoxyethylcarbamoyl)phenoxy)chroman-4-carboxylic acid (0.056 g, 0.108 mmol) in methanol (2 ml) was added 0.5M sodium methanolate in methanol (0.228 ml, 0.114 mmol), and the reaction was stirred for 16 hours. The reaction was concentrated, and the residue was taken up in dichloromethane and hexanes, and concentrated to yield 56 mg of the title compound (95.9% yield). MS (apci) m/z=515.8 (M-Na+2H).

Example 189

Sodium 6-chloro-7-(4-(2-(4-chlorophenyl)-2-fluoroethylcarbamoyl)phenoxy)chroman-4-carboxylate

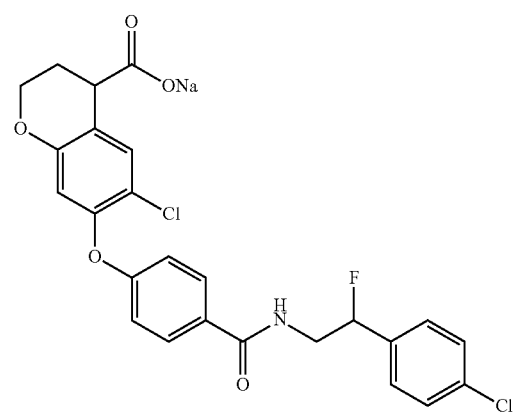

Step A: Preparation of 2-(2,4-dichlorophenyl)-2-(trimethylsilyloxy)acetonitrile To a solution of 2,4-dichlorobenzaldehyde (1.00 g, 5.71 mmol) in neat trimethylsilanecarbonitrile (7.62 ml, 57.1 mmol) was added zinc(II) iodide (0.0912 g, 0.286 mmol). The reaction was stirred for 3 hours, then diluted with EtOAc and washed twice with saturated sodium bicarbonate and once with saturated sodium chloride. The organic layer was dried over anhydrous sodium sulfate, filtered, and concentrated to yield 1.57 g of the title compound (100% yield).

Step B: Preparation of 2-(2,4-dichlorophenyl)-2-fluoroacetonitrile

To a solution of 2-(2,4-dichlorophenyl)-2-(trimethylsilyloxy)acetonitrile (1.57 g, 5.73 mmol) in dichloromethane (20 ml) under argon at −78° C. was added (diethylamino)sulfur trifluoride (1.51 ml, 11.5 mmol) dropwise over 15 minutes. The reaction was stirred at this temperature for 20 minutes, then warmed to 0° C. and allowed to stir for an additional 30 minutes. The reaction was poured onto a mixture of ice water and saturated sodium bicarbonate and allowed to stir for 30 minutes. The mixture was extracted with ether twice, and the combined organic layers were washed with saturated sodium chloride, dried over anhydrous magnesium sulfate, filtered, and concentrated to yield 1.05 g of the title compound (89% yield).

Step C: Preparation of 2-(2,4-dichlorophenyl)-2-fluoroethanamine

To a solution of 2-(2,4-dichlorophenyl)-2-fluoroacetonitrile (0.263 g, 1.29 mmol) in THF (2 ml) was added borane- DMS complex (0.134 ml, 1.42 mmol), and the reaction was heated to reflux under argon for one hour. The reaction was cooled to ambient temperature, and 0.4 ml of concentrated hydrochloric acid were added. The reaction mixture was again heated to reflux for 30 minutes, then cooled to ambient temperature and treated with 1M sodium hydroxide until the pH reached 13. The reaction was extracted three times with ether, and the combined organic layers were washed with saturated sodium chloride, dried over anhydrous potassium carbonate, filtered, and concentrated to yield 217 mg of the title compound (80.9% yield).

Step C: Preparation of ethyl 6-chloro-7-(4-(2-(4-chlorophenyl)-2-fluoroethylcarbamoyl)phenoxy)chroman-4-carboxylate To a solution of 2-(2,4-dichlorophenyl)-2-fluoroethanamine (0.126 g, 0.606 mmol), 4-(6-chloro-4-(ethoxycarbonyl)chroman-7-yloxy)benzoic acid (0.114 g, 0.303 mmol), and 3H-[1,2,3]triazolo[4,5-b]pyridin-3-ol (0.0412 g, 0.303 mmol) in DMF (2 ml) was added N1-((ethylimino)methylene)-N3,N3-dimethylpropane-1,3-diamine hydrochloride (0.0697 g, 0.363 mmol. The reaction was stirred for 16 hours at ambient temperature. It was diluted with EtOAc and washed with 1M hydrochloric acid, saturated sodium bicarbonate, and saturated sodium chloride. The organic layer was dried over anhydrous sodium sulfate, filtered, and concentrated. The crude material was on a Biotage SP1 system eluting with a linear gradient of 5-50% EtOAc in hexanes to yield 161 mg of the title compound (93.8% yield).

Step D: Preparation of 6-chloro-7-(4-(2-(4-chlorophenyl)-2-fluoroethylcarbamoyl)phenoxy)chroman-4-carboxylic acid To a solution of ethyl 6-chloro-7-(4-(2-(2,4-dichlorophenyl)-2-fluoroethylcarbamoyl)phenoxy)chroman-4-carboxylate (0.161 g, 0.284 mmol) in 3:1 THF/ethanol (4 ml) was added sodium hydroxide (0.341 ml, 0.341 mmol), and the reaction was stirred for 3 days at ambient temperature. The reaction was concentrated, taken up in water, acidified with 1M hydrochloric acid, and extracted twice with EtOAc. The combined organic layers were washed with saturated sodium chloride, dried over anhydrous sodium sulfate, filtered, and concentrated to yield 121 mg of the title compound (79.7% yield).

Step E: Preparation of sodium 6-chloro-7-(4-(2-(4-chlorophenyl)-2-fluoroethylcarbamoyl)phenoxy)chroman-4-carboxylate To a solution of 6-chloro-7-(4-(2-(2,4-dichlorophenyl)-2-fluoroethylcarbamoyl)phenoxy)chroman-4-carboxylic acid (0.122 g, 0.226 mmol) in methanol (2 ml) was added 0.5 M sodium methanolate in methanol (0.476 ml, 0.238 mmol), and the reaction was stirred overnight. The reaction was concentrated, taken up in dichloromethane and hexanes, and concentrated again to yield 122 mg of the title compound as a white solid (96.1% yield). MS (apci) m/z=537.7 (M-Na+2H).

TABLE 1 provides additional compounds that were made by methods described herein.

| Ex. # | Structure | Name | MS or $^1$H NMR Data |
|---|---|---|---|
| 190 | 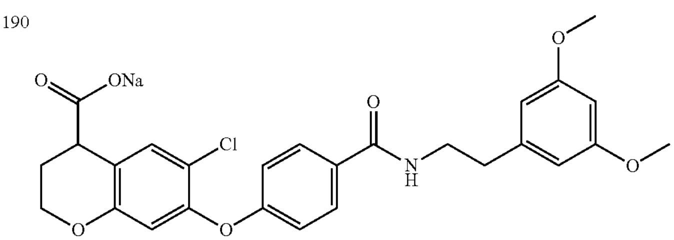 | sodium 6-chloro-7-(4-(3,5-dimethoxyphenethylcarbamoyl)phenoxy) chroman-4-carboxylate | LCMS (APCI) = 512.2 (M − Na + 2H) |
| 191 | 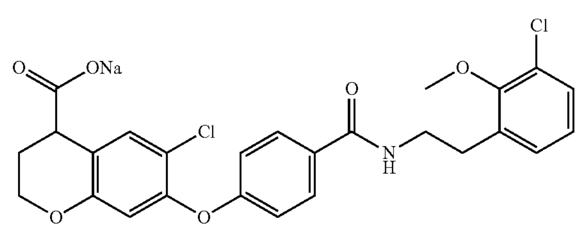 | sodium 6-chloro-7-(4-(3-chloro-2-methoxyphenethylcarbamoyl)phenoxy)chroman-4-carboxylate | LCMS (APCI) = 516.1 (M − Na + 2H) |
| 192 | 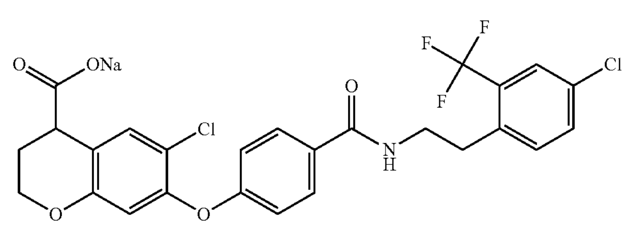 | sodium 6-chloro-7-(4-(4-chloro-2-(trifluoromethyl)phenethylcarbamoyl)phenoxy)chroman-4-carboxylate | LCMS (APCI) = 554.1 (M − Na + 2H) |

TABLE 1-continued provides additional compounds that were made by methods described herein.

| Ex. # | Structure | Name | MS or $^1$H NMR Data |
|---|---|---|---|
| 193 | 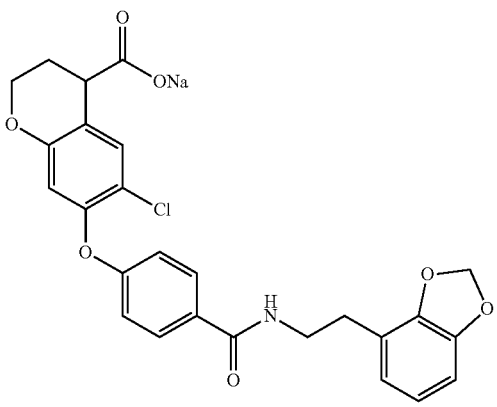 | sodium 7-(4-(2-(benzo[d][1,3]dioxol-4-yl)ethylcarbamoyl)phenoxy)-6-chlorochroman-4-carboxylate | MS (apci) m/z = 495.9 (M − Na + 2H) |
| 194 | 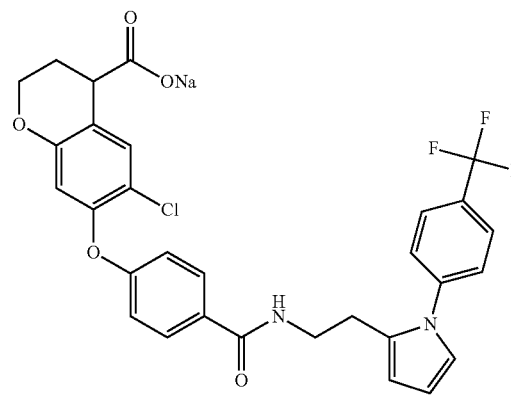 | sodium 6-chloro-7-(4-(2-(1-(4-(trifluoromethyl)phenyl)-1H-pyrrol-2-yl)ethylcarbamoyl)phenoxy)chroman-4-carboxylate | MS (apci) m/z = 584.9 (M − Na + 2H) |
| 195 | 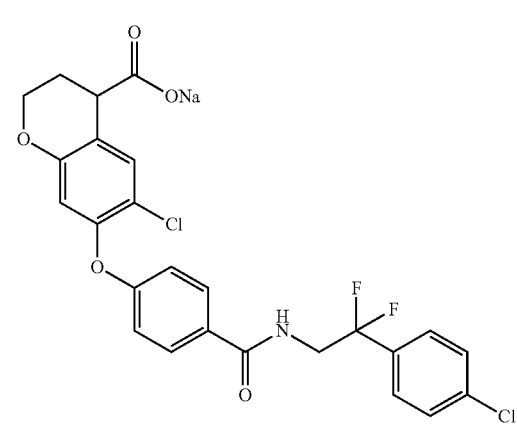 | sodium 6-chloro-7-(4-(2-(4-chlorophenyl)-2,2-difluoroethylcarbamoyl)phenoxy)chroman-4-carboxylate | MS (apci) m/z = 522 (M − Na + 2H). |

TABLE 1-continued provides additional compounds that were made by methods described herein.

| Ex. # | Structure | Name | MS or $^1$H NMR Data |
|---|---|---|---|
| 196 | 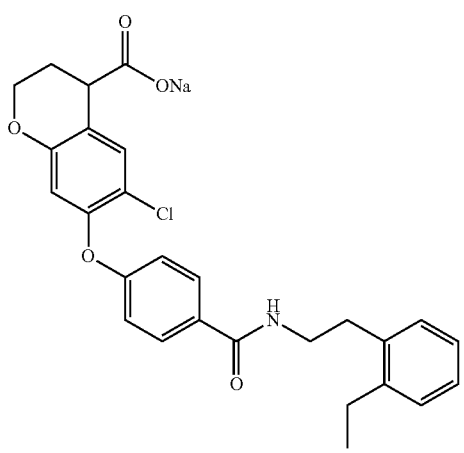 | sodium 6-chloro-7-(4-(2-ethylphenethylcarbamoyl)phenoxy)chroman-4-carboxylate | MS (apci) m/z = 480.0 (M − Na + 2H). |
| 197 | 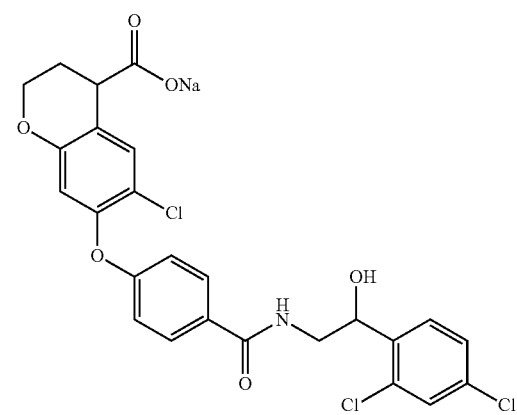 | sodium 6-chloro-7-(4-(2-(2,4-dichlorophenyl)-2-hydroxyethylcarbamoyl)phenoxy)chroman-4-carboxylate | MS (apci) m/z = 537.7 (M − Na + 2H). |
| 198 | 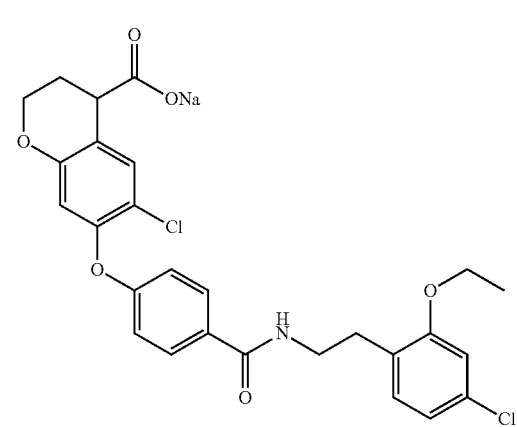 | sodium 6-chloro-7-(4-(4-chloro-2-ethoxyphenethylcarbamoyl)phenoxy)chroman-4-carboxylate | MS (apci) m/z = 530 (M − Na + 2H). |

TABLE 1-continued provides additional compounds that were made by methods described herein.

| Ex. # | Structure | Name | MS or ¹H NMR Data |
|---|---|---|---|
| 199 | 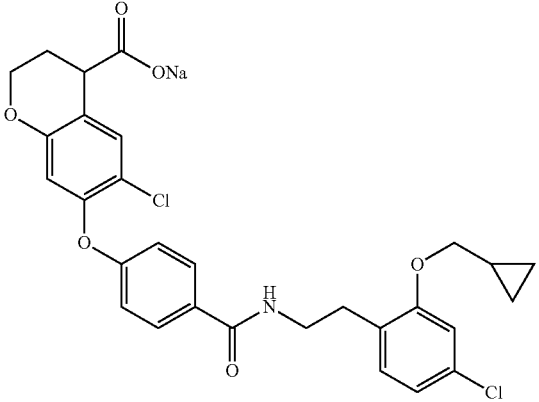 | sodium 6-chloro-7-(4-(4-chloro-2-(cyclopropyl-methoxy)phenethylcarbamoyl)phenoxy)chroman-4-carboxylate | MS (apci) m/z = 556 (M − Na + 2H). |
| 200 | 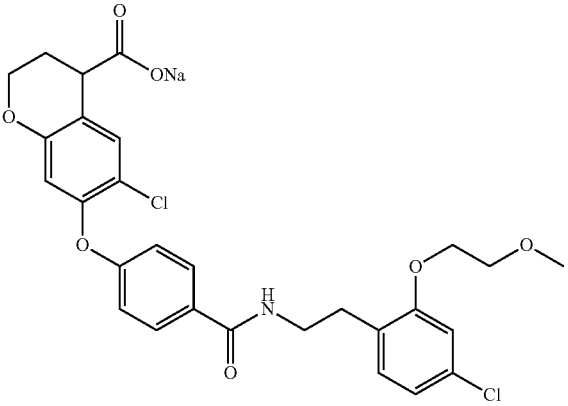 | sodium 6-chloro-7-(4-(4-chloro-2-(2-methoxyethoxy)phenethylcarbamoyl)phenoxy)chroman-4-carboxylate | MS (apci) m/z = 560 (M − Na + 2H). |
| 201 | 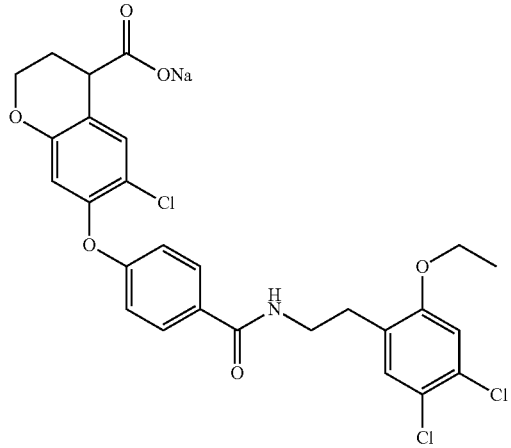 | sodium 6-chloro-7-(4-(4,5-dichloro-2-ethoxyphenethylcarbamoyl)phenoxy)chroman-4-carboxylate | MS (apci) m/z = 564 (M − Na + 2H). |

TABLE 1-continued provides additional compounds that were made by methods described herein.

| Ex. # | Structure | Name | MS or ¹H NMR Data |
|---|---|---|---|
| 202 | 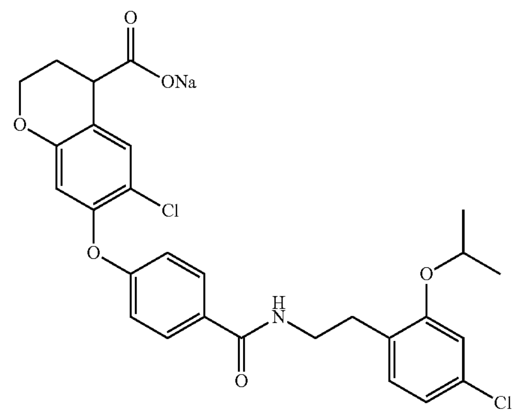 | sodium 6-chloro-7-(4-(4-chloro-2-isopropoxy-phenethylcarbamoyl)phenoxy)chroman-4-carboxylate | MS (apci) m/z = 544 (M − Na + 2H). |
| 203 | 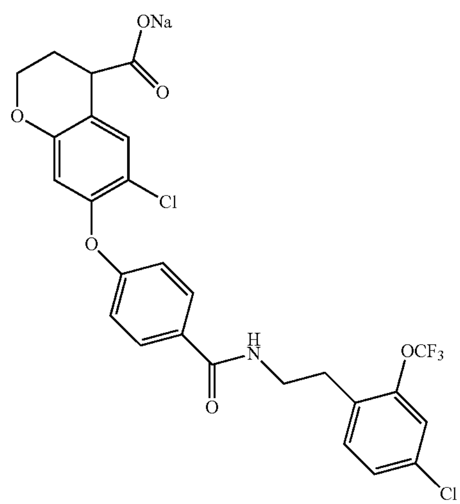 | sodium 6-chloro-7-(4-(4-chloro-2-(trifluoromethoxy)phenethylcarbamoyl)phenoxy)chroman-4-carboxylate | MS (apci) m/z = 570 (M − Na + 2H). |
| 204 | 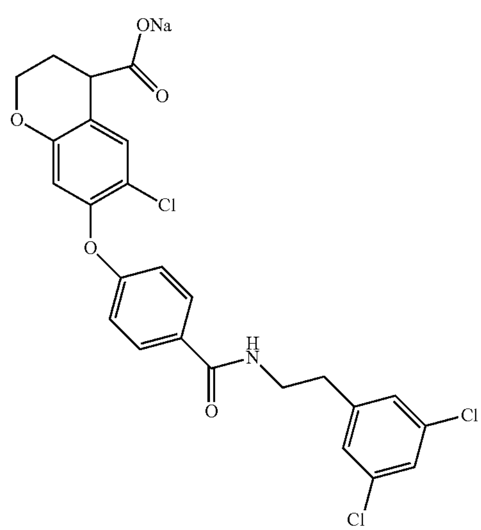 | sodium 6-chloro-7-(4-(3,5-dichlorophenethylcarbamoyl)phenoxy)chroman-4-carboxylate | MS (apci) m/z = 522 (M − Na + 2H). |

TABLE 1-continued provides additional compounds that were made by methods described herein.

| Ex. # | Structure | Name | MS or ¹H NMR Data |
|---|---|---|---|
| 205 | 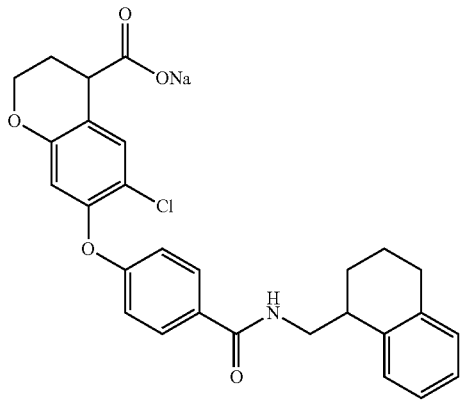 | sodium 6-chloro-7-(4-((1,2,3,4-tetrahydronaphthalen-1-yl)methylcarbamoyl)phenoxy)chroman-4-carboxylate | MS (apci) m/z = 492 (M − Na + 2H). |
| 206 | 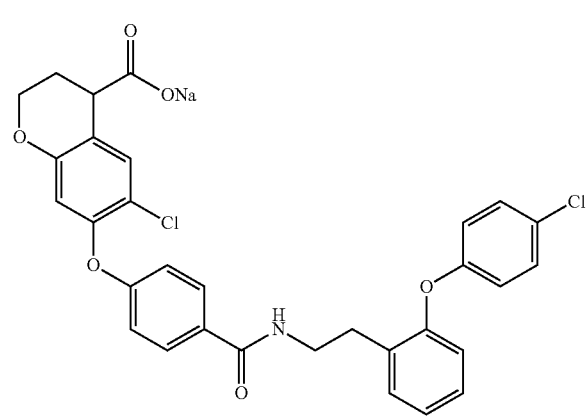 | sodium 6-chloro-7-(4-(2-(4-chlorophenoxy)phenethylcarbamoyl)phenoxy)chroman-4-carboxylate | MS (apci) m/z = 578.1 (M + 2H − Na) |
| 207 | 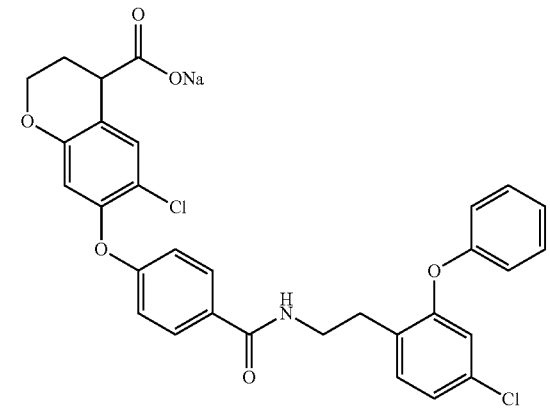 | sodium 6-chloro-7-(4-(4-chloro-2-phenoxyphenethylcarbamoyl)phenoxy)chroman-4-carboxylate | MS (apci) m/z = 578.1 (M + 2H − Na) |

TABLE 1-continued provides additional compounds that were made by methods described herein.

| Ex. # | Structure | Name | MS or $^1$H NMR Data |
|---|---|---|---|
| 208 | 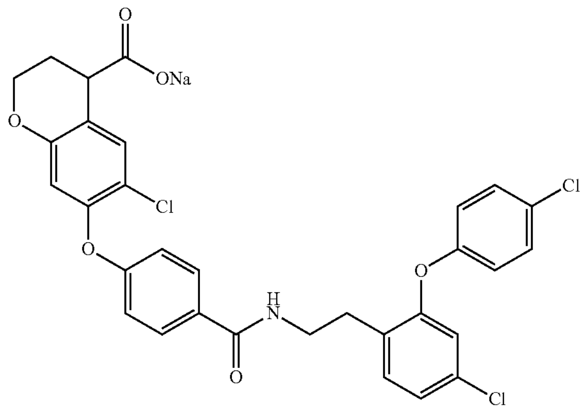 | sodium 6-chloro-7-(4-(4-chloro-2-(4-chlorophenoxy)phenethyl-carbamoyl)phenoxy)chroman-4-carboxylate | MS (apci) m/z = 612.1 (M + 2H − Na) |
| 209 | 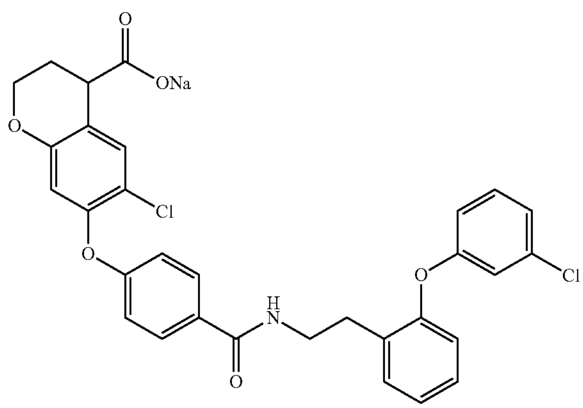 | sodium 6-chloro-7-(4-(2-(3-chlorophenoxy)phenethylcarbamoyl)phenoxy)chroman-4-carboxylate | MS (apci) m/z = 578.1 (M + 2H − Na) |
| 210 | 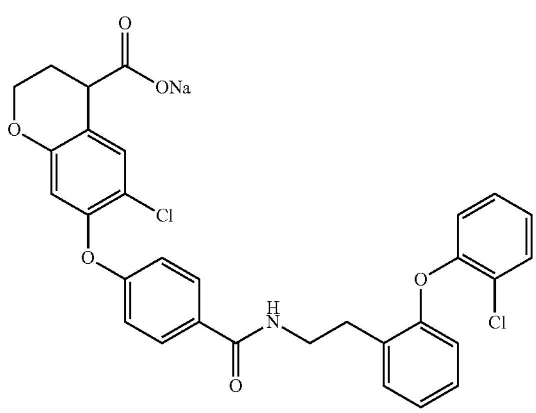 | sodium 6-chloro-7-(4-(2-(2-chlorophenoxy)phenethylcarbamoyl)phenoxy)chroman-4-carboxylate | MS (apci) m/z = 578.1 (M + 2H − Na) |

TABLE 1-continued provides additional compounds that were made by methods described herein.

| Ex. # | Structure | Name | MS or $^1$H NMR Data |
|---|---|---|---|
| 211 | 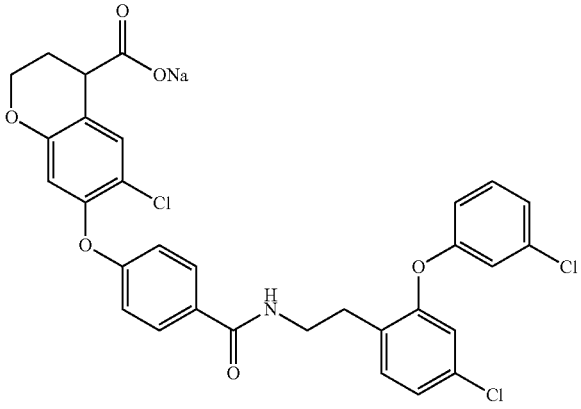 | sodium 6-chloro-7-(4-(4-chloro-2-(3-chlorophenoxy)phenethyl-carbamoyl)phenoxy)chroman-4-carboxylate | MS (apci) m/z = 612.0 (M + 2H − Na) |
| 212 | 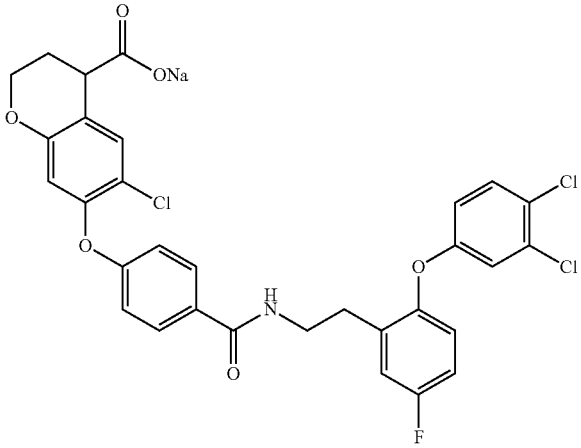 | sodium 6-chloro-7-(4-(2-(3,4-dichlorophenoxy)-5-fluorophenethyl-carbamoyl)phenoxy)chroman-4-carboxylate | MS (apci) m/z = 630.0 (M + 2H − Na) |
| 213 | 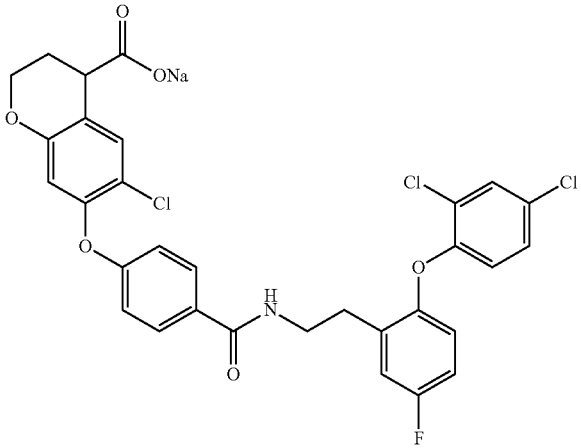 | sodium 6-chloro-7-(4-(2-(2,4-dichlorophenoxy)-5-fluorophenethyl-carbamoyl)phenoxy)chroman-4-carboxylate | MS (apci) m/z = 630.0 (M + 2H − Na) |

217 218

TABLE 1-continued provides additional compounds that were made by methods described herein.

| Ex. # | Structure | Name | MS or ¹H NMR Data |
|---|---|---|---|
| 214 | 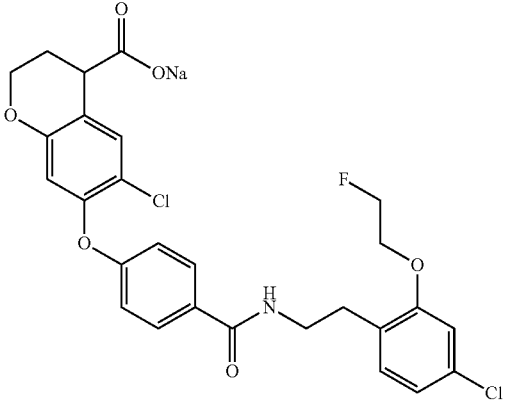 | sodium 6-chloro-7-(4-(4-chloro-2-(2-fluoroethoxy)phenethyl-carbamoyl)phenoxy)chroman-4-carboxylate | MS (apci) m/z = 547.9 (M + 2H − Na) |
| 215 | 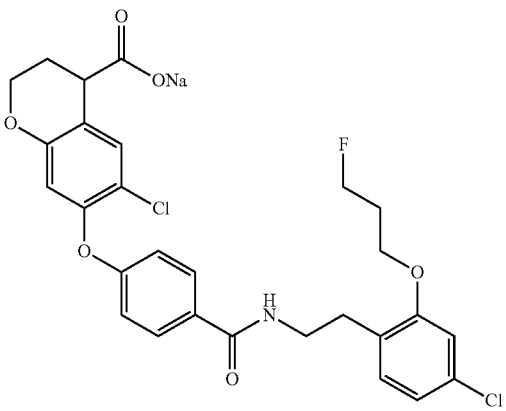 | sodium 6-chloro-7-(4-(4-chloro-2-(3-fluoropropoxy)phenethyl-carbamoyl)phenoxy)chroman-4-carboxylate | MS (apci) m/z = 562 (M + 2H − Na) |
| 216 | 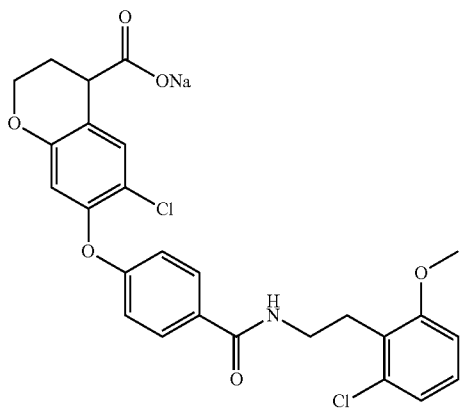 | sodium 6-chloro-7-(4-(2-chloro-6-methoxyphenethyl-carbamoyl)phenoxy)chroman-4-carboxylate | MS (apci): 515.9 (M + 2H − Na) |

TABLE 1-continued provides additional compounds that were made by methods described herein.

| Ex. # | Structure | Name | MS or $^1$H NMR Data |
|---|---|---|---|
| 217 | 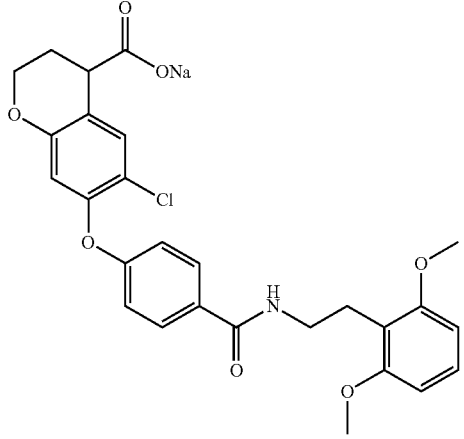 | sodium 6-chloro-7-(4-(2,6-dimethoxyphenethyl-carbamoyl)phenoxy)chroman-4-carboxylate | MS (apci): 512.0 (M + 2H − Na) |
| 218 | 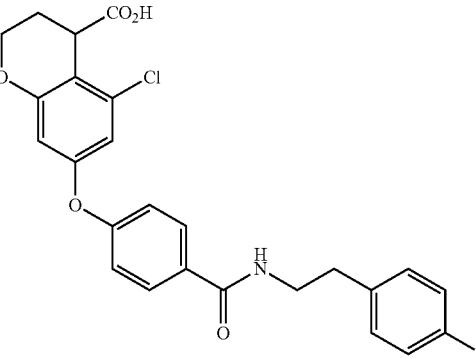 | 5-chloro-7-(4-(4-chlorophenethyl-carbamoyl)phenoxy)chroman-4-carboxylic acid | MS (apci, pos) m/z = 486 |
| 219 | 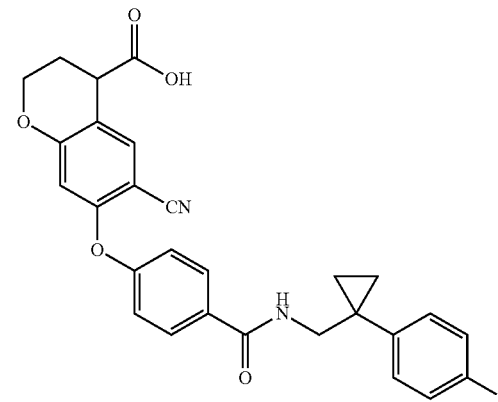 | 7-(4-((1-(4-chlorophenyl)cyclopropyl)methylcarbamoyl)phenoxy)-6-cyanochroman-4-carboxylic acid | MS (apci, pos) m/z = 503 |

TABLE 1-continued provides additional compounds that were made by methods described herein.

| Ex. # | Structure | Name | MS or $^1$H NMR Data |
|---|---|---|---|
| 220 | 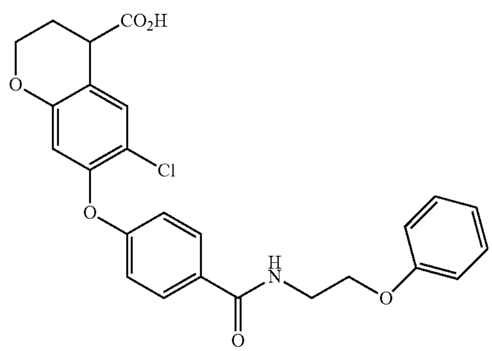 [SMILES: O=C(NCCOc1ccccc1)c1ccc(Oc2cc3c(cc2Cl)C(C(=O)O)CCO3)cc1] | 6-chloro-7-(4-(2-phenoxyethylcarbamoyl)phenoxy)chroman-4-carboxylic acid | MS (apci, pos) m/z = 468 |
| 221 | 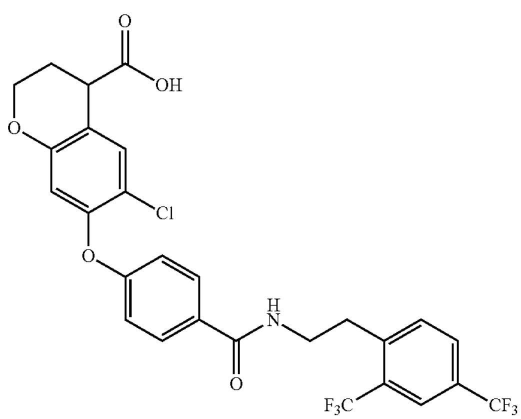 [SMILES: O=C(NCCc1ccc(C(F)(F)F)cc1C(F)(F)F)c1ccc(Oc2cc3c(cc2Cl)C(C(=O)O)CCO3)cc1] | 7-(4-(2,4-bis(trifluoromethyl)phenethylcarbamoyl)phenoxy)-6-chlorochroman-4-carboxylic acid | $^1$H NMR (400 MHz, D$_6$ DMSO) δ 8.02 (d, 1H, J = 8.1 Hz), 7.97 (s, 1H), 7.83-7.81 (c, 2H), 7.76 (d, 1H, J = 8.0 Hz), 7.55 (s, 1H), 6.91 (d, 2H, J = 8.6 Hz), 6.51 (s, 1H), 4.21 (m, 1H), 4.11 (m, 1H), 3.60 (m, 1H), 3.55-3.52 (c, 2H), 3.23 (m, 1H), 3.09 (m, 1H), 2.20 (m, 1H), 1.76 (m, 1H). |
| 222 | 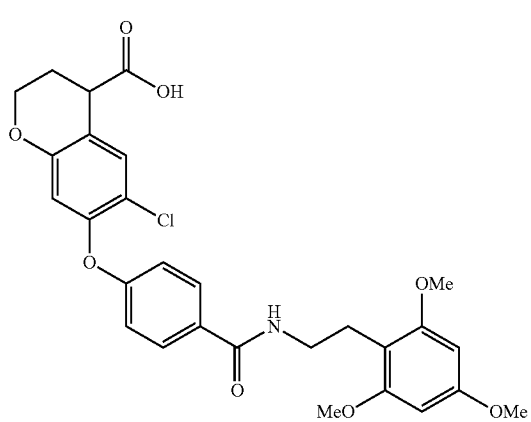 [SMILES: COc1cc(OC)c(CCNC(=O)c2ccc(Oc3cc4c(cc3Cl)C(C(=O)O)CCO4)cc2)c(OC)c1] | 6-chloro-7-(4-(2,4,6-trimethoxyphenethylcarbamoyl)phenoxy)chroman-4-carboxylic acid | MS (apci, pos) m/z = 542 |

TABLE 1-continued provides additional compounds that were made by methods described herein.

| Ex. # | Structure | Name | MS or $^1$H NMR Data |
|---|---|---|---|
| 223 | 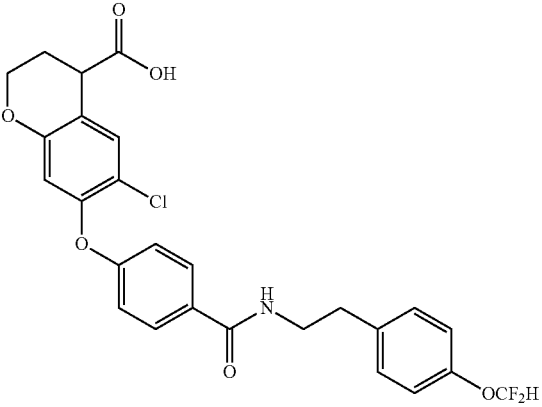 | 6-chloro-7-(4-(4-(difluoromethoxy)phenethylcarbamoyl)phenoxy)chroman-4-carboxylic acid | MS (apci, pos) m/z = 518 |
| 224 | 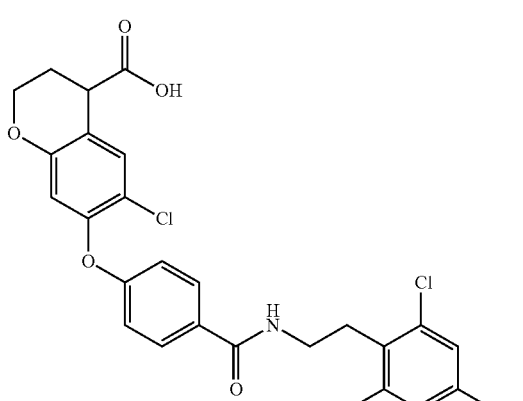 | 6-chloro-7-(4-(2,6-dichloro-4-methoxyphenethyl-carbamoyl)phenoxy)chroman-4-carboxylic acid | MS (apci, pos) m/z = 552 |
| 225 | 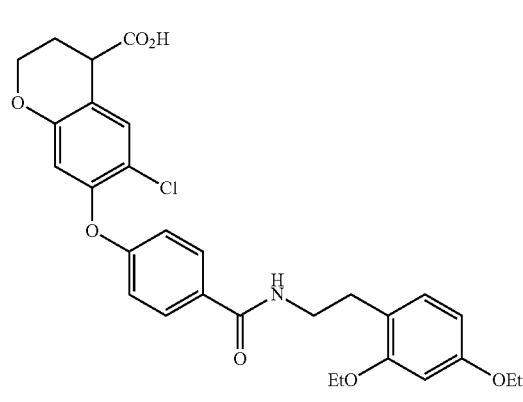 [SMILES: CCOc1ccc(CCNC(=O)c2ccc(Oc3cc4c(cc3Cl)C(C(=O)O)CCO4)cc2)c(OCC)c1] | 6-chloro-7-(4-(2,4-diethoxyphenethyl-carbamoyl)phenoxy)chroman-4-carboxylic acid | MS (apci, pos) m/z = 540 |

TABLE 1-continued provides additional compounds that were made by methods described herein.

| Ex. # | Structure | Name | MS or $^1$H NMR Data |
|---|---|---|---|
| 226 | 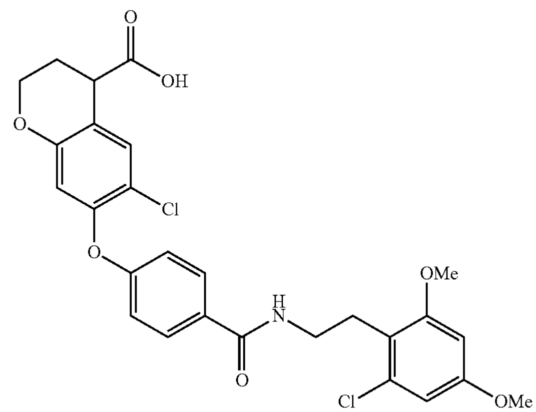 [SMILES: COc1cc(Cl)c(CCNC(=O)c2ccc(Oc3cc4c(cc3Cl)C(C(=O)O)CCO4)cc2)c(OC)c1] | 6-chloro-7-(4-(2-chloro-4,6-dimethoxyphenethyl-carbamoyl)phenoxy)chroman-4-carboxylic acid | MS (esi, pos) m/z = 546 |
| 227 | 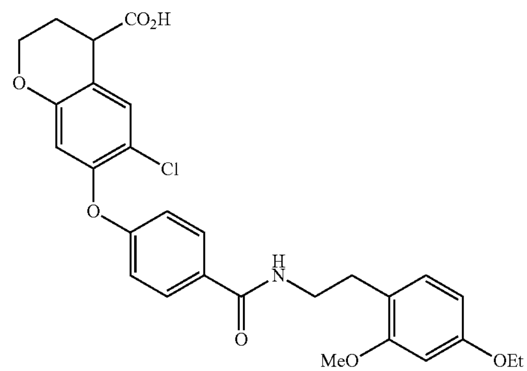 [SMILES: CCOc1ccc(CCNC(=O)c2ccc(Oc3cc4c(cc3Cl)C(C(=O)O)CCO4)cc2)c(OC)c1] | 6-chloro-7-(4-(4-ethoxy-2-methoxyphenethyl-carbamoyl)phenoxy)chroman-4-carboxylic acid | MS (esi + apci, pos) m/z = 526 |
| 228 | 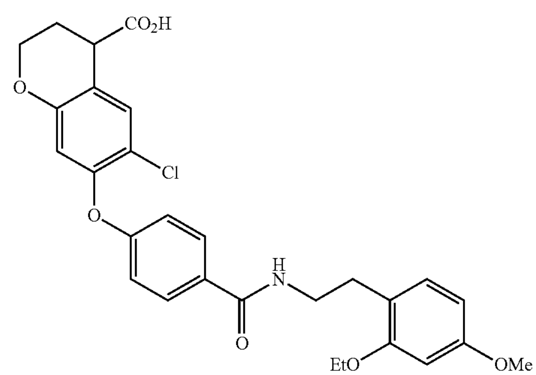 [SMILES: CCOc1cc(OC)ccc1CCNC(=O)c1ccc(Oc2cc3c(cc2Cl)C(C(=O)O)CCO3)cc1] | 6-chloro-7-(4-(2-ethoxy-4-methoxyphenethyl-carbamoyl)phenoxy)chroman-4-carboxylic acid | MS (esi + apci, pos) m/z = 526 |
| 229 | 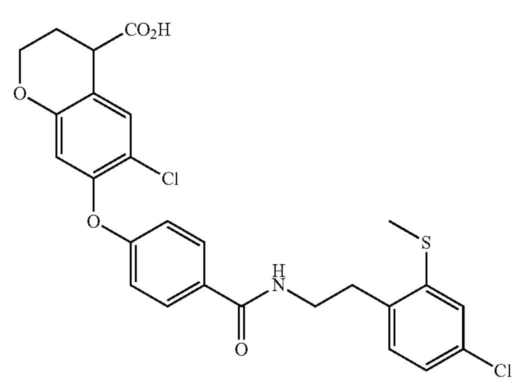 [SMILES: CSc1cc(Cl)ccc1CCNC(=O)c1ccc(Oc2cc3c(cc2Cl)C(C(=O)O)CCO3)cc1] | 6-chloro-7-(4-(4-chloro-2-(methylthio)phenethylcarbamoyl)phenoxy)chroman-4-carboxylic acid | MS (apci, pos) m/z = 532 |

TABLE 1-continued provides additional compounds that were made by methods described herein.

| Ex. # | Structure | Name | MS or ¹H NMR Data |
|---|---|---|---|
| 230 | 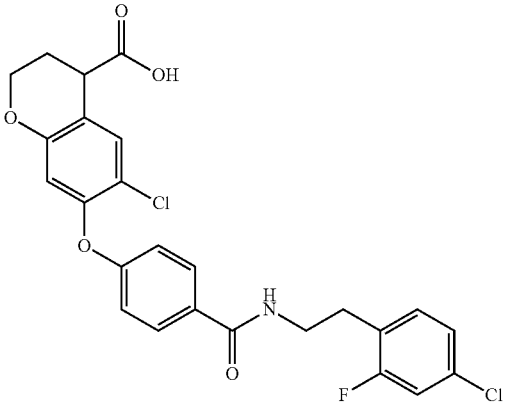 [SMILES: O=C(NCCc1ccc(Cl)cc1F)c1ccc(Oc2cc3c(cc2Cl)C(C(=O)O)CCO3)cc1] | 6-chloro-7-(4-(4-chloro-2-fluorophenethyl-carbamoyl)phenoxy)chroman-4-carboxylic acid | MS (esi + apci, pos) m/z = 504 |
| 231 | 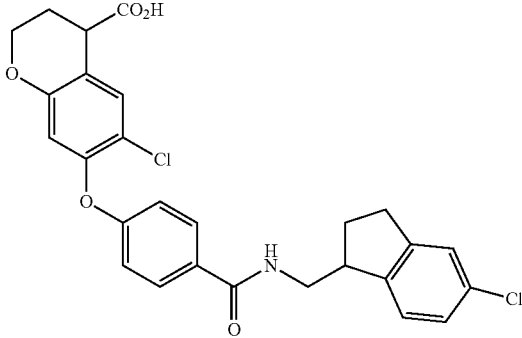 [SMILES: O=C(NCC1CCc2cc(Cl)ccc21)c1ccc(Oc2cc3c(cc2Cl)C(C(=O)O)CCO3)cc1] | 6-chloro-7-(4-((5-chloro-2,3-dihydro-1H-inden-1-yl)methylcarbamoyl)phenoxy)chroman-4-carboxylic acid | MS (apci, pos) m/z = 512 |
| 232 | 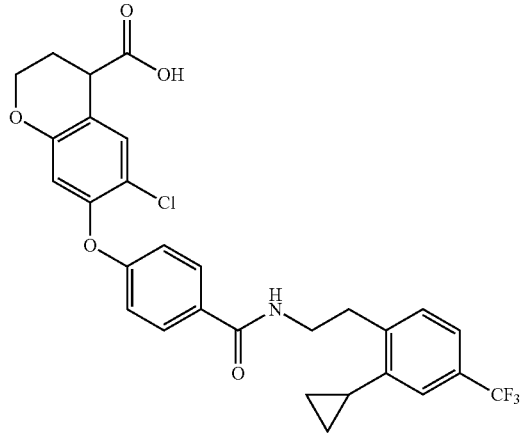 [SMILES: O=C(NCCc1ccc(C(F)(F)F)cc1C1CC1)c1ccc(Oc2cc3c(cc2Cl)C(C(=O)O)CCO3)cc1] | 6-chloro-7-(4-(2-cyclopropyl-4-(trifluoromethyl)phenethylcarbamoyl)phenoxy)chroman-4-carboxylic acid | MS (esi + apci, pos) m/z = 560 |

Example 233

6-Chloro-7-(4-(4-chloro-2-hydroxyphenethylcarbamoyl)phenoxy)chroman-4-carboxylic acid

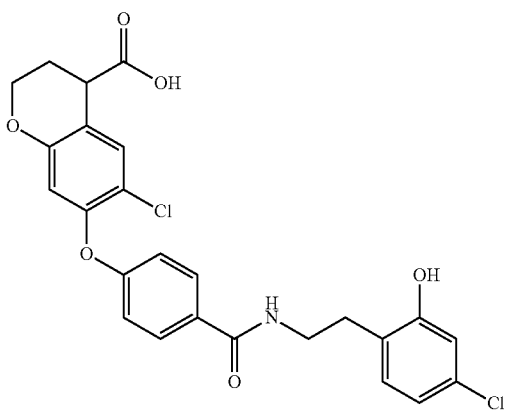

Step A: Preparation of ethyl 6-chloro-7-(4-(4-chloro-2-methoxyphenethylcarbamoyl)phenoxy)chroman-4-carboxylate To a suspension of 2-(4-chloro-2-methoxyphenyl)ethanamine hydrochloride (Preparation 8; 23.4 g, 105 mmol) in DCM (200 ml) was added triethylamine (16.8 ml, 120 mmol), and the mixture was allowed to stir for 30 minutes (solids did not go into solution). To this was added sequentially 4-(6-chloro-4-(ethoxycarbonyl)chroman-7-yloxy)benzoic acid (Preparation 1; 37.8 g, 100 mmol, 1H-benzo[d][1,2,3]triazol-1-ol hydrate (15.4 g, 100 mmol), and N1-((ethylimino)methylene)-N3,N3-dimethylpropane-1,3-diamine hydrochloride (23.1 g, 120 mmol), and the reaction was allowed to stir overnight (all solids went into solution after 2 hours). The reaction was diluted with EtOAc (600 ml) and washed with 600 mL portions of 1M HCl, saturated aqueous bicarbonate, and brine. The organic layer was dried over sodium sulfate, filtered, and concentrated. The residue was taken up in hot ethyl acetate (500 ml) and was crystallized by the addition of hexanes (1.5 L) to yield ethyl 6-chloro-7-(4-(4-chloro-2-methoxyphenethylcarbamoyl)phenoxy)chroman-4-carboxylate (51.1 g, 93.9 mmol).

Step B: Preparation of 6-chloro-7-(4-(4-chloro-2-methoxyphenethylcarbamoyl)phenoxy)chroman-4-carboxylic acid To a solution of ethyl 6-chloro-7-(4-(4-chloro-2-methoxyphenethylcarbamoyl)phenoxy)chroman-4-carboxylate (31.0 g, 56.9 mmol) in 3:1 THF/EtOH (200 ml) was added sodium hydroxide (120 ml, 120 mmol), and the reaction was allowed to stir overnight at ambient temperature, at which point it was complete as determined by thin layer chromatography. The reaction was concentrated to about 25% volume, taken up in 100 ml of EtOH and 100 ml of water, and acidified with 10 ml of concentrated HCl with stirring. The product initially oiled out, but became a solid. The solids were collected by filtration and washed with 200 ml of water to yield 6-chloro-7-(4-(4-chloro-2-methoxyphenethylcarbamoyl)phenoxy)chroman-4-carboxylic acid (24.7 g, 47.8 mmol) as a white solid.

Step C: Preparation of 6-Chloro-7-(4-(4-chloro-2-hydroxyphenethylcarbamoyl)phenoxy)chroman-4-carboxylic acid To a stirred, chilled (0° C.) solution of boron trichloride in dichloromethane (13.6 mL; 1.0 M; 7 eq.) was added, portionwise over 2 minutes, solid 6-chloro-7-(4-(4-chloro-2-methoxyphenethylcarbamoyl)phenoxy)chroman-4-carboxylic acid (1.0 g; 1.94 mmol) under nitrogen atmosphere. The resulting mixture was allowed to warm to ambient temperature, stirred for 8 hours and then heated to 35° C. for 24 hours. The reaction was quenched with 5 mL water (significant effervescence observed while adding first 2 mL) and then 6 mL of saturated $Na_2CO_3$ was added to bring the pH to 4. During the last 1 mL of addition, significant amounts of precipitates formed in the lower organic layer. The warm bath was removed and replaced with an ice bath. The material was stirred for 5 minutes in ice bath, then solids collected on a medium frit, washing once with 5 mL chilled MTBE. This material was purified via Biotage chromatography with methanol in ethyl acetate to provide the desired 6-chloro-7-(4-(4-chloro-2-hydroxyphenethylcarbamoyl)phenoxy)chroman-4-carboxylic acid (195 mg). MS (apci, neg) m/z=500. $^1$H NMR (400 MHz, D6 DMSO) δ 8.45 (t, 1H), 7.82, (d, 2H), 7.46 (s, 1H), 7.06 (d, 1H), 6.95 (d, 2H), 6.83 (d, 1H), 6.75 (dd, 1H), 6.60 (s, 1H), 4.22 (m, 1H), 4.12 (t, 1H), 3.72 (br s, 1H), 3.60 (t, 1H), 2.76 (t, 2H), 2.22 (m, 1H), 1.99 (m, 1H), 1.76 (m, 1H).

Example 234

Enantiomer 2 of 6-chloro-7-(4-(4-chloro-2-cyclopropylphenethylcarbamoyl)phenoxy)chroman-4-carboxylic acid and preparation of sodium salt

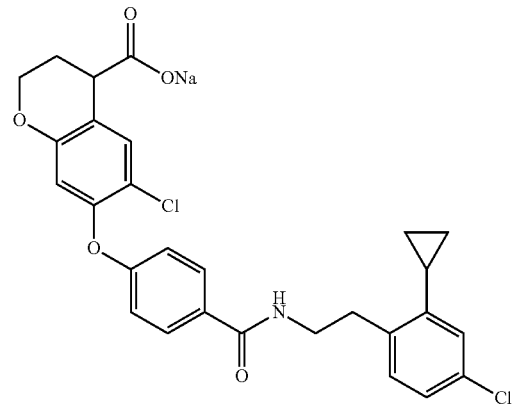

Step A: Preparation of Ethyl 7-(4-(2-bromo-4-chlorophenethylcarbamoyl)phenoxy)-6-chlorochroman-4-carboxylate To a stirred solution of 4-(6-chloro-4-(ethoxycarbonyl)chroman-7-yloxy)benzoic acid (Preparation 1; 1.32 g; 3.52 mmol), 1-hydroxybenzotriazole hydrate (0.59 g; 3.85 mmol) and 2-(2-bromo-4-chlorophenyl)ethanamine (Preparation 5; 0.904 g; 3.85 mmol) in dry dimethylformamide (10 mL) was added 1-ethyl-(3-dimethylaminopropyl) carbodiimide hydrochloride (0.806 g; 4.02 mmol) at ambient temperature. After stirring at ambient temperature for 5 hours, the solution was diluted with 100 mL of water, stirred for 10 minutes longer and then extracted with ethyl acetate (3×15 mL). The combined organic layers were dried over sodium sulfate, filtered and concentrated in vacuo. The residue was purified by silica gel chromatography (Biotage 40M), eluting with hexane and ethyl acetate to provide ethyl 7-(4-(2-bromo-4-chlorophenethylcarbamoyl)phenoxy)-6-chlorochroman-4-carboxylate as a white solid (1.21 g). MS (apci, pos) m/z=594.

Step B: Preparation of Ethyl 6-chloro-7-(4-(4-chloro-2-cyclopropylphenethylcarbamoyl)phenoxy)chroman-4-carboxylate To a stirred suspension of ethyl 7-(4-(2-bromo-4-chlorophenethylcarbamoyl)phenoxy)-6-chlorochroman-4-carboxylate (129 mg; 0.22 mmol) in 2 mL toluene was added successively water (0.1 mL), potassium phosphate (138 mg; 0.65 mmol), tricyclohexylphosphine (24 mg; 0.087 mmol), and cyclopropylboronic acid (0.435 mmol) at ambient temperature with stirring. A balloon of nitrogen with a three-way purge valve was attached, and the flask was evacuated and refilled five times with nitrogen. Palladium (II) acetate (10 mg; 0.043 mmol) was added, and again the flask was evacuated and refilled five times with nitrogen. The mixture was stirred in an oil bath set to 100° C. under the nitrogen balloon. After 4 hours the mixture was cooled to ambient temperature. The mixture was diluted with 10 mL EtOAc and 5 mL water. The mixture was transferred to a separatory funnel and after shaking, the organic layer was separated, dried over sodium sulfate and evaporated to give a brown oil. This material was purified by silica gel chromatography on a Biotage 25S column, eluting with 75/25 hexane/EtOAc to provide 83 mg of ethyl 6-chloro-7-(4-(4-chloro-2-cyclopropylphenethylcarbamoyl)phenoxy)chroman-4-carboxylate as a colorless oil. MS (apci, pos) m/z=554.

Step C: Preparation of 6-Chloro-7-(4-(4-chloro-2-cyclopropylphenethyl carbamoyl)phenoxy)chroman-4-carboxylic acid To a stirred solution of ethyl 6-chloro-7-(4-(4-chloro-2-cyclopropylphenethylcarbamoyl)phenoxy)chroman-4-carboxylate (83 mg; 0.15 mmol) in a mixture of 1.4 mL tetrahydrofuran and 0.7 mL ethanol at ambient temperature was added 0.60 mL of 1M aqueous sodium hydroxide. The resulting slightly cloudy mixture was vigorously stirred at ambient temperature for 1 hour, after which the reaction was determined to be complete by thin layer chromatography (90/10/1 chloroform/methanol/HOAc). The reaction mixture was diluted with 5 mL EtOAc and 2.5 mL of 1M HCl, then transferred to a separatory funnel. After shaking, the organic layer was washed with 2 mL brine, then dried over sodium sulfate and evaporated to give 61 mg of 6-chloro-7-(4-(4-chloro-2-cyclopropylphenethylcarbamoyl)phenoxy)chroman-4-carboxylic acid as a colorless oil. MS (apci, pos) m/z=526

Step D: Isolation of Enantiomer 2 of 6-chloro-7-(4-(4-chloro-2-cyclopropylphenethylcarbamoyl)phenoxy)chroman-4-carboxylic acid The racemic mixture of 6-chloro-7-(4-(4-chloro-2-cyclopropylphenethylcarbamoyl)phenoxy)chroman-4-carboxylic acid was dissolved in methanol and resolved via supercritical fluid chromatography employing a CHIRALCEL® OJ-H column (3×15 cm) eluting with methanol/carbon dioxide at 100 bar, using 1 mL injections and a flow rate of 70 mL/min Collection of fractions containing peak 2 and removal of volatiles provided Enantiomer 2 of 6-chloro-7-(4-(4-chloro-2-cyclopropylphenethylcarbamoyl)phenoxy)chroman-4-carboxylic acid. MS (apci, pos) m/z=526. Chiral purity (ee) >98% as measured with CHIRALPAK® QD-AX column in comparison to racemic material.

Step E: Preparation of the sodium salt of Enantiomer 2 of 6-chloro-7-(4-(4-chloro-2-cyclopropylphenethylcarbamoyl)phenoxy)chroman-4-carboxylic acid The material obtained in Step D (peak 2; 83 mg) was dissolved in 1 mL methanol, and 0.026 mL of 25% sodium methoxide in methanol was added. The solvent was evaporated, and the residue evaporated from ether to give 60 mg of Enantiomer 2 of 6-chloro-7-(4-(4-chloro-2-cyclopropylphenethylcarbamoyl)phenoxy)chroman-4-carboxylic acid, sodium salt as an off-white solid. MS (apci, pos): m/z=526. $^1$H NMR (400 MHz, D6 DMSO) δ 8.58 (t, 1H), 7.82 (d, 2H), 7.55 (s, 1H), 7.17 (d, 1H), 7.14 (dd, 1H), 6.91 (m, 3H), 6.52 (s, 1H), 4.21 (dt, 1H), 4.11 (m, 1H), 3.47 (q, 2H), 3.22 (t, 1H), 2.99 (t, 2H), 2.20 (m, 1H), 2.10 (m, 1H), 1.78 (m, 1H), 1.09 (t, 1H), 0.96 (m, 2H), 0.69 (m, 2H). Optical rotation: $[\alpha]^{25}_D = -16.63°$ (c=1.00, MeOH).

During the chiral separation described in Step D, fractions containing peak 1 were collected to provide Enantiomer 1 of 6-chloro-7-(4-(4-chloro-2-cyclopropylphenethylcarbamoyl)phenoxy)chroman-4-carboxylic acid. MS (apci, pos) m/z=526. Chiral purity (ee) >98% as measured with CHIRALPAK® QD-AX column in comparison to racemic material. The sodium salt of Enantiomer 1 was then prepared in a manner similar to that provided in Step E. MS (apci, pos) m/z=526. The sodium salt of Enantiomer 1 was found to be less active than the sodium salt of Enantiomer 2 when tested in an assay described in Example A.

Example 235

Enantiomer 2 of 6-chloro-7-(4-(4-cyclopropyl-2-methoxyphenethylcarbamoyl)phenoxy)chroman-4-carboxylic acid and preparation of sodium salt

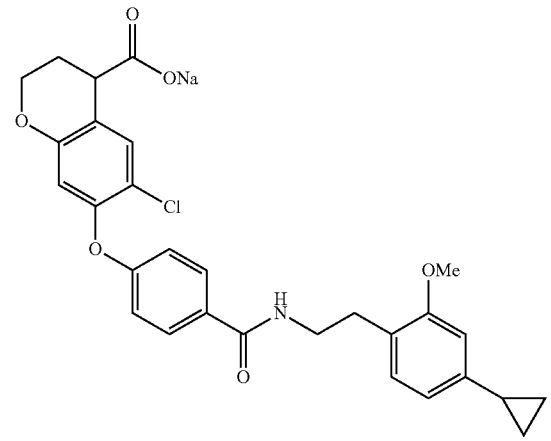

Step A: Preparation of ethyl 7-(4-(2-methoxy-4-bromophenethylcarbamoyl)phenoxy)-6-chlorochroman-4-carboxylate To a stirred solution of 4-(6-chloro-4-(ethoxycarbonyl)chroman-7-yloxy)benzoic acid (Preparation 1; 1.90 g; 5.04 mmol), 1-hydroxybenzotriazole hydrate (0.85 g; 5.55 mmol) and 2-(2-methoxy-4-bromophenyl)ethanamine (Preparation 6; 1.28 g; 5.55 mmol) in dry dimethylformamide (15 mL) was added 1-ethyl-(3-dimethylaminopropyl) carbodiimide hydrochloride (1.16 g; 6.05 mmol) at ambient temperature. After stirring at ambient temperature for 4 hours, the solution was diluted with 150 mL of water, stirred for 10 minutes longer and then extracted with ethyl acetate (3×15 mL). Aqueous HCl (1M, 50 mL) was added to enable layer separation. The combined organic layers were dried over sodium sulfate, filtered and concentrated in vacuo. The residue was purified by silica gel chromatography (Biotage 40M), eluting with hexane and ethyl acetate to provide ethyl 7-(4-(2-methoxy-4-bromophenethylcarbamoyl)phenoxy)-6-chlorochroman-4-carboxylate as a light yellow solid (1.81 g). MS (apci, pos) m/z=590.

Step B: Preparation of ethyl 7-(4-(2-methoxy-4-cyclopropylphenethylcarbamoyl)phenoxy)-6-chlorochroman-4-carboxylate To a stirred suspension of 7-(4-(2-methoxy-4-bromophenethylcarbamoyl)phenoxy)-6-chlorochroman-4-carboxylate (130 mg; 0.22 mmol) in 2 mL toluene was added successively 0.1 mL water, potassium phosphate (141 mg; 0.66 mmol), tricyclohexylphosphine (25 mg; 0.08 mmol), and cyclopropylboronic acid (38 mg; 0.44 mmol) at ambient temperature with stirring. A balloon of nitrogen with a three-way purge valve was attached, and the flask was evacuated and refilled five times with nitrogen. Palladium(II) acetate (10 mg; 0.04 mmol) was added, and again the flask was evacuated and refilled five times with nitrogen. The mixture was then stirred in an oil bath set to 100° C. under the nitrogen balloon. After 3.5 hours the mixture was cooled to ambient temperature, and the reaction was determined to be complete by thin layer chromatography (50/50 hexane/EtOAc). The mixture was diluted with 10 mL EtOAc and 5 mL water. The mixture was transferred to a separatory funnel and after shaking, the organic layer was dried over sodium sulfate and evaporated to give a brown oil. The crude material was purified by silica gel chromatography on a Biotage 25S column, eluting with 75/25 hexane/EtOAc to give 73 mg of ethyl 7-(4-(2-methoxy-4-cyclopropylphenethylcarbamoyl)phenoxy)-6-chlorochroman-4-carboxylate as a colorless oil. MS (apci, pos) m/z=550.

Step C: Preparation of 6-chloro-7-(4-(4-cyclopropyl-2-methoxyphenethylcarbamoyl)phenoxy)chroman-4-carboxylic acid To a stirred solution of ethyl 7-(4-(2-methoxy-4-cyclopropylphenethylcarbamoyl)phenoxy)-6-chlorochroman-4-carboxylate (0.07 g; 0.133 mmol) in a mixture of 1.2 mL THF and 0.6 mL ethanol at ambient temperature was added 0.53 mL of 1M aqueous NaOH. The resulting slightly cloudy mixture was vigorously stirred at ambient temperature. After 1 hour the reaction mixture was diluted with 6 mL EtOAc and 3 mL of 1M aqueous HCl, then transferred to a separatory funnel. After shaking, the organic layer was washed with 2 mL brine, then dried over sodium sulfate and evaporated to give 62 mg of 6-chloro-7-(4-(4-cyclopropyl-2-methoxyphenethylcarbamoyl)phenoxy)chroman-4-carboxylic acid as a colorless oil. MS (apci, pos) m/z=523.

Step D: Isolation of Enantiomer 2 of 6-chloro-7-(4-(4-cyclopropyl-2-methoxyphenethylcarbamoyl)phenoxy)chroman-4-carboxylic acid The racemic mixture of 6-chloro-7-(4-(4-cyclopropyl-2-methoxyphenethylcarbamoyl)phenoxy)chroman-4-carboxy-lic acid was dissolved in methanol and resolved via supercritical fluid chromatography employing a CHIRALCEL® OJ-H column (3×15 cm) eluting with methanol/carbon dioxide at 100 bar, using 1 mL injections and a flow rate of 60 mL/min. Collection of fractions containing peak 2 and removal of volatiles provided Enantiomer 2 of 6-chloro-7-(4-(4-cyclopropyl-2-methoxyphenethylcarbamoyl)phenoxy)chroman-4-carboxylic acid. MS (apci, pos) m/z=522. Chiral purity (ee) >98% as measured with CHIRALPAK® QD-AX column in comparison to racemic material.

Step E: Preparation of the sodium salt of Enantiomer 2 of 6-chloro-7-(4-(4-cyclopropyl-2-methoxyphenethylcarbamoyl)phenoxy)chroman-4-carboxylic acid The material obtained above (peak 2; 6-chloro-7-(4-(4-cyclopropyl-2-methoxyphenethylcarbamoyl)phenoxy)chroman-4-carboxylic acid; 10.7 g, 20.5 mmol) was taken up in 40 ml THF and 75 ml EtOH. The solution was treated with sodium methoxide (41.0 ml of 0.5 M in methanol, 20.5 mmol). The mixture remained a solution and was stirred for 5 minutes. The sides of flask were rinsed with 50 ml ethanol and the mixture was concentrated in vacuo. EtOH (100 mL) was added and the mixture was concentrated in vacuo. The residue was put under high vacuum at 55° C. (sand bath temperature) for 60 hours to provide sodium (S)-6-chloro-7-(4-(4-cyclopropyl-2-methoxyphenethylcarbamoyl)phenoxy)chroman-4-carboxylate (11.3 g, 20.8 mmol) as a white solid. MS (apci, pos) m/z=522. $^1$H NMR (400 MHz, D6 DMSO) δ 7.82 (d, 2H), 7.56 (s, 1H), 6.99 (d, 1H), 6.91 (dd, 2H), 6.66 (s, 1H), 6.56 (d, 1H), 6.52 (m, 1H), 4.23 (m, 1H), 4.12 (m, 1H), 3.77 (s, 3H), 3.38 (m, 2H), 3.27 (m, 1H), 2.74 (t, 2H), 2.21 (m, 1H), 1.84 (m, 2H), 0.90 (m, 2H), 0.65 (m, 2H).

During the chiral separation described in Step D, fractions containing peak 1 were collected to provide Enantiomer 1 of 6-chloro-7-(4-(4-cyclopropyl-2-methoxyphenethylcarbamoyl)phenoxy)chroman-4-carboxylic acid. MS (apci, pos) m/z=522. Chiral purity (ee) >98% as measured with CHIRALPAK® QD-AX column in comparison to racemic material. The sodium salt of Enantiomer 1 was then prepared in a manner similar to that provided in Step E. MS (apci, pos) m/z=522. The sodium salt of Enantiomer 1 was found to be less active than the sodium salt of Enantiomer 2 when tested in an assay described in Example A.

Example 236

Enantiomer 2 of 6-chloro-7-(4-(2,4-dichloro-6-methoxyphenethylcarbamoyl)phenoxy)chroman-4-carboxylic acid and preparation of sodium salt

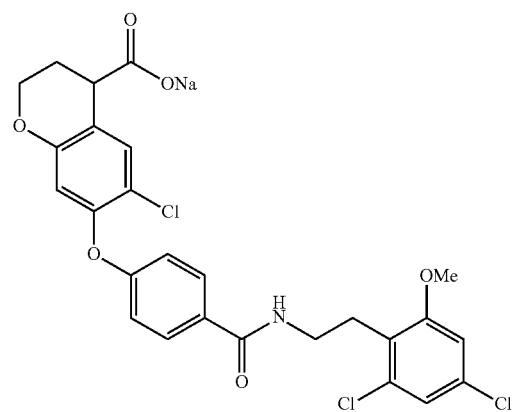

Step A: Preparation of Ethyl 6-chloro-7-(4-(2,4-dichloro-6-methoxyphenethylcarbamoyl)phenoxy)chroman-4-carboxylate To a stirred solution of 4-(6-chloro-4-(ethoxycarbonyl)chroman-7-yloxy)benzoic acid (Preparation 1; 0.75 g; 2.0 mmol), 1-hydroxybenzotriazole hydrate, and 2-(2,4-dichloro-6-methoxyphenyl)ethanamine (Preparation 7; 0.48 g, 2.19 mmol) in 6 mL DMF at ambient temperature was added solid 1-ethyl-(3-dimethylaminopropyl)carbodiimide hydrochloride (0.46 g; 2.4 mmol). The resulting solution was stirred at ambient temperature overnight for convenience. The solution was diluted with 60 mL water and after stirring for 10 minutes, the mixture was transferred to a separatory funnel and extracted with 30 mL EtOAc. 1M HCl (30 mL) was added to enable layer separation. The organic layer was dried over sodium sulfate and evaporated. The residue was purified by silica gel chromatography on a Biotage 40M column, eluting with 70/30 hexane/EtOAc, to give 0.56 g of ethyl 6-chloro-7-(4-(2,4-dichloro-6-methoxyphenethylcarbamoyl)phenoxy)chroman-4-carboxylate as a white glass. MS (apci, pos) m/z=578.

Step B: Preparation of 6-chloro-7-(4-(2,4-dichloro-6-methoxyphenethylcarbamoyl)phenoxy)chroman-4-carboxylic acid To a stirred solution of 6-chloro-7-(4-(2,4-dichloro-6-methoxyphenethylcarbamoyl)phenoxy)chroman-4-carboxylate (0.56 g; 0.97 mmol) in a mixture of 10 mL tetrahydrofuran and 5 mL ethanol at ambient temperature was added 3.9 mL of 1M aqueous sodium hydroxide. The resulting slightly cloudy mixture was vigorously stirred at ambient temperature the reaction mixture was poured into a separatory funnel containing 100 mL ethyl acetate and 50 mL 1M aqueous hydrochloric acid. After shaking, the organic layer was washed with 20 mL brine, then dried over sodium sulfate and evaporated to give 0.60 of light yellow oil. To convert to the sodium salt, the material was dissolved in 10 mL methanol, and 0.22 mL of 25% sodium methoxide in methanol was added. The solvent was evaporated, and the residue evaporated from ether to give 0.54 g of 6-chloro-7-(4-(2,4-dichloro-6-methoxyphenethylcarbamoyl)phenoxy)chroman-4-carboxylic acid as an off-white glass. MS (apci, pos) m/z=550. MS (apci, neg) m/z=548.

Step C: Isolation of Enantiomer 2 of 6-chloro-7-(4-(2,4-dichloro-6-methoxyphenethylcarbamoyl)phenoxy)chroman-4-carboxylic acid The racemic mixture of 6-chloro-7-(4-(2,4-dichloro-6-methoxyphenethylcarbamoyl)phenoxy)chroman-4-carboxylic acid was dissolved in methanol and resolved via supercritical fluid chromatography employing a CHIRALCEL® OJ-H column (3×15 cm) eluting with methanol/carbon dioxide at 100 bar, using 1 mL injections and a flow rate of 70 mL/min. Collection of fractions containing peak 2 and removal of volatiles provided Enantiomer 2 of 6-chloro-7-(4-(4-cyclopropyl-2-methoxyphenethylcarbamoyl)phenoxy)chroman-4-carboxylic acid. MS (apci, pos) m/z=550. Chiral purity (ee) >98% as measured with CHIRALPAK® QD-AX column in comparison to racemic material.

Step D: Preparation of the sodium salt of Enantiomer 2 of 6-chloro-7-(4-(2,4-dichloro-6-methoxyphenethylcarbamoyl)phenoxy)chroman-4-carboxylic acid The material obtained in Step C (peak 2; 0.56 g; 0.97 mmol)) dissolved in 10 mL methanol, and 0.22 mL of 25% sodium methoxide in methanol was added. The solvent was evaporated, and the residue evaporated from ether to give 0.54 g of the sodium salt of Enantiomer 2 of 6-chloro-7-(4-(2,4-dichloro-6-methoxyphenethylcarbamoyl)phenoxy)chroman-4-carboxylic acid as an off-white glass. MS (apci, pos) m/z=550. MS (apci, neg) m/z=548. $^1$H NMR (400 MHz, D6 DMSO) 8.50 (t, 1H), 7.80 (d, 2H), 7.56 (s, 1H), 7.14 (d, 1H), 7.07 (d, 2H), 6.53 (s, 1H), 4.23 (dt, 1H), 4.13 (m, 1H), 3.79 (s, 3H), 3.38 (q, 2H), 3.29 (t, 1H), 3.17 (s, 2H), 2.21 (m, 1H), 1.81 (m, 1H).

During the chiral separation described in Step C, fractions containing peak 1 were collected to provide Enantiomer 1 of 6-chloro-7-(4-(2,4-dichloro-6-methoxyphenethylcarbamoyl)phenoxy)chroman-4-carboxylic acid. MS (apci, pos) m/z=550. Chiral purity (ee) >98% as measured with CHIRALPAK® QD-AX column in comparison to racemic material. The sodium salt of Enantiomer 1 was then prepared in a manner similar to that provided in Step D. MS (apci, pos) m/z=550. The sodium salt of Enantiomer 1 was found to be less active than the sodium salt of Enantiomer 2 when tested in an assay described in Example A.

Example 237

Enantiomer 2 of 6-chloro-7-(4-(4-chloro-2-methoxyphenethylcarbamoyl)phenoxy)chroman-4-carboxylic acid and preparation of sodium salt

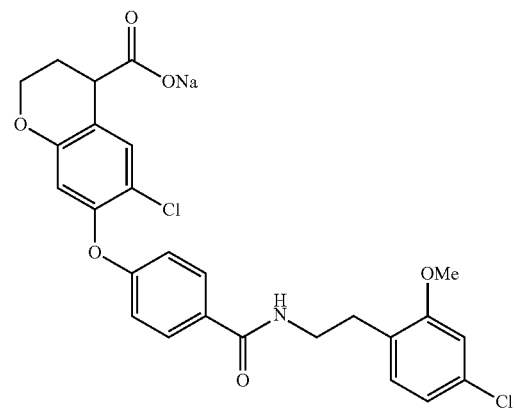

Step A: Preparation of ethyl 6-chloro-7-(4-(4-chloro-2-methoxyphenethylcarbamoyl)phenoxy)chroman-4-carboxylate To a suspension of 2-(4-chloro-2-methoxyphenyl)ethanamine hydrochloride (Preparation 8; 23.4 g, 105 mmol) in DCM (200 ml) was added triethylamine (16.8 ml, 120 mmol), and the mixture was allowed to stir for 30 minutes (solids did not go into solution). To this was added sequentially 4-(6-chloro-4-(ethoxycarbonyl)chroman-7-yloxy)benzoic acid (Preparation 1; 37.8 g, 100 mmol, 1H-benzo[d][1,2,3]triazol-1-ol hydrate (15.4 g, 100 mmol), and N1-((ethylimino)methylene)-N3,N3-dimethylpropane-1,3-diamine hydrochloride (23.1 g, 120 mmol), and the reaction was allowed to stir overnight (all solids went into solution after 2 hours). The reaction was diluted with EtOAc (600 ml) and washed with 600 mL portions of 1M HCl, saturated aqueous bicarbonate, and brine. The organic layer was dried over sodium sulfate, filtered, and concentrated. The residue was taken up in hot ethyl acetate (500 ml) and was crystallized by the addition of hexanes (1.5 L) to yield ethyl 6-chloro-7-(4-(4-chloro-2-methoxyphenethylcarbamoyl)phenoxy)chroman-4-carboxylate (51.1 g, 93.9 mmol).

Step B: Preparation of 6-chloro-7-(4-(4-chloro-2-methoxyphenethylcarbamoyl)phenoxy)chroman-4-carboxylic acid To a solution of ethyl 6-chloro-7-(4-(4-chloro-2-methoxyphenethylcarbamoyl)phenoxy)chroman-4-carboxylate (31.0 g, 56.9 mmol) in 3:1 THF/EtOH (200 ml) was added sodium hydroxide (120 ml, 120 mmol), and the reaction was allowed to stir overnight at ambient temperature, at which point it was complete as determined by thin layer chromatography. The reaction was concentrated to about 25% volume, taken up in 100 ml of EtOH and 100 ml of water, and acidified with 10 ml of concentrated HCl with stirring. The product initially oiled out, but became a solid. The solids were collected by filtration and washed with 200 ml of water to yield 6-chloro-7-(4-(4-chloro-2-methoxyphenethylcarbamoyl) phenoxy)chroman-4-carboxylic acid (24.7 g, 47.8 mmol) as a white solid.

Step C: Isolation of Enantiomer 2 of 6-chloro-7-(4-(4-chloro-2-methoxyphenethylcarbamoyl)phenoxy) chroman-4-carboxylic acid The racemic mixture of 6-chloro-7-(4-(4-chloro-2-methoxyphenethylcarbamoyl)phenoxy)chroman-4-carboxylic acid was dissolved in methanol and resolved via supercritical fluid chromatography employing a CHIRALCEL® OJ-H column (3×15 cm) eluting with methanol/carbon dioxide at 100 bar, using 1 mL injections and a flow rate of 70 mL/min. Collection of fractions containing peak 2 and removal of volatiles provided Enantiomer 2 of 6-chloro-7-(4-(4-chloro-2-methoxyphenethylcarbamoyl)phenoxy)chroman-4-carboxylic acid. MS (apci, pos) m/z=516. Chiral purity (ee) >98% as measured with CHIRALPAK® QD-AX column in comparison to racemic material.

Step D: Preparation of the sodium salt of Enantiomer 2 of 6-chloro-7-(4-(4-chloro-2-methoxyphenethylcarbamoyl)phenoxy)chroman-4-carboxylic acid The material obtained above (peak 2; 32.4 g, 62.7 mmol) was suspended in THF (55 ml) and EtOH (100 ml) was added followed by sodium methanolate in methanol (125 ml, 62.7 mmol), and the reaction was allowed to stir for 2 minutes, at which point it all crashed out of solution. The mixture was diluted with EtOH (300 ml), and was concentrated on the rotary evaporator. The residue was taken up in 500 ml of EtOH and concentrated twice to remove any residual MeOH to give 6-chloro-7-(4-(4-chloro-2-methoxyphenethylcarbamoyl)phenoxy)chroman-4-carboxylic acid, sodium salt of Enantiomer 2 as free flowing solid. MS (apci, pos) m/z=516. $^1$H NMR (400 MHz, D6 DMSO) δ 8.42 (br s, 1H), 7.79 (m, 2H), 7.54 (s, 1H), 7.14 (d, 1H), 7.02 (s, 1H), 6.91 (m, 3H), 6.51 (s, 1H), 4.20 (m, 1H), 4.11 (m, 1H), 3.80 (s, 3H), 3.41 (m, 2H), 3.19 (m, 1H), 2.78 (m, 2H), 2.19 (m, 1H), 1.76 (m, 1H). Optical rotation: $[\alpha]^{25}_D$=−17.46° (c=1.00, MeOH).

During the chiral separation described in Step C, fractions containing peak 1 were collected to provide Enantiomer 1 of 6-chloro-7-(4-(4-chloro-2-methoxyphenethylcarbamoyl) phenoxy)chroman-4-carboxylic acid. MS (apci, pos) m/z=516. Chiral purity (ee) >98% as measured with CHIRALPAK® QD-AX column in comparison to racemic material. The sodium salt of Enantiomer 1 was then prepared in a manner similar to that provided in Step D. The sodium salt of Enantiomer 1 was found to be less active than the sodium salt of Enantiomer 2 when tested in an assay described in Example A.

Example 238

Enantiomer 2 of 6-chloro-7-(4-(2-methoxy-4-(trifluoromethyl)phenethylcarbamoyl)phenoxy)chroman-4-carboxylic acid and preparation of sodium salt

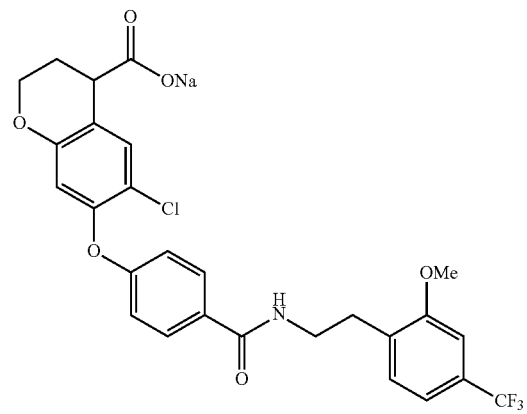

Step A: Preparation of ethyl 6-chloro-7-(4-(2-methoxy-4-(trifluoromethyl)phenethylcarbamoyl)phenoxy)chroman-4-carboxylate A portion of 4-(6-chloro-4-(ethoxycarbonyl)chroman-7-yloxy)benzoic acid (Preparation 1; 0.7 g, 1.86 mmol) was diluted with dichloromethane (1 mL) followed by the addition of oxalyl chloride in dichloromethane (1.02 ml, 2.04 mmol) and DMF (1 drop). After stirring for 10 minutes, 2-(2-methoxy-4-(trifluoromethyl)phenyl)ethanamine (Preparation 9; 0.448 g, 2.04 mmol) and DIEA (1.13 ml, 6.50 mmol) were added, and the reaction was stirred for 2 hours. The reaction was loaded directly onto a biotage 25 cartridge and eluted with 5% ethyl acetate/hexanes to 75% ethyl acetate/hexanes to yield ethyl 6-chloro-7-(4-(2-methoxy-4-(trifluoromethyl)phenethylcarbamoyl)phenoxy)chroman-4-carboxylate (624 mg, 1.08 mmol, 58.1% yield).

Step B: Preparation of 6-chloro-7-(4-(2-methoxy-4-(trifluoromethyl)phenethylcarbamoyl)phenoxy)chroman-4-carboxylic acid Ethyl 6-chloro-7-(4-(2-methoxy-4-(trifluoromethyl)phenethylcarbamoyl)phenoxy)chroman-4-carboxylate (100 mg, 0.173 mmol) was diluted with tetrahydrofuran (1 mL) followed by the addition of sodium hydroxide (692 μL of a 1 M aqueous solution, 0.692 mmol) and ethanol (500 μL). After stirring for 2 hours, the reaction was diluted with ethyl acetate and 2N aqueous HCl. The layers were separated and the organic layer was dried over MgSO$_4$, filtered and concentrated. The material was purified using two 0.5 mm preparative silica gel plates eluting with 10% methanol/dichloromethane to yield 6-chloro-7-(4-(2-methoxy-4-(trifluoromethyl)phenethylcarbamoyl)phenoxy)chroman-4-carboxylic acid (61 mg, 0.111 mmol, 64.1% yield). $^1$H NMR (400 MHz, D6 DMSO) δ 8.48 (t, 1H), 7.82 (d, 2H), 7.44 (s, 1H), 7.35 (d, 1H), 7.23 (m, 2H), 6.96 (d, 2H), 6.61 (s, 1H), 4.24 (m, 1H), 4.08 (m, 1H), 3.87 (s, 3H), 3.82 (t, 1H), 3.47 (q, 1H), 3.17 (d, 1H), 2.89 (t, 2H), 2.21 (m, 1H), 2.05 (m, 1H).

Step C: Isolation of Enantiomer 2 of 6-chloro-7-(4-(2-methoxy-4-(trifluoromethyl)phenethylcarbamoyl)phenoxy)chroman-4-carboxylic acid The racemic mixture of 6-chloro-7-(4-(2-methoxy-4-(trifluoromethyl)phenethylcarbamoyl)phenoxy)chroman-4-carboxylic acid was dissolved in methanol and resolved via supercritical fluid chromatography employing a CHIRALCEL® OJ-H column (3×15 cm) eluting with methanol/carbon dioxide at 100 bar, using 1 mL injections and a flow rate of 70 mL/min. Collection of fractions containing peak 2 and removal of volatiles provided Enantiomer 2 of 6-chloro-7-(4-(2-methoxy-4-(trifluoromethyl)phenethylcarbamoyl)phenoxy)chroman-4-carboxylic acid. Chiral purity (ee) >98% as measured with CHIRALPAK® QD-AX column in comparison to racemic material. $^1$H NMR (400 MHz, D6 DMSO) δ 7.86 (m, 2H), 7.51 (s, 1H), 7.42 (d, 1H), 7.19 (m, 2H), 6.78 (m, 2H), 6.36 (s, 1H), 4.20 (dt, 1H), 4.09 (m, 1H), 3.86 (s, 3H), 3.36 (t, 2H), 3.21 (t, 1H), 2.79 (t, 2H), 2.18 (m, 1H), 1.77 (m, 1H).

Step D: Preparation of the sodium salt of Enantiomer 2 of 6-chloro-7-(4-(2-methoxy-4-(trifluoromethyl)phenethylcarbamoyl)phenoxy)chroman-4-carboxylic acid Enantiomer 2 of 6-chloro-7-(4-(2-methoxy-4-(trifluoromethyl)phenethylcarbamoyl)phenoxy) chroman-4-carboxylic acid (50 mg, 0.091 mmol) was diluted with THF (300 µL) followed by the addition of sodium methoxide (182 µL, 0.091 mmol). After stirring for 1 hour, the reaction was concentrated and placed under vacuum overnight. The residue was re-suspended in ethanol and concentrated. The material was dried under vacuum at 60° C. for 5 hours and then at ambient temperature overnight to yield the sodium salt of Enantiomer 2 of 6-chloro-7-(4-(2-methoxy-4-(trifluoromethyl)phenethylcarbamoyl)phenoxy)chroman-4-carboxylic acid (40 mg, 0.073 mmol) as a white solid.

Example 239

Enantiomer 2 of 6-chloro-7-(4-(2,4-dimethoxyphenethylcarbamoyl)phenoxy)chroman-4-carboxylic acid and preparation of sodium salt

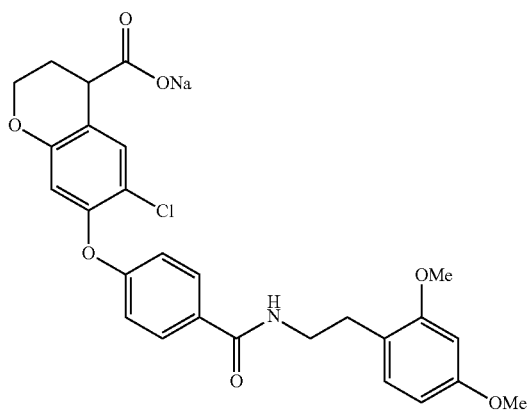

Step A: Preparation of ethyl 6-chloro-7-(4-(2,4-dimethoxyphenethyl carbamoyl)phenoxy)chroman-4-carboxylate 4-(6-Chloro-4-(ethoxycarbonyl)chroman-7-yloxy)benzoic acid (Preparation 1; 9.099 ml, 3.185 mmol) in DMF was treated sequentially with N-ethyl-N-isopropylpropan-2-amine (0.8321 ml, 4.777 mmol), 2-(2,4-dimethoxyphenyl)ethanamine hemisulfate (commercially available from ChemBridge Corporation; 0.95 g; 2.07 mmol), N1-((ethylimino)methylene)-N3,N3-dimethylpropane-1,3-diamine hydrochloride (0.7326 g, 3.822 mmol), and 3H-[1,2,3]triazolo[4,5-b]pyridin-3-ol (0.1300 g, 0.9554 mmol) at ambient temperature. The reaction was stirred for 14 hours. The reaction was partitioned between ethyl acetate and brine, the organic layer dried in vacuo, filtered, concentrated and purified on silica gel. Elution with 20 to 75% ethyl acetate-hexanes provided ethyl 6-chloro-7-(4-(2,4-dimethoxyphenethylcarbamoyl)phenoxy)chroman-4-carboxylate (1.255 g, 2.324 mmol) as an off white solid.

Step B: Preparation of 6-chloro-7-(4-(2,4-dimethoxyphenethyl carbamoyl)phenoxy)chroman-4-carboxylic acid Ethyl 6-chloro-7-(4-(2,4-dimethoxyphenethylcarbamoyl)phenoxy)chroman-4-carboxylate (1.25 g, 2.31 mmol) in 2:1 THF-Ethanol (25 mL) was treated with sodium hydroxide (9.26 ml, 9.26 mmol) at ambient temperature. After 3 hours, HPLC showed complete and clean conversion to a more polar peak. The reaction was diluted with ethyl acetate and acidified with hydrogen chloride (9.72 ml, 9.72 mmol). Brine was added and the reaction transferred to separatory funnel. The mixture was extracted with ethyl acetate. The organic layer showed a single spot (10% MeOH in CHCl$_3$ with a few drops of AcOH). The ethyl acetate layer was dried over sodium sulfate, filtered, and concentrated in vacuo to give 1.2 g of 6-chloro-7-(4-(2,4-dimethoxyphenethylcarbamoyl)phenoxy)chroman-4-carboxylic acid as a white solid. MS (apci, pos) m/z=512.

Step C: Isolation of Enantiomer 2 of 6-chloro-7-(4-(2,4-dimethoxyphenethylcarbamoyl)phenoxy)chroman-4-carboxylic acid The racemic mixture of 6-chloro-7-(4-(2,4-dimethoxyphenethylcarbamoyl)phenoxy)chroman-4-carboxylic acid was dissolved in methanol and resolved via supercritical fluid chromatography employing a CHIRALCEL® OJ-H column (3×15 cm) and eluting with methanol/carbon dioxide at 100 bar, using 1 mL injections and a flow rate of 70 mL/min. Collection of fractions containing peak 2 and removal of volatiles provided Enantiomer 2 of 6-chloro-7-(4-(2,4-dimethoxyphenethylcarbamoyl)phenoxy)chroman-4-carboxylic acid. Chiral purity (ee) >98% as measured with CHIRALPAK® QD-AX column in comparison to racemic material.

Step D: Preparation of the sodium salt of Enantiomer 2 of 6-chloro-7-(4-(2,4-dichloro-6-methoxyphenethylcarbamoyl)phenoxy)chroman-4-carboxylic acid The material obtained above (peak 2; 32 mg, 0.063 mmol) was dissolved in 3:1 THF-MeOH (2 ml total volume) was treated with sodium methanolate, 0.5 M in MeOH (125 µL, 0.063 mmol) at ambient temperature with rapid stirring. After 10 minutes, the reaction was concentrated in vacuo to a white semi-solid that was suspended in ethyl acetate and concentrated to a white solid. The solids were suspended in ethanol, and the suspension was concentrated in vacuo (4 torr on rotary evaporator at 50° C.) and the resulting solids were dried under high vacuum for 24 hours to give 33 mg of the sodium salt of Enantiomer 2 as a white solid. MS (apci, pos) m/z=512. MS (apci, neg) m/z=510.

During the chiral separation described in Step C, fractions containing peak 1 were collected to provide Enantiomer 1 of 6-chloro-7-(4-(2,4-dimethoxyphenethylcarbamoyl)phenoxy)chroman-4-carboxylic acid. Chiral purity (ee) >98% as measured with CHIRALPAK® QD-AX column in comparison to racemic material. The sodium of Enantiomer 1 was then prepared in a manner similar to that described in Step D. MS (apci, pos) m/z=512. The sodium salt of Enantiomer 1 was found to be less active than the sodium salt of Enantiomer 2 when tested in an assay described in Example A.

What is claimed is:

1. A method of treating an allergic inflammatory disease selected from asthma, dermatitis, allergic rhinitis, urticaria, anaphylaxis, angioedemea, allergies, contact hypersensitivity, drug hypersensitivity, and allergic conjunctivitis in a mammal, comprising administering a therapeutically effective amount of a compound of Formula I

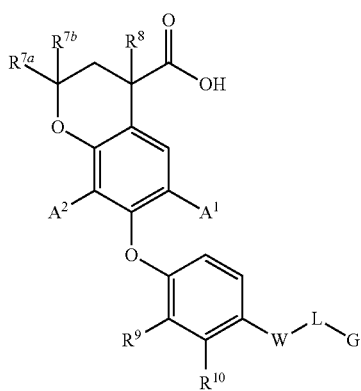

I or a pharmaceutically acceptable salt thereof, to said mammal in need thereof, wherein:
$A^1$ is hydrogen, CN, Cl, F, Br, OMe, (1-4C alkyl) or cyclopropyl;
$A^2$ is hydrogen, Cl, Br, F, (1-4C alkyl) or cyclopropyl;
W is —C(=O)NR$^1$— or —NR$^2$C(=O)—;
$R^1$ and $R^2$ are each hydrogen or methyl;
L is a bond, —(CR$^3$R$^4$)$_n$—(CR$^a$R$^b$)$_m$—(CR$^5$R$^6$)—*, (2-4C)alkenylene, —O(1-4C alkyl)-*, -(1-4C alkyl)-O—*, -(1-4C alkyl)-S—*, (3-6C)cycloalkylene, or hetCyc$^1$, wherein the * indicates the point of attachment to G, provided that when W is —NR$^2$C(=O)— then L is not —(CH=CH)—;
m=0, 1 or 2;
n=0 or 1;
$R^a$ and $R^b$ are independently selected from hydrogen and (1-4C alkyl);
$R^3$ is hydrogen, (1-4C alkyl) or CH$_2$OH;
$R^4$ is hydrogen or methyl;
$R^5$ is hydrogen, (1-4C alkyl), OH, —O(1-4C alkyl) or F;
$R^6$ is hydrogen, F or methyl,
or $R^5$ and $R^6$ together with the carbon to which they are attached form a cyclopropyl ring;
hetCyc$^1$ is a group having the formula

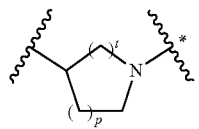

where t is 1 or 2 and p is 0 or 1, and the * indicates the point of attachment to G;
G is Ar$^1$, Ar$^2$, naphthyl, a benzo-fused (5-6C)cycloalkyl ring optionally substituted with one or more substituents independently selected from Cl and OMe, a benzo-fused 5-6 membered heterocyclic ring having 1-2 heteroatoms independently selected from O and N, a (3-6C)cycloalkyl ring optionally substituted with one or more substituents independently selected from (1-4C)alkyl, an oxaspirononanyl ring, or t-butyl;
Ar$^1$ is phenyl optionally substituted with one or more substituents independently selected from F, Cl, Br, CF$_3$, (1-4C)alkyl, OH, —O(1-4C alkyl), —S(1-3C alkyl), —SCF$_3$, cyclopropyl, —CH$_2$N(1-3C alkyl)$_2$, —O-(2-3C)fluoroalkyl, —O-(1-3C) difluoroalkyl —O-(1-3C)trifluoroalkyl, —OCH$_2$(cyclopropyl), and (3-4C)alkynyl;
Ar$^2$ is phenyl which is substituted with Ar$^3$, —O—Ar$^4$, hetAr$^1$ or —O-hetAr$^2$, wherein Ar$^2$ is optionally further substituted with one or more substituents independently selected from F, Cl and CF$_3$;
Ar$^3$ is phenyl optionally substituted with one or more substituents independently selected from F, Cl, Br and (1-4C alkyl);
Ar$^4$ is phenyl optionally substituted with one or more substituents independently selected from F, Cl, Br and (1-4C alkyl);
hetAr$^1$ is a 6-membered heteroaryl having 1-2 nitrogen atoms and optionally substituted with one or more substituents independently selected from (1-4C alkyl);
hetAr$^2$ is a 6-membered heteroaryl having 1-2 nitrogen atoms and optionally substituted with one or more substituents independently selected from (1-4C alkyl) and CF$_3$;
$R^{7a}$, $R^{7b}$ and $R^8$ are each independently hydrogen or methyl;
$R^9$ is hydrogen, methyl, fluoro or NO$_2$; and
$R^{10}$ is hydrogen, methyl or fluoro.

2. The method of claim 1, where W is —C(=O)NR$^1$—.

3. The method of claim 1, wherein:
L is selected from a bond, —(CR$^3$R$^4$)$_n$—(CR$^a$R$^b$)$_m$—(CR$^5$R$^6$)—*, and (3-6C)cycloalkylene; and
G is selected from Ar$^1$, Ar$^2$ and a (3-6C)cycloalkyl ring.

4. The method of claim 3, wherein L is selected from a bond and —(CR$^3$R$^4$)$_n$—(CR$^a$R$^b$)$_m$—(CR$^5$R$^6$)—*.

5. The method of claim 1, wherein L is selected from hetCyc$^1$, —O(1-4C alkyl)-*, -(1-4C alkyl)-O—* and -(1-4C alkyl)-S—*.

6. The method of claim 1, wherein G is Ar$^1$ or Ar$^2$.

7. The method of claim 1, wherein:
Ar$^1$ is phenyl optionally substituted with one or more substituents independently selected from F, Cl, Br, CF$_3$, methyl, ethyl, propyl, tert-butyl, OH, methoxy, ethoxy, propoxy, isopropoxy, tert-butoxy, SMe, SCF$_3$, cyclopropyl, CH$_2$NMe$_2$, OCH$_2$CH$_2$F, OCH$_2$CH$_2$CH$_2$F, OCHF$_2$, OCF$_3$, —OCH$_2$(cyclopropyl), and propynyl;
Ar$^3$ is selected from phenyl, 2-chlorophenyl, 3-chlorophenyl, 4-chlorophenyl, 3-methylphenyl, 4-methylphenyl, 3,4-dimethylphenyl, and 2,3-dimethylphenyl;

—O—Ar⁴ is selected from groups having the formula:

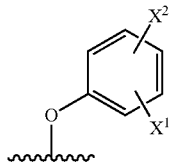

where $X^1$ and $X^2$ are independently selected from fluoro, chloro and bromo;
hetAr¹ is selected from a pyridyl and pyrimidyl ring, each of which is optionally substituted with one or more (1-4C alkyl) groups; and
O-hetAr² is selected from pyridinyloxy and pyrimidinyloxy ring, each of which is optionally substituted with $CF_3$.

8. The method of claim 1, wherein G is a (3-6C)cycloalkyl ring.

9. The method of claim 1, wherein $A^1$ is selected from Cl, CN and cyclopropyl, and $A^2$ is selected from H, Cl and cyclopropyl.

10. The method of claim 9, wherein $A^1$ is CN, Cl or cyclopropyl.

11. The method of claim 10, wherein $A^1$ is CN.

12. The method of claim 10, wherein $A^1$ is Cl.

13. The method of claim 10, wherein $A^2$ is selected from hydrogen and cyclopropyl.

14. The method of claim 1, wherein
$A^1$ is CN, Cl, or cyclopropyl;
$A^2$ is hydrogen, Cl, Br, or cyclopropyl;
W is —C(=O)NH—;
L is a bond or —$(CR^3R^4)_n$—$(CR^aR^b)_m$—$(CR^5R^6)$—; and
G is $Ar^1$, $Ar^2$, naphthyl or a (3-6C)cycloalkyl ring optionally substituted with one or more substituents independently selected from (1-4C)alkyl.

15. The method of claim 14, wherein G is $Ar^1$, wherein $Ar^1$ is phenyl optionally substituted with one or more substituents independently selected from F, Cl, Br, $CF_3$, methyl, ethyl, propyl, tert-butyl, OH, methoxy, ethoxy, propoxy, isopropoxy, tert-butoxy, SMe, $SCF_3$, cyclopropyl, $CH_2NMe_2$, $OCH_2CH_2F$, $OCH_2CH_2CH_2F$, $OCHF_2$, $OCF_3$, —$OCH_2$(cyclopropyl), and propynyl.

16. The method of claim 15, wherein L is a bond or $CH_2CH_2$.

17. The method of claim 16, wherein $Ar^1$ is substituted with one to three of said substituents.

18. The method of claim 17, wherein $R^{7a}$, $R^{7b}$ and $R^8$ are each hydrogen.

19. The method of claim 18, wherein $R^9$ and $R^{10}$ are each hydrogen.

20. The method of claim 1, wherein said compound is selected from:
6-Cyano-7-(4-(4-chlorophenylcarbamoyl)phenoxy)chroman-4-carboxylic acid;
7-(4-(4-chlorophenylcarbamoyl)phenoxy)-6-cyano-4-methylchroman-4-carboxylic acid;
7-(4-(4-Chlorophenylcarbamoyl)phenoxy)-6-cyano-2,2-dimethylchroman-4-carboxylic acid;
6-Cyano-7-(4-(2,4-dichlorophenylcarbamoyl)phenoxy)chroman-4-carboxylic acid;
6-Cyano-7-(4-(phenethylcarbamoyl)phenoxy)chroman-4-carboxylic acid;
6-Cyano-7-(4-(2,3-dihydro-1H-inden-2-ylcarbamoyl)phenoxy)chroman-4-carboxylic acid;
7-(4-(4-Chlorobenzyloxycarbamoyl)phenoxy)-6-cyano-chroman-4-carboxylic acid;
6-Cyano-7-(4-(3,4-dichlorophenylcarbamoyl)phenoxy)chroman-4-carboxylic acid;
6-Chloro-7-(4-(4-chlorophenethylcarbamoyl)-2-nitrophenoxy)chroman-4-carboxylic acid;
6-Chloro-7-(4-(4-chlorophenethylcarbamoyl)phenoxy)chroman-4-carboxylic acid;
6-Chloro-7-(4-(4-chlorophenethylcarbamoyl)phenoxy)chroman-4-carboxylic acid;
6-chloro-7-(4-(phenethylcarbamoyl)phenoxy)chroman-4-carboxylic acid;
6-chloro-7-(4-(4-phenylbutylcarbamoyl)phenoxy)chroman-4-carboxylic acid;
6-chloro-7-(4-(4-(3-chlorophenyl)butylcarbamoyl)phenoxy)chroman-4-carboxylic acid;
6-chloro-7-(4-(4-(4-chlorophenyl)butylcarbamoyl)phenoxy)chroman-4-carboxylic acid;
(Z)-6-chloro-7-(4-(4-(2-chlorophenyl)but-3-enylcarbamoyl)phenoxy)chroman-4-carboxylic acid;
6-chloro-7-(4-(4-(2-chlorophenyl)butylcarbamoyl)phenoxy)chroman-4-carboxylic acid;
(Z)-6-chloro-7-(4-(4-(2,4-dichlorophenyl)but-3-enylcarbamoyl)phenoxy)chroman-4-carboxylic acid;
6-chloro-7-(4-(4-(2,4-dichlorophenyl)butylcarbamoyl)phenoxy)chroman-4-carboxylic acid;
6-chloro-7-(4-(2-methylphenethylcarbamoyl)phenoxy)chroman-4-carboxylic acid;
6-chloro-7-(4-(2,4-dimethylphenethylcarbamoyl)phenoxy)chroman-4-carboxylic acid;
6-chloro-7-(4-(4-methylphenethylcarbamoyl)phenoxy)chroman-4-carboxylic acid;
7-(4-(4-bromophenethylcarbamoyl)phenoxy)-6-chlorochroman-4-carboxylic acid;
6-chloro-7-(4-(4-cyclopropylphenethylcarbamoyl)phenoxy)chroman-4-carboxylic acid;
6-chloro-7-(4-(2-cyclopropylethylcarbamoyl)phenoxy)chroman-4-carboxylic acid;
6-chloro-7-(4-(2-(2'-chlorobiphenyl-4-yl)ethylcarbamoyl)phenoxy)chroman-4-carboxylic acid;
6-chloro-7-(4-(4-chloro-2-methylphenethylcarbamoyl)phenoxy)chroman-4-carboxylic acid;
7-(4-(4-bromo-2-chlorophenethylcarbamoyl)phenoxy)-6-chlorochroman-4-carboxylic acid;
6-chloro-7-(4-(2-(2',3-dichlorobiphenyl-4-yl)ethylcarbamoyl)phenoxy)chroman-4-carboxylic acid;
6-chloro-7-(4-(2-chloro-4-cyclopropylphenethylcarbamoyl)phenoxy)chroman-4-carboxylic acid;
6-chloro-7-(4-(2-(3-chlorobiphenyl-4-yl)ethylcarbamoyl)phenoxy)chroman-4-carboxylic acid;
7-(4-(2-bromo-4-chlorophenethylcarbamoyl)phenoxy)-6-chlorochroman-4-carboxylic acid;
6-chloro-7-(4-(2-(2',5-dichlorobiphenyl-2-yl)ethylcarbamoyl)phenoxy)chroman-4-carboxylic acid;
6-chloro-7-(4-(4-chloro-2-cyclopropylphenethylcarbamoyl)phenoxy)chroman-4-carboxylic acid;
7-(4-(4-bromo-2-methoxyphenethylcarbamoyl)phenoxy)-6-chlorochroman-4-carboxylic acid;
6-chloro-7-(4-(4-cyclopropyl-2-methoxyphenethylcarbamoyl)phenoxy)chroman-4-carboxylic acid;
6-chloro-7-(4-(2,4-dichloro-6-methoxyphenethylcarbamoyl)phenoxy)chroman-4-carboxylic acid;
8-bromo-6-chloro-7-(4-(4-chlorophenethylcarbamoyl)phenoxy)chroman-4-carboxylic acid;
7-(4-(4-chlorophenethylcarbamoyl)phenoxy)-6,8-dicyclopropylchroman-4-carboxylic acid;

6,8-dicyclopropyl-7-(4-(2,4-dichlorophenethylcarbamoyl)phenoxy)chroman-4-carboxylic acid;
7-(4-(4-chlorophenethylcarbamoyl)phenoxy)-6-cyclopropylchroman-4-carboxylic acid;
6-cyclopropyl-7-(4-(2,4-dichlorophenethylcarbamoyl)phenoxy)chroman-4-carboxylic acid;
6-chloro-8-cyclopropyl-7-(4-(2,4-dichlorophenethylcarbamoyl)phenoxy)chroman-4-carboxylic acid;
6-Cyano-7-(4-(4-((dimethylamino)methyl)phenethylcarbamoyl)phenoxy)chroman-4-carboxylic acid
6-Cyano-7-(4-(1,2,3,4-tetrahydroisoquinolin-7-ylcarbamoyl)phenoxy)chroman-4-carboxylic acid;
6,8-dichloro-7-(4-(4-chlorophenethylcarbamoyl)phenoxy)chroman-4-carboxylic acid;
7-(4-((2-Phenylcyclopropyl)carbamoyl)phenoxy)-6-cyano-3,4-dihydro-2H-chromene-4-carboxylic acid;
7-(4-((3-Methoxyphenethyl)carbamoyl)phenoxy)-6-cyano-3,4-dihydro-2H-chromene-4-carboxylic acid;
7-(4-((4-Fluorophenethyl)carbamoyl)phenoxy)-6-cyano-3,4-dihydro-2H-chromene-4-carboxylic acid;
7-(4-((4-(Trifluoromethyl)phenethyl)carbamoyl)phenoxy)-6-cyano-3,4-dihydro-2H-chromene-4-carboxylic acid;
7-(4-((2-(4-Chlorophenyl)cyclopropyl)carbamoyl)phenoxy)-6-cyano-3,4-dihydro-2H-chromene-4-carboxylic acid;
7-(4-(chroman-3-ylcarbamoyl)phenoxy)-6-cyanochroman-4-carboxylic acid
6-Cyano-7-(4-(6-methoxy-1,2,3,4-tetrahydronaphthalen-2-ylcarbamoyl)phenoxy)chroman-4-carboxylic acid;
6-Cyano-7-(4-(naphthalen-1-ylmethylcarbamoyl)phenoxy)chroman-4-carboxylic acid;
6-Cyano-7-(4-(2-(naphthalen-1-yl)ethylcarbamoyl)phenoxy)chroman-4-carboxylic acid;
6-Cyano-7-(4-(2-(naphthalen-2-yl)ethylcarbamoyl)phenoxy)chroman-4-carboxylic acid;
7-(4-(4-tert-Butylphenethylcarbamoyl)phenoxy)-6-cyanochroman-4-carboxylic acid;
7-(4-(2-(Biphenyl-4-yl)ethylcarbamoyl)phenoxy)-6-cyanochroman-4-carboxylic acid;
7-(4-(2-Biphenyl-4-yl)ethylcarbamoyl)phenoxy)-6-chlorochroman-4-carboxylic acid;
6-chloro-7-(4-((R)-2-phenylpropylcarbamoyl)phenoxy)chroman-4-carboxylic acid;
6-chloro-7-(4-((S)-2-phenylpropylcarbamoyl)phenoxy)chroman-4-carboxylic acid;
6-chloro-7-(4-(2-(4-chlorophenyl)propylcarbamoyl)phenoxy)chroman-4-carboxylic acid;
6-chloro-7-(4-(2-methoxyphenethylcarbamoyl)phenoxy)chroman-4-carboxylic acid;
6-chloro-7-(4-(2-(trifluoromethoxy)phenethylcarbamoyl)phenoxy)chroman-4-carboxylic acid;
6-chloro-7-(4-(2-phenoxyphenethylcarbamoyl)phenoxy)chroman-4-carboxylic acid;
6-Cyano-7-(4-(3',4'-dimethylbiphenyl-3-ylcarbamoyl)phenoxy)chroman-4-carboxylic acid;
7-(4-(Biphenyl-3-ylcarbamoyl)phenoxy)-6-cyanochroman-4-carboxylic acid;
7-(4-(Biphenyl-4-ylcarbamoyl)phenoxy)-6-cyanochroman-4-carboxylic acid;
7-(4-(4'-Chlorobiphenyl-4-ylcarbamoyl)phenoxy)-6-cyanochroman-4-carboxylic acid;
6-Cyano-7-(4-(3-(2-methylpyrimidin-4-yl)phenylcarbamoyl)phenoxy)chroman-4-carboxylic acid;
6-Chloro-7-(4-(4'-chloro-6-fluorobiphenyl-3-ylcarbamoyl)phenoxy)chroman-4-carboxylic acid;
6-Cyano-7-(4-(1,2,3,4-tetrahydronaphthalen-2-ylcarbamoyl)phenoxy)chroman-4-carboxylic acid;
7-(4-(5-Chloro-2,3-dihydro-1H-inden-2-ylcarbamoyl)phenoxy)-6-cyanochroman-4-carboxylic acid;
7-(4-(4-Chlorophenylcarbamoyl)phenoxy)-6-cyanochroman-4-carboxylic acid;
6-Cyano-7-(4-(4-(trifluoromethyl)phenylcarbamoyl)phenoxy)chroman-4-carboxylic acid;
6-Cyano-7-(4-(naphthalen-2-ylcarbamoyl)phenoxy)chroman-4-carboxylic acid;
6-chloro-7-(4-(3-(4-chlorophenyl)propylcarbamoyl)phenoxy)chroman-4-carboxylic acid;
6-chloro-7-(4-(3-phenylpropylcarbamoyl)phenoxy)chroman-4-carboxylic acid;
6-chloro-7-(4-(2-chlorophenethylcarbamoyl)phenoxy)chroman-4-carboxylic acid;
6-chloro-7-(4-(2,6-dichlorophenethylcarbamoyl)phenoxy)chroman-4-carboxylic acid;
6-chloro-7-(4-(2,4-difluorophenethylcarbamoyl)phenoxy)chroman-4-carboxylic acid;
6-chloro-7-(4-(2-chloro-6-fluorophenethylcarbamoyl)phenoxy)chroman-4-carboxylic acid;
6-chloro-7-(4-(3-hydroxyphenethylcarbamoyl)phenoxy)chroman-4-carboxylic acid;
6-chloro-7-(4-(4-hydroxyphenethylcarbamoyl)phenoxy)chroman-4-carboxylic acid;
6-chloro-7-(4-(4-fluorophenethylcarbamoyl)phenoxy)chroman-4-carboxylic acid;
6-chloro-7-(4-(2-(naphthalen-1-yl)ethylcarbamoyl)phenoxy)chroman-4-carboxylic acid;
6-chloro-7-(4-(2-(naphthalen-2-yl)ethylcarbamoyl)phenoxy)chroman-4-carboxylic acid;
6-chloro-7-(4-(2,5-dimethoxyphenethylcarbamoyl)phenoxy)chroman-4-carboxylic acid;
6-chloro-7-(4-(2,3-dimethoxyphenethylcarbamoyl)phenoxy)chroman-4-carboxylic acid;
7-(4-(5-bromo-2-methoxyphenethylcarbamoyl)phenoxy)-6-chlorochroman-4-carboxylic acid;
7-(4-(2-bromophenethylcarbamoyl)phenoxy)-6-chlorochroman-4-carboxylic acid;
7-(4-(2-(biphenyl-2-yl)ethylcarbamoyl)phenoxy)-6-chlorochroman-4-carboxylic acid;
6-chloro-7-(4-(2-cyclopropylphenethylcarbamoyl)phenoxy)chroman-4-carboxylic acid;
6-chloro-7-(4-(2-(4'-chlorobiphenyl-2-yl)ethylcarbamoyl)phenoxy)chroman-4-carboxylic acid;
6-chloro-7-(4-(2-(3'-chlorobiphenyl-2-yl)ethylcarbamoyl)phenoxy)chroman-4-carboxylic acid;
6-chloro-7-(4-(2-(2'-chlorobiphenyl-2-yl)ethylcarbamoyl)phenoxy)chroman-4-carboxylic acid;
6-chloro-7-(4-(2-chloro-4-fluorophenethylcarbamoyl)phenoxy)chroman-4-carboxylic acid;
6-chloro-7-(4-(2-chloro-4-(trifluoromethyl)phenethylcarbamoyl)phenoxy)chroman-4-carboxylic acid;
6-chloro-7-(4-(4-chloro-2-methoxyphenethylcarbamoyl)phenoxy)chroman-4-carboxylic acid;
6-chloro-7-(4-(2-chloro-4-methoxyphenethylcarbamoyl)phenoxy)chroman-4-carboxylic acid;
6-chloro-7-(4-(4-fluoro-2-methoxyphenethylcarbamoyl)phenoxy)chroman-4-carboxylic acid;
6-chloro-7-(4-(2-methoxy-4-(trifluoromethyl)phenethylcarbamoyl)phenoxy)chroman-4-carboxylic acid;
6-chloro-7-(4-(2,5-dichlorophenethylcarbamoyl)phenoxy)chroman-4-carboxylic acid;
6-chloro-7-(4-(5-chloro-2-fluorophenethylcarbamoyl)phenoxy)chroman-4-carboxylic acid;

6-chloro-7-(4-(2,4-dichlorophenethylcarbamoyl)-phenoxy)chroman-4-carboxylic acid;
Enantiomer 2 of 6-chloro-7-(4-(2,4-dichlorophenethylcarbamoyl)-phenoxy)chroman-4-carboxylic acid;
6-chloro-7-(4-(2,4-dichlorophenethylcarbamoyl)-phenoxy)chroman-4-carboxylic acid;
6-Cyano-7-(4-(4'-methylbiphenyl-3-ylcarbamoyl)phenoxy)chroman-4-carboxylic acid;
6-Cyano-7-(4-(3'-methylbiphenyl-3-ylcarbamoyl)phenoxy)chroman-4-carboxylic acid;
6-Cyano-7-(4-(2',3'-dimethylbiphenyl-3-ylcarbamoyl)phenoxy)chroman-4-carboxylic acid;
7-(4-(2-(benzo[d][1,3]dioxol-5-yl)ethylcarbamoyl)phenoxy)-6-chlorochroman-4-carboxylic acid;
6-chloro-7-(4-((2,3-dihydro-1H-inden-2-yl)methylcarbamoyl)phenoxy)chroman-4-carboxylic acid;
6-chloro-7-(4-(2-(p-tolylthio)ethylcarbamoyl)phenoxy)chroman-4-carboxylic acid;
6-chloro-7-(4-(2-(4-chlorophenylthio)ethylcarbamoyl)phenoxy)chroman-4-carboxylic acid;
6-chloro-7-(4-(2-ethoxyphenethylcarbamoyl)phenoxy)chroman-4-carboxylic acid;
6-chloro-7-(4-(2-(2-chlorophenoxy)ethylcarbamoyl)phenoxy)chroman-4-carboxylic acid;
7-(4-(2-tert-butoxyphenethylcarbamoyl)phenoxy)-6-chlorochroman-4-carboxylic acid;
6-chloro-7-(4-(2-(methylthio)phenethylcarbamoyl)phenoxy)chroman-4-carboxylic acid;
6-chloro-7-(4-(4-(methylthio)phenethylcarbamoyl)phenoxy)chroman-4-carboxylic acid;
6-chloro-7-(4-(1-(3-chlorophenyl)pyrrolidin-3-ylcarbamoyl)phenoxy)chroman-4-carboxylic acid;
6-chloro-7-(4-(1-(3-chlorophenyl)piperidin-4-ylcarbamoyl)phenoxy)chroman-4-carboxylic acid;
6-chloro-7-(4-(1-(3-(trifluoromethyl)phenyl)azetidin-3-ylcarbamoyl)phenoxy)chroman-4-carboxylic acid;
6-chloro-7-(4-(1-(3-(trifluoromethyl)phenyl)pyrrolidin-3-ylcarbamoyl)phenoxy)chroman-4-carboxylic acid;
6-chloro-7-(4-(1-(3-(trifluoromethyl)phenyl)piperidin-4-ylcarbamoyl)phenoxy)chroman-4-carboxylic acid;
6-chloro-7-(4-(1-(2,4-dichlorophenyl)piperidin-4-ylcarbamoyl)phenoxy)chroman-4-carboxylic acid;
6-chloro-7-(4-((S)-1-(3-chlorophenyl)piperidin-3-ylcarbamoyl)phenoxy)chroman-4-carboxylic acid;
6-Cyano-7-(4-((2,3-dihydro-1H-inden-2-yl)methylcarbamoyl)phenoxy)chroman-4-carboxylic acid;
7-(4-(4-tert-Butylcyclohexylcarbamoyl)phenoxy)-6-cyanochroman-4-carboxylic acid;
7-(4-(4-Chlorophenylcarbamoyl)phenoxy)chroman-4-carboxylic acid;
7-(4-(4-Chlorophenethylcarbamoyl)-2-methylphenoxy)-6-cyanochroman-4-carboxylic acid;
6-Cyano-7-(4-((R)-2-phenylpropylcarbamoyl)phenoxy)chroman-4-carboxylic acid;
6-Cyano-7-(4-((S)-2-phenylpropylcarbamoyl)phenoxy)chroman-4-carboxylic acid;
7-(4-(1-(4-Chlorophenyl)propan-2-ylcarbamoyl)phenoxy)-6-cyanochroman-4-carboxylic acid;
7-(4-(4-Chloro-3-methoxyphenethylcarbamoyl)phenoxy)-6-cyanochroman-4-carboxylic acid;
7-(4-(3-tert-Butylphenylcarbamoyl)phenoxy)-6-cyanochroman-4-carboxylic acid;
6-Cyano-7-(4-(3-isopropoxyphenylcarbamoyl)phenoxy)chroman-4-carboxylic acid;
6-chloro-7-(4-(3,4-dichlorobenzylcarbamoyl)phenoxy)chroman-4-carboxylic acid;
6-chloro-7-(4-(4-(trifluoromethyl)phenethylcarbamoyl)phenoxy)chroman-4-carboxylic acid;
6-chloro-7-(4-(3,4-dichlorophenethylcarbamoyl)phenoxy)chroman-4-carboxylic acid;
6-chloro-7-(4-(2,3-dichlorophenethylcarbamoyl)phenoxy)chroman-4-carboxylic acid;
6-chloro-7-(4-(4-methoxyphenethylcarbamoyl)phenoxy)chroman-4-carboxylic acid;
6-chloro-7-(4-(3,4-dimethoxyphenethylcarbamoyl)phenoxy)chroman-4-carboxylic acid;
7-(4-(4-tert-butylphenethylcarbamoyl)phenoxy)-6-chlorochroman-4-carboxylic acid;
6-chloro-7-(4-(3-methoxyphenethylcarbamoyl)phenoxy)chroman-4-carboxylic acid;
6-chloro-7-(4-(2,4-dimethoxyphenethylcarbamoyl)phenoxy)chroman-4-carboxylic acid;
6-chloro-7-(4-(3-fluorophenethylcarbamoyl)phenoxy)chroman-4-carboxylic acid;
6-chloro-7-(4-(3-methylphenethylcarbamoyl)phenoxy)chroman-4-carboxylic acid;
6-chloro-7-(4-(4-(trifluoromethylthio)phenethylcarbamoyl)phenoxy)chroman-4-carboxylic acid;
6-chloro-7-(4-(3,5-dichlorophenethylcarbamoyl)phenoxy)chroman-4-carboxylic acid;
6-chloro-7-(4-(3-phenoxyphenethylcarbamoyl)phenoxy)chroman-4-carboxylic acid;
6-chloro-7-(4-(3-chlorophenethylcarbamoyl)phenoxy)chroman-4-carboxylic acid;
6-chloro-7-(4-(3-(trifluoromethyl)phenethylcarbamoyl)phenoxy)chroman-4-carboxylic acid;
6-chloro-7-(4-(2-(trifluoromethyl)phenethylcarbamoyl)phenoxy)chroman-4-carboxylic acid;
6-chloro-7-(4-(2-fluorophenethylcarbamoyl)phenoxy)chroman-4-carboxylic acid;
6-Cyano-7-(4-(3-(trifluoromethyl)phenylcarbamoyl)phenoxy)chroman-4-carboxylic acid;
Cis-6-Chloro-7-(4-(4-phenylcyclohexylcarbamoyl)phenoxy)chroman-4-carboxylic acid;
Trans-6-Chloro-7-(4-(4-phenylcyclohexylcarbamoyl)phenoxy)chroman-4-carboxylic acid;
7-(4-(4-tert-butylcyclohexylcarbamoyl)phenoxy)-6-chlorochroman-4-carboxylic acid;
6-Chloro-7-(4-(4,4-dimethylcyclohexylcarbamoyl)phenoxy)chroman-4-carboxylic acid;
6-Chloro-7-(4-(3-phenylcyclohexylcarbamoyl)phenoxy)chroman-4-carboxylic acid;
6-Chloro-7-(4-(3-(3-chlorophenyl)cyclohexylcarbamoyl)phenoxy)chroman-4-carboxylic acid;
6-Chloro-7-(4-(3-(4-methylphenyl)cyclohexylcarbamoyl)phenoxy)chroman-4-carboxylic acid;
6-Chloro-7-(4-(3-(4-methoxyphenyl)cyclohexylcarbamoyl)phenoxy)chroman-4-carboxylic acid;
6-Chloro-7-(4-(3-(4-(methylthio)phenyl)cyclohexylcarbamoyl)phenoxy)chroman-4-carboxylic acid;
6-Chloro-7-(4-(3-(3-methoxyphenyl)cyclohexylcarbamoyl)phenoxy)chroman-4-carboxylic acid;
6-chloro-7-(4-(3-(4-chlorophenyl)cyclohexylcarbamoyl)phenoxy)chroman-4-carboxylic acid;
6-chloro-7-(4-(3-phenylcyclopentylcarbamoyl)phenoxy)chroman-4-carboxylic acid;
6-Chloro-7-(4-(3-p-tolylcyclopentylcarbamoyl)phenoxy)chroman-4-carboxylic acid;
6-Chloro-7-(4-(3-(3-chlorophenyl)cyclopentylcarbamoyl)phenoxy)chroman-4-carboxylic acid;
6-chloro-7-(4-(3-(4-chlorophenyl)cyclopentylcarbamoyl)phenoxy)chroman-4-carboxylic acid;

6-chloro-7-(4-(3-(3-methylphenyl)cyclopentylcarbamoyl)phenoxy)chroman-4-carboxylic acid;
6-chloro-7-(4-(3-(3-(trifluoromethyl)phenyl)cyclopentylcarbamoyl)phenoxy)chroman-4-carboxylic acid;
6-chloro-7-(4-(3-(3-fluorophenyl)cyclopentylcarbamoyl)phenoxy)chroman-4-carboxylic acid;
6-chloro-7-(4-(3-(3-(methylthio)phenyl)cyclopentylcarbamoyl)phenoxy)chroman-4-carboxylic acid;
6-chloro-7-(4-(3-(3,4-dichlorophenyl)cyclopentylcarbamoyl)phenoxy)chroman-4-carboxylic acid;
6-chloro-7-(4-(3-(4-methoxyphenyl)cyclopentylcarbamoyl)phenoxy)chroman-4-carboxylic acid;
6-chloro-7-(4-(3-(4-(methylthio)phenyl)cyclopentylcarbamoyl)phenoxy)chroman-4-carboxylic acid;
6-chloro-7-(4-(4-(4-chlorophenyl)cyclohexylcarbamoyl)phenoxy)chroman-4-carboxylic acid;
6-chloro-7-(4-(3-phenylcyclobutylcarbamoyl)phenoxy)chroman-4-carboxylic acid;
6-chloro-7-(4-(1-(4-chlorophenyl)-3-hydroxypropan-2-ylcarbamoyl)phenoxy)chroman-4-carboxylic acid;
6-chloro-7-(4-(3,3-dimethylbutylcarbamoyl)phenoxy)chroman-4-carboxylic acid;
6-chloro-7-(4-(2-cyclohexylethylcarbamoyl)phenoxy)chroman-4-carboxylic acid;
6-chloro-7-(4-(4-chlorophenethylcarbamoyl)-2-methylphenoxy)chroman-4-carboxylic acid;
6-chloro-7-(4-(2,4-dichlorophenethylcarbamoyl)-2-methylphenoxy)chroman-4-carboxylic acid;
6-chloro-7-(4-(2,4-dichlorophenethylcarbamoyl)-3-methylphenoxy)chroman-4-carboxylic acid;
6-chloro-7-(4-(2-(4-chlorophenyl)-2-hydroxyethylcarbamoyl)phenoxy)chroman-4-carboxylic acid;
6-chloro-7-(4-(2-(2-chlorophenyl)-2-hydroxyethylcarbamoyl)phenoxy)chroman-4-carboxylic acid;
6-chloro-7-(4-(2-cyclopentylethylcarbamoyl)phenoxy)chroman-4-carboxylic acid;
7-(4-(1-oxaspiro[4.4]nonan-3-ylcarbamoyl)phenoxy)-6-chlorochroman-4-carboxylic acid;
6-chloro-7-(4-(2-(4-chlorophenyl)-2-methoxyethylcarbamoyl)phenoxy)chroman-4-carboxylic acid;
6-chloro-7-(4-(2-(4-chlorophenyl)-2-fluoroethylcarbamoyl)phenoxy)chroman-4-carboxylic acid;
6-chloro-7-(4-(3,5-dimethoxyphen-ethylcarbamoyl)phenoxy)chroman-4-carboxylic acid;
6-chloro-7-(4-(3-chloro-2-methoxyphen-ethylcarbamoyl)phenoxy)chroman-4-carboxylic acid;
6-chloro-7-(4-(4-chloro-2-(trifluoro-methyl)phenethylcarbamoyl)phenoxy)chroman-4-carboxylic acid;
7-(4-(2-(benzo[d][1,3]dioxol-4-yl)ethylcarbamoyl)phenoxy)-6-chlorochroman-4-carboxylic acid;
6-chloro-7-(4-(2-(1-(4-(trifluoromethyl)phenyl)-1H-pyrrol-2-yl)ethylcarbamoyl)phenoxy)chroman-4-carboxylic acid;
6-chloro-7-(4-(2-(4-chlorophenyl)-2,2-difluoroethylcarbamoyl)phenoxy)chroman-4-carboxylic acid;
6-chloro-7-(4-(2-ethylphenethylcarbamoyl)phenoxy)chroman-4-carboxylic acid;
6-chloro-7-(4-(2-(2,4-dichlorophenyl)-2-hydroxyethylcarbamoyl)phenoxy)chroman-4-carboxylic acid;
6-chloro-7-(4-(4-chloro-2-ethoxyphen-ethylcarbamoyl)phenoxy)chroman-4-carboxylic acid;
6-chloro-7-(4-(4-chloro-2-(cyclopropyl-methoxy)phenethylcarbamoyl)phenoxy)chroman-4-carboxylic acid;
6-chloro-7-(4-(4-chloro-2-(2-methoxyethoxy)phenethylcarbamoyl)phenoxy)chroman-4-carboxylic acid;
6-chloro-7-(4-(4,5-dichloro-2-ethoxyphenethylcarbamoyl)phenoxy)chroman-4-carboxylic acid;
6-chloro-7-(4-(4-chloro-2-isopropoxy-phenethylcarbamoyl)phenoxy)chroman-4-carboxylic acid;
6-chloro-7-(4-(4-chloro-2-(trifluoromethoxy)phenethylcarbamoyl)phenoxy)chroman-4-carboxylic acid;
6-chloro-7-(4-(3,5-dichlorophen-ethylcarbamoyl)phenoxy)chroman-4-carboxylic acid;
6-chloro-7-(4-((1,2,3,4-tetrahydronaphthalen-1-yl)methylcarbamoyl)phenoxy)chroman-4-carboxylic acid;
6-chloro-7-(4-(2-(4-chlorophenoxy)phenethylcarbamoyl)phenoxy)chroman-4-carboxylic acid;
6-chloro-7-(4-(4-chloro-2-phenoxyphen-ethylcarbamoyl)phenoxy)chroman-4-carboxylic acid;
6-chloro-7-(4-(4-chloro-2-(4-chlorophenoxy)phenethylcarbamoyl)phenoxy)chroman-4-carboxylic acid;
6-chloro-7-(4-(2-(3-chlorophenoxy)phenethylcarbamoyl)phenoxy)chroman-4-carboxylic acid;
6-chloro-7-(4-(2-(2-chlorophenoxy)phenethylcarbamoyl)phenoxy)chroman-4-carboxylic acid;
6-chloro-7-(4-(4-chloro-2-(3-chlorophenoxy)phenethylcarbamoyl)phenoxy)chroman-4-carboxylic acid;
6-chloro-7-(4-(2-(3,4-dichlorophenoxy)-5-fluorophenethylcarbamoyl)phenoxy)chroman-4-carboxylic acid;
6-chloro-7-(4-(2-(2,4-dichlorophenoxy)-5-fluorophenethylcarbamoyl)phenoxy)chroman-4-carboxylic acid;
6-chloro-7-(4-(4-chloro-2-(2-fluoroethoxy)phenethylcarbamoyl)phenoxy)chroman-4-carboxylic acid;
6-chloro-7-(4-(4-chloro-2-(3-fluoropropoxy)phenethylcarbamoyl)phenoxy)chroman-4-carboxylic acid;
6-chloro-7-(4-(2-chloro-6-methoxyphen-ethylcarbamoyl)phenoxy)chroman-4-carboxylic acid;
6-chloro-7-(4-(2,6-dimethoxyphen-ethylcarbamoyl)phenoxy)chroman-4-carboxylic acid;
5-chloro-7-(4-(4-chlorophenethylcarbamoyl)phenoxy)chroman-4-carboxylic acid;
7-(4-((1-(4-chlorophenyl)cyclopropyl)methylcarbamoyl)phenoxy)-6-cyanochroman-4-carboxylic acid;
6-chloro-7-(4-(2-phenoxyethylcarbamoyl)phenoxy)chroman-4-carboxylic acid;
7-(4-(2,4-bis(trifluoromethyl)phenethylcarbamoyl)phenoxy)-6-chlorochroman-4-carboxylic acid;
6-chloro-7-(4-(2,4,6-trimethoxyphenethylcarbamoyl)phenoxy)chroman-4-carboxylic acid;
6-chloro-7-(4-(4-(difluoromethoxy)phenethylcarbamoyl)phenoxy)chroman-4-carboxylic acid;
6-chloro-7-(4-(2,6-dichloro-4-methoxyphenethylcarbamoyl)phenoxy)chroman-4-carboxylic acid;
6-chloro-7-(4-(2,4-diethoxyphenethylcarbamoyl)phenoxy)chroman-4-carboxylic acid;
6-chloro-7-(4-(2-chloro-4,6-dimethoxyphenethylcarbamoyl)phenoxy)chroman-4-carboxylic acid;
6-chloro-7-(4-(4-ethoxy-2-methoxyphenethylcarbamoyl)phenoxy)chroman-4-carboxylic acid;
6-chloro-7-(4-(2-ethoxy-4-methoxyphenethylcarbamoyl)phenoxy)chroman-4-carboxylic acid;
6-chloro-7-(4-(4-chloro-2-(methylthio)phenethylcarbamoyl)phenoxy)chroman-4-carboxylic acid;
6-chloro-7-(4-(4-chloro-2-fluorophenethylcarbamoyl)phenoxy)chroman-4-carboxylic acid;
6-chloro-7-(4-((5-chloro-2,3-dihydro-1H-inden-1-yl)methylcarbamoyl)phenoxy)chroman-4-carboxylic acid;
6-chloro-7-(4-(2-cyclopropyl-4-(trifluoromethyl)phenethylcarbamoyl)phenoxy)chroman-4-carboxylic acid;
6-Chloro-7-(4-(4-chloro-2-hydroxyphenethylcarbamoyl)phenoxy)chroman-4-carboxylic acid;
Enantiomer 2 of 6-chloro-7-(4-(4-chloro-2-cyclopropylphenethylcarbamoyl)phenoxy)chroman-4-carboxylic acid;

Enantiomer 2 of 6-chloro-7-(4-(4-cyclopropyl-2-methoxyphenethylcarbamoyl)phenoxy)chroman-4-carboxylic acid;

Enantiomer 2 of 6-chloro-7-(4-(2,4-dichloro-6-methoxyphenethylcarbamoyl)phenoxy)chroman-4-carboxylic acid;

Enantiomer 2 of 6-chloro-7-(4-(4-chloro-2-methoxyphenethylcarbamoyl)phenoxy)chroman-4-carboxylic acid;

6-chloro-7-(4-(2-methoxy-4-(trifluoromethyl)phenethylcarbamoyl)phenoxy)chroman-4-carboxylic acid;

Enantiomer 2 of 6-chloro-7-(4-(2-methoxy-4-(trifluoromethyl)phenethyl-carbamoyl)phenoxy)chroman-4-carboxylic acid;

Enantiomer 2 of 6-chloro-7-(4-(2,4-dimethoxyphenethylcarbamoyl)phenoxy)chroman-4-carboxylic acid;

or a pharmaceutically acceptable salt thereof.

21. The method of claim 20, wherein said compound is Enantiomer 2 of 6-chloro-7-(4-(4-chlorophenethylcarbamoyl)phenoxy)chroman-4-carboxylic acid.

22. The method of claim 20, wherein said compound is sodium 6,8-dichloro-7-(4-(4-chlorophenethylcarbamoyl)phenoxy)chroman-4-carboxylate.

23. The method of claim 20, wherein said compound is the sodium salt of Enantiomer 2 of 6-chloro-7-(4-(2,4-dichlorophenethylcarbamoyl)-phenoxy)chroman-4-carboxylate.

24. The method of claim 20, wherein said compound is 6-chloro-7-(4-(4-chloro-2-hydroxyphenethylcarbamoyl)phenoxy)chroman-4-carboxylic acid.

25. The method of claim 20, wherein said compound is the sodium salt of Enantiomer 2 of 6-chloro-7-(4-(4-chloro-2-cyclopropylphenethylcarbamoyl)phenoxy)chroman-4-carboxylic acid.

26. The method of claim 20, wherein said compound is the sodium salt of Enantiomer 2 of 6-chloro-7-(4-(4-cyclopropyl-2-methoxyphenethylcarbamoyl)phenoxy)chroman-4-carboxylic acid.

27. The method of claim 20, wherein said compound is the sodium salt of Enantiomer 2 of 6-chloro-7-(4-(4-chloro-2-methoxyphenethylcarbamoyl)phenoxy)chroman-4-carboxylic acid.

28. The method of claim 1, wherein said allergic inflammatory disease is selected from asthma, dermatitis and allergic rhinitis.

29. The method of claim 28, wherein said allergic inflammatory disease is asthma.

30. The method of claim 29, wherein said asthma is mild-to-moderate asthma, severe asthma, refractory asthma, steroid-resistant asthma, steroid-insensitive asthma, or exercise-induced asthma.

31. The method of claim 30, wherein said asthma is mild-to-moderate asthma.

* * * * *